US007749981B2

(12) United States Patent
Boyer et al.

(10) Patent No.: US 7,749,981 B2
(45) Date of Patent: *Jul. 6, 2010

(54) DRUG-ELUTING STENTS COATED WITH NON-NUCLEOTIDE P2Y$_{12}$ RECEPTOR ANTAGONIST COMPOUND

(75) Inventors: José L. Boyer, Chapel Hill, NC (US); James G. Douglass, III, Apex, NC (US); Sammy R. Shaver, Chapel Hill, NC (US)

(73) Assignee: Inspire Pharmaceuticals, Inc., Durham, NC (US)

( * ) Notice: Subject to any disclaimer, the term of this patent is extended or adjusted under 35 U.S.C. 154(b) by 1248 days.

This patent is subject to a terminal disclaimer.

(21) Appl. No.: 11/267,941

(22) Filed: Nov. 4, 2005

(65) Prior Publication Data
US 2006/0121086 A1 Jun. 8, 2006

Related U.S. Application Data

(63) Continuation-in-part of application No. 11/124,619, filed on May 5, 2005, now Pat. No. 7,335,648.

(51) Int. Cl.
*A01N 43/04* (2006.01)
*A61K 31/70* (2006.01)
(52) U.S. Cl. ...................... 514/46; 536/27.23
(58) Field of Classification Search .................. None
See application file for complete search history.

(56) References Cited

U.S. PATENT DOCUMENTS

| 3,321,463 | A | 5/1967 | Moffatt et al. | 260/211.5 |
|---|---|---|---|---|
| 4,794,174 | A | 12/1988 | Secrist | 536/26 |
| 5,049,550 | A | 9/1991 | Zamecnik | 514/47 |
| 5,409,937 | A | 4/1995 | Whittaker | 514/303 |
| 5,681,823 | A | 10/1997 | Kim et al. | 514/47 |
| 5,747,496 | A | 5/1998 | Cox et al. | 514/258 |
| 6,037,343 | A | 3/2000 | Ali | 514/252 |
| 6,040,317 | A | 3/2000 | Duggan et al. | 514/317 |
| 6,048,865 | A * | 4/2000 | Baraldi | 514/46 |
| 6,297,232 | B1 | 10/2001 | Bonnert et al. | 514/211.03 |
| 6,369,064 | B1 | 4/2002 | Brown et al. | 514/258 |
| 6,503,954 | B1 * | 1/2003 | Bhat et al. | 514/772.2 |
| 6,908,624 | B2 | 6/2005 | Hossainy et al. | 424/242 |
| 2003/0077312 | A1 * | 4/2003 | Schmulewicz et al. | 424/426 |
| 2004/0030380 | A1 * | 2/2004 | Shulze et al. | 623/1.42 |
| 2004/0220133 | A1 | 11/2004 | Boyer et al. | 514/47 |
| 2005/0159388 | A1 | 7/2005 | Plourde et al. | |
| 2006/0129225 | A1 * | 6/2006 | Kopia et al. | 623/1.13 |
| 2007/0123544 | A1 * | 5/2007 | Plourde et al. | 514/261.1 |

FOREIGN PATENT DOCUMENTS

| EP | 0 066 918 A | 12/1982 |
|---|---|---|
| EP | 1 348 466 A2 | 10/2003 |
| WO | WO 98/28300 | 7/1998 |
| WO | WO 99/05142 | 2/1999 |
| WO | WO 99/05143 | 2/1999 |
| WO | WO 99/05144 | 2/1999 |
| WO | WO 99/06053 | 2/1999 |
| WO | WO 99/41254 | 8/1999 |
| WO | WO 00/04021 | 1/2000 |
| WO | WO 00/33080 | 6/2000 |
| WO | WO 01/36438 | 5/2001 |
| WO | WO 01/40243 | 6/2001 |
| WO | WO 01/40246 | 6/2001 |
| WO | WO 01/94368 | 12/2001 |
| WO | WO 02/16381 | 2/2002 |
| WO | WO 02/096428 | 12/2002 |
| WO | WO 2005/040174 | 5/2005 |
| WO | WO 2005/097814 | 10/2005 |

OTHER PUBLICATIONS

George A Patani and Edmond J. LaVoie, Bioisosterism: A Rational Approach in Drug Design, Chem. Rev., 1996, 96 (8), 3147-3176.*
Sudha R. Vippagunta, Harry G. Brittain and David J.W. Grant, Crystalline Solids, Advanced Drug Delivery Reviews 48 (2001), 3-26.*
T. J. Pulvirenti, J.L. Yin, X. Chaufour, C. McLachlan, B.D. Hambly, M.R. Bennett and J. A. Carden, P2X (purinergic) receptor redistribution in rabbit aorta following injury to endotherlial cells and cholesterol feeding, Journal of Neurocytology; Sep. 200; 29, 9; p. 623-631.*
STN structure search, CAPlus, Aug. 17, 2009, pp. 396-401.*
Adamiak and Stawiński, "A Highly Effective Route to N,N'-Disubstituted Ureas Under Mild Conditions. An Application to the Synthesis of tRNA Anticodon Loop Fragments Containing Ureidonucleosides," Tetrahedron Letters No. 22, pp. 1935-1936, (1977).
André, et al., "P2Y$_{12}$ regulates platelet adhesion/activation, thrombus growth, and thrombus stability in injured arteries," *J. Clin. Invest.*, 112: 398-406 (2003).
Antiplatelet Trialists' Collaboration, "Collaborative overview of randomized trials of antiplatelet therapy Prevention of death, myocardial antiplatelet therapy in various categories of patients," *Br. Med. J.* 308: 81-106 (1994).
Antiplatelet Trialists' Collaboration, "Collaborative overview of randomized trials of antiplatelet therapy—II: Maintenance of vascular antiplatelet therapy," *Br. Med. J.* 308: 159-168 (1994).

(Continued)

*Primary Examiner*—Robert A Wax
*Assistant Examiner*—Lyndsey Beckhardt
(74) *Attorney, Agent, or Firm*—Howrey LLP; Viola T. Kung

(57) ABSTRACT

The present invention provides a drug-eluting stent, wherein the stent is coated with one or more non-nucleotide P2Y$_{12}$ receptor antagonist compounds or a pharmaceutically acceptable salt, solvate, or hydrate thereof. When the stent is placed in a narrowed or damaged arterial vessel, a therapeutically effective amount of the P2Y$_{12}$ receptor antagonist compound is eluted continuously from the stent to the local environment of the stent. The P2Y$_{12}$ receptor antagonist compound-eluting stents are useful in preventing thrombosis and restenosis, and are effective in inhibiting the contraction of vascular smooth muscle cells, inhibiting cell proliferation, and reducing inflammation.

19 Claims, No Drawings

OTHER PUBLICATIONS

Anzai and Uzawa, "Cyclonucleoside Formation and Ring Cleavage in the Reaction of 2',3'-O-Isopropylideneadenosine with Benzoyl Chloride and Its Substituted Derivatives," *J.Org. Chem.* 49:5076-5080 (1984).

Baraldi, et al., "Novel $N^6$-(Substituted-phenylcarbamoyl)adenosine-5'-uronamides as Potent Agonists for $A_3$ Adenosine Receptors," *Journal of Medicinal Chemistry* 39(3): 802-806 (1996).

Baraldi, et al., "Synthesis and Biological Activity of a New Series of $N^6$-Arylcarbamoyl, 2-(Ar)alkynyl-$N^6$-arylcarbamoyl, and $N^6$-Carboxamido Derivatives of Adenosine-5'-N-ethyluronamide as $A_1$ and $A_3$ Adenosine Receptor Agonists," Journal of Medicinal Chemistry 41:3174-3185 (1998).

Baraldi, et al., "Synthesis and Biological Evaluation of Novel $N^6$[4-(Substituted)sulfonamideophenylcarbamoyl]adenosine-5'-uronamides as $A_3$ Adenosine Receptor Agonists," *Journal of Medicinal Chemistry* 47:5535-5540 (2004).

Bennett, et al., "Thrombotic Thrombocytopenic Purpura Associated with Clopidogrel," *N. Engl. J. Med.* 342: 1771-1777 (2000).

Bennett, et al., "Thrombotic Thrombocytopenic Purpura Associated with Ticlopidine," *Ann. Intern. Med.* 128: 541-544 (1998).

Bernat, et al., "Effect of Various Antiplatelet Agents on Acute Arterial Thrombosis in the Rat," *Thromb. Haemostas.* 70: 812-826 (1993).

Brown, et al., "Matrix Metalloproteinase Inhibitors Containing a (Carboxyalkyl)amino Zinc Ligand: Modification of the P1 and P2' Residues," *J. Med. Chem.* 37(5): 674-688 (1994).

Bush, et al., "Effects of the selective thromboxane synthetase inhibitor dazoxiben on variations in cyclic blood flow in stenosed canine coronary arteries," *Circulation* 69: 1161-1170 (1984).

Camaioni, et al., "Adenosine Receptor Agonists: Synthesis and Biological Evaluation of the Diastereoisomers of 2-(3-Hydroxy-3-phenyl-1-propyn-1-yl)NECA," *Bioorganic & Medicinal Chemistry* 5(12): 2267-2275 (1997).

Cristalli, et al., "2-Aralkynyl and 2-Heteroalkynyl Derivativse of Adenosine-5'-N-ethyluronamide as Selective $A_{2a}$ Adenosine Receptor Agonists," *Journal of Medicinal Chemistry* 38(9): 1462-1472 (1995).

Dangelmaier, et al., "Potentiation of Thromboxane $A_2$-induced Platelet Secretion by Gi Signaling through the Phosphoinositide-3 Kinase Pathway," *Thromb. Haemostas.* 85: 341-348 (2001).

Doorty et al., "Poly(N-isopropylacrylamide) co-polymer films as potential vehicles for delivery of an antimitotic agent to vascular smooth muscle cells", *Cardiovascular Pathology* 12:105-110; 2003.

Folts, et al., "Platelet Aggregation in Partially Obstructed Vessels and its Elimination with Aspirin," *Circulation* 54: 365-370 (1976).

Frederick et al., "The Protective Dose of the Potent GPIIb/IIIa Antagonist SC-54701A is Reduced When Used in Combination with Aspirin and Heparin in a Canine Model of Coronary Artery Thrombosis," *Circulation* 93: 129-134 (1996).

Gachet, C., "ADP Receptors of Platelets and their Inhibition," *Thromb. Haemostas.* 86: 222-232 (2001).

Garcia-Echeverria, C., "A base labile handle for solid phase organic chemistry," *Tetrahedron Lett.*, 38: 8933-8937 (1997).

Geiger, et al., "Specific Impairment of Human Platelet $P2Y_{AC}$ ADP Receptor-Mediated Signaling by the Antiplatelet Drug Clopidogrel," *Arterioscler. Thromb. Vasc. Biol.* 19: 2007-2011 (1999).

Hass, et al., "A Randomized Trial Comparing Ticlopidine Hydrochloride with Aspirin for the Prevention of Stroke in High-Risk Patients," *N. Engl. J. Med.* 321: 501-507 (1989).

Hechler, et al., "A Role of the Fast ATP-gated $P2X_1$ Cation Channel in Thrombosis of Small Arteries In Vivo," *J. Exp. Med.*198: 661-667 (2003).

Herbert, et al., "Inhibitory Effect of Clopidogrel on Platelet Adhesion and Intimal Proliferation After Arterial Injury in Rabbits," *Arterioscl. Thromb.* 13: 1171-1179 (1993).

Hourani, et al., "Effects of the $P_2$-purinoceptor antagonist, suramin, on human platelet aggregation induced by adenosine 5'-diphosphate," *Br. J. Pharmacology* 105: 453-457 (1992).

Humphries, R.G., et al., "Pharmacological profile of the novel P2T-Purinoceptor antagonist, FPL 67085 in vitro and in the anaestheized rat in vitro," Br. J. Pharmacol.115:1110-1116 (1995).

Ingall, et al., "Antagonists of the Platelet $P_{2T}$ Receptor: A Novel Approach to Antithrombotic Therapy," *J. Med. Chem.* 42: 213-220 (1999).

Jacobson, et al., "Structure-Activity Relationships of 9-Alkyladenine and Ribose-Modified Adenosine Derivatives at Rat $A_3$ Adenosine Receptors," *Journal of Medicinal Chemistry* 38(10): 1720-12735 (1995).

Jagroop, et al., "Both the ADP receptors $P2Y_1$ and $P2Y_{12}$, play a roll in controlling shape change in human platelets," *Platelets* 14: 15-20 (2003).

Kapetanakis et al., "Clopidogrel administration prior to coronary artery bypass grafting surgery: the cardiologist's panacea or the surgeon's headache?", *Eur. Heart J.* 26:576-583; 2005.

Kavanagh et al., "Local drug delivery in restenosis injury: thermoresponsive co-polymers as potential drug delivery systems", *Pharmacology & Therapeutics* 102:1-15; 2004.

Lee, et al., "N-Alkoxysulfamide, N-Hydroxysulfamide, and Sulfamate Analogues of Methionyl and Isoleucyl Adenylates as Inhibitors of Methionyl-tRNA and Isoleucyl-tRNA Synthetases," Bioorganic & *Medicinal Chemistry Letters* 13(6): 1087-1092 (2003).

Lekstrom and Bell, "Aspirin in the Prevention of Thrombosis," *Medicine* 70: 161-177 (1991).

Lyga and Secrist III, "Synthesis of Chain-Extended and C-6' Functionalized Precursors of the Nucleoside Antibiotic Sinefungin," *Journal of Organic Chemistry* 48(12): 1982-1988 (1983).

Maffrand, et al., "ADP Plays a Key Role in Thrombogenesis in Rats," *Thromb. Haemostas.* 59: 225-230 (1988).

McKee, et al., "Aspirin Resistance in Cardiovascular Disease: A Review of Prevalence, Mechanisms, and Clinical Significance," *Thromb. Haemostas.* 88: 711-715 (2002).

Mickelson, et al., "Antiplatelet Antibody [7E3 F(ab')$_2$] Prevents Rethrombosis After Recombinant Tissue-Type Plasminogen Activator-Induced Coronary Artery Thrombolysis in a Canine Model," *Circulation* 81: 617-627 (1990).

Mitsunobu, O., "The Use of Diethyl Azodicarboxylate and Triphenylphosphine in Synthesis and Transformation of Natural Products," *Synthesis* 1-28 (1981).

Moffatt, et al., "Nucleoside polyphosphates. VIII. New and Improved Syntheses of Uridine Diphosphate Glucose and Flavin Adenine Dinucleotide Using Nucleoside-5' Phosphoramidates", *Journal of the American Chemical Society*, 80, 3756-61 (1958).

Muni et al., "Coronary drug-eluting stent development: Issues in trial design", *American Heart Journal* 149:415-433; 2005.

Neuhaus, et al., "Safety Observations from the Pilot Phase of the Randomized r-Hirudin for Improvement of Thrombolysis (HIT-III) Study," *Circulation*, 90: 1638-1642 (1994).

Quinn and Fitzgerald, "Ticlopidine and Clopidogrel," *Circulation* 100: 1667-1672 (1999).

Romson, J., et al., "Electrical Induction of Coronary Artery Thrombosis in the Ambulatory Canine: A model for In Vivo Evaluation of Anti-Thrombotic Agents," Thromb. Res. 17:841-853 (1980).

Santosh and Balasubramanian, "A Facile and Stereoselective Synthesis of Arylethers of Vicinal Bromohydrins by Mitsunobu Reaction," *Synthetic Communications*, 24(8): 1049-1062 (1994).

Savi, et al., "Identification and Biological Activity of the Active Metabolite of Clopidogrel," *Thromb. Haemostas.* 84: 891-896 (2000).

Secrist III and Talekar, "5'-C-Chain-extended Adenosine Derivatives Related to Sinefungin, Synthesis and Biological Activity," *Nucleosides & Nucleotides* 9(4): 619-627 (1990).

Shebuski, et al., "Acceleration of Recombinant Tissue-Type Plasminogen Activator-Induced Thrombolysis and Prevention of Reocclusion by the Combination of Heparin and the Arg-Gly-Asp-Containing Peptide Bitistatin in a Canine Model of Coronary Thrombosis," *Circulation* 82: 169-177 (1990).

Springthorpe, Abstracts of Papers, MEDI-016, 225th ACS Natl. Mtg., New Orleans, LA, Mar. 2003.

The EPIC investigators; Califf, R.M. coordinating author; "Use of a Monoclonal Antibody Directed Against the Platelet Glycoprotein IIb/IIIa Receptor in High-Risk Coronary Angioplasty," *New Engl. J. Med.* 330: 956-961 (1994).

The GUSTO IIa investigators; "Randomized Trial of Intravenous Heparin Versus Recombinant Hirudin for Acute Coronary Syndromes," *Circulation* 90: 1631-1637 (1994).

The IMPACT-II investigators; "Randomised placebo-controlled trial of effect of eptifibatide on complications of percutaneous coronary intervention: IMPACT-II," *Lancet* 349: 1422-1428 (1997).

The RESTORE investigators; "Effects of Platelet Glycoprotein IIb/IIIa Blockade with Tirofiban on Adverse Cardiac Events in Patients with Unstable Angina or Acute Myocardial Infarction Undergoing Coronary Angioplasty," *Circulation* 96: 1445-1453 (1997).

The TIMI 9a investigators; "Hirudin in Acute Myocardial Infarction," *Circulation* 90: 1624-1630 (1994).

Tschopp, J.F., et al., "Inhibition of coronary artery reocclusion after thrombolysis with an RGD-containing peptide with no significant effect on bleeding time," Coron. Artery Dis. 4:809-817(1993).

Weber, et al., "Low-Dose Aspirin Versus Anticoagulants for Prevention of Coronary Graft Occlusion,"*Am. J. Cardiol* 66: 1461-1468 (1990).

Wihlborg et al., "ADP Receptor P2Y12 is Expressed in Vascular Smooth Muscle Cells and Stimulates Contraction in Human Blood Vessels", *Arterioscl. Thromb. Vasc. Biol.* 24:1810-1815; 2004.

Gershlick et al., "Inhibition of Restenosis With a Paclitaxel-Eluting, Polymer-Free Coronary Stent, The European evaLUation of pacliTaxel Eluting Stent (ELUTES) Trial," in Circulation, Journal of the American Heart Association, 2004, 109, pp. 487-493.

* cited by examiner

DRUG-ELUTING STENTS COATED WITH NON-NUCLEOTIDE P2Y$_{12}$ RECEPTOR ANTAGONIST COMPOUND

This application is a continuation-in-part of U.S. application Ser. No. 11/124,619, filed May 5, 2005 now U.S. Pat. No. 7,335,648; which is incorporated herein by reference in its entirety.

TECHNICAL FIELD

This invention relates to non-nucleotide compounds and methods of making and using such compounds in the prevention or treatment of diseases or conditions associated with platelet aggregation, including thrombosis, stroke and myocardial infarction in humans and other mammals, and for inhibition of platelet aggregation in blood and blood-related products. This invention also relates to drug-eluting stents, wherein a therapeutically effective amount of a non-nucleotide P2Y$_{12}$ receptor antagonist compound is eluted continuously from the stent to the local environment of the stent, when the stent is placed in a narrowed or damaged arterial vessel.

BACKGROUND OF THE INVENTION

Hemostasis is the spontaneous process of arresting bleeding from damaged blood vessels. Upon injury, precapillary vessels contract within seconds, and thrombocytes, or blood platelets, bind to the exposed subendothelial matrix of an injured vessel by a process called platelet adhesion. Platelets also stick to each other in a phenomenon known as platelet aggregation to form stable platelet aggregates that quickly help stop or slow blood outflow from injured vessels.

An intravascular thrombus can result from pathological disturbances of hemostasis, or by the rupture of atherosclerotic plaques. Platelet adhesion and aggregation are critical events in intravascular thrombosis. Activated under conditions of high shear blood flow in diseased vessels or by the release of mediators from other circulating cells and damaged endothelial cells lining the vessel, platelets and other cells accumulate at a site of vessel injury to form a thrombus, and recruit more platelets to the developing thrombus. The thrombus can grow to sufficient size to block off arterial blood vessels. Thrombi can also form in areas of stasis or slow blood flow in veins. Venous thrombi can easily detach portions of themselves, creating emboli that travel through the circulatory system. This process can result in blockade of other vessels, such as pulmonary arteries. Blockages of this sort can result in pathological outcomes such as pulmonary embolism. Thus, arterial thrombi cause serious disease by local blockade, whereas the morbidity and mortality associated with venous thrombi arise primarily after distant blockade, or embolization. Conditions associated with pathological thrombus formation include venous thromboembolism, thrombophlebitis, deep vein thrombosis, arterial embolism, coronary and cerebral arterial thrombosis, unstable angina, myocardial infarction, stroke, transient ischemic attack, cerebral embolism, renal embolism and pulmonary embolism.

A number of converging pathways lead to platelet aggregation. Whatever the initial stimulus, the final common event is crosslinking of platelets by binding of fibrinogen to a membrane binding site, glycoprotein IIb/IIIa (GP IIb/IIIa, also known as integrin $\alpha_{IIb}\beta_3$). Antagonists of the GP IIb/IIIa receptor have been shown to produce potent antithrombotic effects (Ali, U.S. Pat. No. 6,037,343; Duggan, et al., U.S. Pat. No. 6,040,317). GP IIb/IIIa antagonists include functionblocking antibodies like Abciximab (ReoPro®), cyclic peptides and peptidomimetic compounds (The EPIC investigators; Califf, R. M., coordinating author, New Engl. J. Med. 330: 956-961 (1994); The IMPACT-II investigators, Lancet 349:1422-1428 (1997); The RESTORE investigators, Circulation 96: 1445-1453 (1997)). The clinical efficacy of some of these newer drugs, such as Abciximab, is impressive, but recent trials have found that these approaches are associated with an increased risk of major bleeding, sometimes necessitating blood transfusion (The EPIC investigators; Califf, R. M., coordinating author, New Engl. J. Med. 330: 956-961 (1994)). Also, administration of this class of antiplatelet agent appears to be limited to intravenous methods.

Thrombin can produce platelet aggregation independently of other pathways but substantial quantities of thrombin are unlikely to be present without prior activation of platelets by other mechanisms. Thrombin inhibitors, such as hirudin, are highly effective antithrombotic agents. However, functioning as both antiplatelet and anti-coagulant agents, thrombin inhibitors again can produce excessive bleeding (The TIMI 9a Investigators, Circulation, 90: 1624-1630 (1994); The GUSTO IIa Investigators, Circulation, 90: 1631-1637 (1994); Neuhaus, et al., Circulation, 90: 1638-1642 (1994)).

Various antiplatelet agents have been studied as inhibitors of thrombus formation. Some agents such as aspirin and dipyridamole have come into use as prophylactic antithrombotic agents, and others have been the subjects of clinical investigations. To date, therapeutic agents such as the disintegrins, and the thienopyridines ticlopidine (TICLID®) and clopidogrel (PLAVIX®) have been shown to have utility as platelet aggregation inhibitors, although they can produce a substantial number of side effects and have limited effectiveness in some patients. (Hass, et al., N. Engl. J. Med., 321: 501-507 (1989); Weber, et al., Am. J Cardiol. 66: 1461-1468 (1990); Lekstrom and Bell, Medicine 70: 161-177 (1991)). In particular, the use of the thienopyridines in antiplatelet therapies has been shown to increase the incidence of potentially life threatening thrombotic thrombocytopenic purpura (Bennett, et al., N. Engl. J. Med., 342: 1771-1777 (2000)). Aspirin, which has a beneficial effect on the inhibition of platelet aggregation (Antiplatelet Trialists' Collaboration, Br. Med. J. 308: 81-106 (1994); Antiplatelet Trialists' Collaboration, Br. Med. J. 308: 159-168 (1994)), acts by inhibiting the synthesis of prostaglandins. Its well-documented, high incidence of gastric side effects, however, limits its usefulness in many patients. In addition, aspirin resistance has been observed in some individuals (McKee, et al., Thromb. Haemost. 88: 711-715 (2002)).

Many studies have demonstrated that adenosine 5'-diphosphate (ADP) plays a key role in the initiation and progression of arterial thrombus formation (Bernat, et al., Thromb. Haemostas. 70: 812-826 (1993)); Maffrand, et al., Thromb. Haemostas. 59: 225-230 (1988); Herbert, et al., Arterioscl. Thromb. 13: 1171-1179 (1993)). ADP induces inhibition of adenylyl cyclase and modulation of intracellular signaling pathways such as activation of phosphoinositide-3 kinase (PI3K), influx and mobilization of intracellular $Ca^{+2}$, secretion, shape change, and platelet aggregation (Dangelmaier, et al. Thromb Haemost. 85: 341-348 (2001)). ADP-induced platelet aggregation is triggered by its binding to specific receptors expressed in the plasma membrane of the platelet. There are at least three different P2 receptors expressed in human platelets: P2X$_1$, P2Y$_1$, and P2Y$_{12}$. The P2X$_1$ receptor is a ligand-gated cation channel that is activated by ATP, resulting in a transient influx of extracellular calcium. This receptor has been implicated in the regulation of platelet shape change, and recent evidence suggests its participation in thrombus formation in small arteries under high shear forces. (Jagroop, et al., *Platelets* 14:15-20 (2003); Hechler, et al., *J. Exp. Med.* 198: 661-667 (2003)). The P2Y$_1$ receptor is a G protein-coupled receptor that is activated by ADP, and is responsible for calcium mobilization from intracellular stores, platelet shape change and initiation of aggregation. The P2Y$_{12}$ receptor, also referred to as the P2Y$_{ac}$ and P2$_T$ receptor, is a G protein-coupled receptor that is activated by ADP and is responsible for inhibition of adenylyl cyclase and activation of PI3K. Activation of P2Y$_{12}$ is required for platelet secretion and stabilization of platelet aggregates (Gachet, *Thromb. Haemost.* 86: 222-232 (2001); André, et al., *J. Clin. Invest.*, 112: 398-406 (2003)).

ADP-induced platelet aggregation requires the simultaneous activation of both P2Y$_1$ and P2Y$_{12}$ receptors, and therefore, aggregation can be inhibited by blockade of either receptor. Several authors have demonstrated that ADP-induced aggregation is inhibited in a concentration-dependent manner by analogues of adenosine triphosphate (ATP). ATP, itself, is a weak and nonselective, but competitive, P2Y$_1$ and P2Y$_{12}$ receptor antagonist. Ingall, et al. (*J. Med. Chem.* 42: 213-220 (1999)) have reported that modification of the polyphosphate side chain of ATP along with substitution of the adenine moiety at the C$^2$-position, resulted in compounds that inhibited the P2$_T$ receptor (or P2Y$_{12}$ receptor). Zamecnik (U.S. Pat. No. 5,049,550) has disclosed a method for inhibiting platelet aggregation by administration of a diadenosine tetraphosphate-like compound, App(CH$_2$)ppA. Kim and Zamecnik (U.S. Pat. No. 5,681,823) have disclosed P$^1$, P$^4$-(dithio)-P$^2$, P$^3$-(monochloromethylene)-5', 5'''-diadenosine-P$^1$, P$^4$-tetraphosphate as an antithrombotic agent.

Nucleotide P2Y$_{12}$ antagonists have been developed, however, there is still a need for compounds that have improved oral bioavailability and blood stability.

Thienopyridines, ticlopidine and clopidogrel react covalently with the P2Y$_{12}$ receptor and produce irreversible platelet inhibition in vivo (Quinn and Fitzgerald, *Circulation* 100: 1667-1672 (1999); Geiger, et al., *Arterioscler. Thromb. Vasc. Biol.* 19: 2007-2011 (1999); Savi, et al., *Thromb Haemost.* 84: 891-896 (2000)). Patients treated with thienopyridines usually require 2-3 days of therapy to observe significant inhibition of platelet aggregation, however, and maximal inhibition usually is observed between 4 to 7 days after initiation of treatment. Also, the platelet inhibitory effect of thienopyridines persists up to 7-10 days after the therapy is discontinued, and both ticlopidine and clopidogrel produce a significant prolongation of the bleeding time (from 1.5 to 2-fold over control). Because of the prolonged effect of thienopyridines, these drugs need to be discontinued for 7 to 10 days prior to elective surgery, leaving the patient unprotected from a possible thrombotic event during that period. Recently, the association of thienopyridine treatment with events of thrombotic thrombocytopenic purpura has been reported (Bennett, et al., *N. Engl. J. Med.* 342: 1773-1777 (2000); Bennett, et al., *Ann. Intern. Med.* 128: 541-544 (1998)).

Derivatives of 5,7-disubstituted-1,2,3-triazolol[4,5-d]pyrimidin-3-yl-cyclopentanes and -tetrahydrofurans have been disclosed as antagonists of the P2T- (or P2Y$_{12}$) receptor on platelets (Cox, et al., U.S. Pat. No. 5,747,496, and related patents; Bonnert, et al., U.S. Pat. No. 6,297,232; WO 98/28300; Brown, et al., WO 99/41254; WO 99/05144; Hardern, et al. WO 99/05142; WO 01/36438; and Guile, et al. WO 99/05143) for use in the treatment of platelet aggregation disorders.

Guile, et al. (WO 00/04021) disclose the use of triazolo[4,5-d]pyrimidine compounds in therapy. Brown, et al. (U.S. Pat. No. 6,369,064) disclose the use of Triazolo(4,5-d)pyrimidine compounds in the treatment of myocardial infarction and unstable angina. Dixon, et al. (WO 02/096428) disclose the use of 8-azapurine derivatives in combination with other antithrombotic agents for antithrombotic therapy. Springthorpe discloses AZD6140 as a potent, selective, orally active P2Y$_{12}$ receptor antagonist which is now in Phase I clinical trials (Abstracts of Papers, 225$^{th}$ ACS National Meeting, New Orleans, La.; March, 2003; MEDI-016). WO 02/016381 discloses a method of preventing or treating diseases or conditions associated with platelet aggregation using mononucleoside polyphosphates and dinucleoside polyphosphates.

Stents are typically slotted metal tubes, which can be expanded by a balloon in an angioplastied artery, providing a rigid structural support for the arterial wall. The use of coronary stents for the treatment of patients with acute coronary syndrome has increased significantly during the past years. With coronary stents implanted in more than 2 million people worldwide, some doctors and researchers are now concerned about a long-term problem of blood clots inside the stents that is observed in some patients who have received stents.

In-stent restenosis is caused primarily due to hyperplasia of smooth muscle cells in the intimal layer of the vessel wall (so-called neointimal hyperplasia) and, to a much lesser extent, mural thrombus. On the molecular and cellular levels, the initial vascular injury caused by both inflation of intracoronary balloons and the metal of the stent itself results in denudation of the intima and stretching of the media and adventitia, in addition, both macrophages and polymorphonuclear neutrophils migrate to the site of damage, where they release chemokines. These chemokines serve to increase the amount of matrix metalloproteinase, which leads to remodeling of the extracellular matrix and stimulate smooth muscle cell migration. The wound healing reaction stimulates platelets, growth factor and smooth muscle cell activation, followed by smooth muscle cell and fibroblast migration and proliferation into the injured area. Smooth muscle cells are also stimulated to increase the expression of genes involved in cell division. It is both the interaction and the extent of these processes that lead to neointimal hyperplasia and in-stent restenosis, which are characterized by a marked proliferative response produced by the stent as has been demonstrated by histological examinations. Stenting also raises the systemic levels of inflammatory markers such as C-reactive protein and interleukin-6.

Recently, stents are coated with agents that reduce or prevent exaggerated neointimal proliferation, and thereby, restenosis. For example, paclitaxel-eluting stents inhibit the proliferation of smooth muscle cells, and sirolimus-eluting stents inhibits the inflammation response of the arterial wall. One problem with these stents is that the drugs also inhibit the regeneration of the endothelium destroyed during the expansion of the narrowed artery, creating a potential risk of thrombosis. Thus, the placement of these stents often requires the treatment by systemic administration of antithrombotic drugs.

There is a need in the area of cardiovascular and cerebrovascular therapeutics for improved stents.

SUMMARY OF THE INVENTION

This invention is directed to methods of preventing or treating diseases or conditions associated with platelet aggregation or where the aggregation of platelets inhibits treatment options. This invention is directed to methods of preventing or treating thrombosis and related disorders. This invention is further directed to methods of inhibiting platelet aggregation in blood and blood products comprising platelets, such as stored blood.

The method comprises administering to a mammalian subject or to a sample comprising blood or platelet-comprising material, a composition comprising one or more non-nucleotide $P2Y_{12}$ receptor antagonist compound that effectively binds to $P2Y_{12}$ receptors on platelets, preferably in a reversible manner, and thereby causes a inhibition of the ADP-induced platelet aggregation response in blood or in a platelet-comprising material. The compounds useful for the methods are compounds of general Formula I, III-XII, and/or tautomers thereof, and/or pharmaceutically-acceptable hydrates, solvates, and/or salts thereof.

The invention also provides novel compounds and pharmaceutical compositions. The compounds of Formulae I, and III-XII are useful in that they possess antagonist activity at platelet $P2Y_{12}$ receptors.

Optionally, the compounds of this invention can be used in combination with other compounds useful for the treatment of platelet aggregation disorders or diseases.

The present invention also provides a drug-eluting stent, wherein the stent is coated with one or more non-nucleotide $P2Y_{12}$ receptor antagonist compounds of general Formula I, or a pharmaceutically acceptable salt, solvate, or hydrate thereof. When the stent is placed in a vessel, a therapeutically effective amount of the $P2Y_{12}$ receptor antagonist compound is eluted to the local environment of the stent. The $P2Y_{12}$ receptor antagonist compound-eluting stents are useful in preventing thrombosis and restenosis, and are effective in inhibiting the contraction of vascular smooth muscle cells, inhibiting cell proliferation, and reducing inflammation.

DETAILED DESCRIPTION OF THE INVENTION

Definitions

When present, unless otherwise specified, the following terms are generally defined as, but are not limited to, the following:

Alkyl groups are from 1 to 12 carbons inclusively, either straight chained or branched, with or without unsaturation and with or without heteroatoms, are more preferably from 2 to 8 carbons inclusively, and most preferably 2 to 6 carbons inclusively.

Alkenyl groups are from 1 to 12 carbons inclusively, either straight or branched containing at least one double bond but may contain more than one double bond, with or without heteroatoms.

Alkynyl groups are from 1 to 12 carbons inclusively, either straight or branched containing at least one triple bond but may contain more than one triple bond, and additionally may contain one or more double bonded moieties, with or without heteroatoms.

Cycloalkyl groups from 3 to 12 carbons inclusively, more preferably from 3 to 10 carbons inclusively, and most preferably 3 to 6 carbons inclusively, with or without unsaturation, and with or without heteroatoms.

Aralkyl groups are from 1 to 8 carbons inclusively in the alkyl portion, are more preferably from 1 to 6 carbons inclusively in the alkyl portion, and most preferably are 1 to 4 carbons inclusively in the alkyl portion; as included in the alkyl definition above, the alkyl portion of an aralkyl group can include one or more positions of unsaturation such as a double bond or a triple bond in the chain when the chain includes two or more carbon atoms; the alkyl portion of an aralkyl group can also include one or more heteroatoms and/ or substituents; the aryl portion of an aralkyl group can be a monocyclic or polycyclic moiety from 3 to 8 carbons inclusively per ring in the aryl portion, more preferably from 4 to 6 carbons inclusively per ring, and most preferably 5 to 6 carbons inclusively per ring; the aryl portion of an aralkyl group can also bear one or more substituents and/or heteroatoms.

Aryl groups are either monocyclic or polycyclic, are from 3 to 8 carbons inclusively per ring, are more preferably from 4 to 6 carbons inclusively per ring, and are most preferably 5 to 6 carbons inclusively per ring; aryl groups can also bear substituents and/or heteroatoms.

Heteroaralkyl groups are from 1 to 8 carbons inclusively in the alkyl portion, are more preferably from 1 to 6 carbons inclusively in the alkyl portion, and most preferably are 1 to 4 carbons inclusively in the alkyl portion; as included in the alkyl definition above, the alkyl portion of a heteroaralkyl group can include one or more positions of unsaturation such as a double bond or a triple bond in the chain when the chain includes two or more carbon atoms; the alkyl portion of a heteroaralkyl group can also include one or more heteroatoms and/or substituents; the heteroaryl portion of a heteroaralkyl group can be a monocyclic or polycyclic moiety from 3 to 8 carbons inclusively per ring in the heteroaryl portion and containing from 1 to 4 heteroatoms inclusively per ring, more preferably from 4 to 6 carbons inclusively per ring, and most preferably 5 to 6 carbons inclusively per ring; the heteroaryl portion of an heteroaralkyl group can also bear one or more substituents and/or heteroatoms.

Heteroaryl groups are either monocyclic or polycyclic, contain from 1 to 4 heteroatoms inclusively per ring, are from 3 to 8 atoms inclusively per ring, are more preferably from 4 to 6 atoms inclusively per ring, and are most preferably 5 to 6 atoms inclusively per ring; heteroaryl groups can also bear substituents and/or heteroatoms.

Substituents on the foregoing groups can be, but are not limited to, hydroxy, nitro, methoxy, fluoro, chloro, bromo, iodo, methyl, ethyl, propyl, butyl, thioalkyl, alkoxy, carboxyl, carboxamido, alkylsulfonyl, alkylsulfonylamino, sulfonamido, cyano, amino, substituted amino, trifluoromethyl, trifluoromethoxy, phenyl, pyridyl, imidazolyl, cyclopropyl, cyclopentyl, and cyclohexyl; and preferred heteroatoms are oxygen, nitrogen, and sulfur.

A desired substituent on a chain or ring (in place of a hydrogen at a position) is one selected from the given alkyl, aryl, halogen, aralkyl, carboxy, alkoxycarbonyl, hydroxyl, acyloxy, alkoxy, aryloxy or aralkoxy classes or from other classes, which provides a compound with good-to-excellent $P2Y_{12}$ receptor-binding properties, but which does not yield a compound with undesirable properties like chemical instability in a formulation, or one with levels of toxicity that are not well-tolerated by a treated mammal, or especially, not well-tolerated by a human.

Diastereomers are stereoisomers (isomers of identical constitution but differing three-dimensional architecture), which do not bear a mirror-image relation to each other.

Pharmaceutically acceptable salts are salts that retain the desired biological activity of the parent compound and do not impart undesired toxicological effects. Pharmaceutically acceptable salt forms include various polymorphs as well as the amorphous form of the different salts derived from acid or base additions. The acid addition salts can be formed with inorganic or organic acids. Illustrative but not restrictive examples of such acids include hydrochloric, hydrobromic, sulfuric, phosphoric, citric, acetic, propionic, benzoic, napthoic, oxalic, succinic, maleic, malic, mesylic, adipic, lactic, tartaric, salicylic, methanesulfonic, 2-hydroxyethanesulfonic, toluenesulfonic, benzenesulfonic, camphorsulfonic, and ethanesulfonic acids. The pharmaceutically acceptable base addition salts can be formed with metal or organic counterions and include, but are not limited to, alkali metal salts such as sodium or potassium; alkaline earth metal salts such as magnesium or calcium; and ammonium or tetraalkyl ammonium salts, i.e., $NX_4^+$ (wherein X is $C_{1-4}$). Other salts such as hydrochlorides, hydrobromides, mesylates, sulfates, acetates, tartrates, etc., are also contemplated in this invention. Preferred counterions are monovalent ions such as $NH_4^+$, sodium, lithium, potassium, chloride, bromide, bisulfate, and mesylate, with sodium, potassium, chloride and mesylate being most preferred due to ease of manufacture, stability, and physiological tolerance.

Solvates are addition complexes in which a compound is combined with a pharmaceutically acceptable cosolvent in some fixed proportion. Cosolvents include, but are not limited to, water, methanol, ethanol, 1-propanol, isopropanol, 1-butanol, isobutanol, tert-butanol, acetone, methyl ethyl ketone, acetonitrile, ethyl acetate, benzene, toulene, xylene(s), ethylene glycol, dichloromethane, 1,2-dichloroethane, N-methylformamide, N,N-dimethylformamide, N-methylacetamide, pyridine, dioxane, and diethyl ether. Hydrates are solvates in which the cosolvent is water. It is to be understood that the definition of the compound of the present invention encompasses all possible hydrates and solvates, in any proportion, which possess the stated activity.

$P2Y_{12}$ Receptor Antagonist Compounds

The $P2Y_{12}$ receptor antagonist compounds useful for preventing or treating diseases or conditions associated with platelet aggregation and/or platelet activation include compound of general Formula I, and/or tautomers thereof, or a pharmaceutically acceptable salt, solvate, or hydrate thereof:

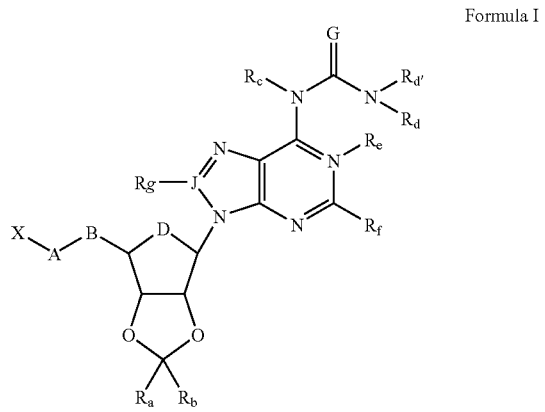

Formula I wherein $R_a$ and $R_b$ are each independently selected from the group consisting of: hydrogen, $C_{1-8}$ alkyl, $C_{1-8}$ alkenyl, $C_{1-8}$ alkynyl, $C_{3-7}$ cycloalkyl, $C_{4-7}$ cycloalkenyl, aralkyl (including saturation and/or unsaturation in the alkylene portion), aryl, and saturated or unsaturated $C_{3-6}$ heterocycle; where all rings or chains optionally can bear one or more desired substituents; or $R_a$ and $R_b$ are taken together to form a ring of 3 to 7 members, with or without substitution, and with or without heteroatoms in place of ring carbon atoms;

$R_c$=H, $C_{1-8}$ alkyl, $C_{3-7}$ cycloalkyl, aralkyl, aryl, or heterocycle, or R(CO)—;

where R is selected from the group consisting of: $C_{1-8}$ alkyl, $C_{1-8}$ alkenyl, $C_{1-8}$ alkynyl, $C_{3-7}$ cycloalkyl, $C_{4-7}$ cycloalkenyl, aryl, aralkyl, heteroaryl, and saturated or unsaturated $C_{3-6}$ heterocycle; where all rings or chains optionally bear one or more desired substituents;

G=O, S, or $NR_d$, where $R_d$ is defined as below;

$R_d$ and $R_{d'}$ are independently selected from the group consisting of: H, $C_{1-8}$ alkyl, $C_{1-8}$ alkenyl, $C_{1-8}$ alkynyl, $C_{3-7}$ cycloalkyl, $C_{4-7}$ cycloalkenyl, $C_{4-11}$ alkylcycloalkyl, $C_{5-11}$ alkylcycloalkenyl, with 1 to 4 carbons in the alkyl portion, aralkyl (including saturation and/or unsaturation in the alkylene portion), aryl, heteroaryl, and saturated or unsaturated $C_{3-6}$ heterocycle; or $R_d$ and $R_{d'}$ groups are taken together to form a ring of 4 to 7 members, with or without unsaturation and with or without heteroatoms in place of ring-carbon units; or $R_d$ or $R_{d'}$ and $R_c$ are taken together to form a ring of 4 to 7 members, with or without unsaturation and with or without heteroatoms in place of ring-carbon units;

$R_e$=O or absent;

$R_f$=H, halogen, $C_{1-8}$ alkyl, $C_{1-8}$ alkenyl, $C_{1-8}$ alkynyl, $C_{3-7}$ cycloalkyl, $C_{4-7}$ cycloalkenyl, $C_{4-11}$ alkylcycloalkyl, $C_{5-11}$ alkylcycloalkenyl, with 1 to 4 carbons in the alkyl portion, aryl, aralkyl (including saturation and/or unsaturation in the alkylene portion), heteroaryl, saturated or unsaturated $C_{3-6}$ heterocycle, —OH, $C_{1-6}$ alkoxy, aryloxy, —SH, $C_{1-6}$ thioalkyl, thioaryl, —[(CO)OR], —[(CO)NRR], amino, —N-substituted amino, or N,N-disubstituted amino; wherein each said substituent on said N-substituted-amino group, or N,N-disubstituted-amino-group of $R_f$ is independently selected from the group consisting of: $C_{1-8}$ alkyl, $C_{1-8}$ alkenyl, $C_{1-8}$ alkynyl, $C_{3-7}$ cycloalkyl, $C_{4-7}$ cycloalkenyl, aryl, aralkyl, heteroaryl, $C_{3-6}$ heterocycle, —[(CO)R] and —[(CO)—NRR]; wherein each R is independently as defined above; or when $R_f$ is —NRR, —[NH(CO)NRR], —[N($C_{1-8}$ alkyl)(CO)NRR], —[N(aryl)(CO)NRR], or [N(aralkyl)(CO)NRR], the R groups of said —NRR unit (N,N-disubstituted-amino-group) in $R_f$ can be taken together such that a ring of 3 to 7 members is formed, with or without heteroatoms in place of the ring-carbon units;

J=N or C, with the proviso that when J=N, then $R_g$ is absent;

when J=C, $R_g$ is selected from the group consisting of: —H, halogen, $C_{1-8}$ alkyl, $C_{1-8}$ alkenyl, $C_{1-8}$ alkynyl, $C_{3-7}$ cycloalkyl, $C_{4-7}$ cycloalkenyl, aralkyl, aryl, —OH, $C_{1-6}$ alkoxy, aryloxy, —SH, $C_{1-6}$ thioalkyl, thioaryl, —[(CO)OR], —[(CO)NRR], and —NRR; wherein each R is independently as defined above; or when $R_g$ is —[(CO)NRR] or —NRR, the R groups of said —NRR unit (N,N-disubstituted-amino-group) in $R_g$ are taken together such that a ring of 3 to 7 members is formed, with or without heteroatoms in place of the ring-carbon units;

D is O, NH, N-acyl, N-alkyl, or C;

A and B are each independently selected from the group consisting of: C, N, substituted N, O, S, S(O), $SO_2$, —$C_{1-3}$ alkylene-, —$C_{1-3}$ heteroalkylene, wherein each said —$C_{1-3}$ alkylene-unit of A and B independently can be saturated or unsaturated, and each carbon of a —$C_{1-3}$ alkylene-unit of B independently can be substituted with 0 to 2 fluorine groups, 0 to 1 methyl groups, 0 to 2 —[(CO)OR] groups, and 0 to 1 —(OR) groups, —$CF_2$—, —(CO)—; —NH(CO)—, —NR(CO)—, —(CO)NH—, —(CO)NR—, —NH(CO)NH—, —NH(CS)NH—, —N(NH)NH—, —N(NR)NH—, —NH(CO)O—, —NH(CS)O—, —O(CO)NH—, —O(CS)NH—, provided that no —S—S— or —O—O— bonds are formed by combination of the -A- and —B— groups; or A and/or B are absent;

X=H, —OR, —COOH, —COOR, —SR, —S(O)RL, —S(O₂)RL, —SO₃H, —S(O₂)NRR, —S(O₂)NR(CO)RL, —NRR, —NR(CO)RL, —N[(CO)RL]₂, —NR(SO₂)RL, —NR(CO)NR(SO₂)RL, —NR(SO₂)NRR, or —NR(SO₂)NR(CO)RL; wherein L is:

H, —CF₃, —CF₂CF₃, C₁₋₈ alkyl, C₁₋₈ alkenyl, C₁₋₈ alkynyl, C₃₋₇ cycloalkyl, C₄₋₇ cycloalkenyl, C₄₋₁₁ alkylcycloalkyl, C₅₋₁₁ alkylcycloalkenyl, with 1 to 4 carbons in the alkyl portion, saturated or unsaturated heteroaryl, aryl, aralkyl (including saturation and/or unsaturation in the alkylene portion), saturated or unsaturated C₃₋₆ heterocycle, C₁₋₆ alkoxy, aralkoxy, aryloxy, N,N-disubstituted-amino, N-substituted-amino, or unsubstituted-amino; where all rings or chains optionally bear one or more desired substituents; or when L is N-substituted-amino, or N,N-disubstituted-amino, each substituent of said amino group of L is selected from the group consisting of: C₁₋₈ alkyl, C₁₋₈ alkenyl, C₁₋₈ alkynyl, C₃₋₇ cycloalkyl, C₄₋₇ cycloalkenyl, aryl, heteroaryl, aralkyl, and C₃₋₆ heterocycle;

when L is N,N-disubstituted-amino, the two substituents independently selected from the group above are taken together to form a ring of 3 to 7 members, wherein said formed ring thereon bears the remaining features of said selected substituents before said ring formation;

optionally can be made for any one-carbon-unit within either or both of said C₁₋₃ alkylene units of A and B, provided that fewer than three said heteroatom-containing-unit for -one-carbon-unit substitutions on the -A-B— chain are made, no —S—S—, or —O—O— bonds are formed in the X-A-B— chain by said substitution or substitutions of a heteroatom-containing-unit for a -one-carbon-unit on the -A-B— chain, and no said heteroatom substitution is made such that the said replacement heteroatom connects directly to the tetrahydrofuran ring shown in Formula I;

wherein the R groups of a —NRR unit (N,N-disubstituted-amino-group) in X optionally can be taken together such that a ring of 3 to 7 members is formed, with or without heteroatoms in place of the ring-carbon units;

with the proviso that when X=H, then at least one of $R_a$ or $R_b$ must be H; or X is a group as provided in Formula II:

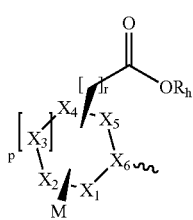

Formula II wherein:

$X_6$ is the attachment point to the moiety defined by A-B;

the ring defined by $X_1$-$X_6$ is taken to mean a ring with or without unsaturation;

$X_1$-$X_6$ are independently C, N, O, or S; and when any of $X_1$-$X_5$ is C, the carbon atom bears an H when doubly bonded in an unsaturated ring, or a substituent M, as defined below; or when any of $X_1$-$X_5$ is C, the carbon atom bears two H when singly bonded in a saturated ring, or one H plus one substituent M, or two substituents M without H, with the proviso that any such moiety with one or two M substituents is of sufficient chemical stability;

when any of $X_1$-$X_5$ is N in an saturated ring, the nitrogen atom bears an H or substituents such as alkyl or acyl;

any of $X_1$-$X_5$ can be absent, with the proviso that at least two of $X_1$-$X_5$ are present, such that the ring described by $X_1$-$X_6$ consists of at least three atoms;

with the provisos that no two adjacent atoms $X_1$-$X_6$ can both be O or S, and that the ring shown in Formula II contains no more than four heteroatoms, and that the shown pendant —CO₂$R_h$ unit in Formula II is a substituent on the ring described in Formula II;

p=0, 1, or 2;

r=0 or 1;

$R_h$ is H, a physiologically-relevant cation forming a carboxylate salt, alkyl, aryl, or aralkyl, with the resultant moiety C(O)OR$_h$ preferably having an adjacent relationship to the attachment point of A; preferably $R_h$ is H or alkyl (such as ethyl):

M is selected from the group consisting of: —H, halogen (such as F, Cl, Br), —CF₃, C₁₋₈ alkyl, C₁₋₈ alkenyl, C₁₋₈ alkynyl, C₃₋₇ cycloalkyl, C₄₋₇ cycloalkenyl, aryl, aralkyl, heteroaryl, saturated or unsaturated C₃₋₆ heterocycle, —OH, cyano, saturated or unsaturated C₁₋₆ alkoxy, aralkoxy, aryloxy, —SH, C₁₋₆ thioalkyl, thioaryl, —[(CO)OR], —[(CO)NRR], amino, —N-substituted amino, and N,N-disubstituted amino; wherein each said substituent on said amino of M is independently selected from the group consisting of: C₁₋₈ alkyl, C₁₋₈ alkenyl, C₁₋₈ alkynyl, C₃₋₇ cycloalkyl, C₄₋₇ cycloalkenyl, aryl, aralkyl, heteroaryl, C₃₋₆ heterocycle, —[(CO)R], —[(CO)O—(C₁₋₈ alkyl)], and —[(CO)—NRR]; and more than one moiety M can be present, either the same or different.

Preferably, the furanosyl moiety in Formula I has the 2'- and 3'-oxygen-groups in a cis-orientation relative to one another on the furanose ring. Further, a furanosyl moiety which supports a 2',3'-acetal or -ketal group is, preferably, derived from ribose; other furanose derivatives can be used, however. A preferred stereochemical embodiment of this invention includes, but is not limited to (D)-ribose-(2',3'-acetal or -ketal) compounds of Formula I, such as found in acetals derived from (−)-adenosine.

In one embodiment of the method, the compound of Formula I is selected from the group consisting of:

4-{2,2-Dimethyl-6-[6-(3-phenyl-ureido)-purin-9-yl]-tetrahydro-furo[3,4-d][1,3]dioxol-4-ylmethoxy}-isophthalic acid (1), 5-Amino-2-{2-benzyl-6-[6-(3-phenyl-ureido)-purin-9-yl]-tetrahydro-furo[3,4-d][1,3]dioxol-4-ylmethoxy}-benzoic acid (2), 3-{2,2-Dimethyl-6-[6-(3-phenyl-ureido)-purin-9-yl]-tetrahydro-furo[3,4-d][1,3]dioxol-4-ylmethoxy}-isoxazole-5-carboxylic acid (3), 4-{2,2-Dimethyl-6-[6-(3-phenyl-ureido)-purin-9-yl]-tetrahydro-furo[3,4-d][1,3]dioxol-4-ylmethoxy}-benzoic acid (4), 5-Amino-2-{2,2-dimethyl-6-[6-(3-phenyl-ureido)-purin-9-yl]-tetrahydro-furo[3,4-d][1,3]dioxol-4-ylmethoxy}-N-hydroxy-benzamide (5), 5-Amino-2-{2-benzyl-6-[6-(3-phenyl-ureido)-purin-9-yl]-tetrahydro-furo[3,4-d][1,3]dioxol-4-ylmethoxy}-N-hydroxy-benzamide (6), 6-{2,2-Dimethyl-6-[6-(3-phenyl-ureido)-purin-9-yl]-tetrahydro-furo[3,4-d][1,3]dioxol-4-ylmethoxy}-nicotinamide (7), 6-{2,2-

Dimethyl-6-[6-(3-phenyl-ureido)-purin-9-yl]-tetrahydro-furo[3,4-d][1,3]dioxol-4-ylmethoxy}-nicotinic acid (8), 2-{2,2-Dimethyl-6-[6-(3-phenyl-ureido)-purin-9-yl]-tetrahydro-furo[3,4-d][1,3]dioxol-4-ylmethoxy}-nicotinic acid (9), 5-Chloro-6-{2,2-dimethyl-6-[6-(3-phenyl-ureido)-purin-9-yl]-tetrahydro-furo[3,4-d][1,3]dioxol-4-ylmethoxy}-nicotinic acid (10), 1-{9-[6-(3-Hydroxy-pyridin-2-yloxymethyl)-2,2-dimethyl-tetrahydro-furo[3,4-d][1,3]dioxol-4-yl]-9H-purin-6-yl}-3-phenyl-urea (11), 6-Chloro-2-{2,2-dimethyl-6-[6-(3-phenyl-ureido)-purin-9-yl]-tetrahydro-furo[3,4-d][1,3]dioxol-4-ylmethoxy}-5-fluoro-nicotinic acid (12), 2-{2-Cyclohexyl-6-[6-(3-phenyl-ureido)-purin-9-yl]-tetrahydro-furo[3,4-d][1,3]dioxol-4-ylmethoxy}-nicotinic acid (13), 2-[6-[6-(3-Phenyl-ureido)-purin-9-yl]-2-(2-trifluoromethyl-phenyl)-tetrahydro-furo[3,4-d][1,3]dioxol-4-ylmethoxy]-nicotinic acid (14), 2-{2-(3,4-Dihydro-1H-naphthalenyl)-6-[6-(3-cyclopentyl-ureido)-purin-9-yl]-tetrahydro-furo[3,4-d][1,3]dioxol-4-ylmethoxy}-nicotinic acid (15), 2-{2-(4-Acetylamino-phenyl)-6-[6-(3-cyclopentyl-ureido)-purin-9-yl]-tetrahydro-furo[3,4-d][1,3]dioxol-4-ylmethoxy}-nicotinic acid (16), 2-{2-Phenyl-6-[6-(3-phenyl-ureido)-purin-9-yl]-tetrahydro-furo[3,4-d][1,3]dioxol-4-ylmethoxy}-nicotinic acid (17), 2-{2-Biphenyl-3-yl-6-[6-(3-phenyl-ureido)-purin-9-yl]-tetrahydro-furo[3,4-d][1,3]dioxol-4-ylmethoxy}-nicotinic acid (18), 2-{2-Naphthalen-2-yl-6-[6-(3-phenyl-ureido)-purin-9-yl]-tetrahydro-furo[3,4-d][1,3]dioxol-4-ylmethoxy}-nicotinic acid (19), 2-{2-(2-Bromo-phenyl)-6-[6-(3-ethyl-ureido)-purin-9-yl]-tetrahydro-furo[3,4-d][1,3]dioxol-4-ylmethoxy}-nicotinic acid (20), 2-{2-Benzo[b]thiophen-3-yl-6-[6-(3-phenyl-ureido)-purin-9-yl]-tetrahydro-furo[3,4-d][1,3]dioxol-4-ylmethoxy}-nicotinic acid (21), 2-{6-[6-(3-Cyclopentyl-ureido)-purin-9-yl]-2-phenethyl-tetrahydro-furo[3,4-d][1,3]dioxol-4-ylmethoxy}-nicotinic acid (22), 2-{6-[6-(3-Cyclopentyl-ureido)-purin-9-yl]-2-phenethyl-tetrahydro-furo[3,4-d][1,3]dioxol-4-ylmethoxy}-nicotinic acid (23), 2-{6-[6-(3-Hexyl-ureido)-purin-9-yl]-2-phenyl-tetrahydro-furo[3,4-d][1,3]dioxol-4-ylmethoxy}-nicotinic acid (24), 2-{2-Biphenyl-4-yl-6-[6-(3-hexyl-ureido)-purin-9-yl]-tetrahydro-furo[3,4-d][1,3]dioxol-4-ylmethoxy}-nicotinic acid (25), 2-{6-[6-(3-Ethyl-ureido)-purin-9-yl]-2-phenylethynyl-tetrahydro-furo[3,4-d][1,3]dioxol-4-ylmethoxy}-nicotinic acid (26), 2-{6-[6-(3-Ethyl-ureido)-purin-9-yl]-2-phenethyl-tetrahydro-furo[3,4-d][1,3]dioxol-4-ylmethoxy}-nicotinic acid (27), 2-{6-[6-(3-Cyclopentyl-ureido)-purin-9-yl]-2-p-tolyl-tetrahydro-furo[3,4-d][1,3]dioxol-4-ylmethoxy}-nicotinic acid (28), 2-{2-(2-indanonyl)-6-[6-(3-phenyl-ureido)-purin-9-yl]-tetrahydro-furo[3,4-d][1,3]dioxol-4-ylmethoxy}-nicotinic acid (29), 2-{6-[6-(3-Ethyl-ureido)-purin-9-yl]-2-phenyl-tetrahydro-furo[3,4-d][1,3]dioxol-4-ylmethoxy}-nicotinic acid (30), 2-{2-tert-Butyl-6-[6-(3-phenyl-ureido)-purin-9-yl]-tetrahydro-furo[3,4-d][1,3]dioxol-4-ylmethoxy}-nicotinic acid (31), 3-({2,2-Dimethyl-6-[6-(3-phenyl-ureido)-purin-9-yl]-tetrahydro-furo[3,4-d][1,3]dioxole-4-carbonyl}-amino)-benzoic acid (32), 2-Benzyl-6-[6-(3-phenyl-ureido)-purin-9-yl]-tetrahydro-furo[3,4-d][1,3]dioxole-4-carboxylic acid (33), 1-{2-Benzyl-6-[6-(3-ethyl-ureido)-purin-9-yl]-tetrahydro-furo[3,4-d][1,3]dioxole-4-carbonyl}-pyrrolidine-2-carboxylic acid (34), 1-{6-[6-(3-Benzyl-ureido)-purin-9-yl]-2-phenyl-tetrahydro-furo[3,4-d][1,3]dioxole-4-carbonyl}-pyrrolidine-2-carboxylic acid (35), 1-{2-Benzyl-6-[6-(3-cyclopentyl-ureido)-purin-9-yl]-tetrahydro-furo[3,4-d][1,3]dioxole-4-carbonyl}-pyrrolidine-2-carboxylic acid (36), 1-(9-{2-Benzyl-6-[(3-methylsulfonyl-ureido)-methyl]-tetrahydro-furo[3,4-d][1,3]dioxol-4-yl}-9H-purin-6-yl)-3-phenyl-urea (37), 1-{6-[6-(3-Cyclopentyl-ureido)-purin-9-yl]-2-phenyl-tetrahydro-furo[3,4-d][1,3]dioxole-4-carbonyl}-pyrrolidine-2-carboxylic acid (38), 1-{2-Phenyl-6-[6-(3-phenyl-ureido)-purin-9-yl]-tetrahydro-furo[3,4-d][1,3]dioxole-4-carbonyl}-pyrrolidine-2-carboxylic acid (39), 1-{2-Benzo[b]thiophen-3-yl-6-[6-(3-hexyl-ureido)-purin-9-yl]-tetrahydro-furo[3,4-d][1,3]dioxole-4-carbonyl}-pyrrolidine-2-carboxylic acid (40), 1-{6-[6-(3-Benzyl-ureido)-purin-9-yl]-2-naphthalen-2-yl-tetrahydro-furo[3,4-d][1,3]dioxole-4-carbonyl}-pyrrolidine-2-carboxylic acid (41), 1-(2-Benzyl-6-{6-[3-(2-phenyl-cyclopropyl)-ureido]-purin-9-yl}-tetrahydro-furo[3,4-d][1,3]dioxole-4-carbonyl)-pyrrolidine-2-carboxylic acid (42), 1-{2-Benzyl-6-[6-(3-hexyl-ureido)-purin-9-yl]-tetrahydro-furo[3,4-d][1,3]dioxole-4-carbonyl}-pyrrolidine-2-carboxylic acid (43), 1-{2-(2,4-Difluoro-phenyl)-6-[6-(3-phenyl-ureido)-purin-9-yl]-tetrahydro-furo[3,4-d][1,3]dioxole-4-carbonyl}-pyrrolidine-2-carboxylic acid (44), 2-{2-Benzyl-6-[6-(3-phenyl-ureido)-purin-9-yl]-tetrahydro-furo[3,4-d][1,3]dioxole-4-carbonyl}-amino-3-hydroxy-propionic acid (45), 3-{2,2-Dimethyl-6-[6-(3-phenyl-ureido)-purin-9-yl]-tetrahydro-furo[3,4-d][1,3]dioxol-4-yl}-acrylic acid methyl ester (46), 3-{2,2-Dimethyl-6-[6-(3-phenyl-ureido)-purin-9-yl]-tetrahydro-furo[3,4-d][1,3]dioxol-4-yl}-propionic acid methyl ester (47), 3-(3-{2,2-Dimethyl-6-[6-(3-phenyl-ureido)-purin-9-yl]-tetrahydro-furo[3,4-d][1,3]dioxol-4-yl}-propionylamino)-benzoic acid (48), 1-(3-{2,2-Dimethyl-6-[6-(3-phenyl-ureido)-purin-9-yl]-tetrahydro-furo[3,4-d][1,3]dioxol-4-yl}-propionyl)-pyrrolidine-2-carboxylic acid (49), and 3-{2,2-Dimethyl-6-[6-(3-phenyl-ureido)-purin-9-yl]-tetrahydro-furo[3,4-d][1,3]dioxol-4-yl}-propionic acid (50). The exemplified compounds named above can be in the forms depicted below, or can be pharmaceutically-acceptable salts, -hydrates, or -solvates thereof, where chemically appropriate.

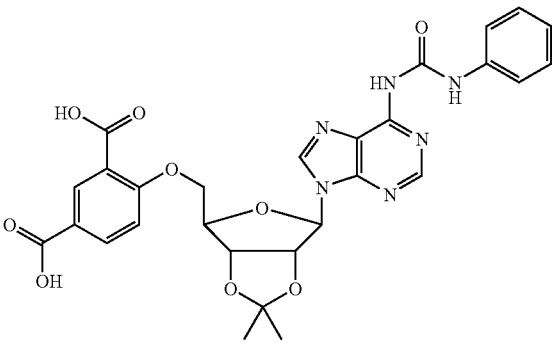

2
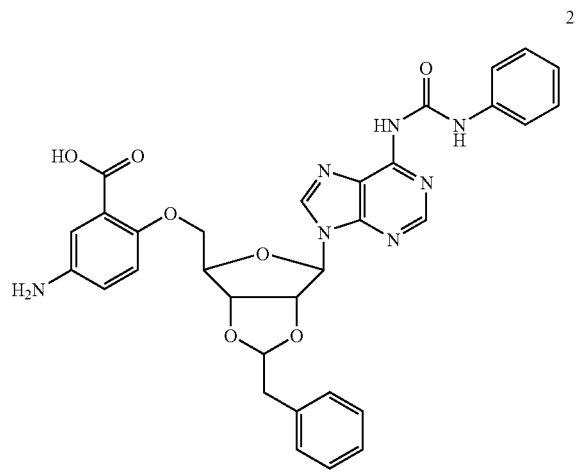
6
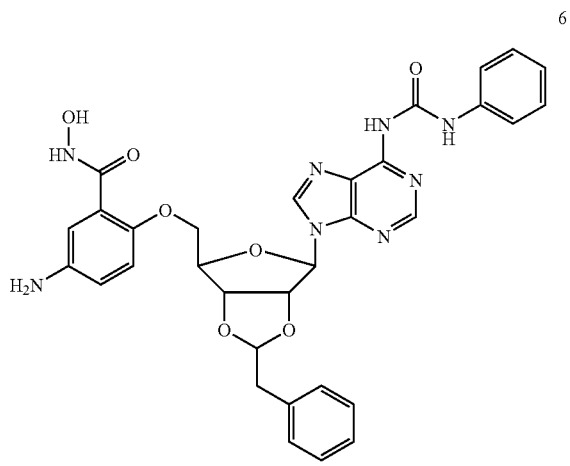
3
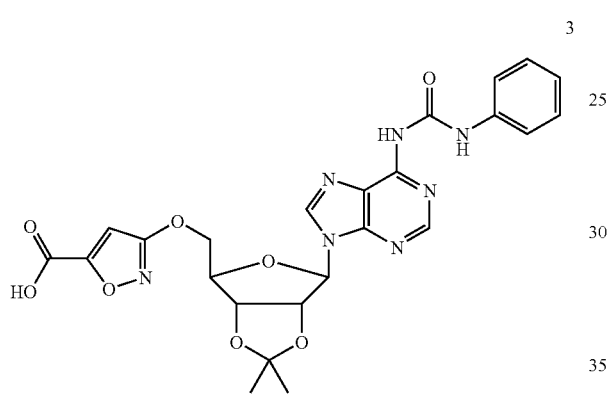
7
4
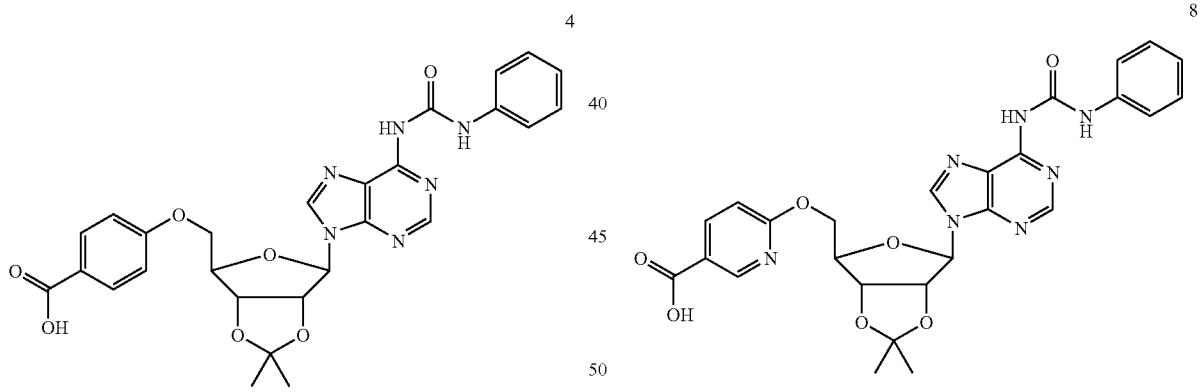
8
5
9
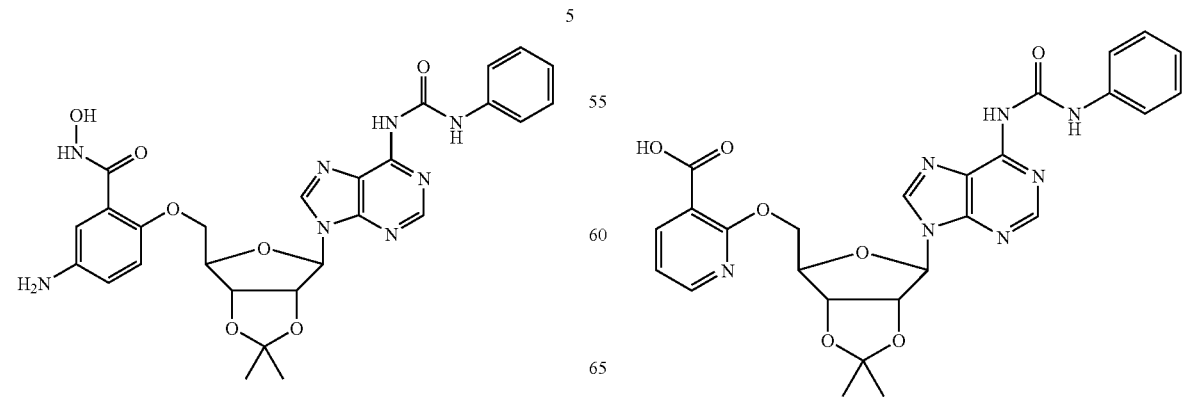

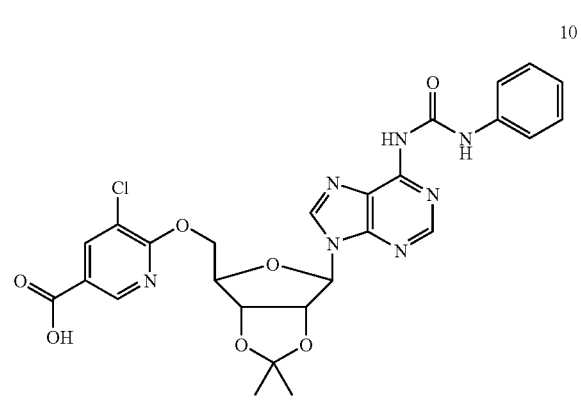
10
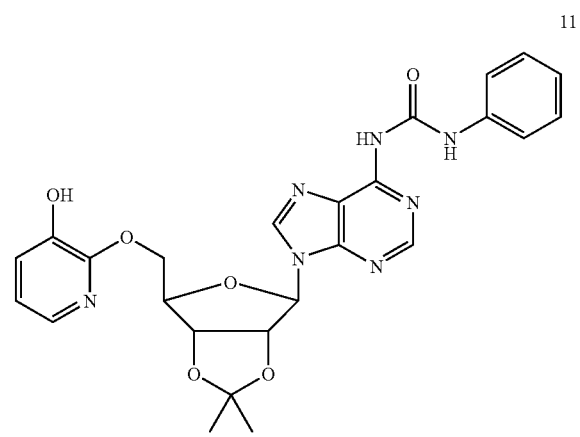
11
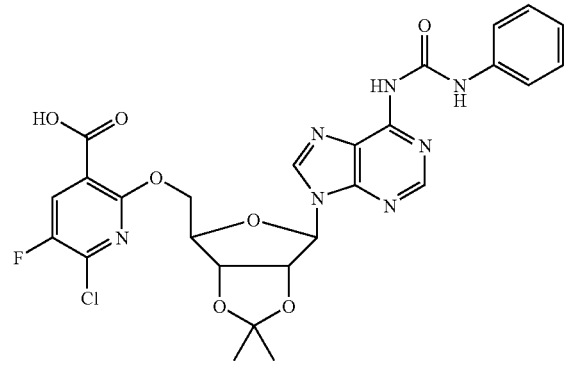
12
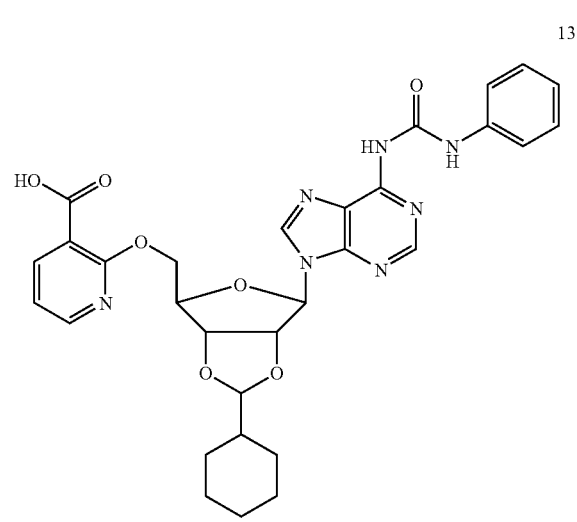

-continued
16
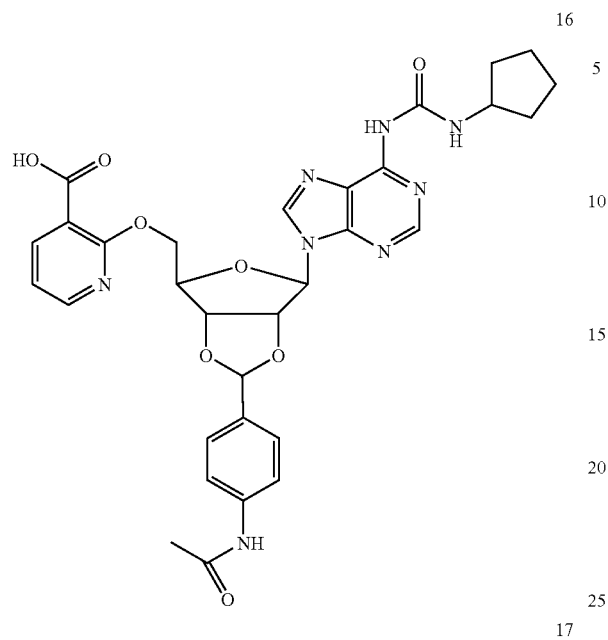
19
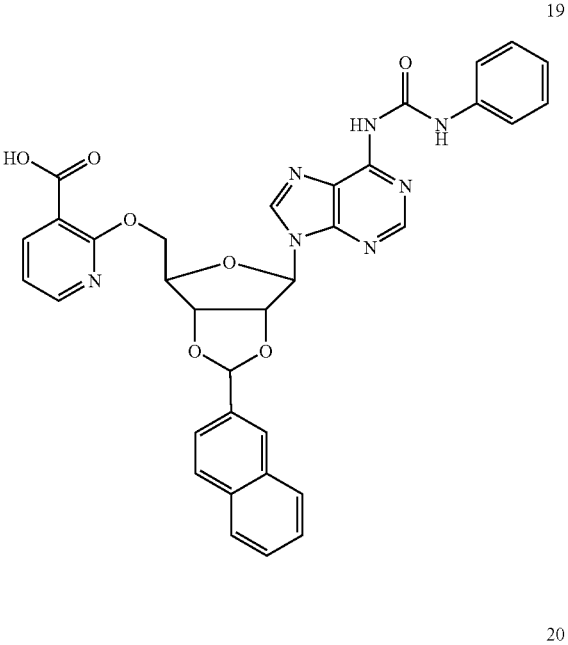
17
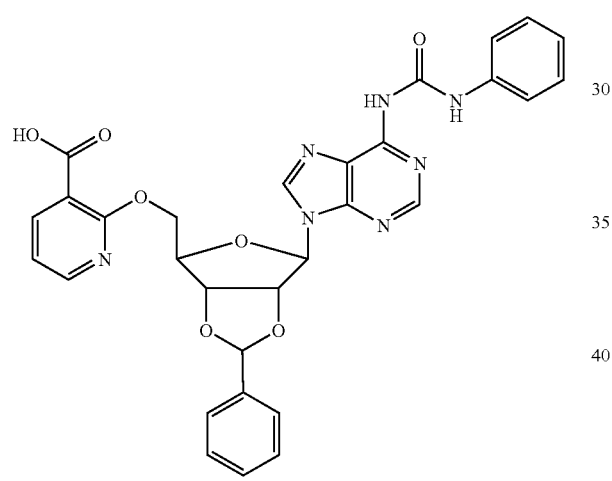
20
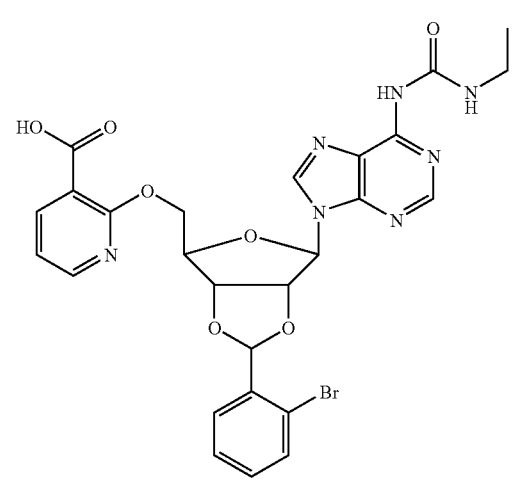
18
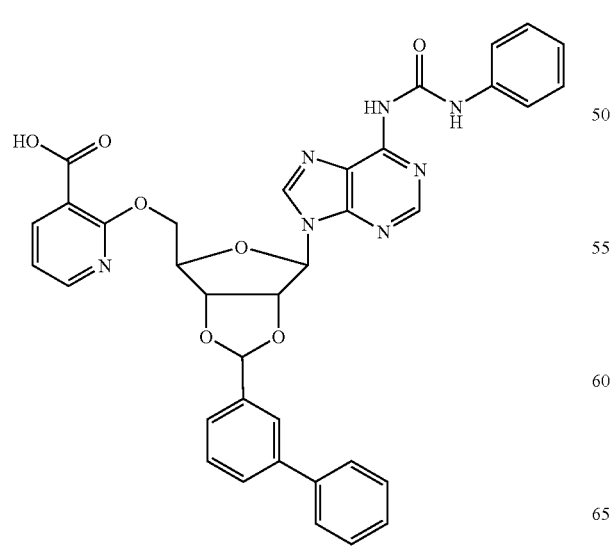
21
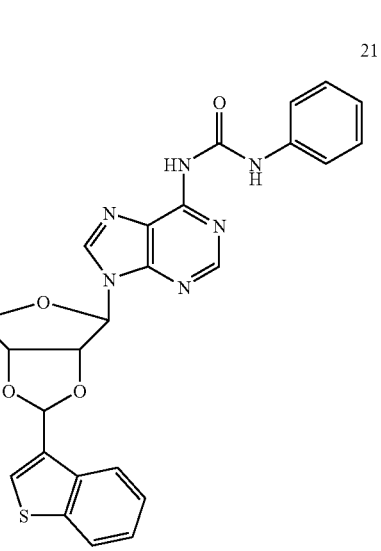

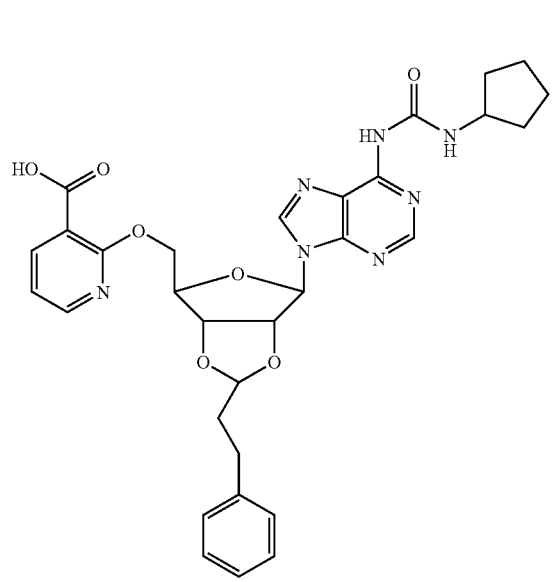
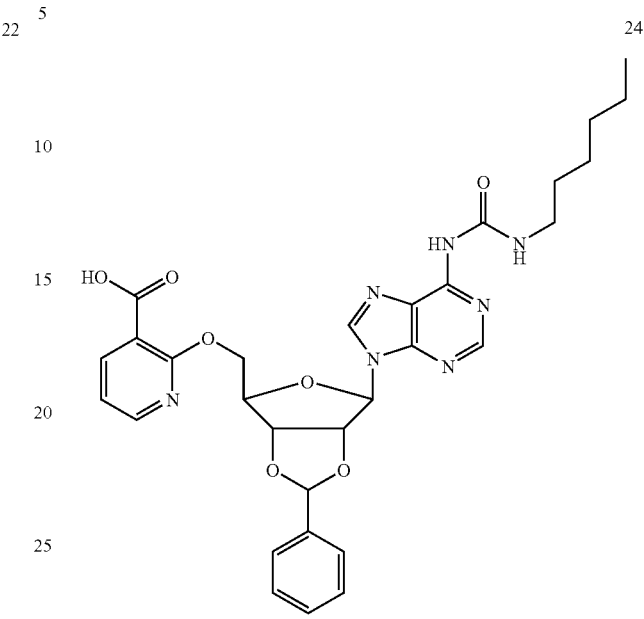

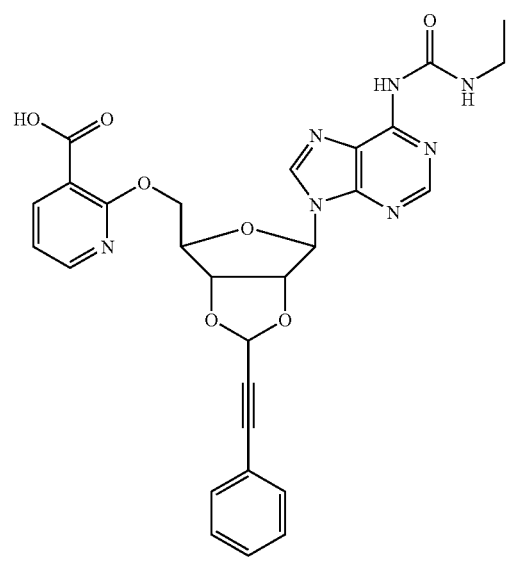
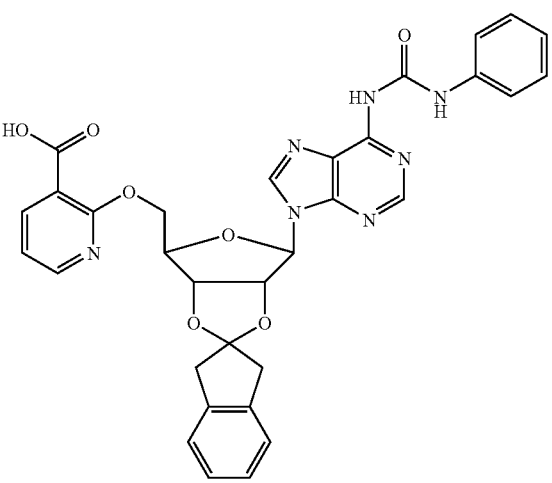
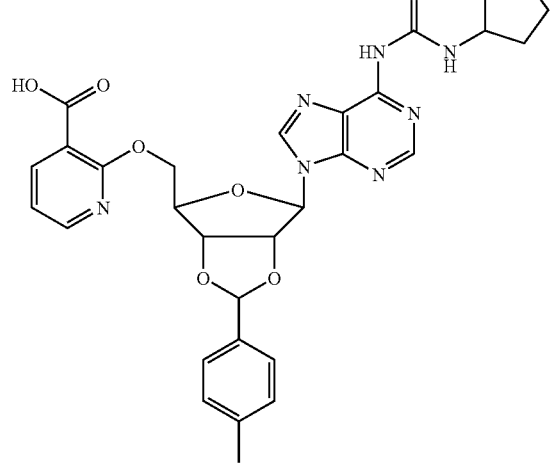

32
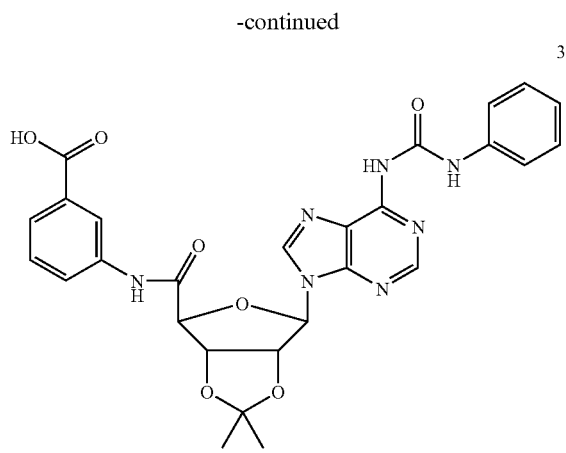
33
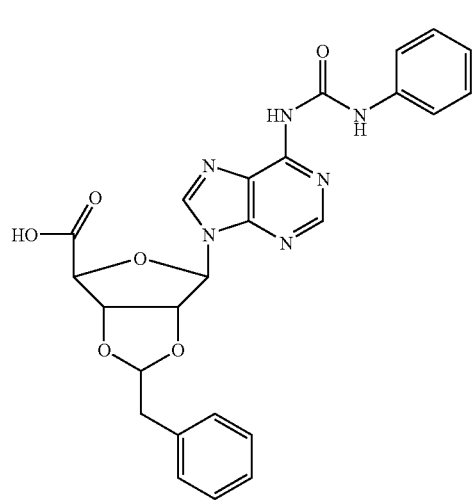
34
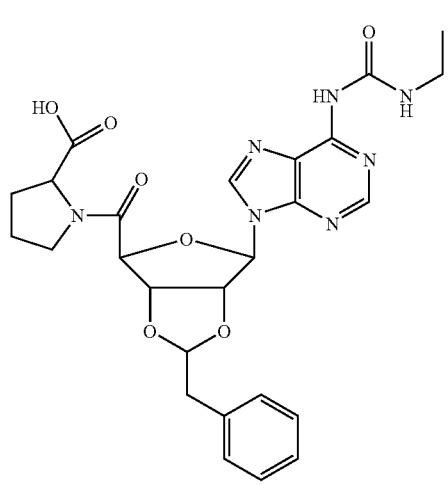
35
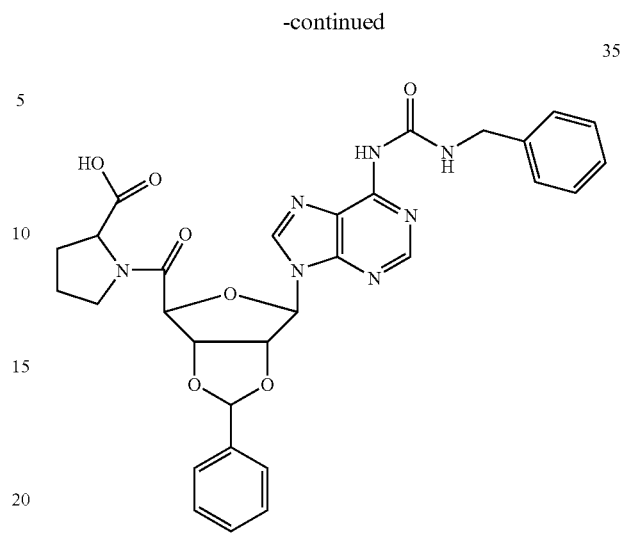
36
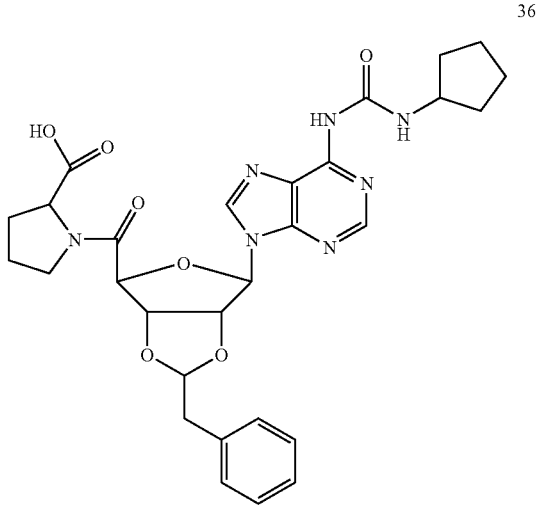
37
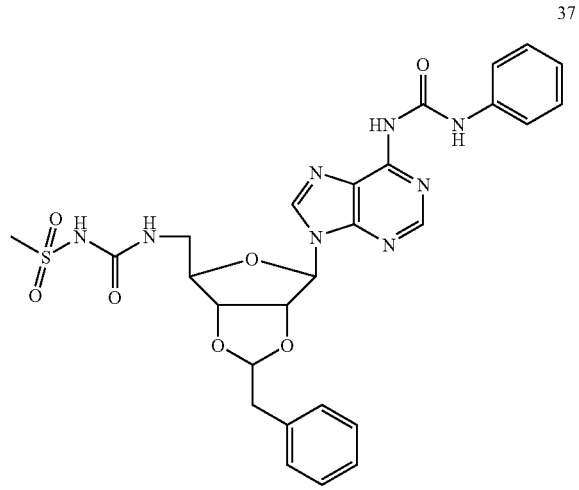

38
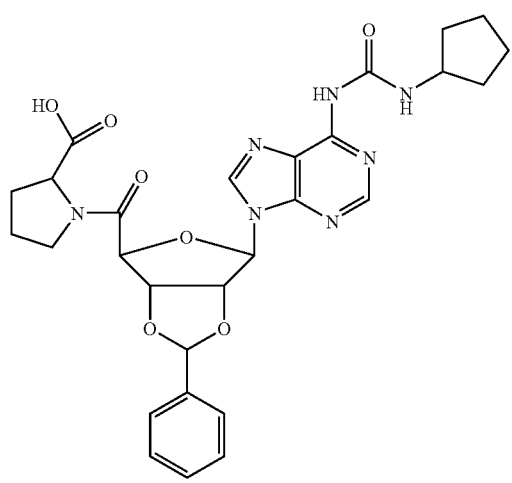
39
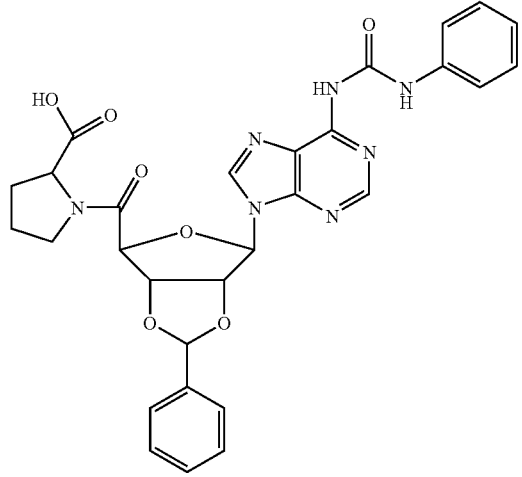
40
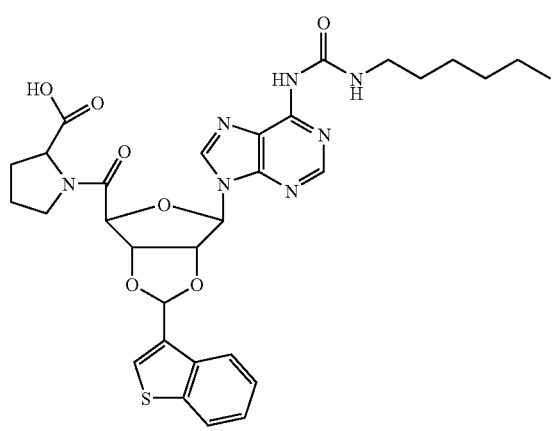
41
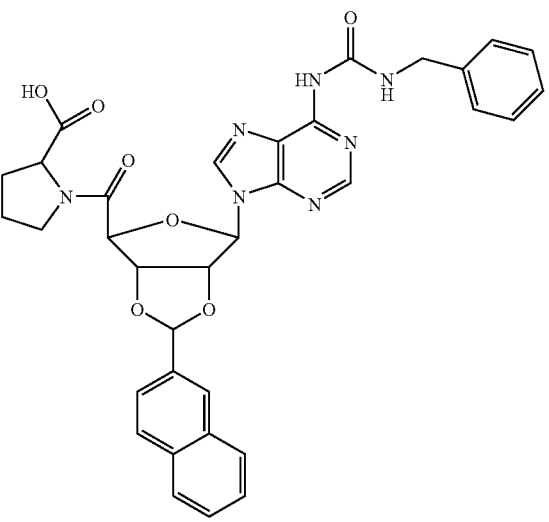
42
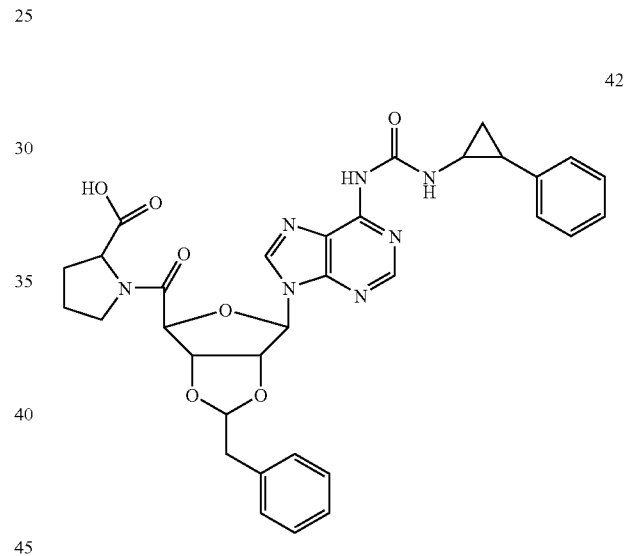
43
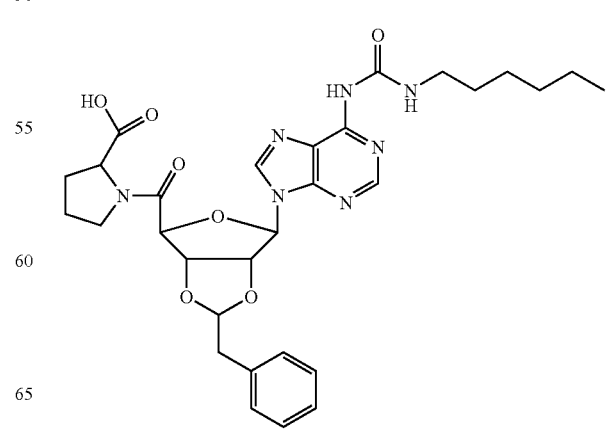

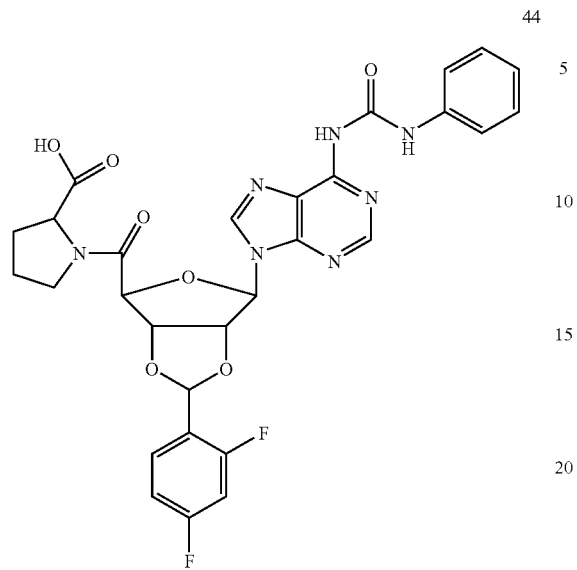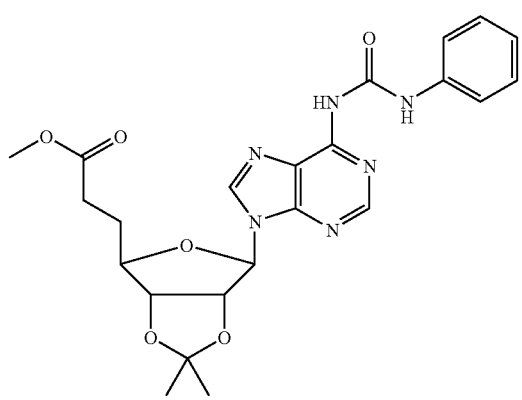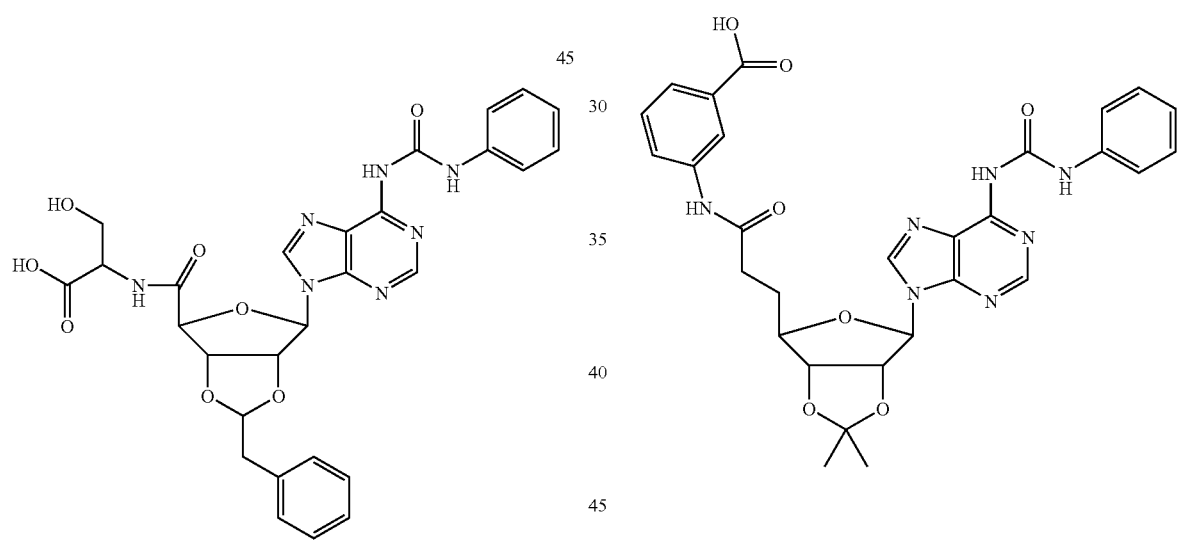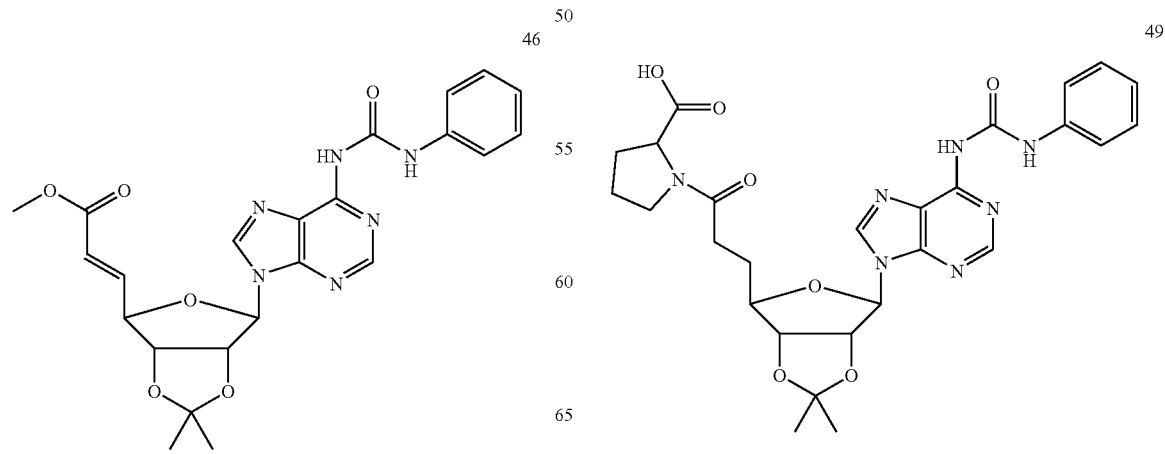

-continued

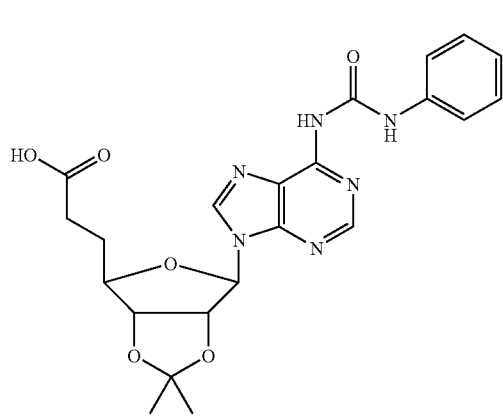

In one embodiment of the present invention, when $R_a$ and $R_b$ are not identical, the compounds depicted in the following structures falling under the definitions of Formulae III-XII represent either one of the two possible diastereomers (which arise from the resultant chiral carbon of the acetal) in pure form, or a mixture of the two diastereomers in any proportion. As a practical matter however, the compounds as depicted represent the pure forms of the diastereomers. Diastereomers are distinct compounds, each with potentially different chemical and biological properties; thus pure forms are preferred as pharmaceutical agents. In addition, there are generally reasons, including but not limited to, the ease of chemical synthesis or separation, chemical or biological stability, toxicity, pharmacokinetic or pharmacodynamic properties in living systems, and the like, to choose between the two possible isomers. While it is possible to resolve such diastereomeric mixtures using chiral chromatographic methods, more preferred is the synthesis of a single diastereomer.

Depending on the acetal in question, the synthesis of a single diastereomer can be achieved in several ways. In some cases, one diastereomer can be selectively generated over the other by carrying out the acetal-forming reaction at a low temperature (such as below 0° C., for example, from −10 to −30° C.). In other cases, a mixture of two diastereomers having different acetal stabilities can be subjected to aqueous acidic conditions, which leads to decomposition of the less-stable diastereomer, while leaving the more stable diastereomer intact. In general, the single diastereomer that survives the decomposition is preferred, since chemical stability is an important attribute for a pharmaceutical product. These principles are exemplified and illustrated in the following compound examples, but as they can be reasonably expanded to related structures; the specific example should not be taken as limiting.

In one embodiment of the present invention, the compound of Formula I is a compound of Formula III:

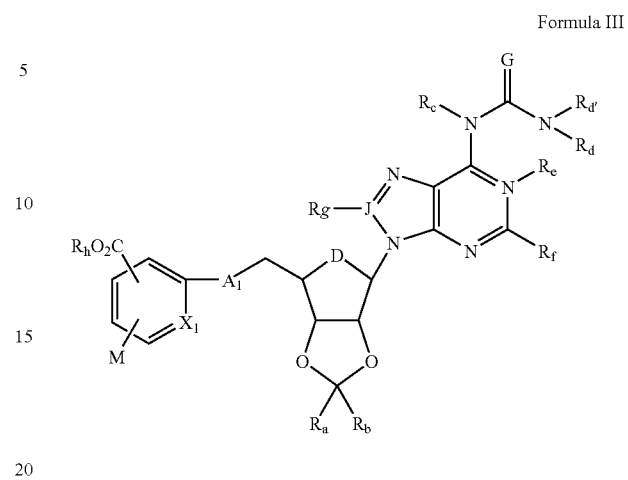

Formula III wherein $R_a$, $R_b$, $R_c$, G, $R_d$, $R_{d'}$, $R_e$, $R_f$, J, $R_g$, and $R_h$ are as defined in Formulae I and II;

$A_1$ is O or $CH_2$;

D is O or $CH_2$;

$X_1$ is selected from the group consisting of: N (nitrogen) and C-M; and

M is independently selected from the group consisting of: —H, halogen, —$CF_3$, $C_{1-8}$ alkyl, cyano, $C_{1-8}$ alkenyl, $C_{1-8}$ alkynyl, $C_{3-7}$ cycloalkyl, $C_{3-7}$ cycloalkenyl, aryl, aralkyl (including saturation and/or unsaturation in the alkylene portion), heteroaryl, saturated or unsaturated $C_{2-6}$ heterocycle, —OH, saturated or unsaturated $C_{1-6}$ alkoxy, aralkoxy, aryloxy, —SH, $C_{1-6}$ thioalkyl, thioaryl, —[(CO)OR], —[(CO)NRR], amino, —N-substituted amino, and N,N-disubstituted amino; wherein each said substituent on said amino of M is independently selected from the group consisting of: $C_{1-8}$ alkyl, $C_{3-7}$ cycloalkyl, aryl, aralkyl, heteroaryl, $C_{2-6}$ heterocycle, —[(CO)R], —[(CO)O—($C_{1-8}$ alkyl)], and —[(CO)—NRR]; and when M is —[(CO)NRR], —[NH(CO)NRR], —[N($C_{1-8}$ alkyl)(CO)NRR], —[N(aryl)(CO)NRR], or —[N(aralkyl)(CO)NRR], the R groups of any said —NRR unit (N,N-disubstituted-amino group) in M are optionally taken together such that a ring of 3 to 7 members is formed, with or without heteroatoms in place of the ring-carbon units.

Particularly useful compounds of Formula III are where the $R_h$=H or alkyl.

Preferred compounds of Formula III are:

wherein G=$A_1$=D=O;

$R_a$=$R_c$=$R_d$=$R_f$=$R_g$=$R_h$=H;

$R_{d'}$=$C_{1-4}$ alkyl, or $C_{3-6}$ cycloalkyl;

$R_e$ is absent;

$X_1$=C or N;

$R_b$=phenyl, benzyl, or styryl;

M=H, halogen, $C_{1-4}$ alkyl, $C_{1-4}$ alkoxy, $CF_3$, cyano, or amino.

Some of the preferred compounds falling under the definition of Formula III are:

-continued
51
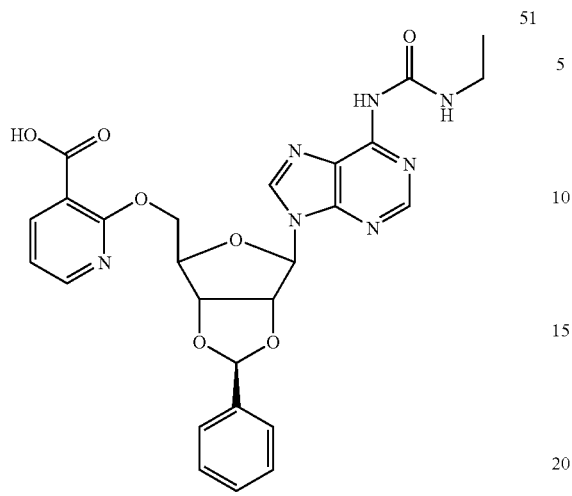
54
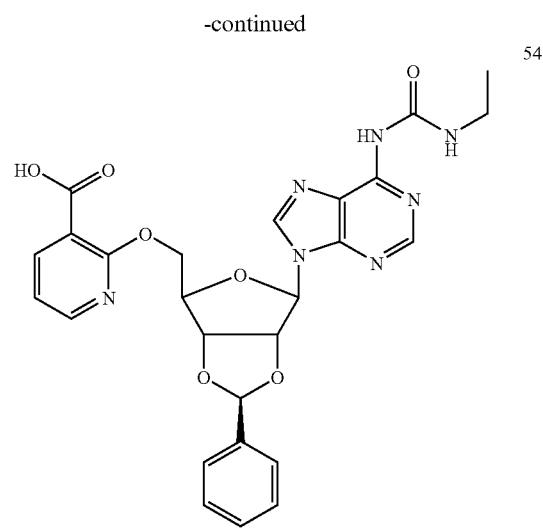
52
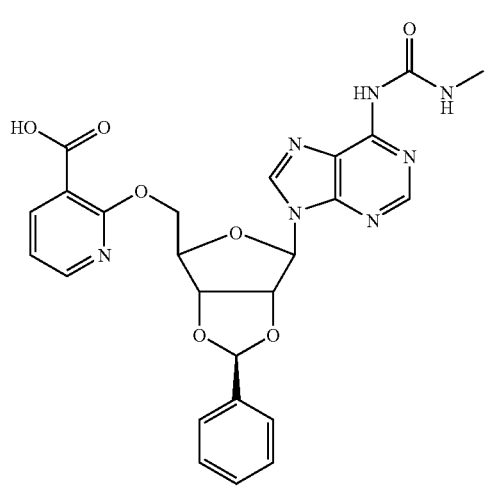
55
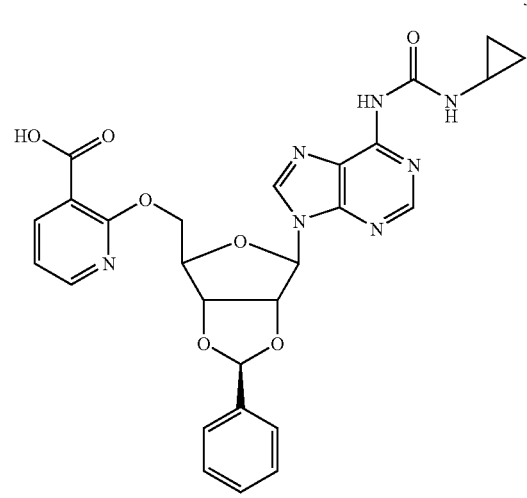
53
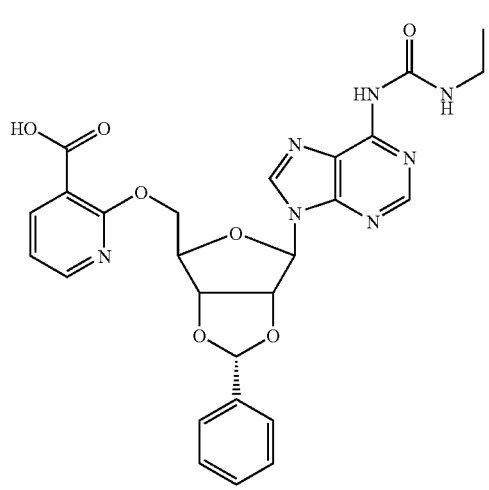
56
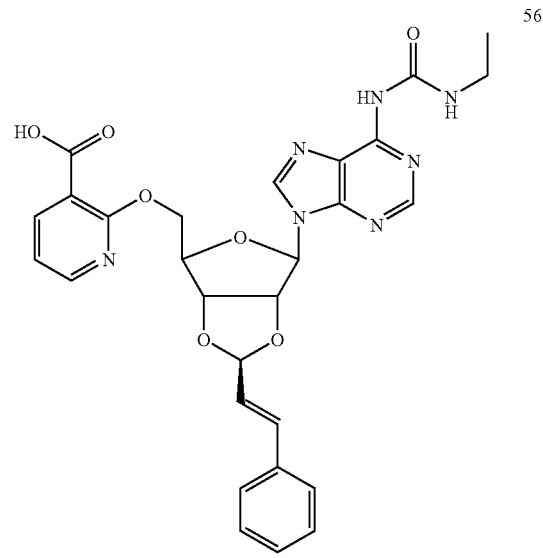

-continued
57
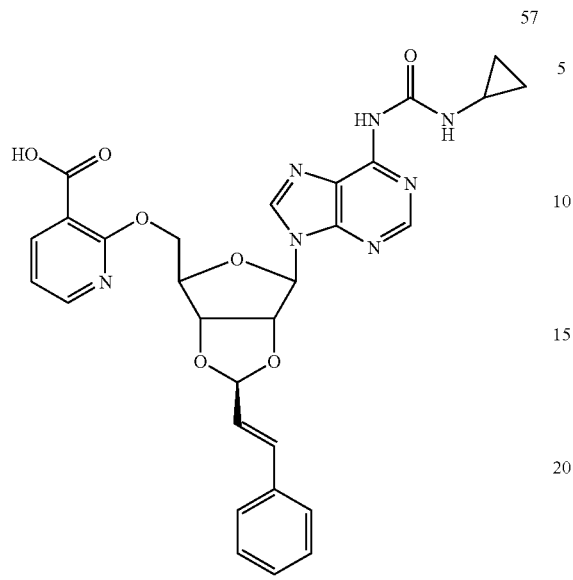
58
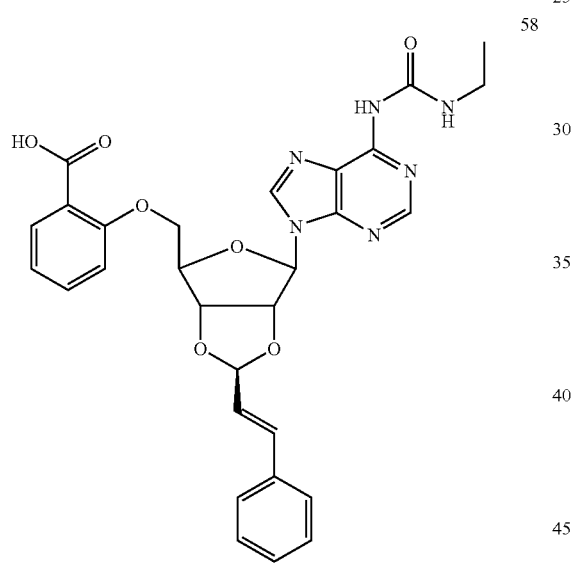
59
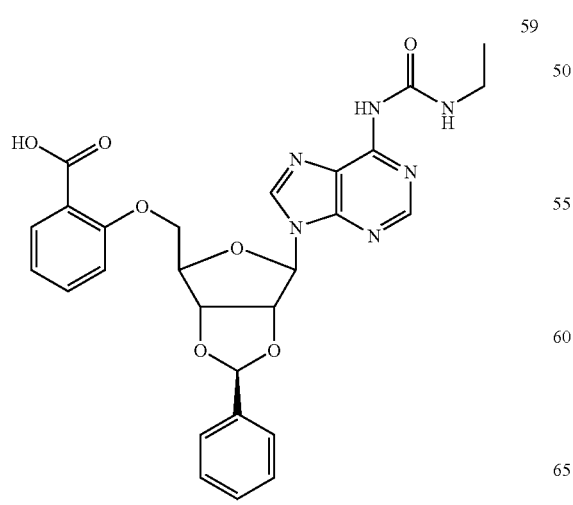
60
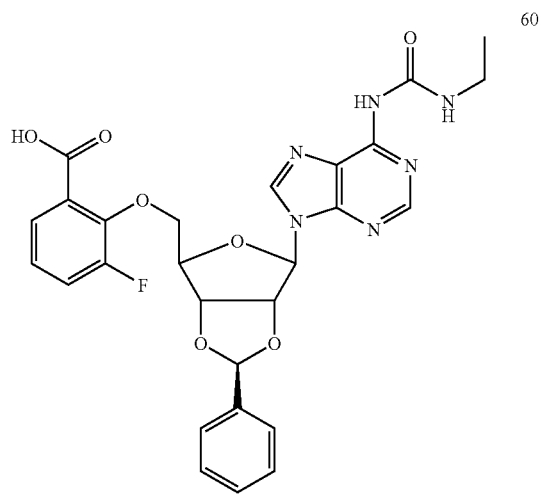
61
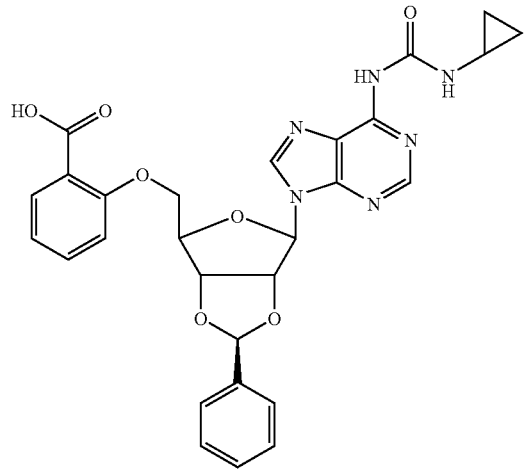
62
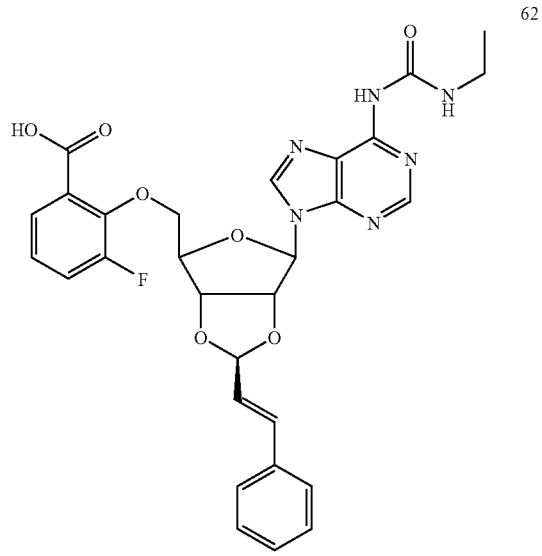

-continued

63

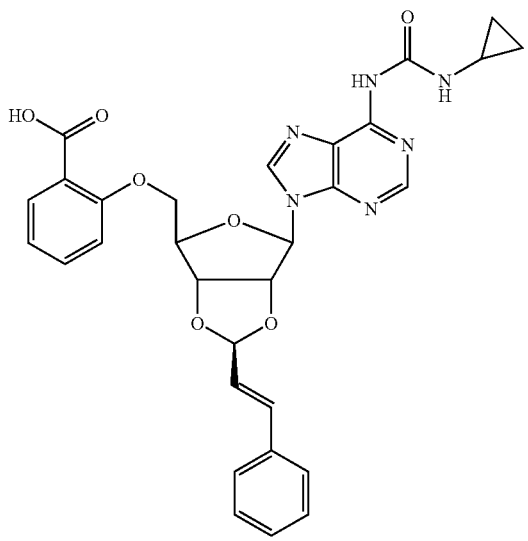

64

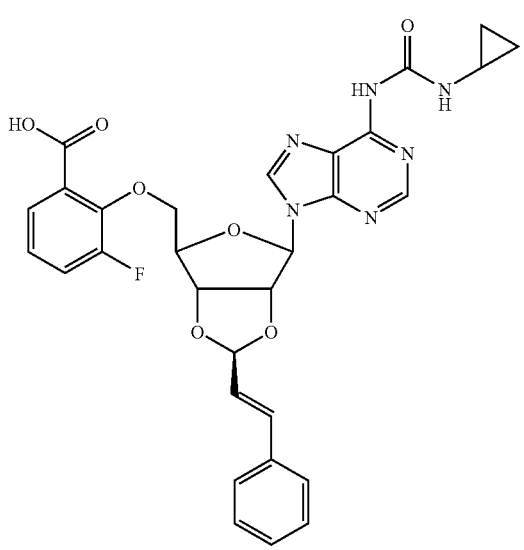

In another embodiment of the present invention, the compound of Formula I is a compound of Formula IV:

Formula IV

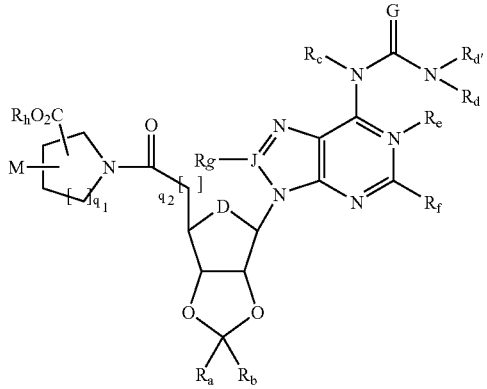

wherein $R_a$, $R_b$, $R_c$, G, D, $R_d$, $R_{d'}$, $R_e$, $R_f$, J, M, $R_g$ and $R_h$ are as defined in Formulae I and II;

$q_1$ and $q_2$ are 0, 1, or 2;

the M and —$CO_2R_h$ groups are independently and optionally attached to any carbon of the pyrrolidine ring; and when M is attached to a carbon that is bonded to the pyrrolidine nitrogen atom (alpha position), then M is not a halogen, hydroxyl, sulfhydryl, or amino group.

Particularly useful groups of compounds are those of Formula IV where $R_h$ is H or alkyl and/or M is H or alkyl.

Preferred compounds of Formula IV are wherein:

$q_1$ is 1 or 2;

$q_2$ is 0 or 1;

G=O;

D=O or C;

$R_a$=$R_c$=$R_d$=$R_f$=$R_g$=H;

$R_e$ is absent;

$R_h$=H or ethyl;

$R_{d'}$=$C_{1-4}$ alkyl, or $C_{3-6}$ cycloalkyl;

$R_b$=phenyl, benzyl, or styryl;

M=H or $C_{1-4}$ alkyl

Some of the preferred compounds falling under the definition of Formula IV are:

65

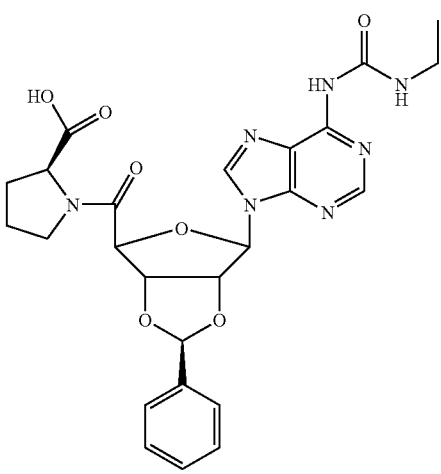

37
66
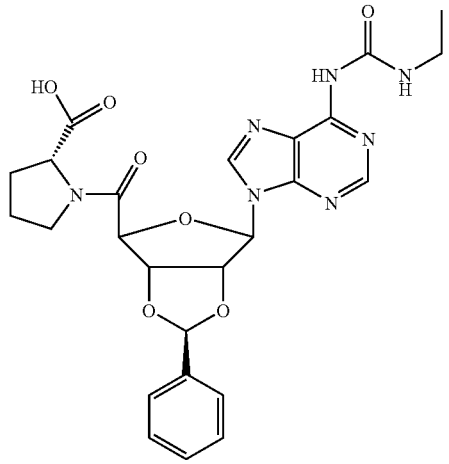
67
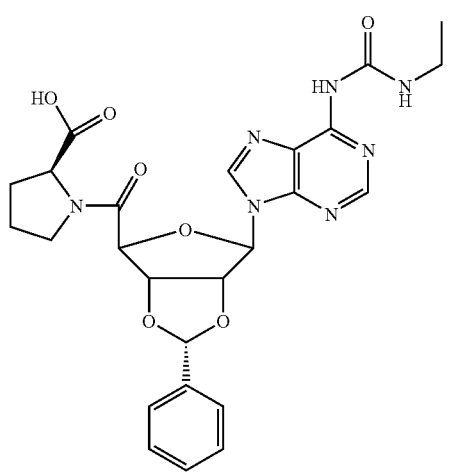
68
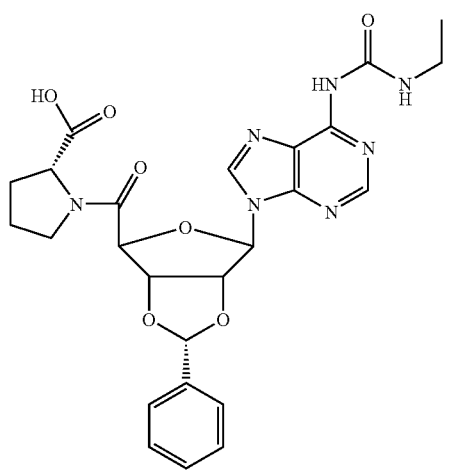
38
69
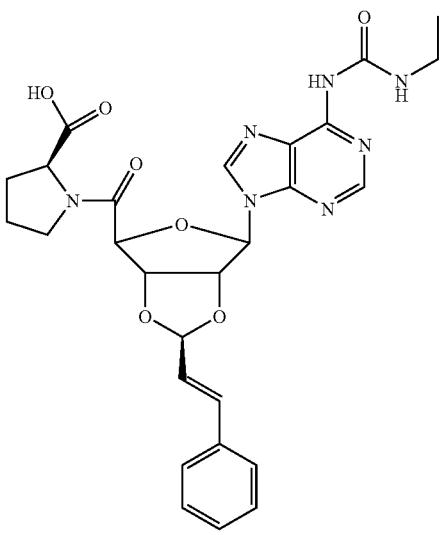
70
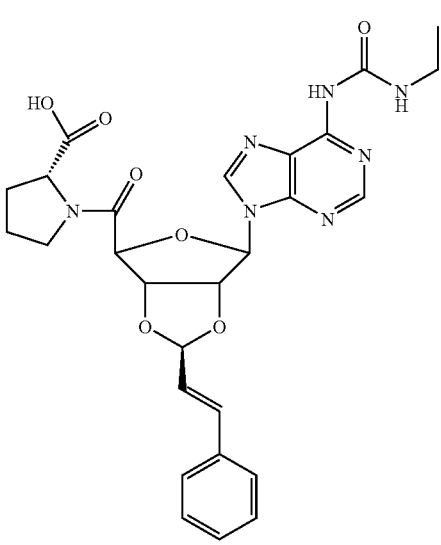
71
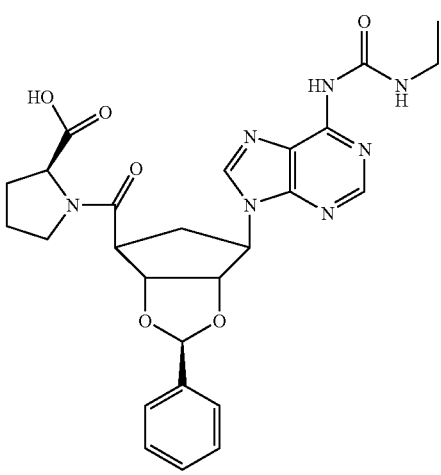

72
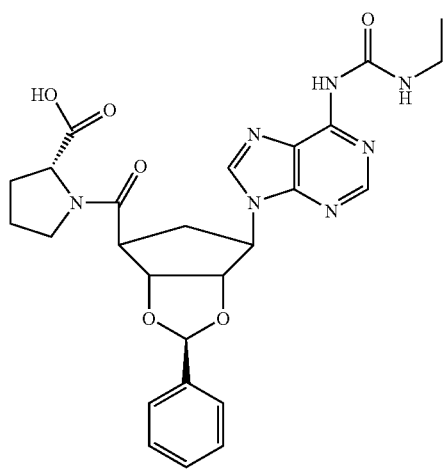
73
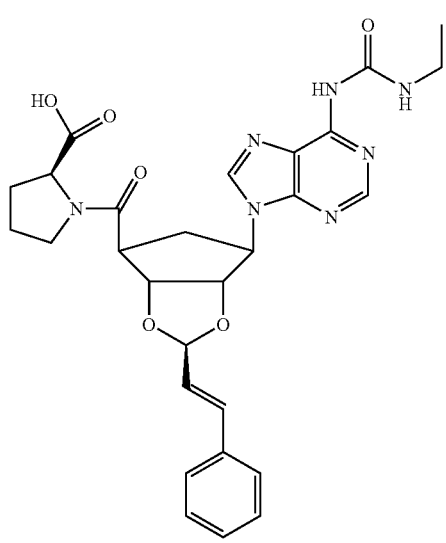
74
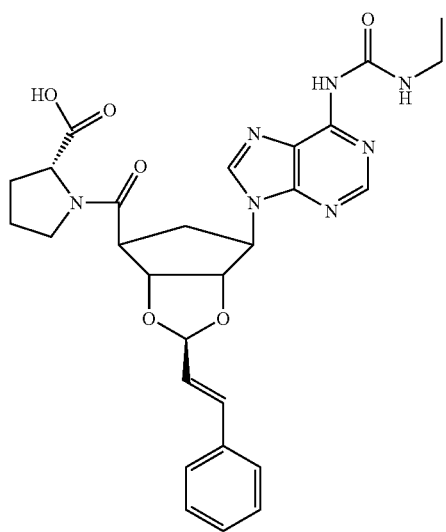
75
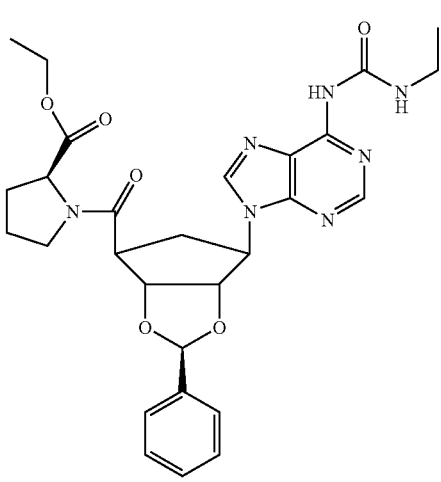
76
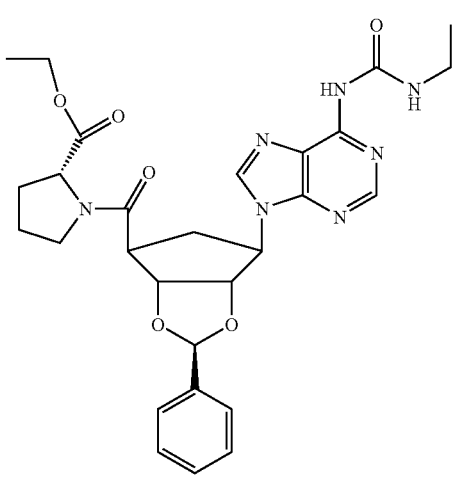
77
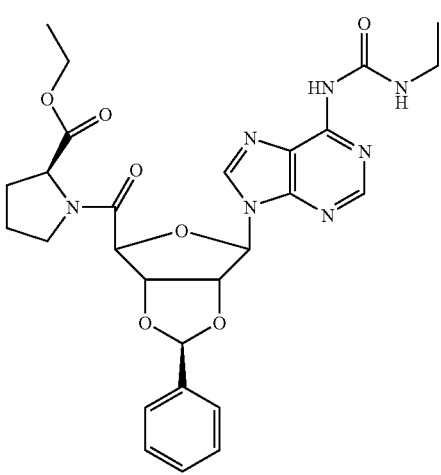

78
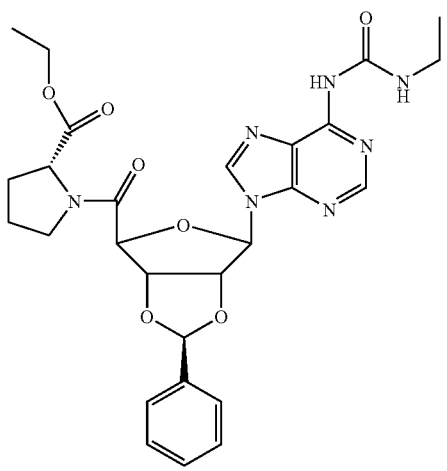
79
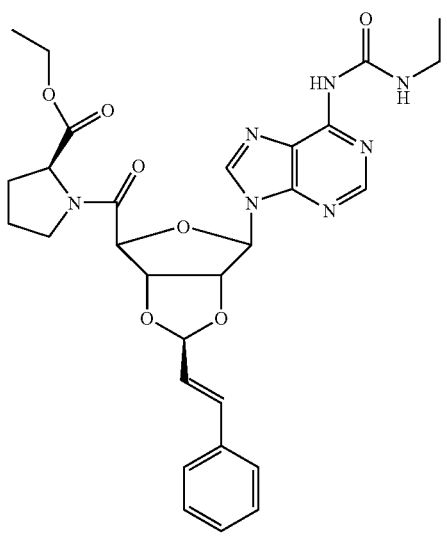
80
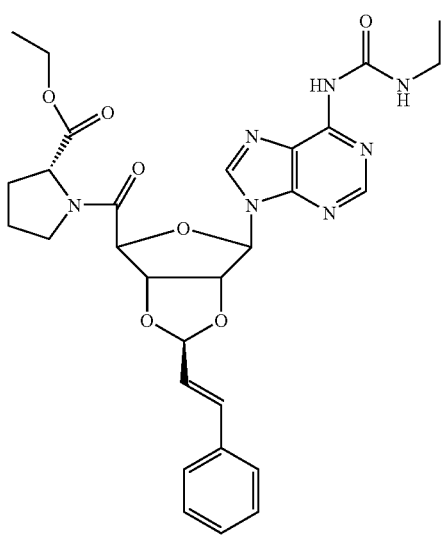
81
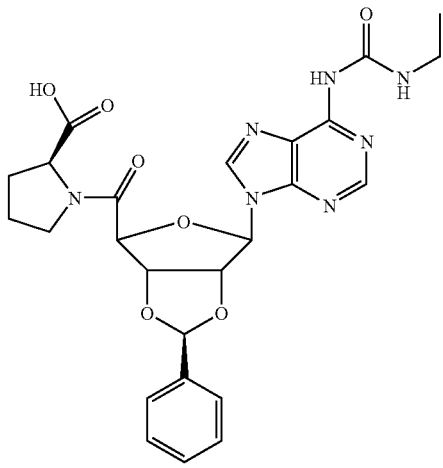
82
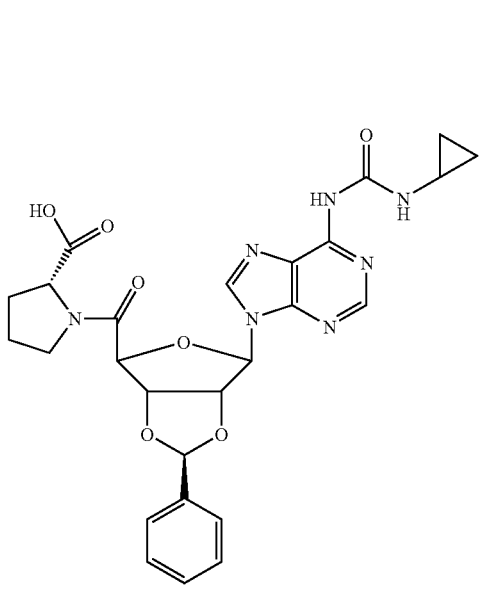
83
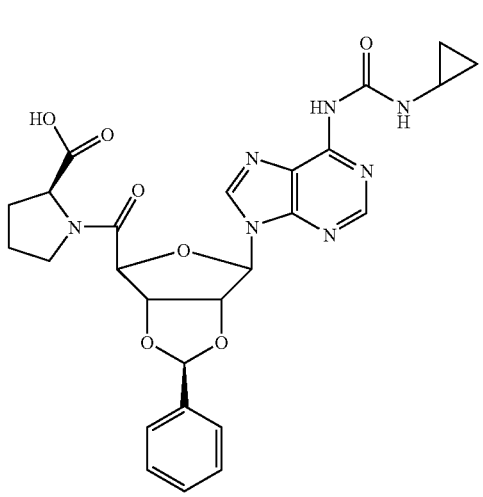

84
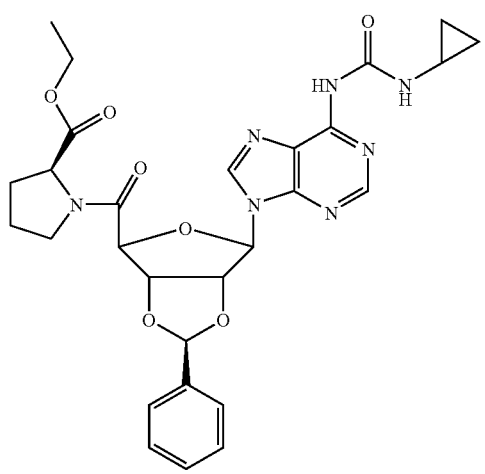
85
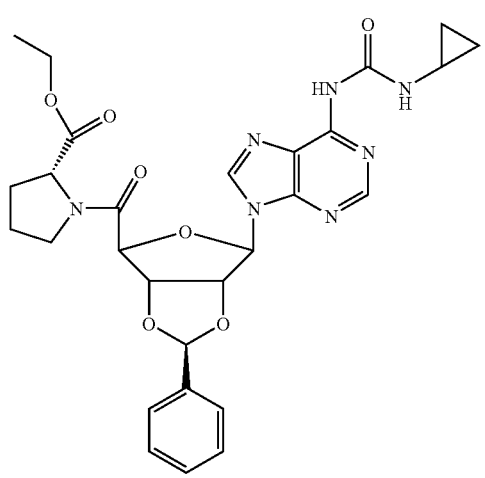
86
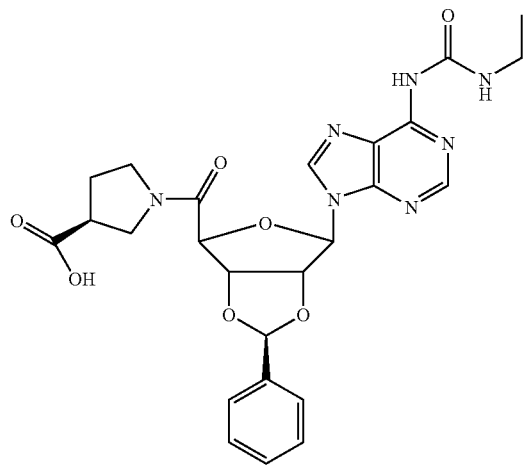
87
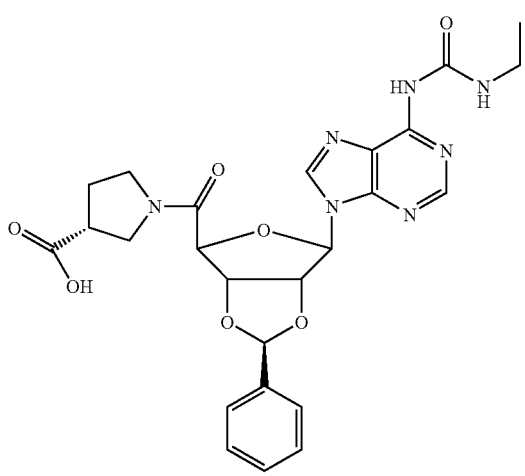
88
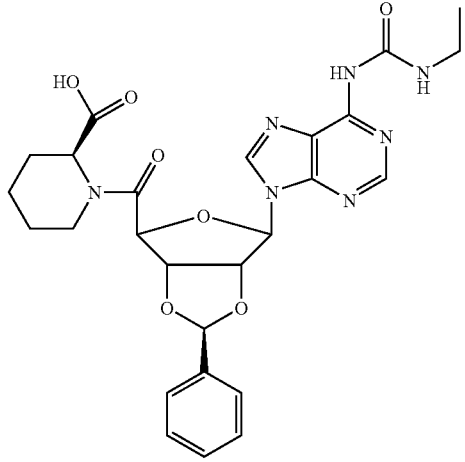
89
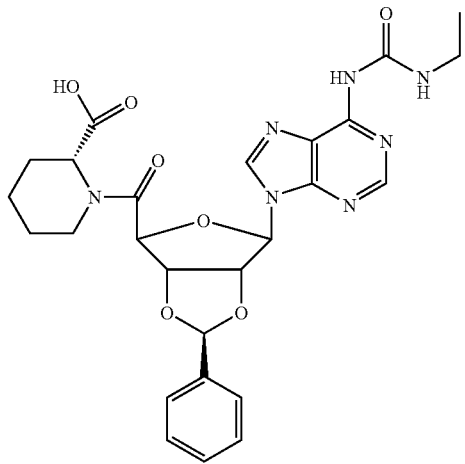

-continued
90
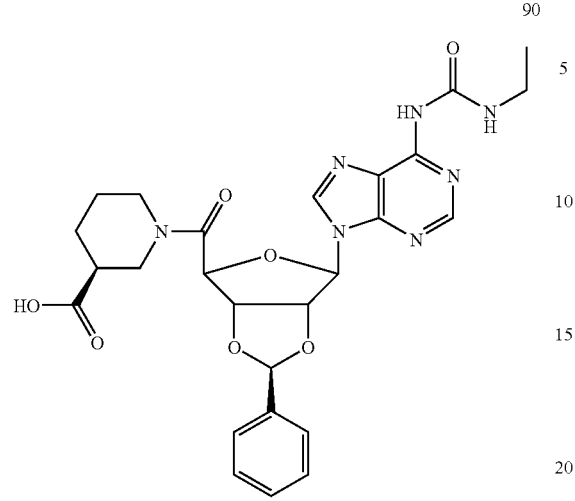
91
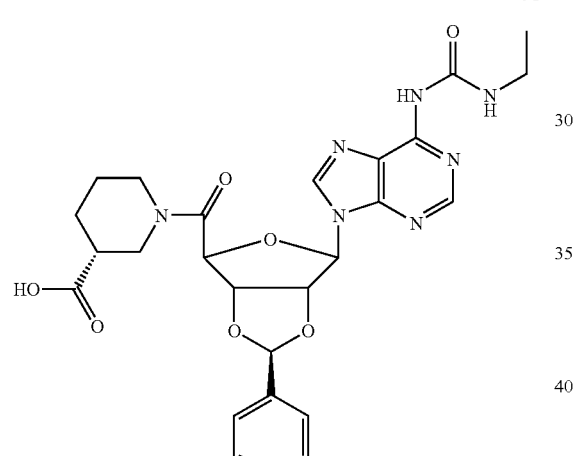
92
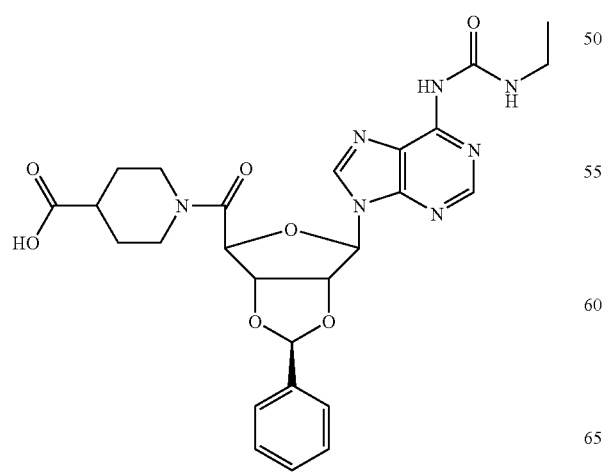
-continued
93
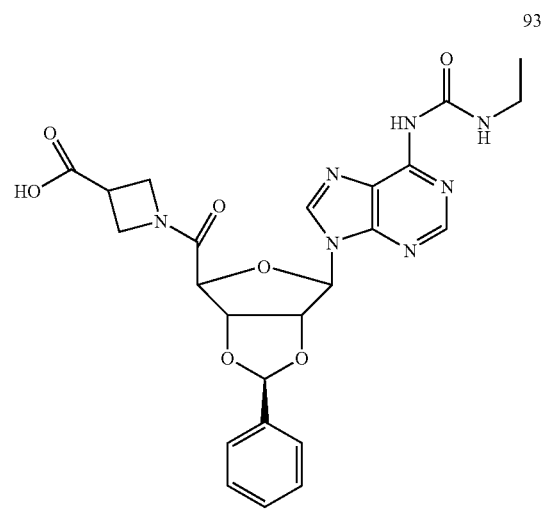
94
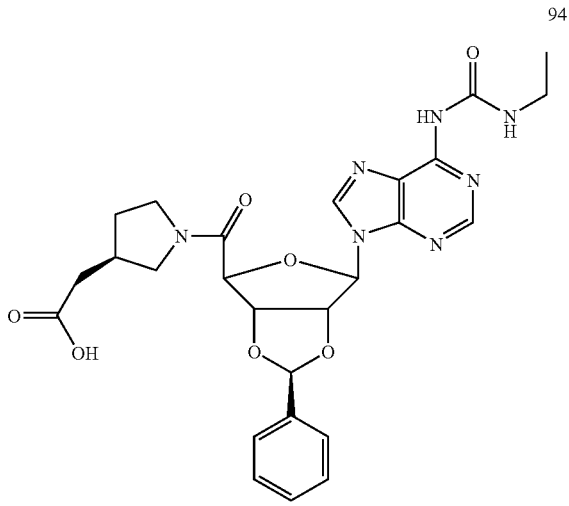
95
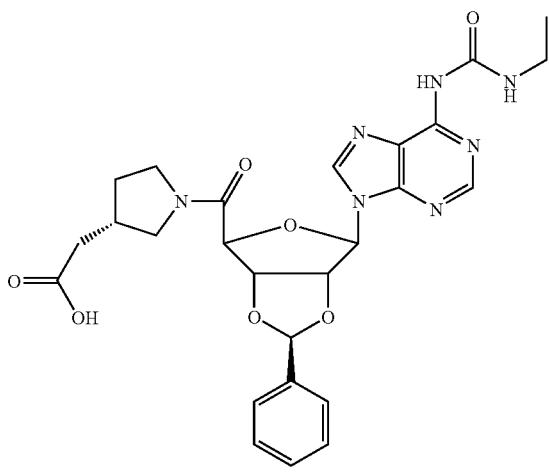

47
48
96
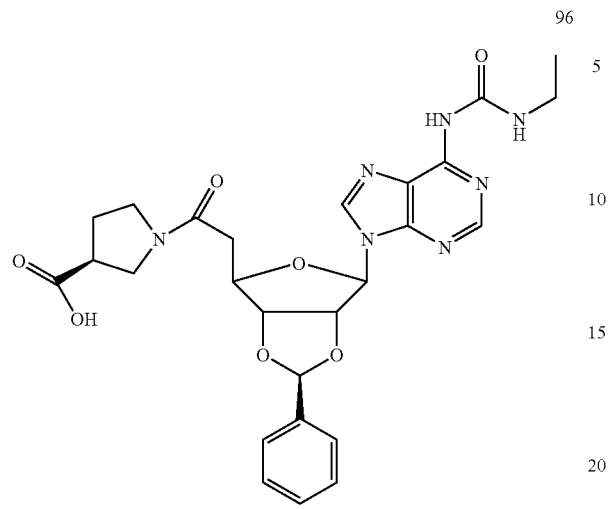
99
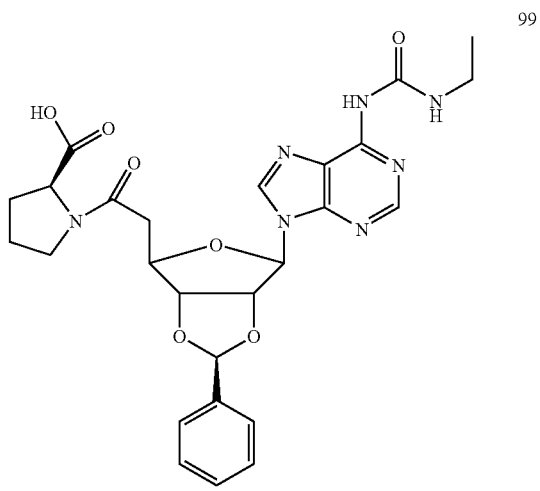
97
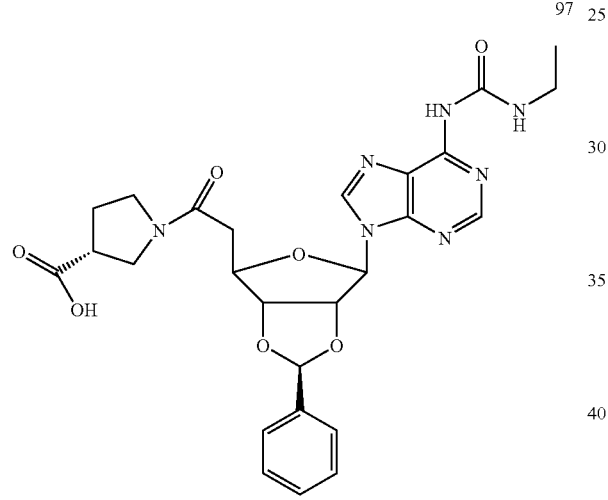
100
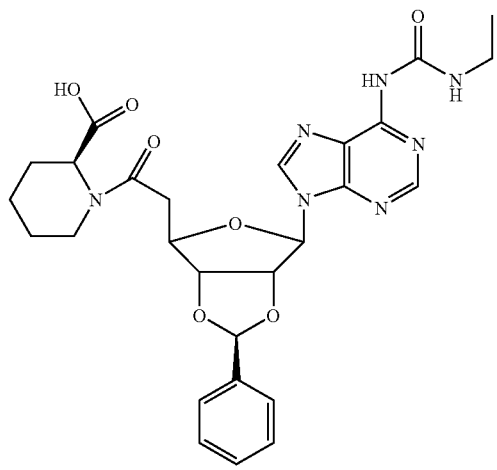
98
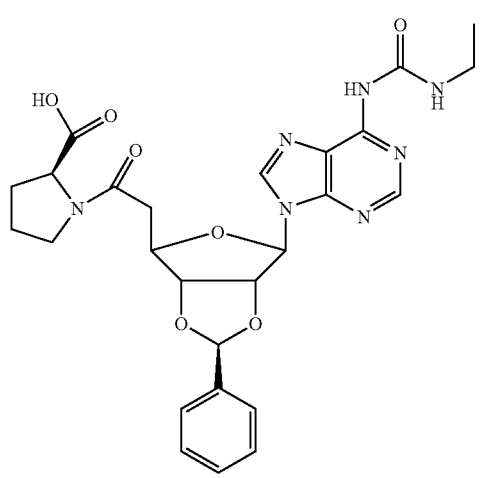
101
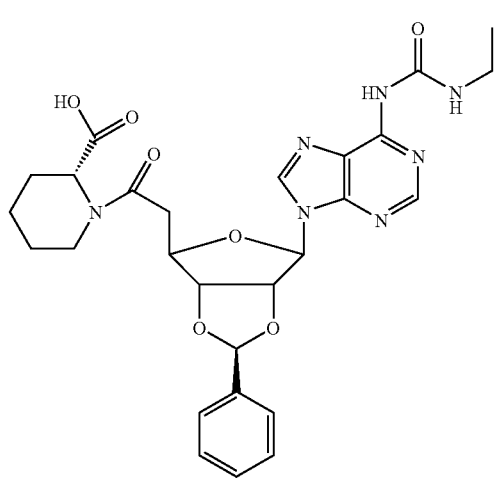

102
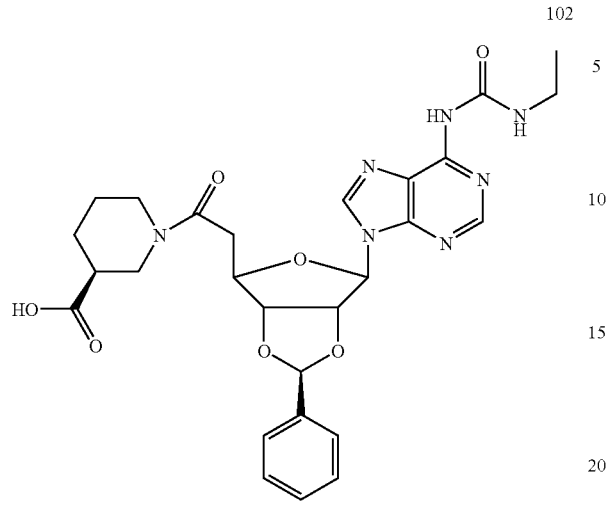
103
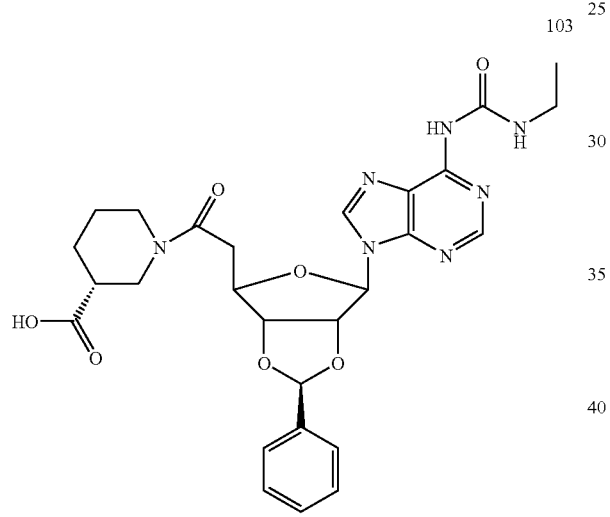
104
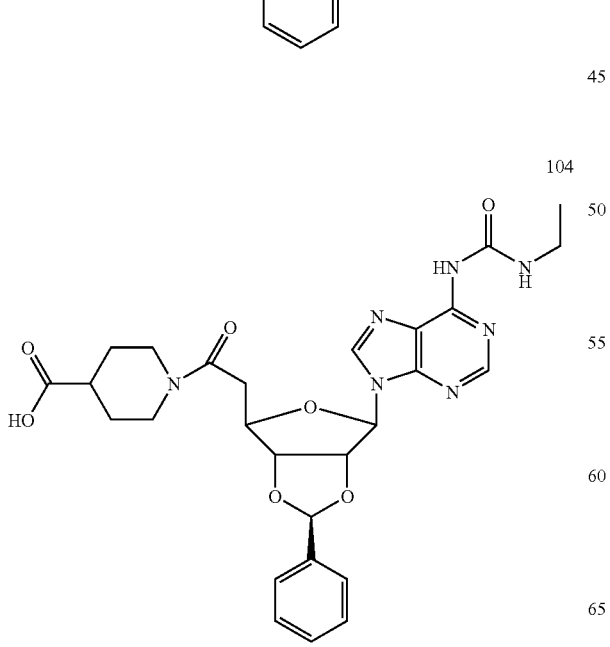
105
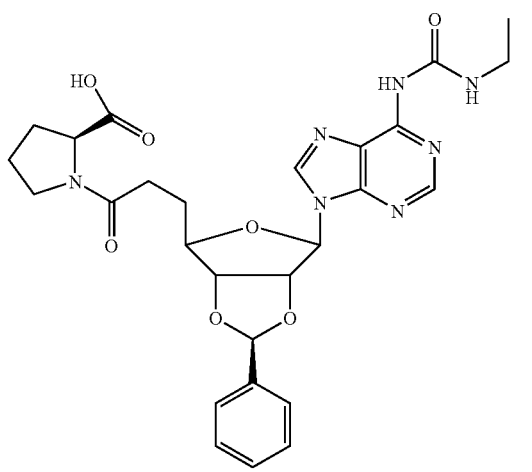
106
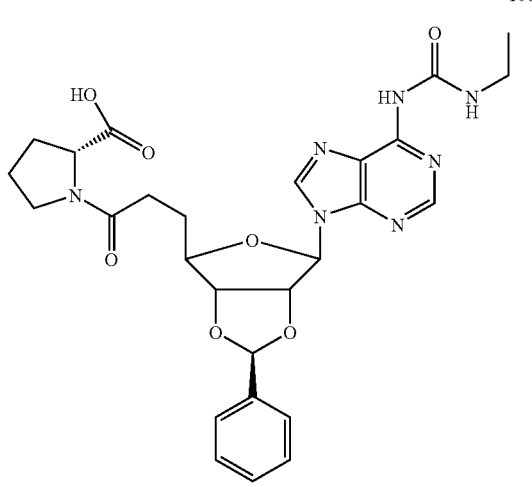
In another embodiment of the present invention, the compound of Formula I is a compound of Formula V:
Formula V
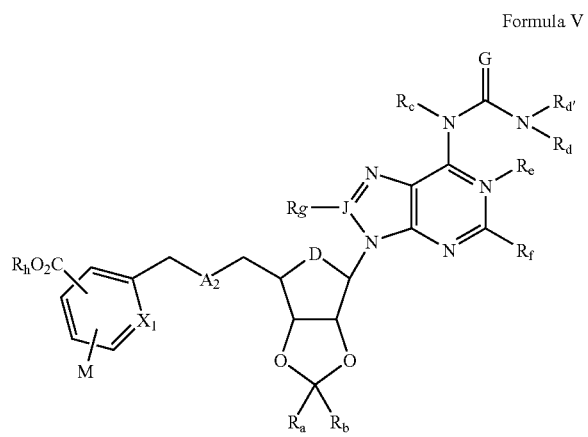
wherein $R_a$, $R_b$, $R_c$, G, D, $R_d$, $R_{d'}$, $R_e$, $R_f$, J, M, $X_1$, $R_g$ and $R_h$ are as defined in Formulae I and II;

$A_2$ is C, O, S, S(O), SO$_2$, or N, where C can be substituted with H or alkyl, and N can be substituted with H, alkyl, or acyl; or $A_2$ is absent.

Preferred compounds of Formula V are wherein:

G=O;

D=O or C;

$R_a$=$R_c$=$R_d$=$R_f$=$R_g$=H;

$R_e$ is absent;

$R_h$=H or ethyl;

$R_{a'}$=$C_{1-4}$ alkyl, or $C_{3-6}$ cycloalkyl;

$A_2$ is C, O, NH, N-methyl, N-acetyl, or absent;

$X_1$=C or N;

$R_b$=phenyl, benzyl, or styryl; and

M=H, halogen, $C_{1-4}$ alkyl, $C_{1-4}$ alkoxy, CF$_3$, cyano, or amino.

Some of the preferred compounds falling under the definition of Formula V are:

53
-continued
112
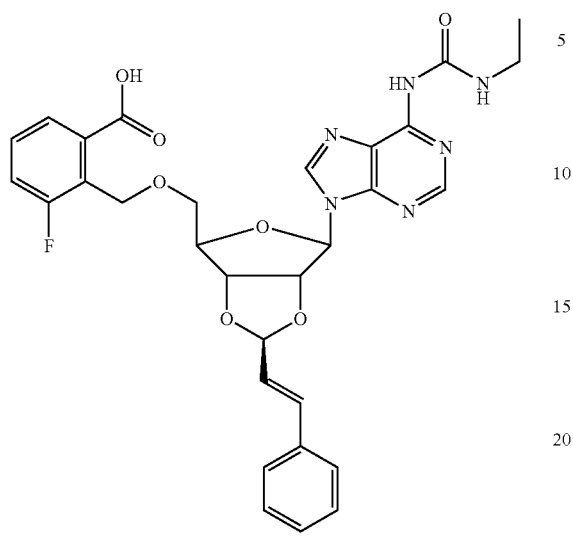
113
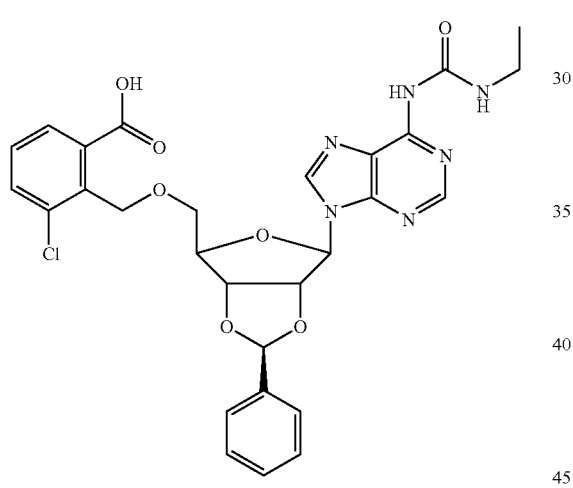
114
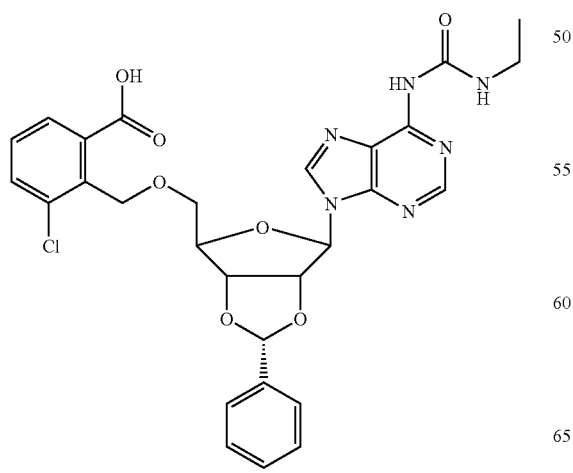
54
-continued
115
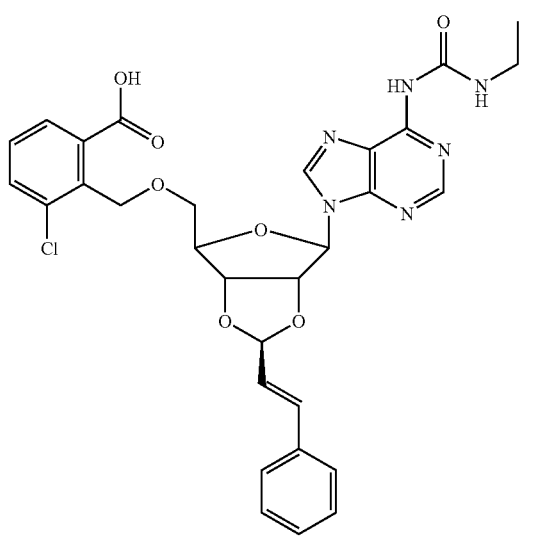
116
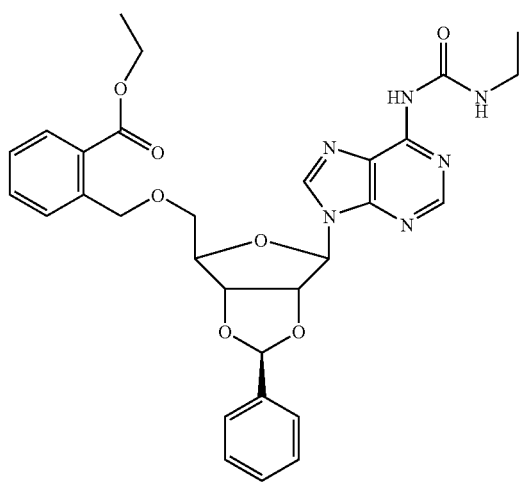
117
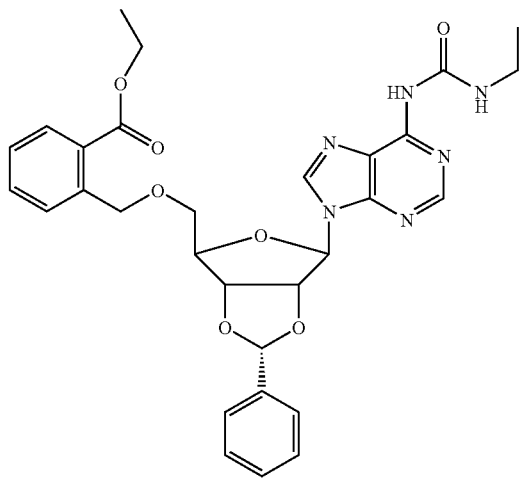

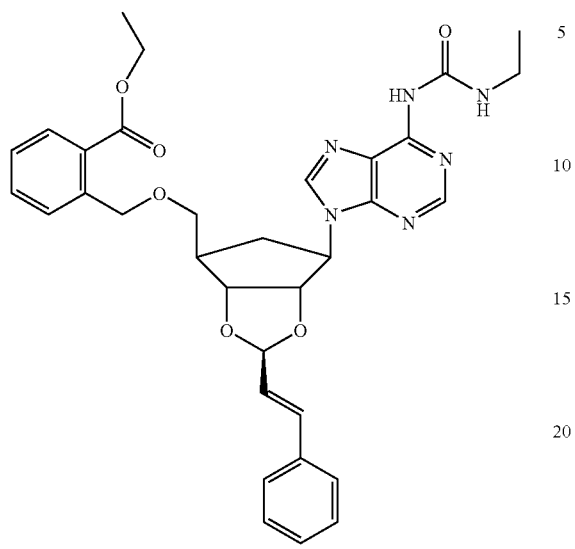
118
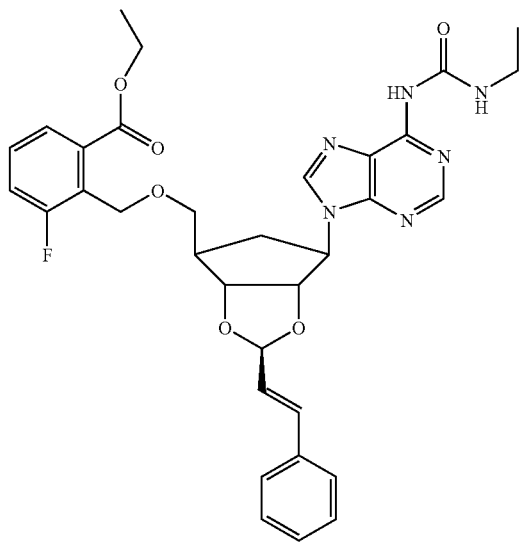
121
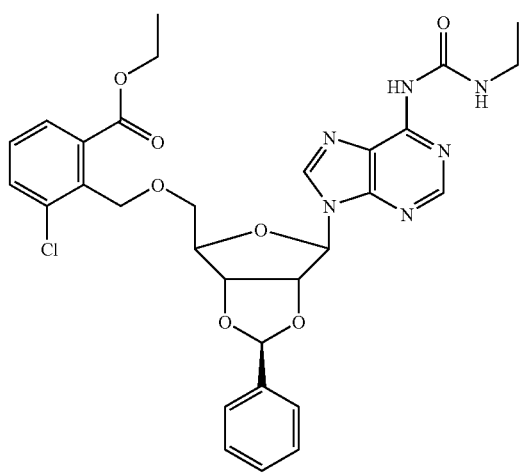
122
119
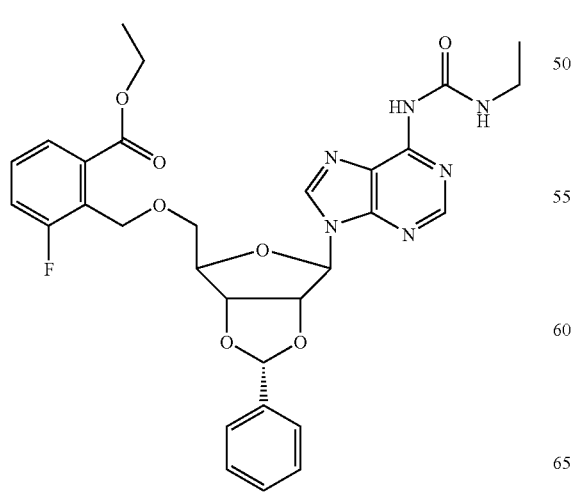
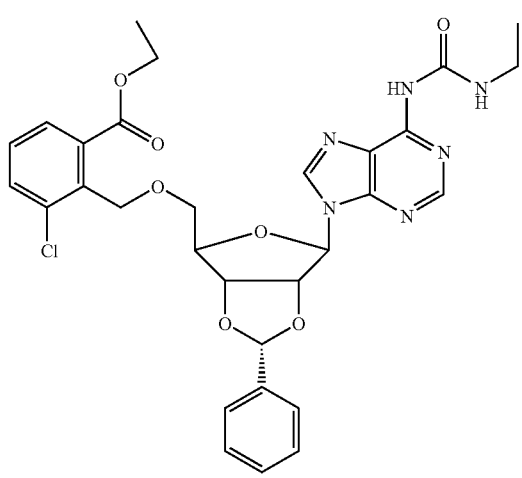
123
120

-continued

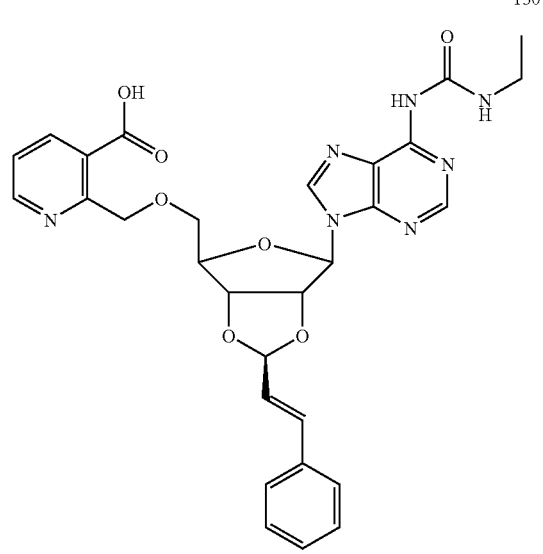
130
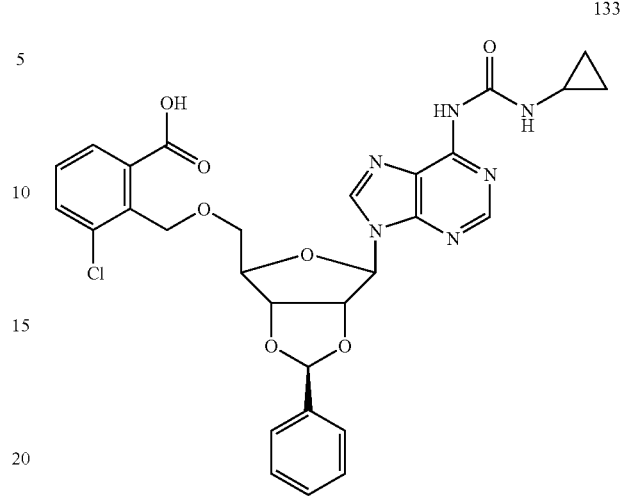
133
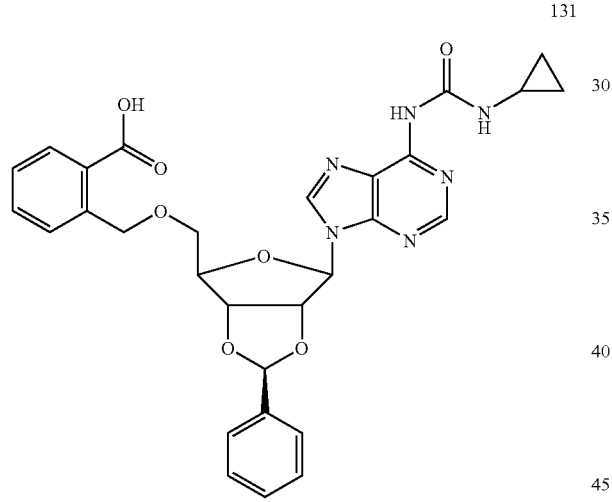
131
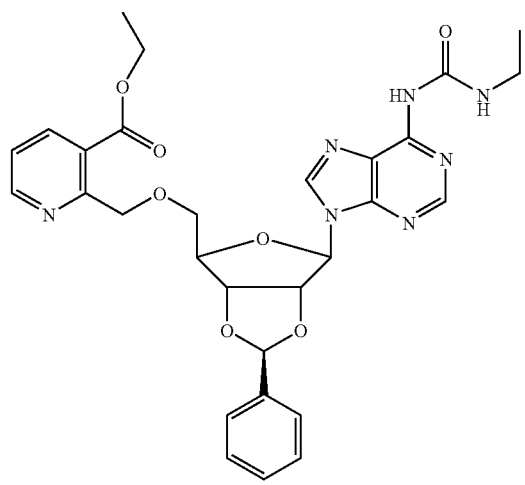
134
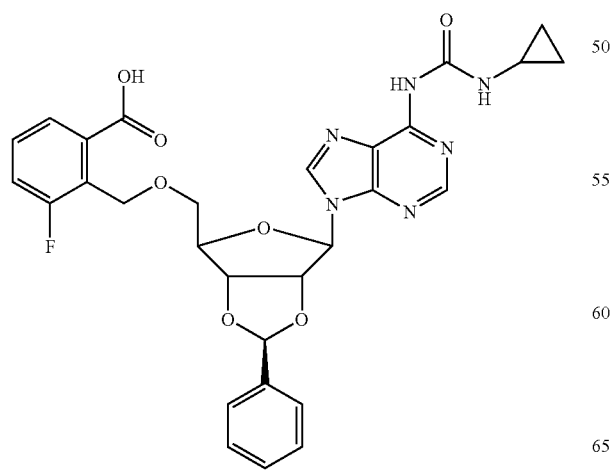
132
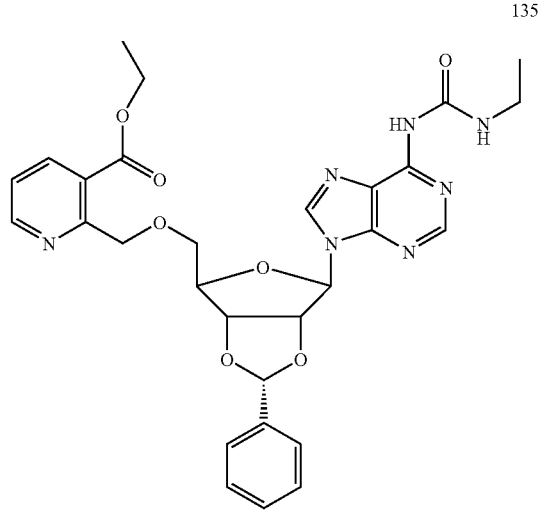
135

136
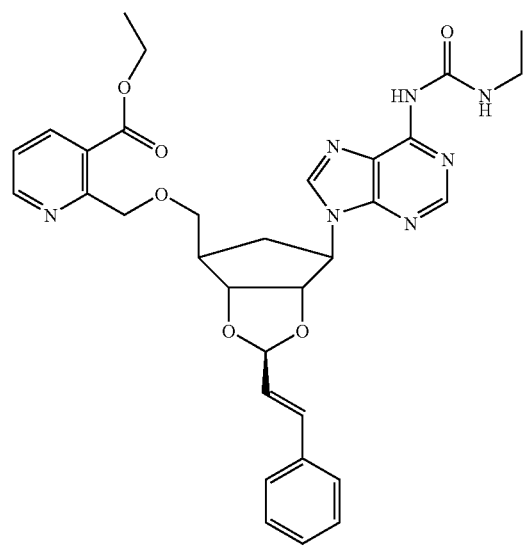
137
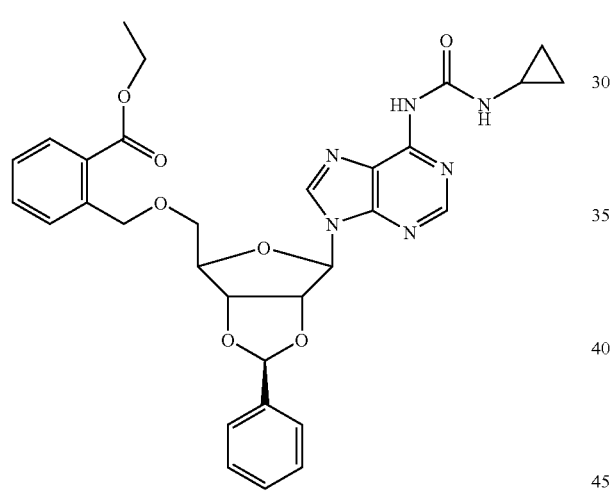
138
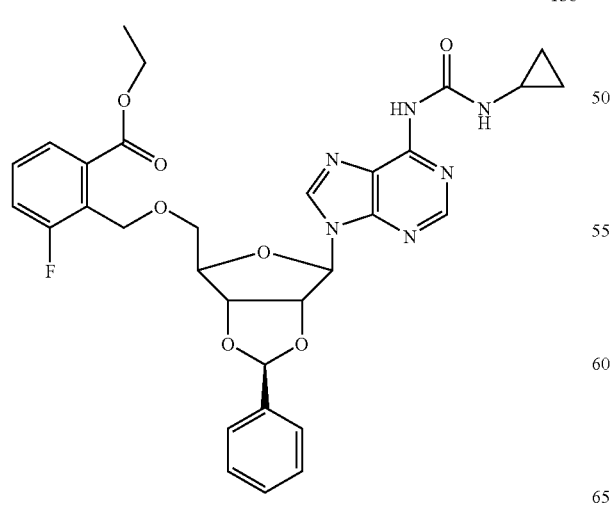
139
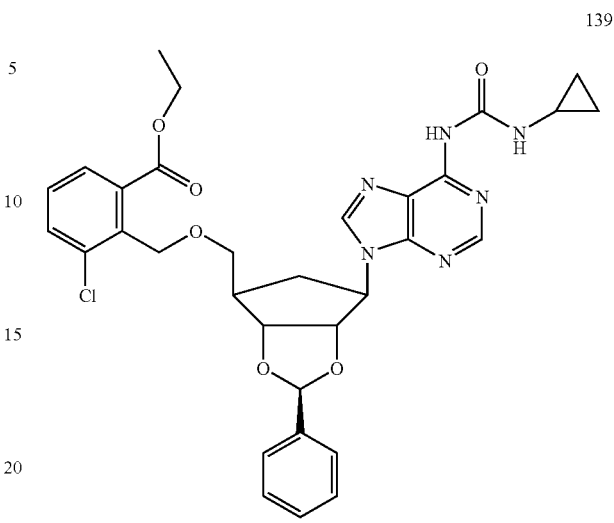
140
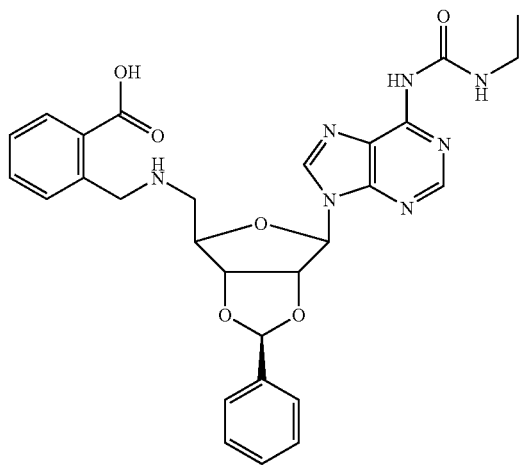
141
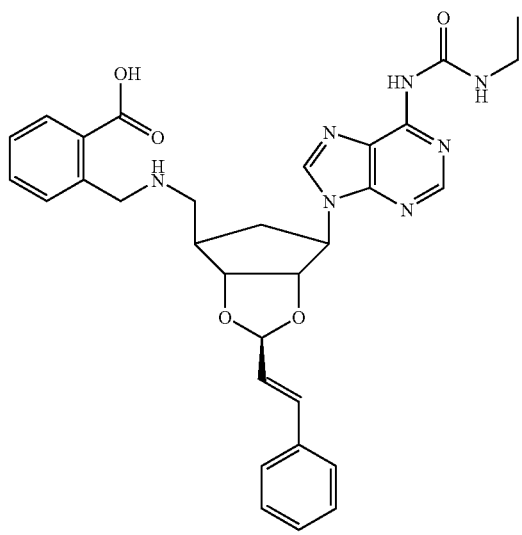

-continued
142
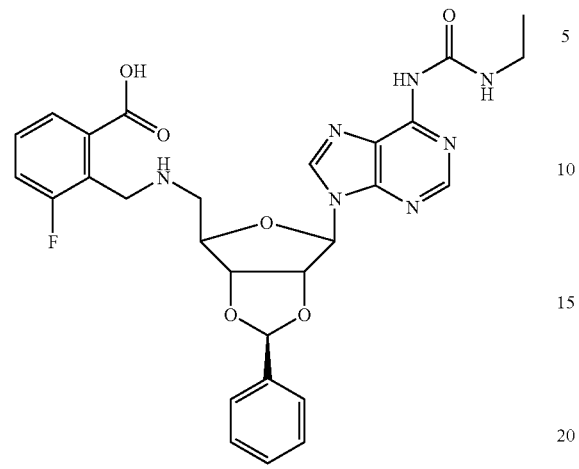
143
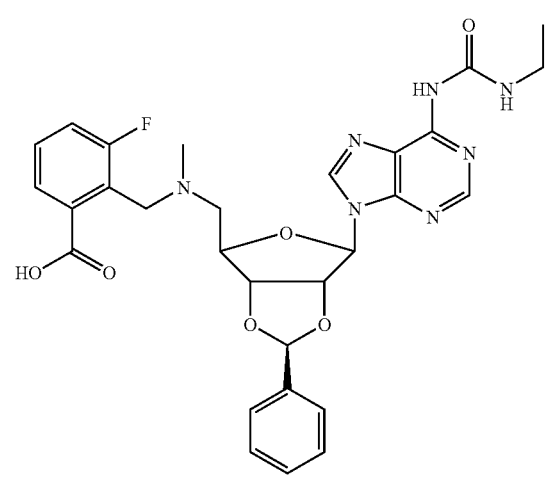
144
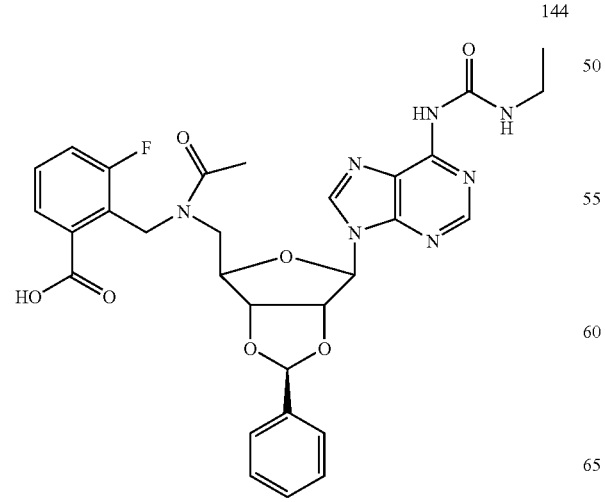
-continued
145
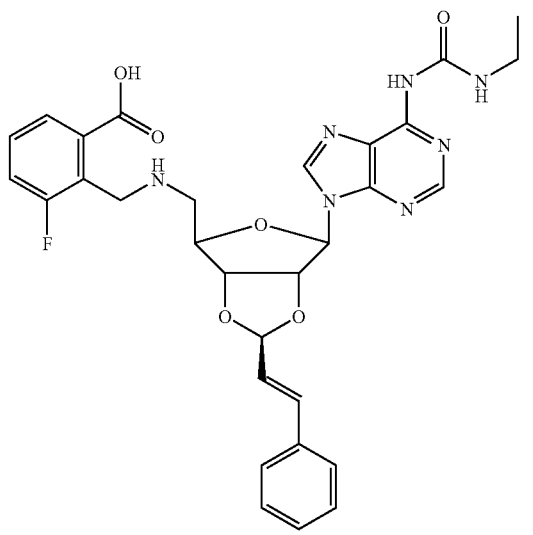
146
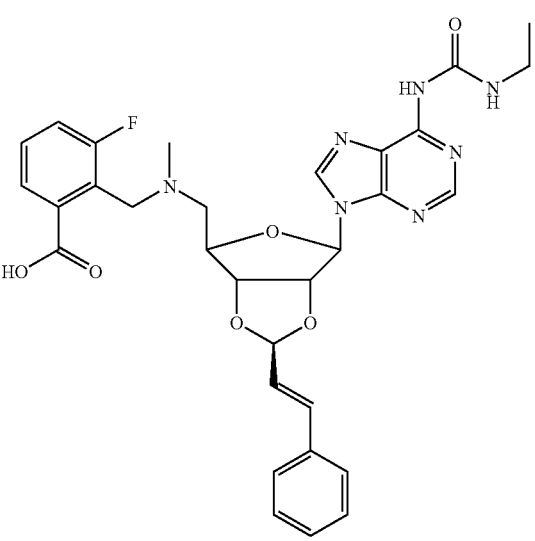
147
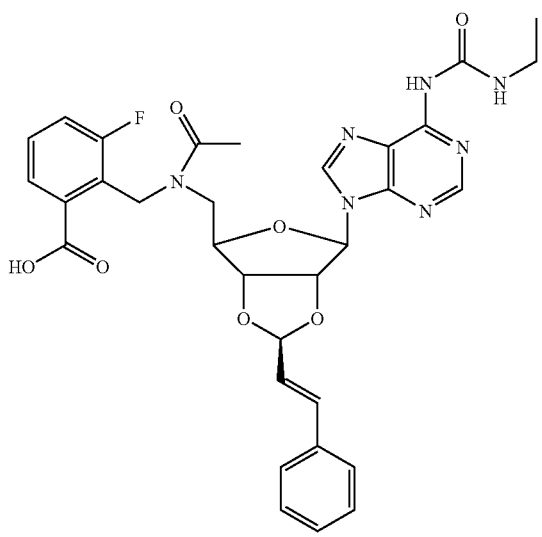

148
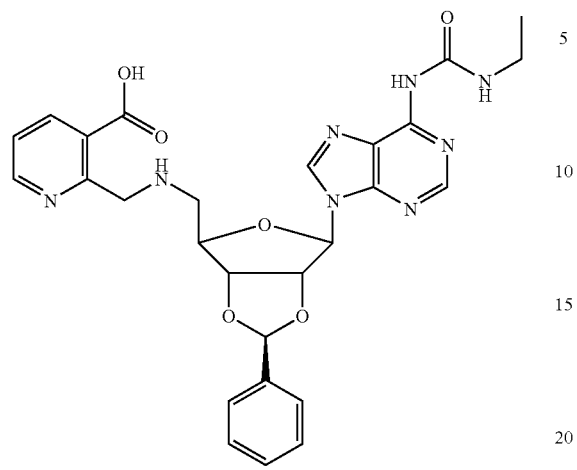
151
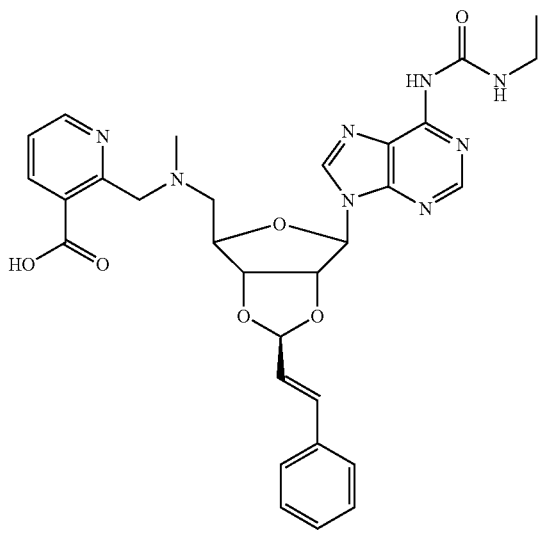
149
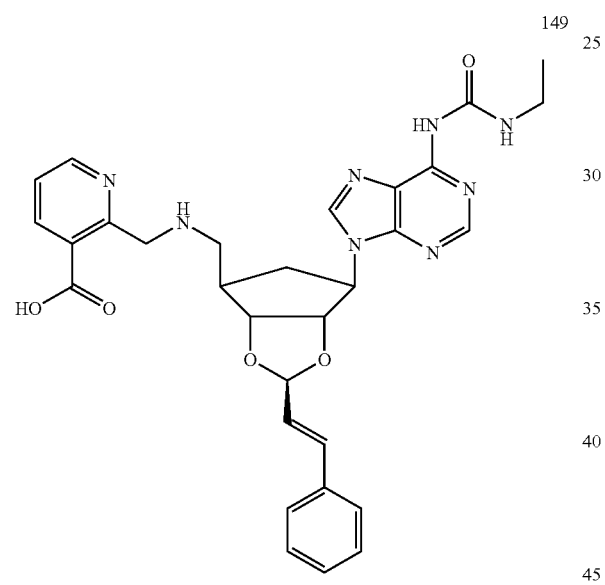
152
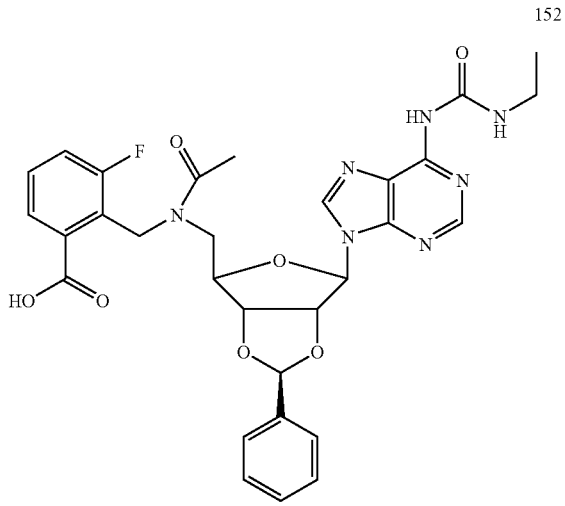
150
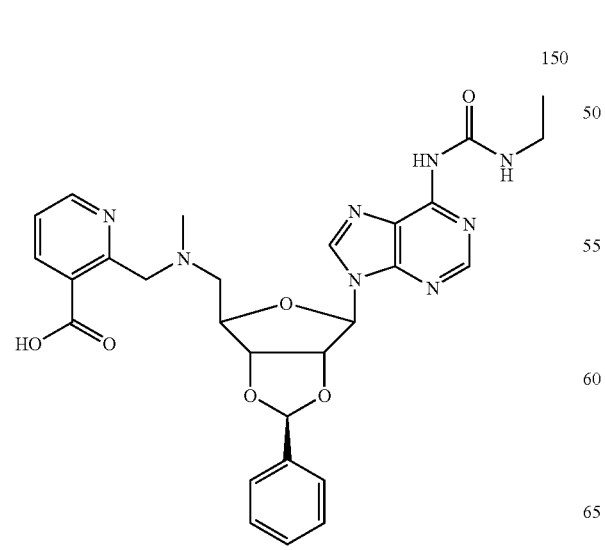
153
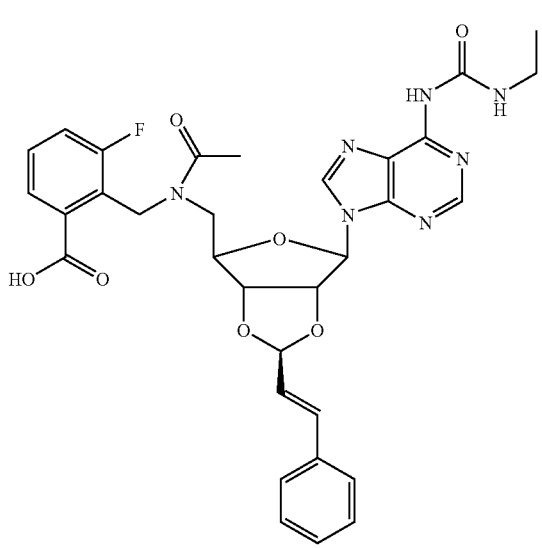

154
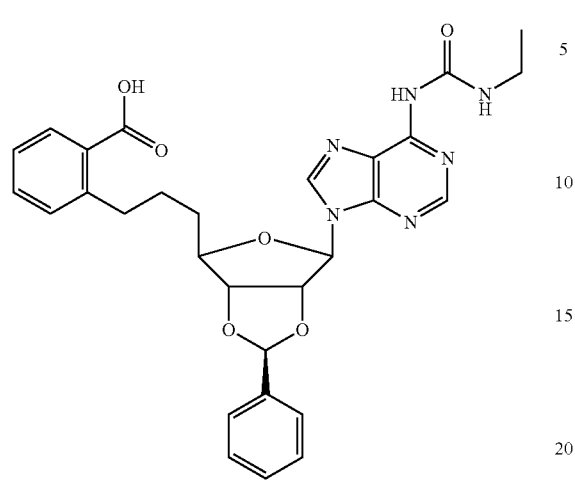
155
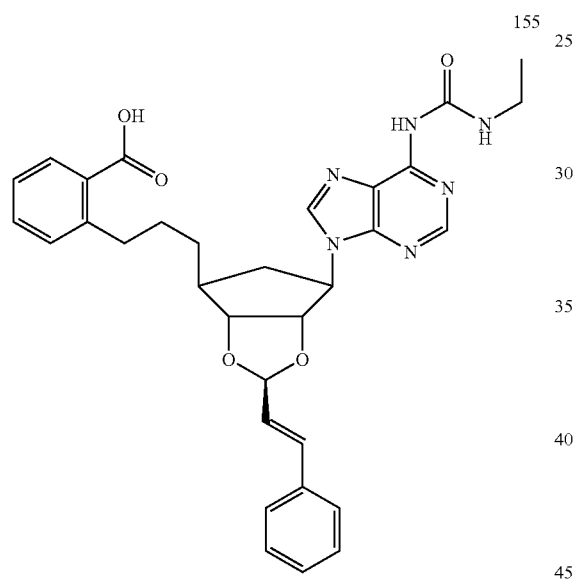
156
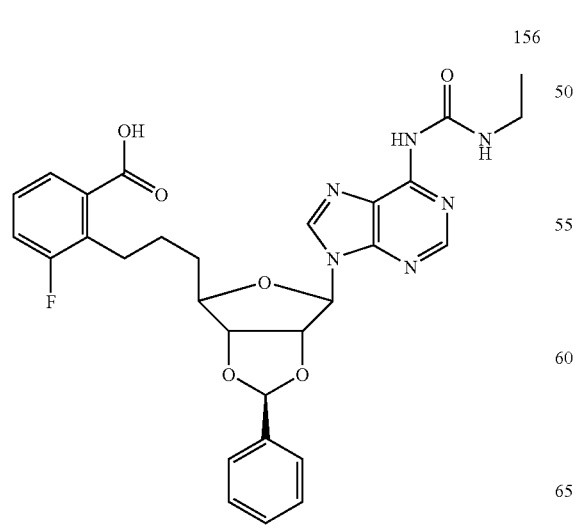
157
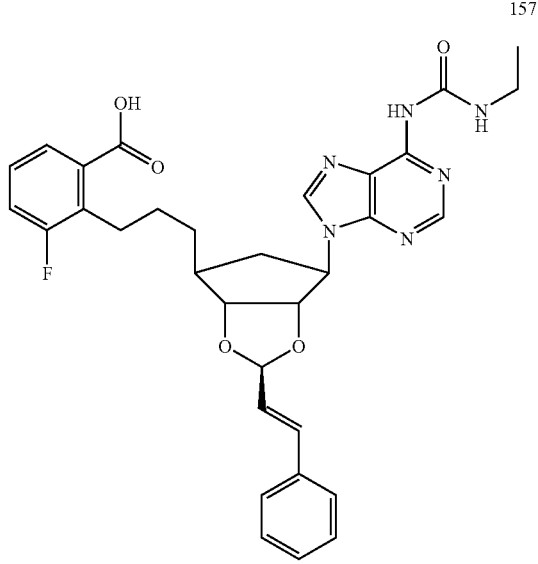
158
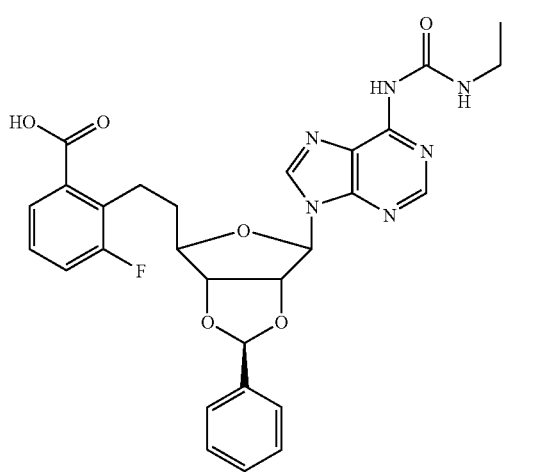
159
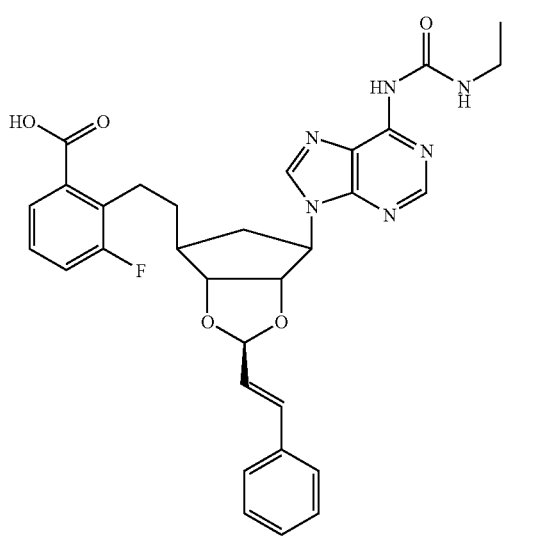

-continued

160

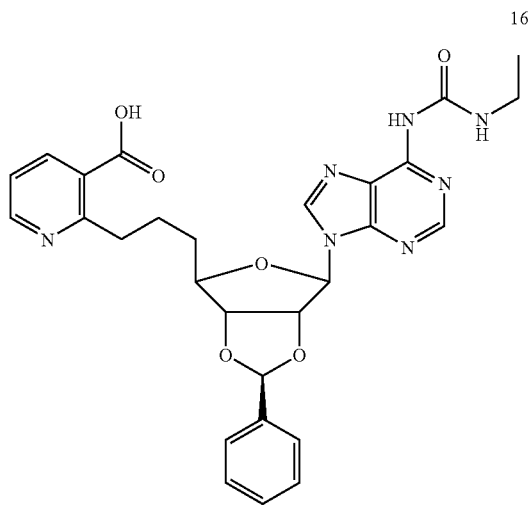

161

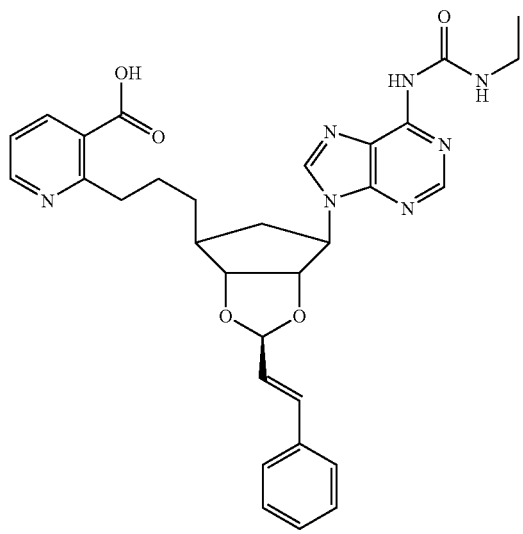

162

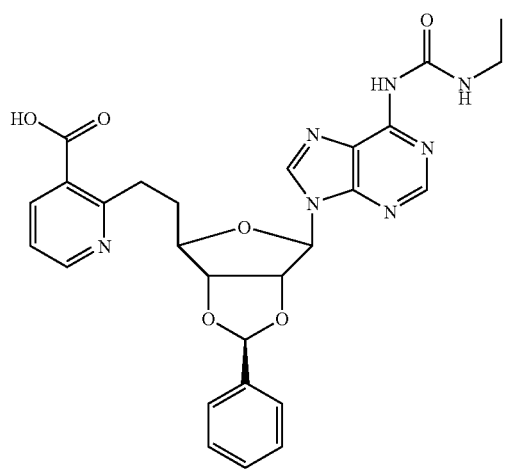

In another embodiment of the method, the compound is a compound of Formula VI:

Formula VI

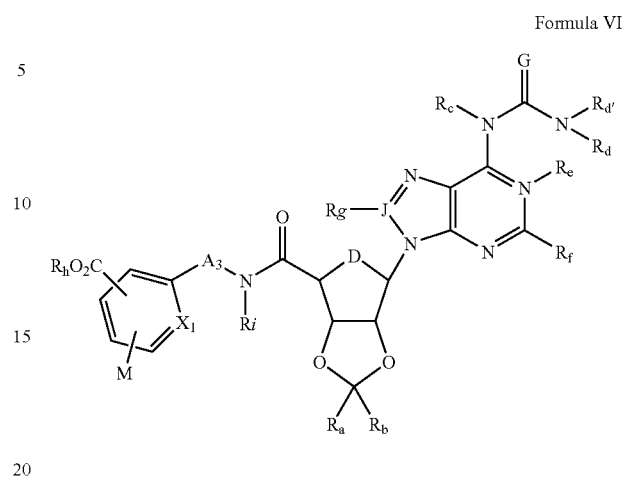

wherein:

$R_a$, $R_b$, $R_c$, G, D, $R_d$, $R_{d'}$, $R_e$, $R_f$, J, M, $X_1$, $R_g$ and $R_h$ are as defined in Formulae I and II;

$A_3$ is C, where C can be substituted with H or alkyl; or $A_3$ is absent;

$R_1$ is H or alkyl.

Preferred compounds of Formula VI are wherein:

G=D=O;

$R_a$=$R_c$=$R_d$=$R_e$=$R_f$=$R_g$=$R_h$=$R_i$=H;

$R_{d'}$=$C_{1-4}$ alkyl, or $C_{3-6}$ cycloalkyl;

$A_3$=$CH_2$, or absent;

$X_1$=C or N;

$R_b$=phenyl, benzyl, or styryl; and

M=H, halogen, $C_{1-4}$ alkyl, $C_{1-4}$ alkoxy, $CF_3$, cyano, or amino.

Some of the preferred compounds falling under the definition of Formula VI are:

163

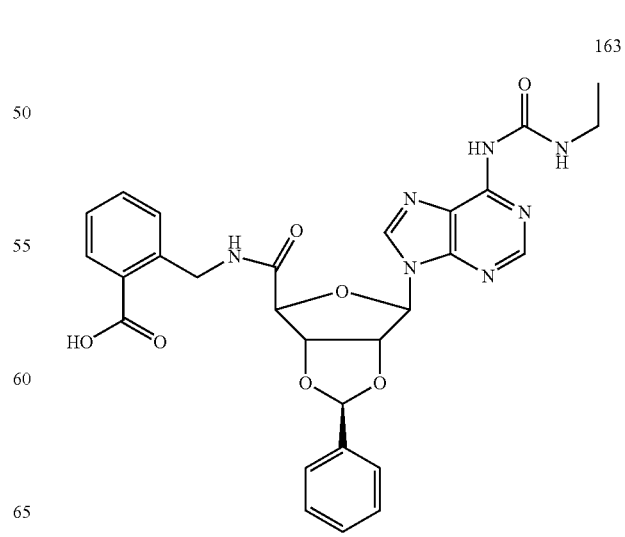

71
164
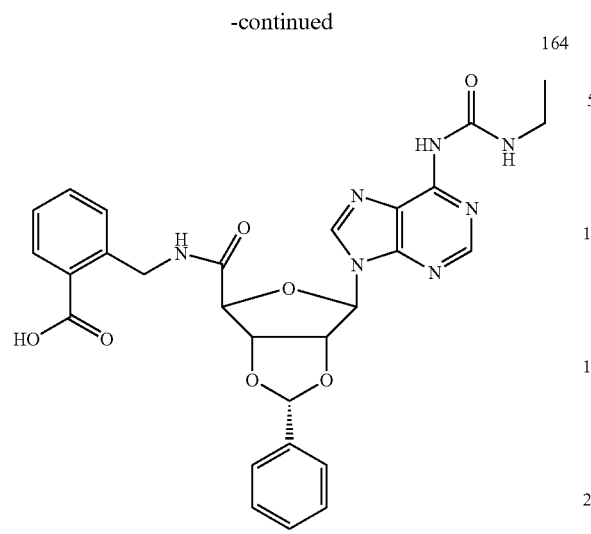
165
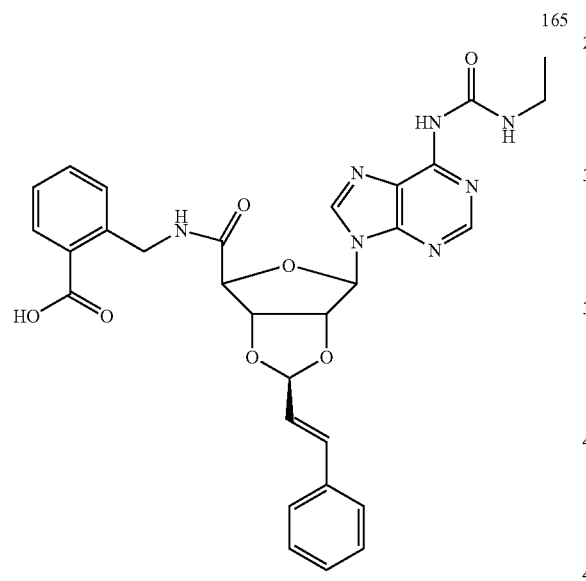
166
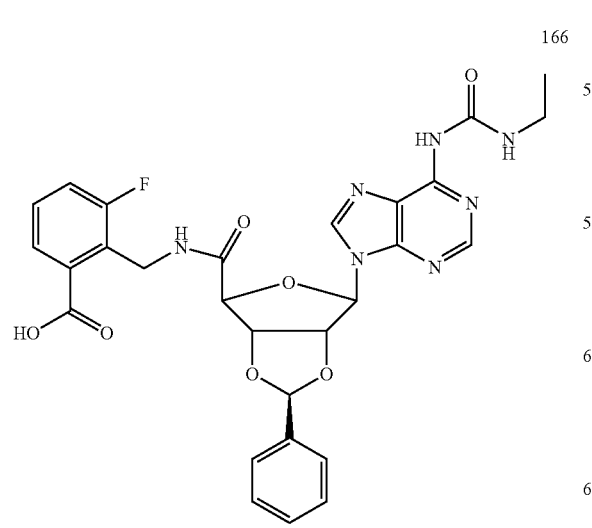
72
167
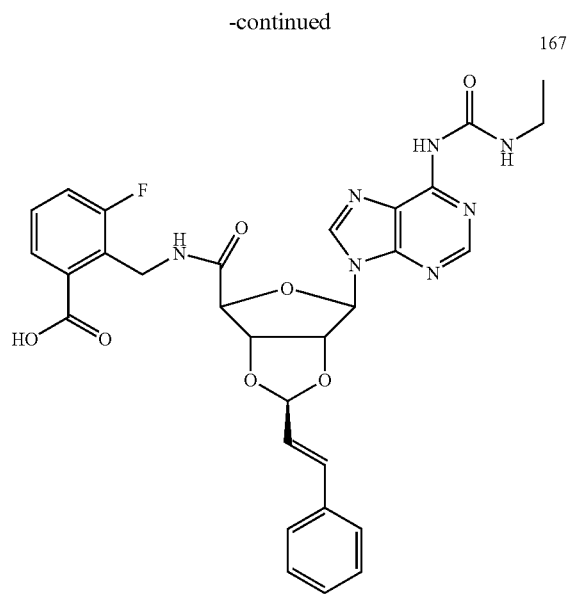
168
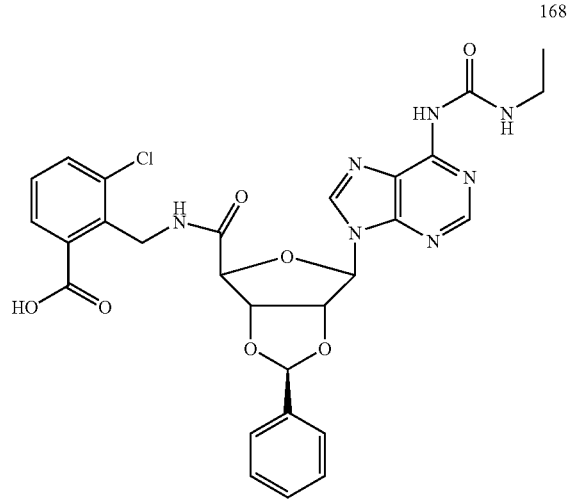
169
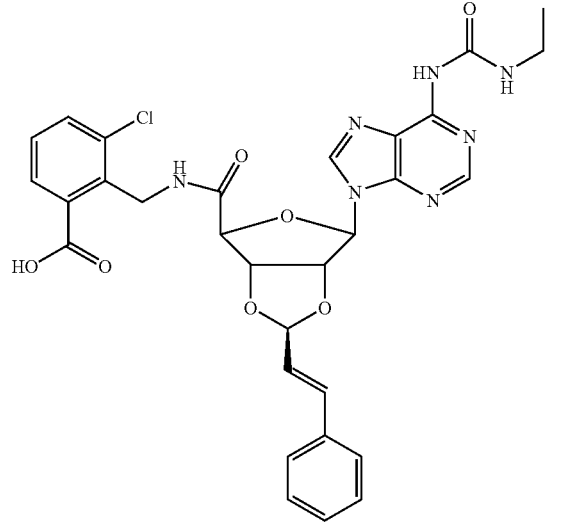

-continued
170
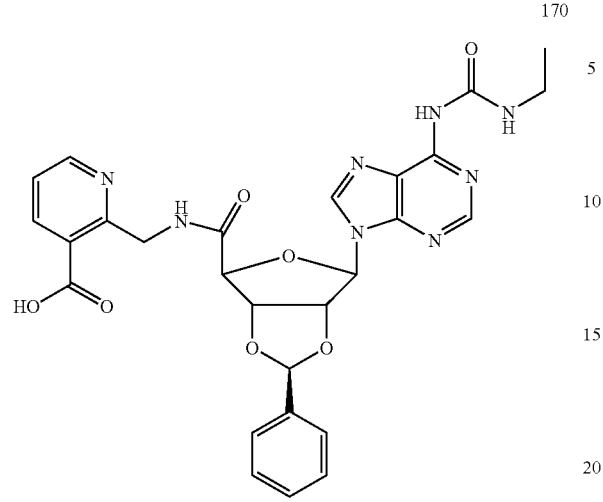
171
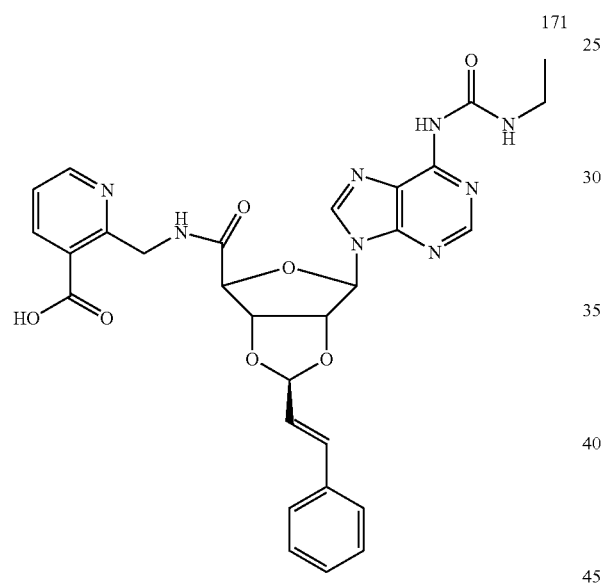
172
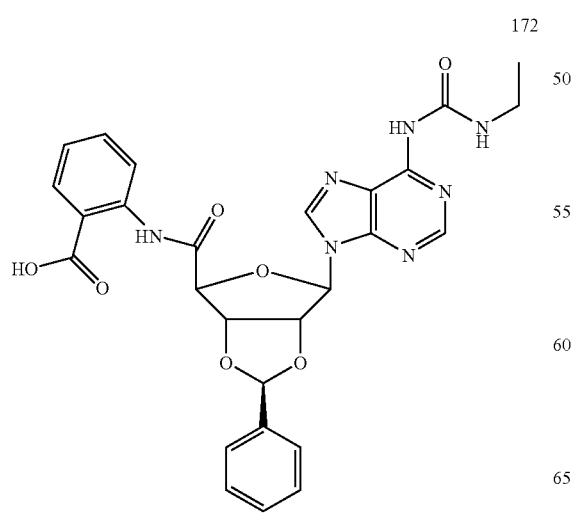
-continued
173
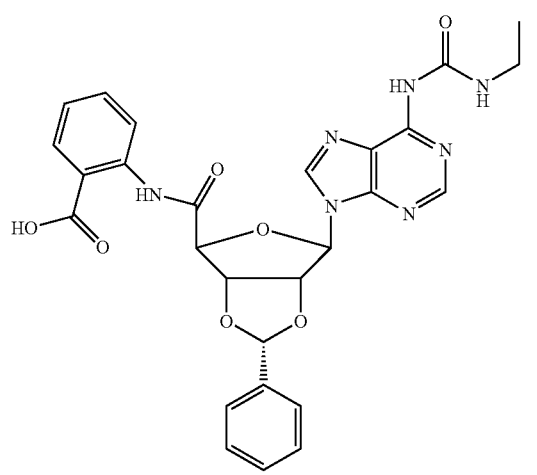
174
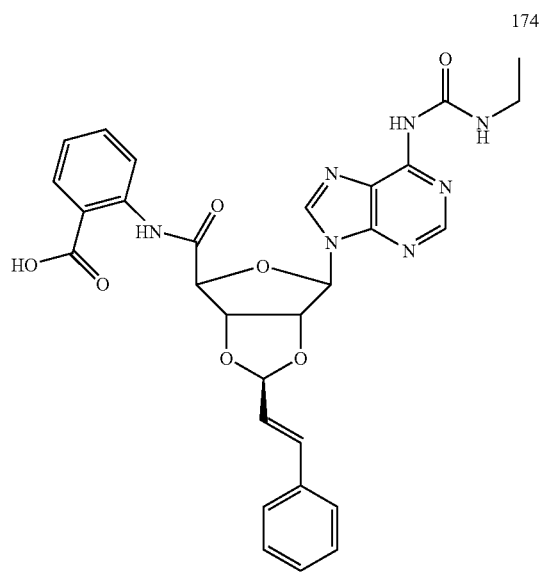
175
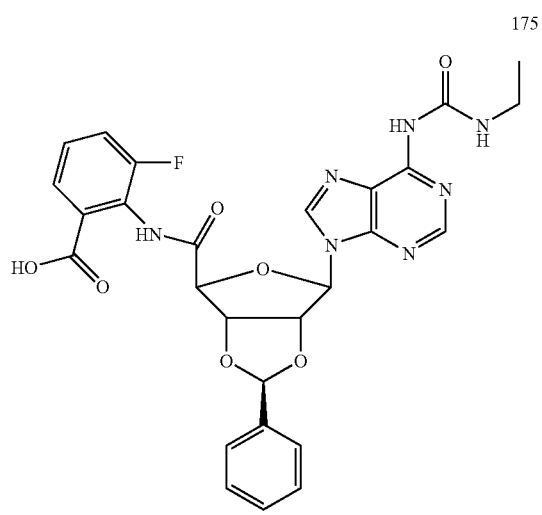

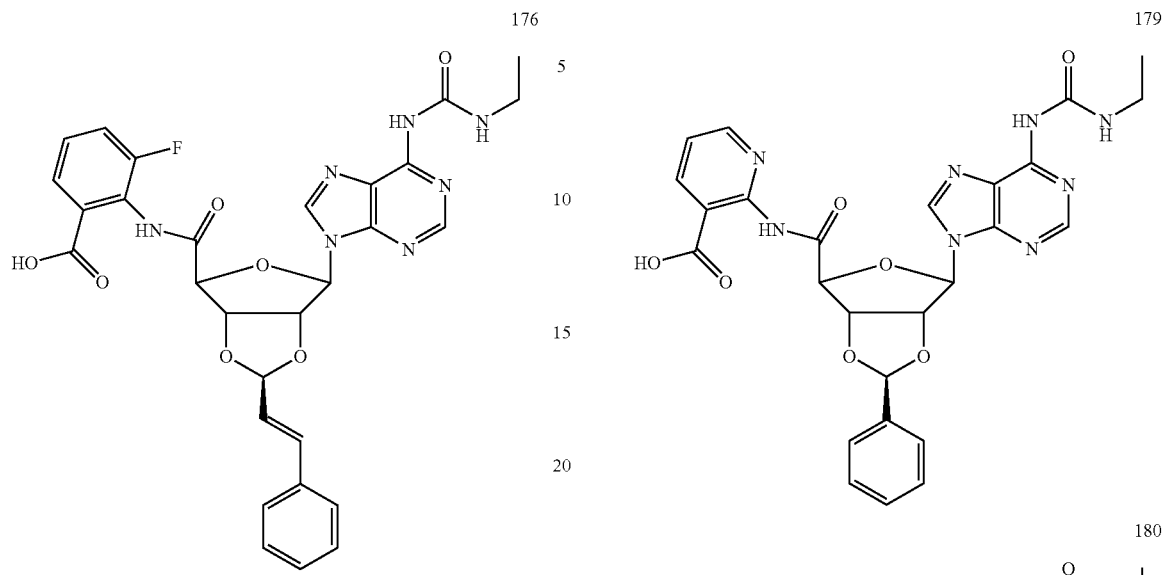
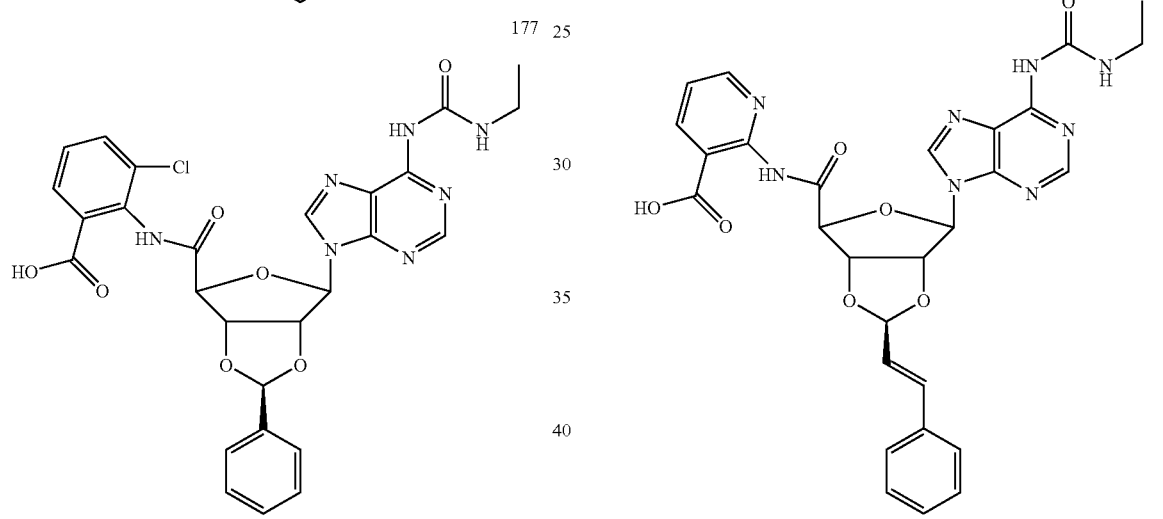
In another embodiment of the present invention, the compound of Formula I is a compound of Formula VII:
Formula VII
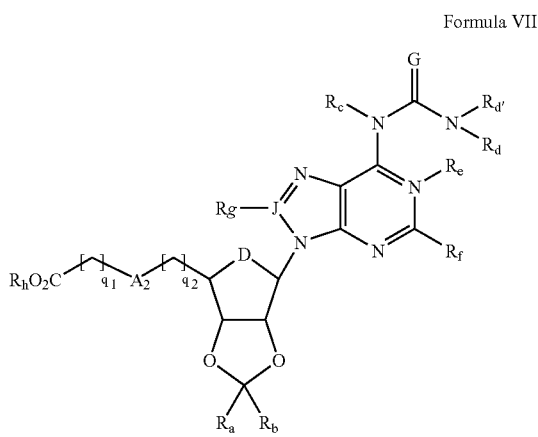

wherein:

$R_a, R_b, R_c, G, D, R_d, R_{d'}, R_e, R_f, J, R_g$ and $R_h$ are as defined in Formulae I and II;

$q_1$ and $q_2$ are independently 0, 1, or 2;

$A_2$ is as previously defined for Formula V, with the proviso that when $q_1$ and/or $q_2$ are 0 and D=O, $A_2$ is C; or $A_2$ is absent.

Preferred compounds of Formula VII are wherein:

G=D=O;

$R_a=R_c=R_d=R_f=R_g=H$;

$R_e$ is absent;

$R_h$=H or ethyl;

$R_{d'}=C_{1-4}$ alkyl, or $C_{3-6}$ cycloalkyl;

$A_2=CH_2$, O, NH, N-methyl, N-acetyl, or absent;

$q_1$ and $q_2$=0 or 1; and $R_b$=phenyl, benzyl, or styryl.

Some of the preferred compounds falling under the definition of Formula VII are:

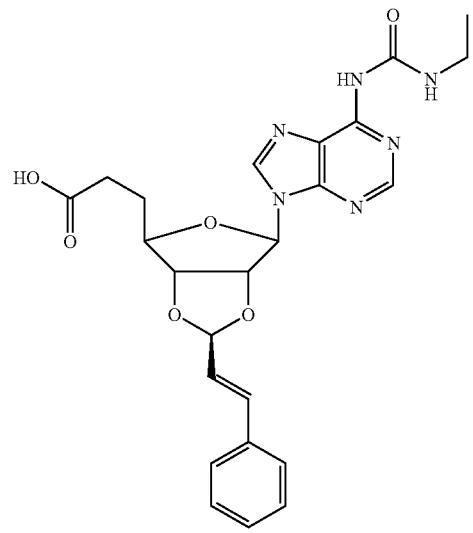

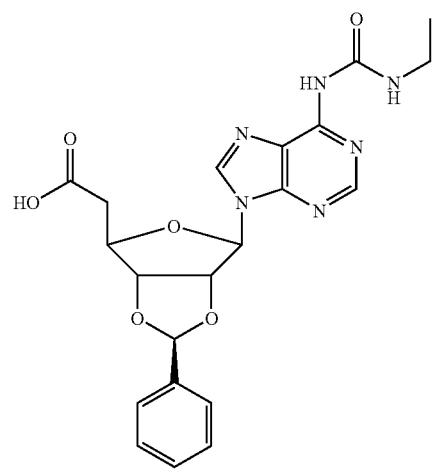

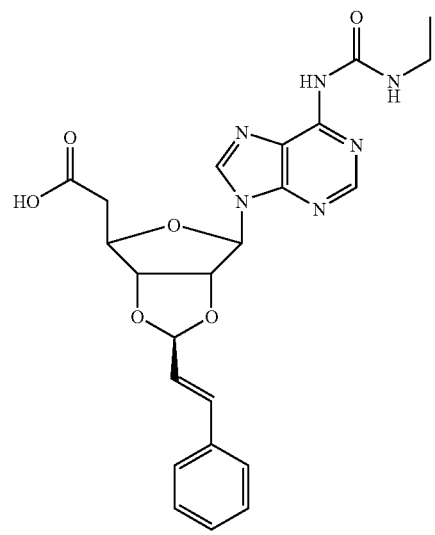

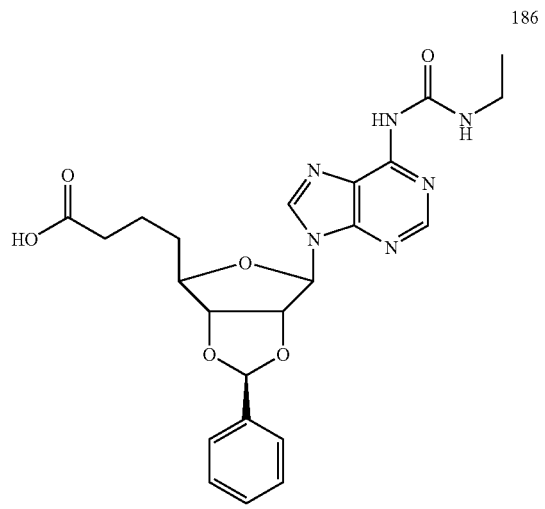
186
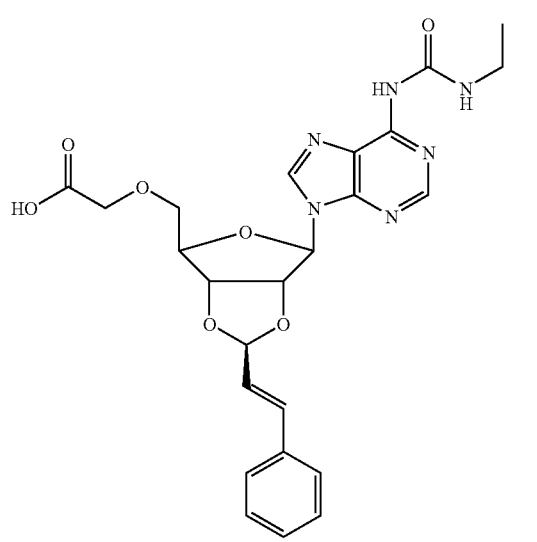
189
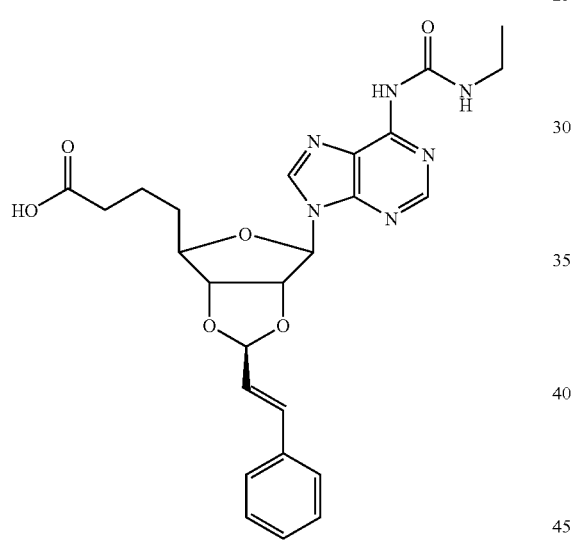
187
190
188
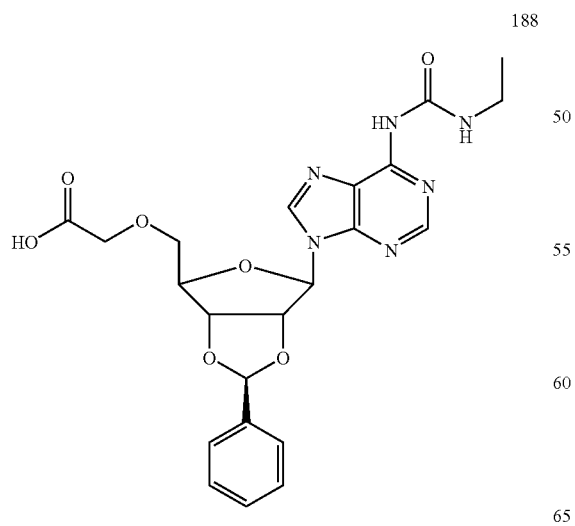
191

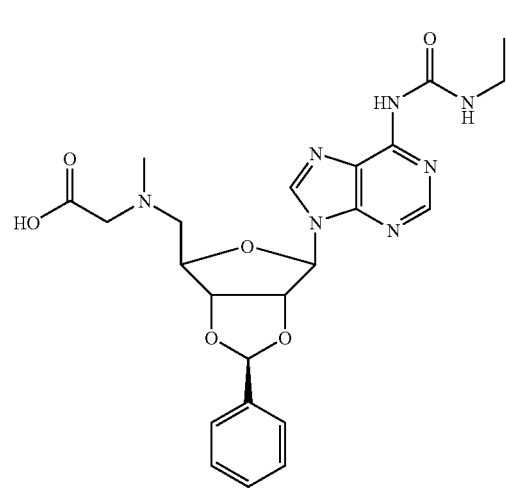
192
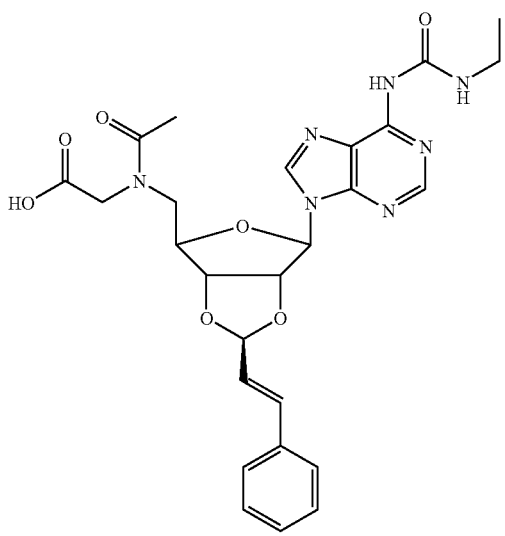
195
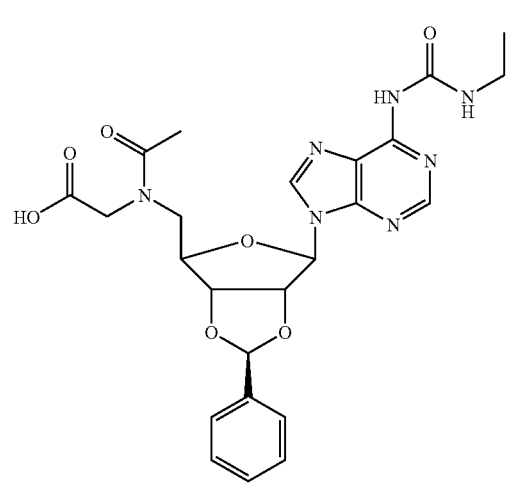
193
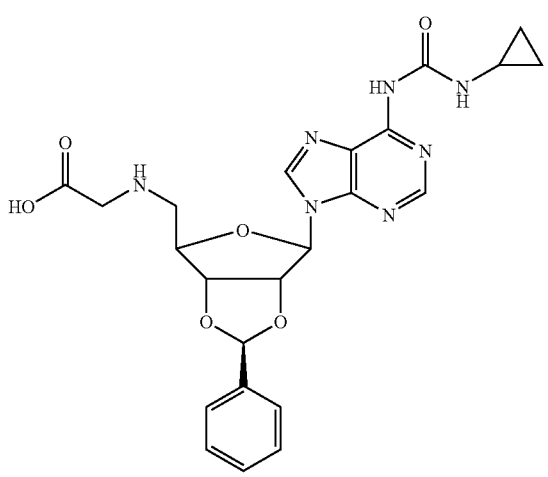
196
194
197

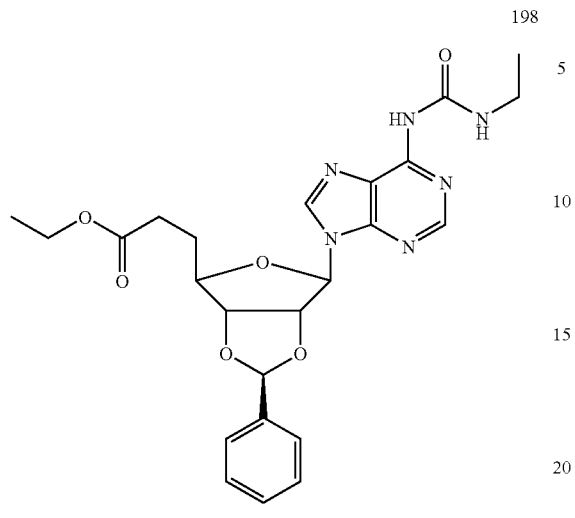
198
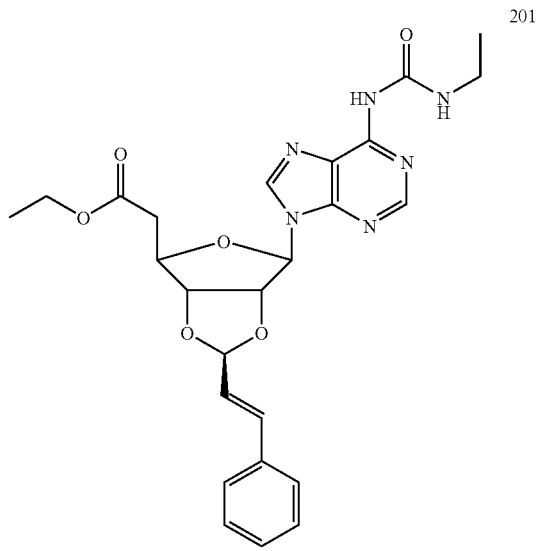
201
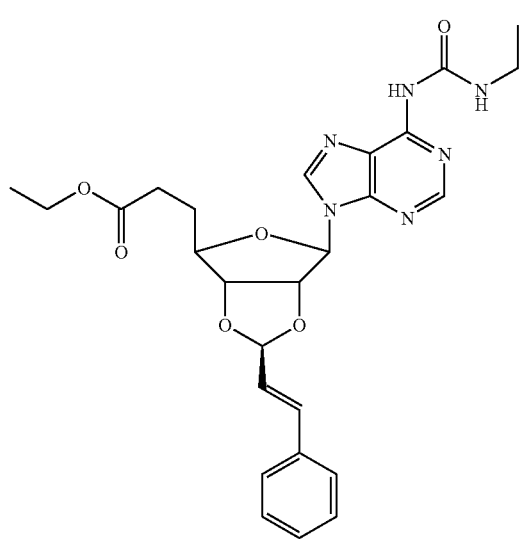
199
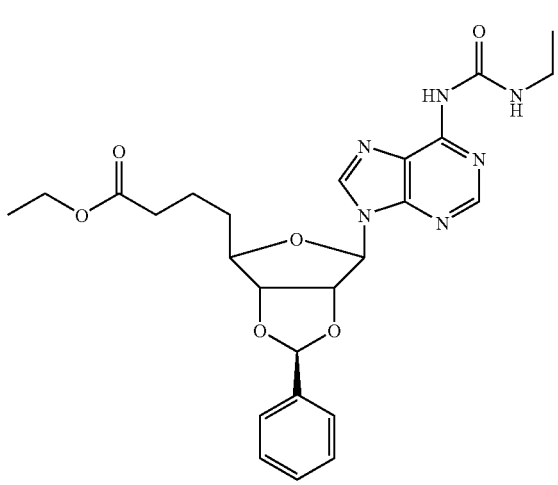
202
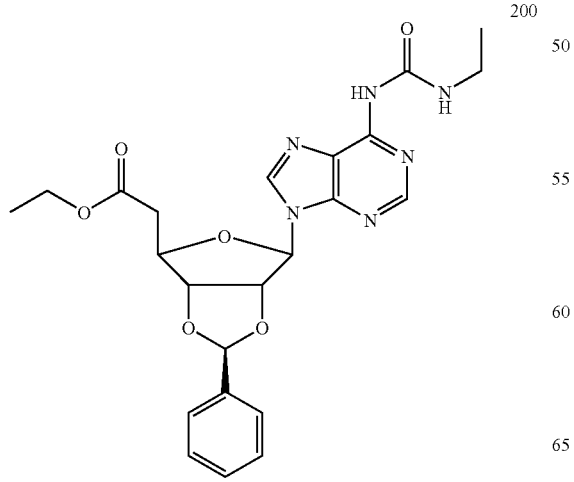
200
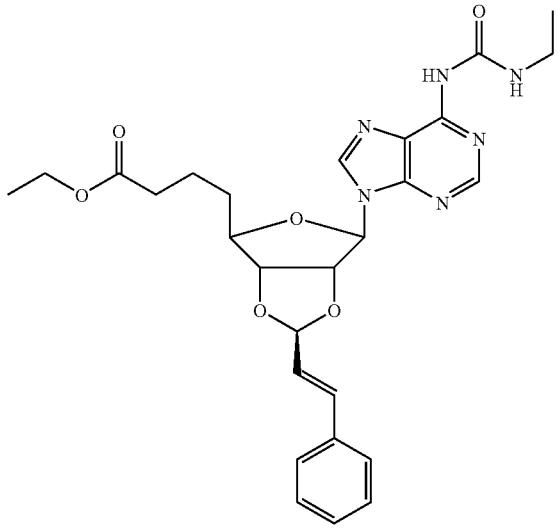
203

85
-continued
204
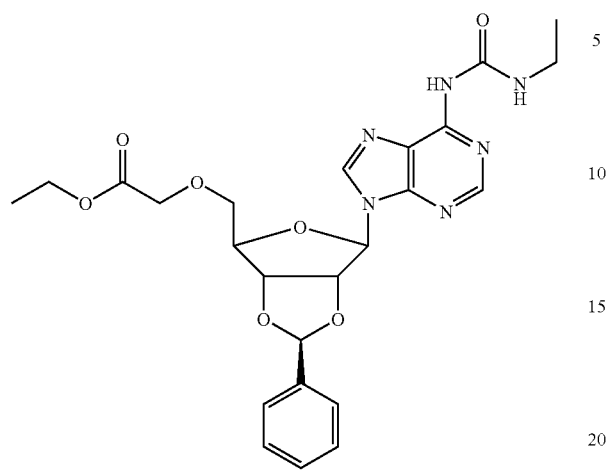
205
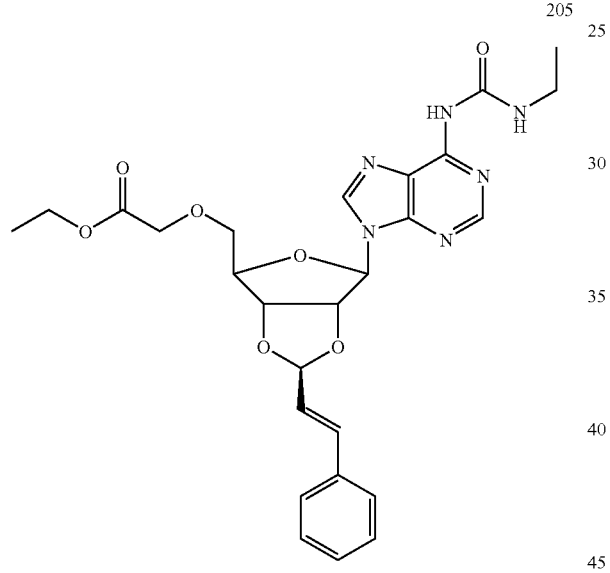
206
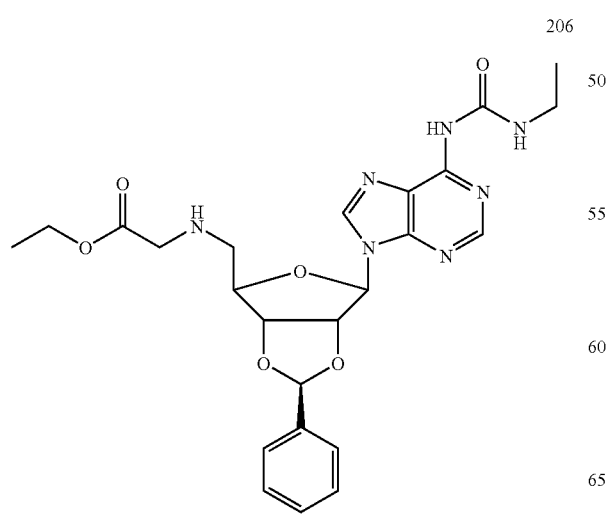
86
-continued
207
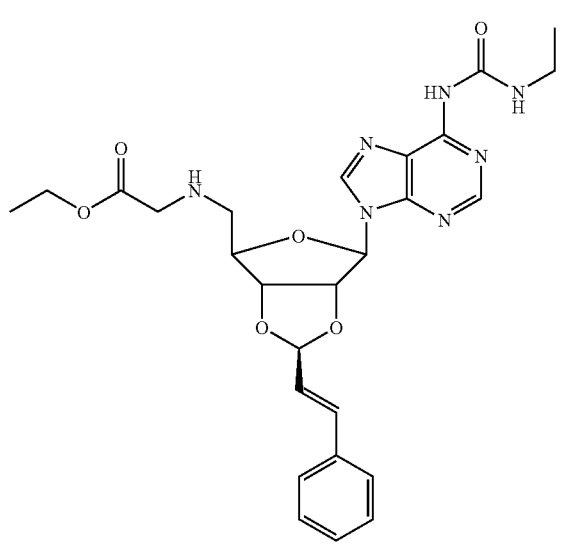
208
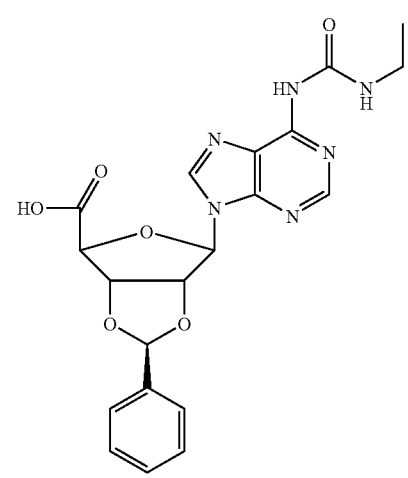
209
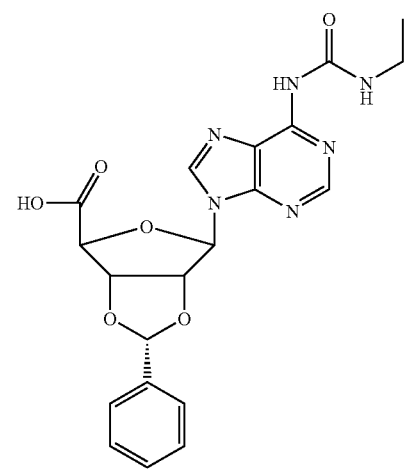

-continued

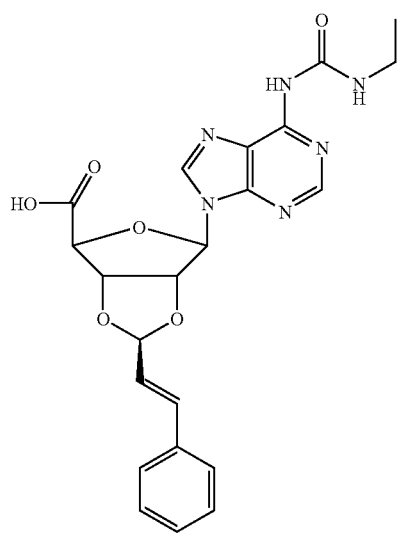
210

In another embodiment of the present invention, the compound of Formula I is a compound of Formula VIII:

Formula VIII

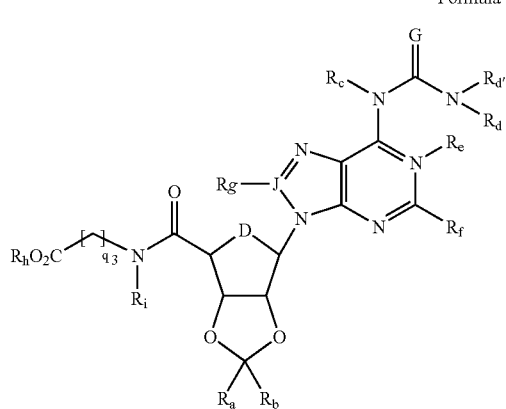

wherein:

$R_a$, $R_b$, $R_c$, G, D, $R_d$, $R_{d'}$, $R_e$, $R_f$, J, $R_g$ and $R_h$ are as defined in Formulae I and II;

$q_3$ is 1, 2, or 3; and $R_i$ is H or alkyl.

Preferred compounds of Formula VIII are wherein:

G=D=O;

$R_a$=$R_c$=$R_d$=$R_f$=$R_g$=H;

$R_e$ is absent;

$R_h$=H or ethyl;

$R_i$ is H or methyl;

$R_{d'}$=$C_{1-4}$ alkyl, or $C_{3-6}$ cycloalkyl;

$q_3$=1 or 2;

$R_b$=phenyl, benzyl, or styryl.

Some of the preferred compounds falling under the definition of Formula VIII are:

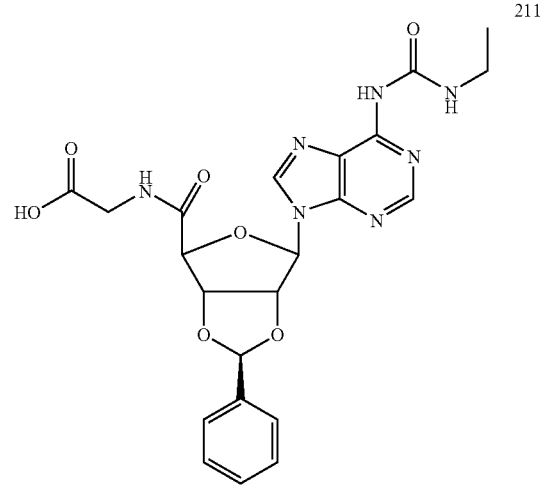
211

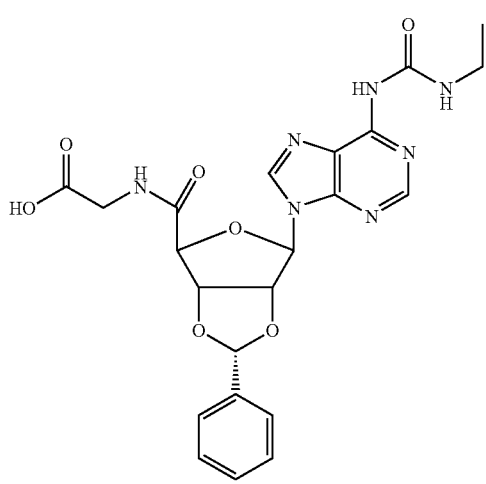
212

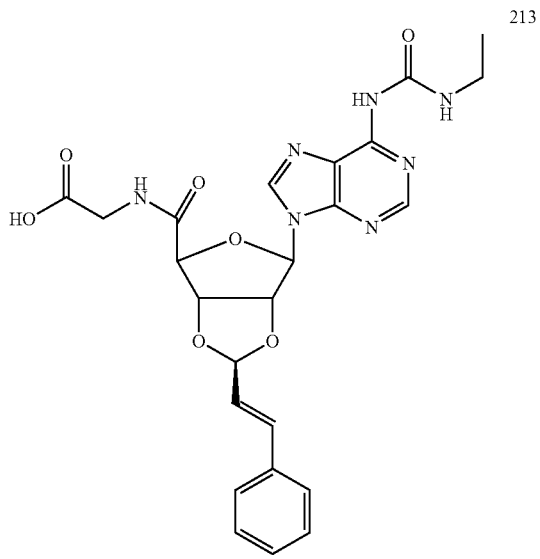
213

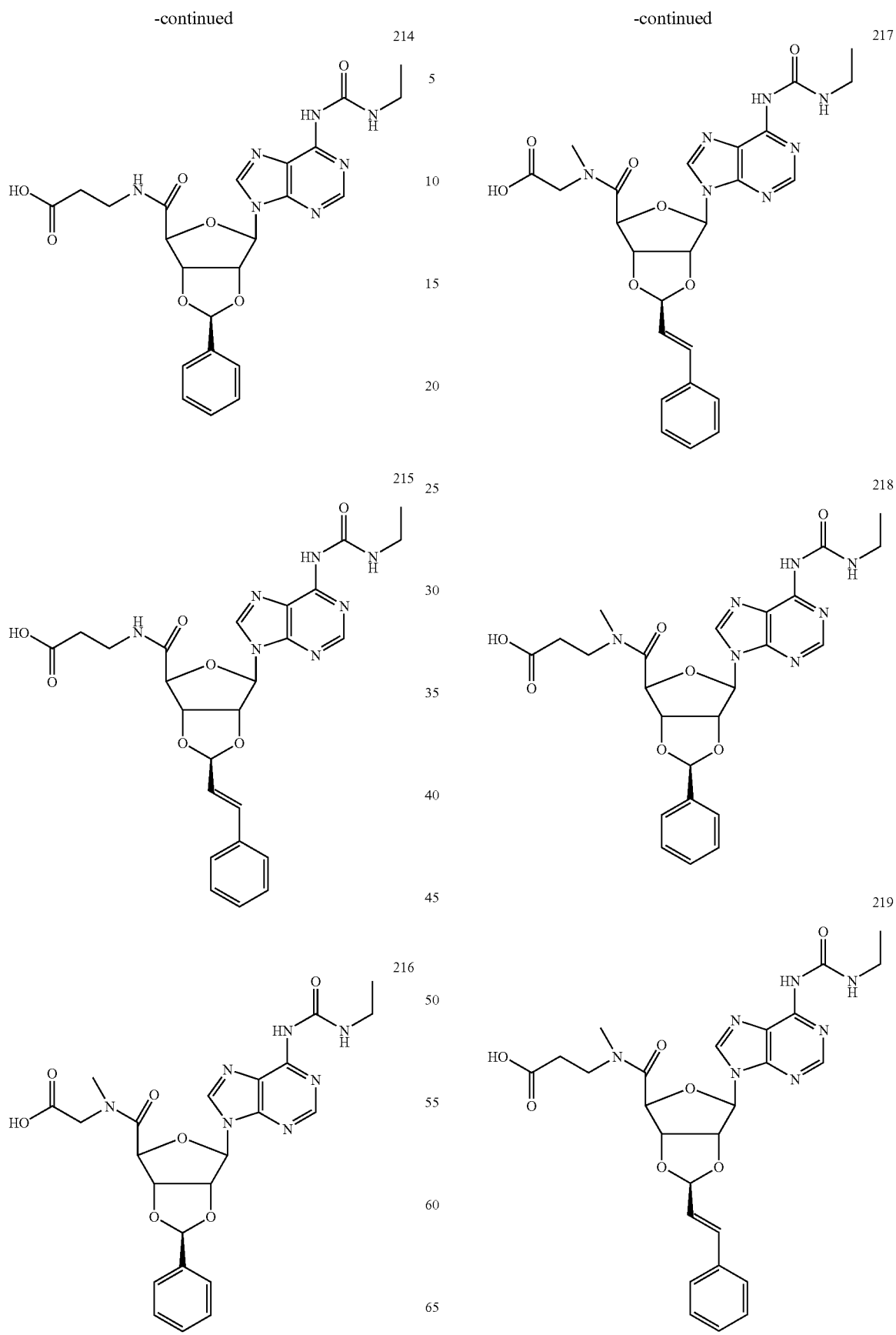

-continued

220

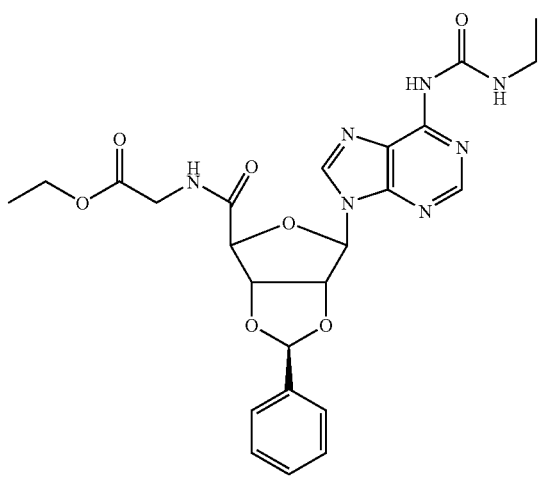

221

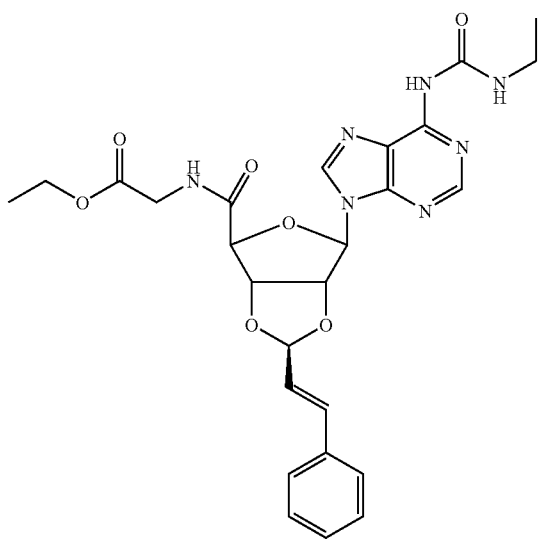

In another embodiment of the present invention, the compound of Formula I is a compound of Formula IX:

Formula IX

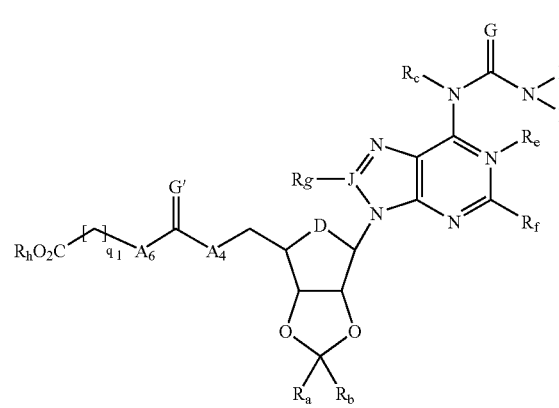

wherein:

$R_a$, $R_b$, $R_c$, G, D, $R_d$, $R_{d'}$, $R_e$, $R_f$, J, $R_g$ and $R_h$ are as defined in Formulae I and II;

$A_4$ and $A_6$ are independently C, N, O, or S, with the proviso that $A_4$ can be absent;

G' is O, or S;

such that the moiety described by $A_4/C(G')/A_6$ is an amide, thioamide, carbamate, thiocarbamate, urea, thiourea, ketone, or thioketone;

$q_1$ is 0, 1, or 2.

Preferred compounds of Formula IX are wherein:

G=G'=O;

$A_4$ and $A_6$ are independently C, N, or O;

$R_a$=$R_c$=$R_d$=$R_e$=$R_f$=$R_g$=$R_h$=H;

$R_{d'}$=$C_{1-4}$ alkyl, or $C_{3-6}$ cycloalkyl;

$q_1$=1; and $R_b$=phenyl, benzyl, or styryl.

Some of the preferred compounds falling under the definition of Formula IX are:

222

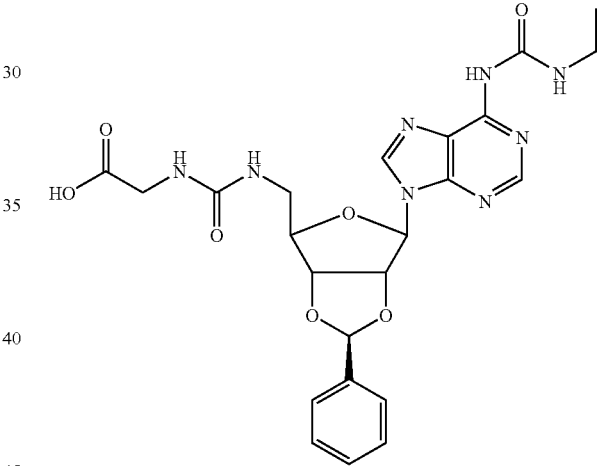

223

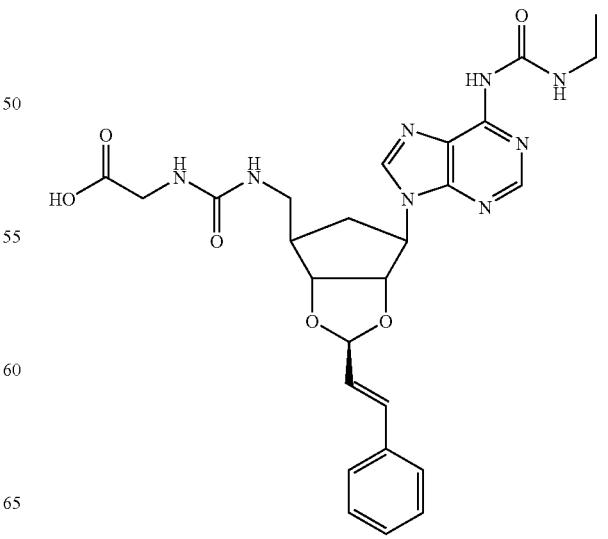

224
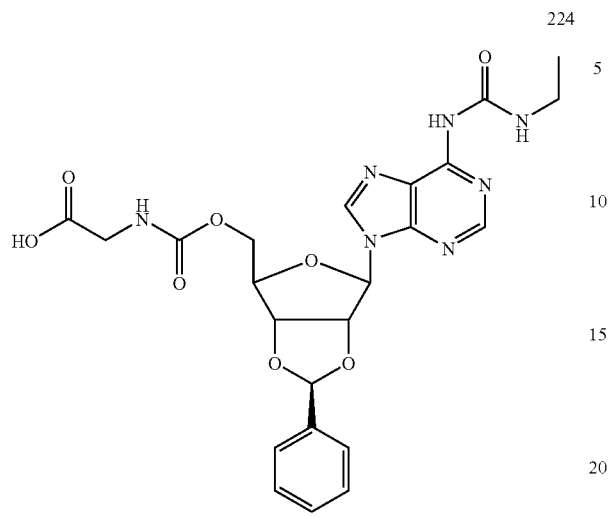
225
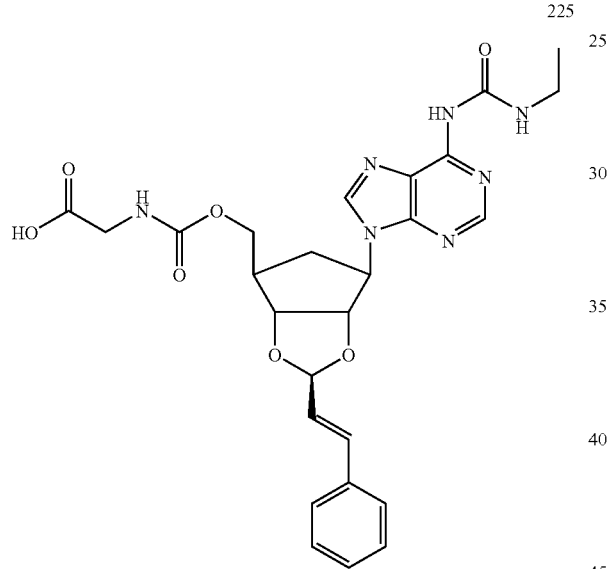
226
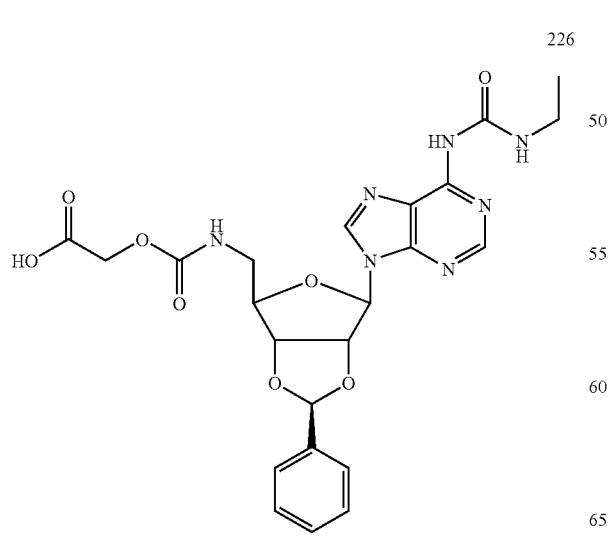
227
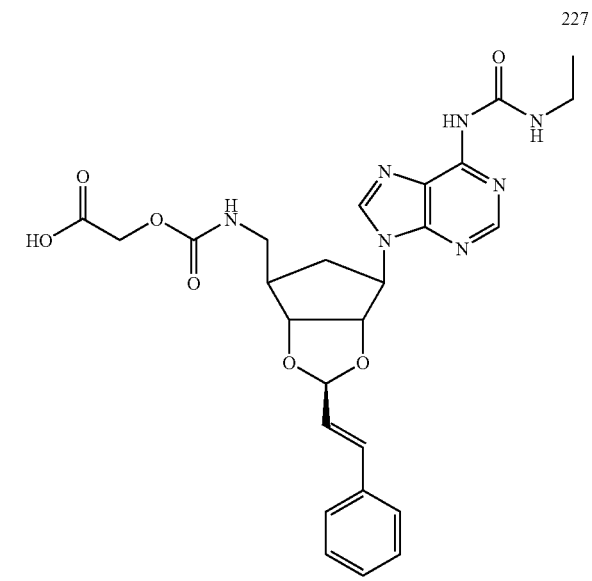
228
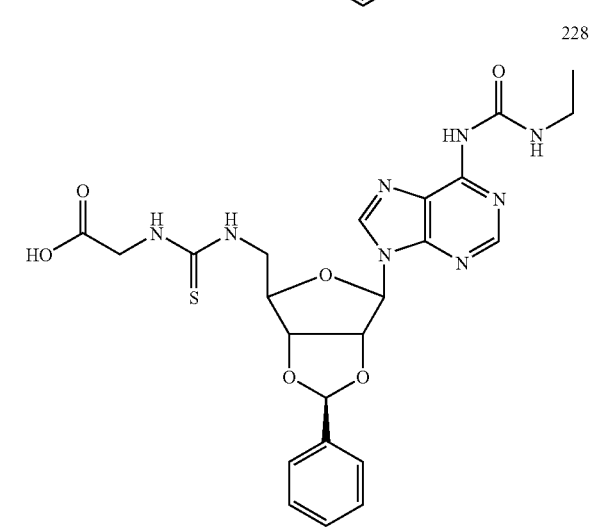
229
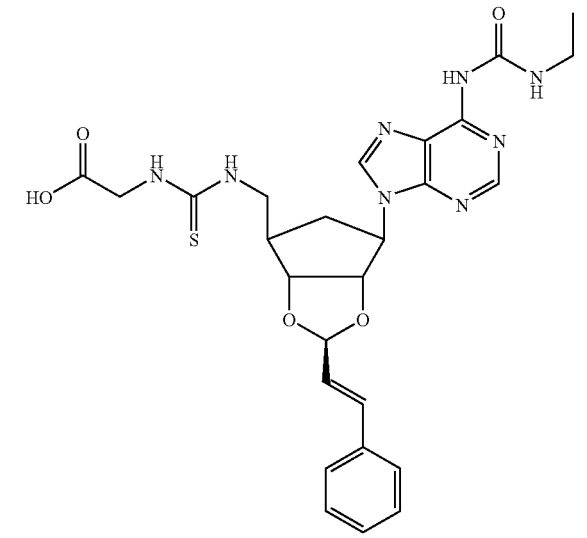

In another embodiment of the present invention, the compound of Formula I is a compound of Formula X:

Formula X wherein:

$R_a$, $R_b$, $R_c$, G, D, $R_d$, $R_{d'}$, $R_e$, $R_f$, J, M, $X_1$, $R_g$ and $R_h$ are as defined in Formulae I and II;

G' is O or S;

$A_6$ is C, N, O, S, or absent; and $R_i$ is H or alkyl;

such that the moiety described by $A_6$/C(G')/$NR_i$ is an amide, thioamide, carbamate, thiocarbamate, urea, or thiourea.

Preferred compounds of Formula X are wherein:

G=G'=O;

D=O or C;

$R_a$=$R_c$=$R_d$=$R_f$=$R_g$=$R_h$=H;

$R_e$ is absent;

$R_i$=H or methyl;

$R_d$=$C_{1-4}$ alkyl, or $C_{3-6}$ cycloalkyl;

$A_6$=$CH_2$, O, NH, or absent;

$X_1$=C or N;

$R_b$=phenyl, benzyl, or styryl; and
M=H, halogen, $C_{1-4}$ alkyl, $C_{1-4}$ alkoxy, $CF_3$, cyano, or amino.
Some of the preferred compounds falling under the definition of Formula X are:
234
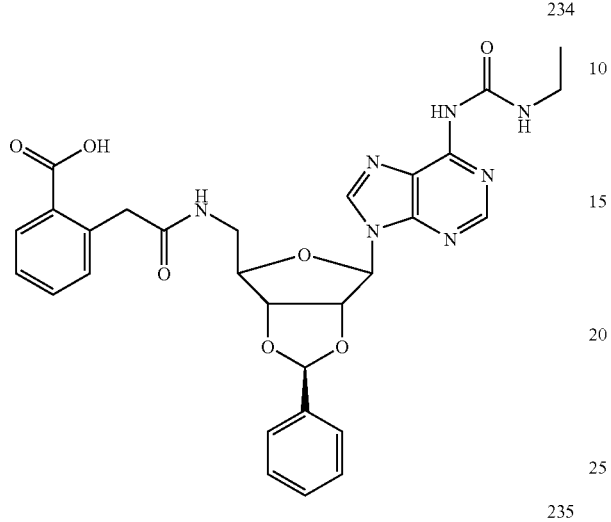
235
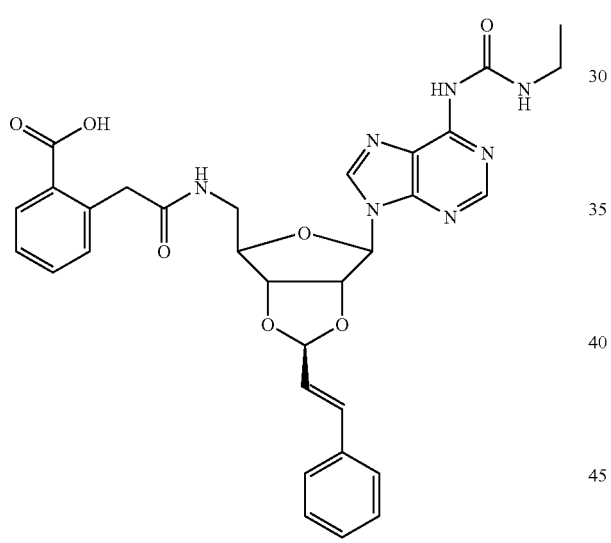
236
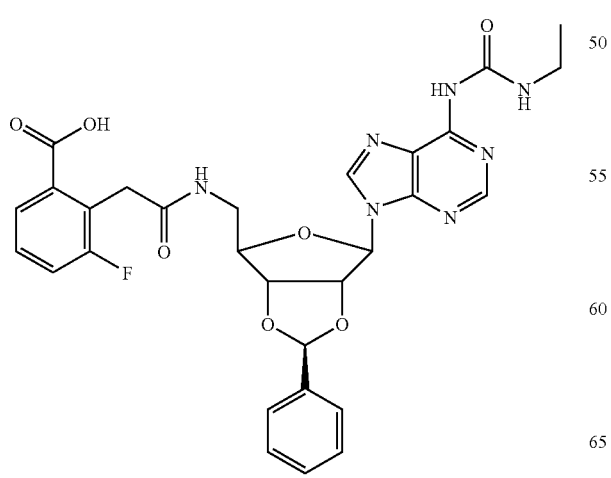
-continued
237
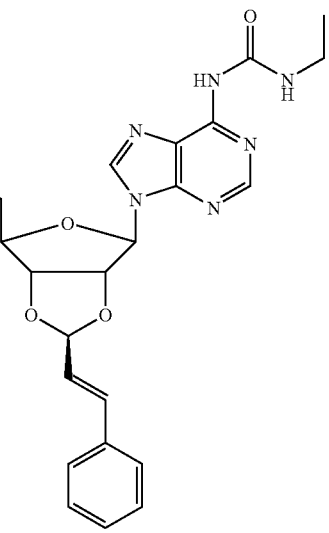
238
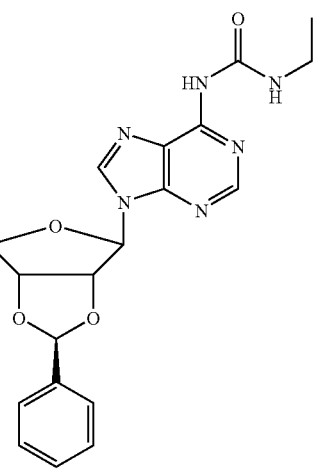
239
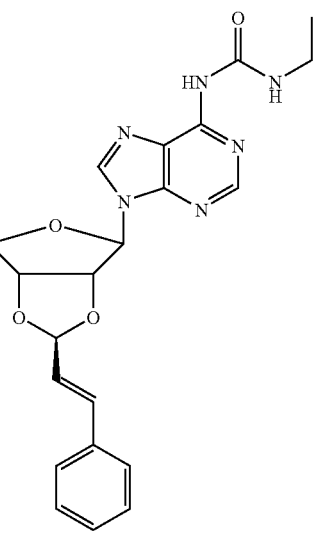

-continued
240
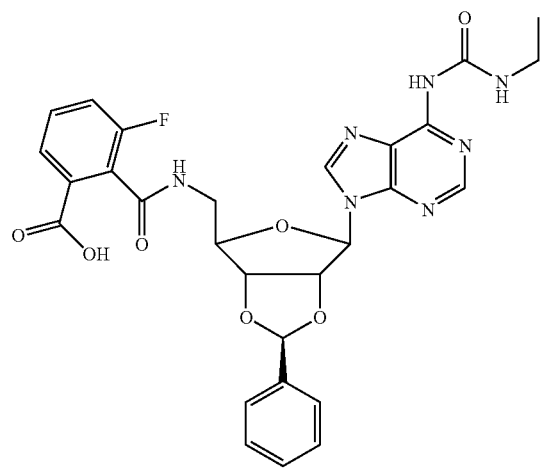
241
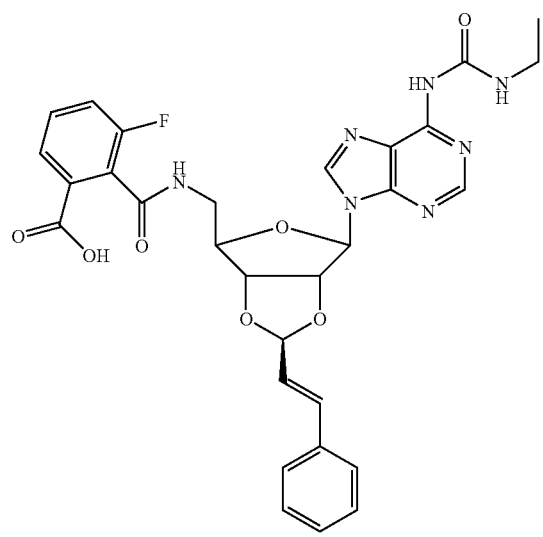
242
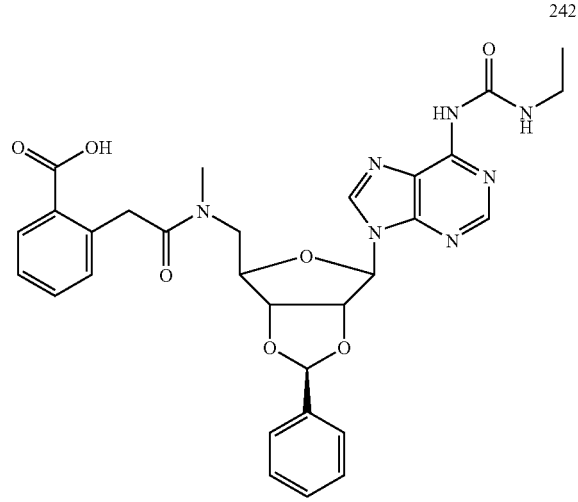
-continued
243
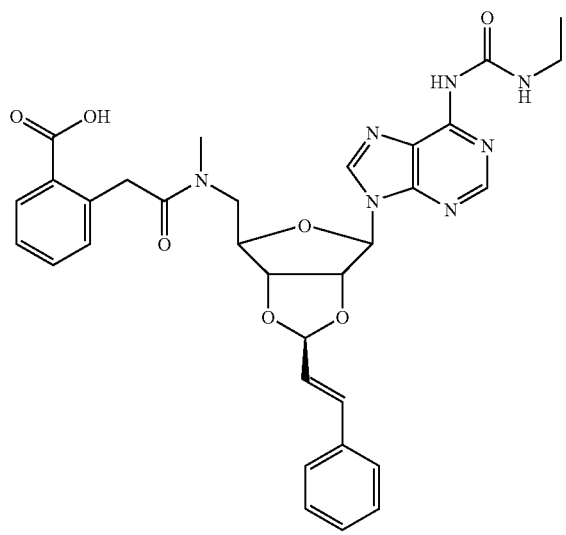
244
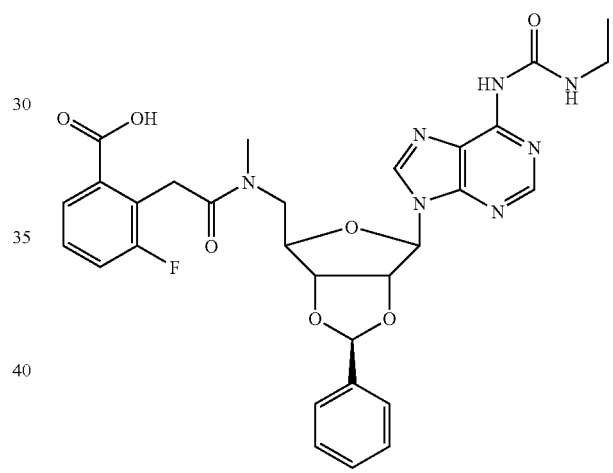
245
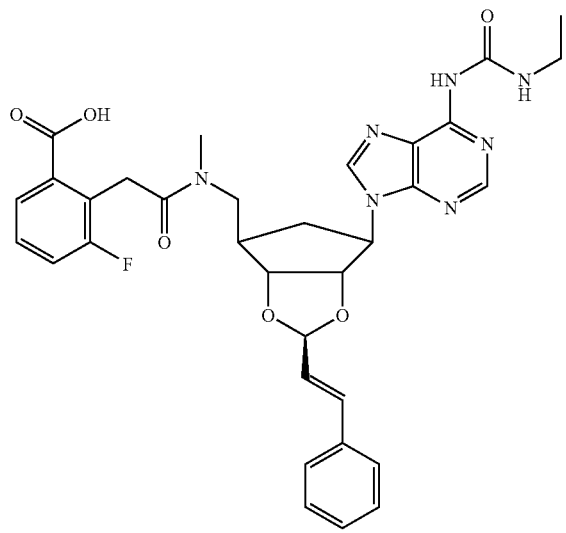

101
-continued
246
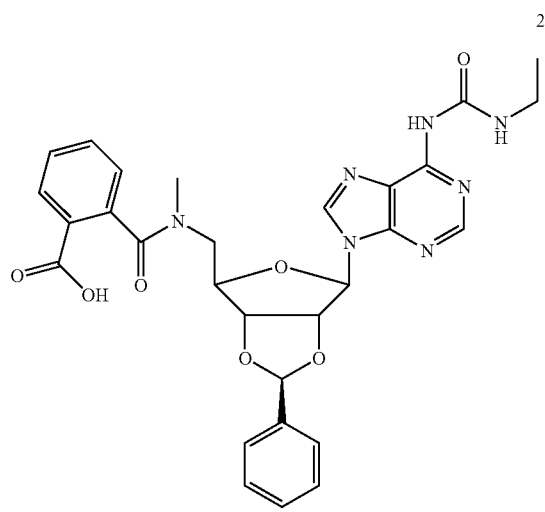
247
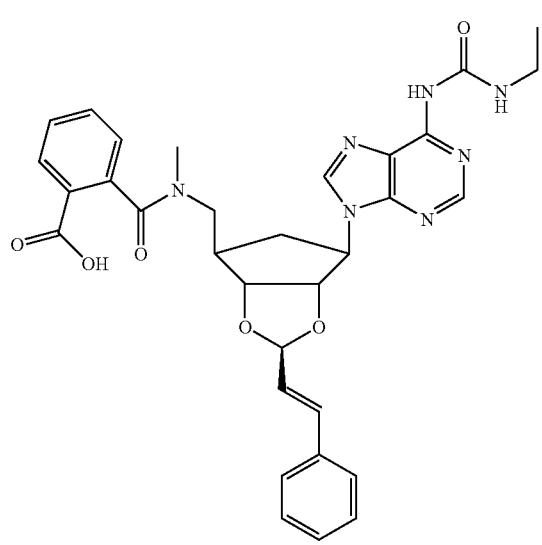
248
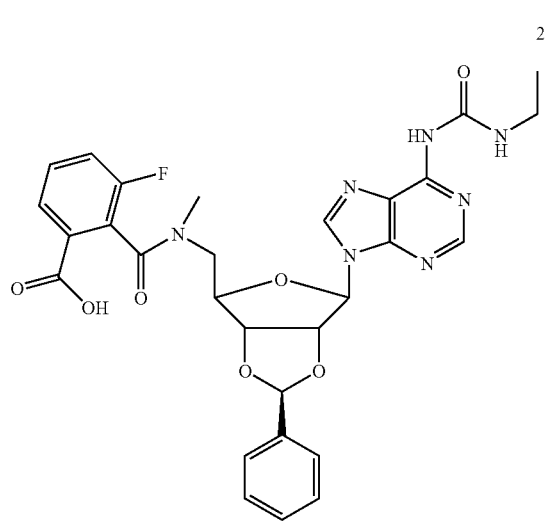
102
-continued
249
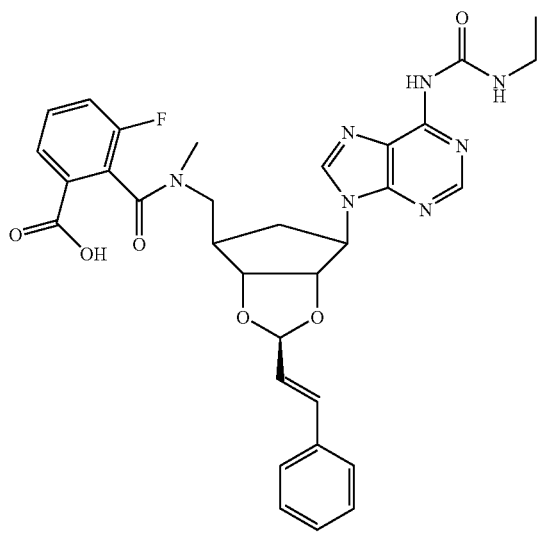
250
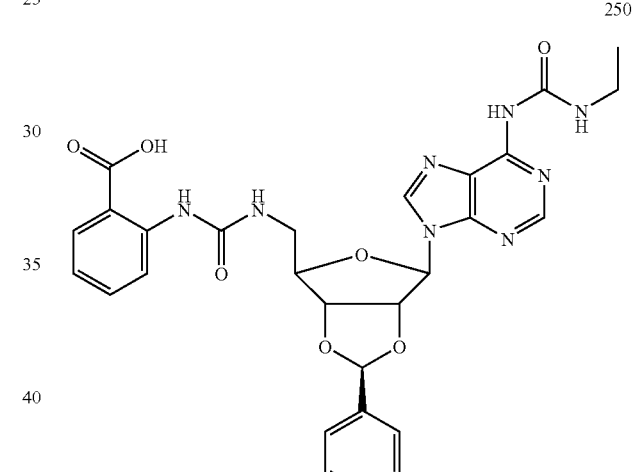
251
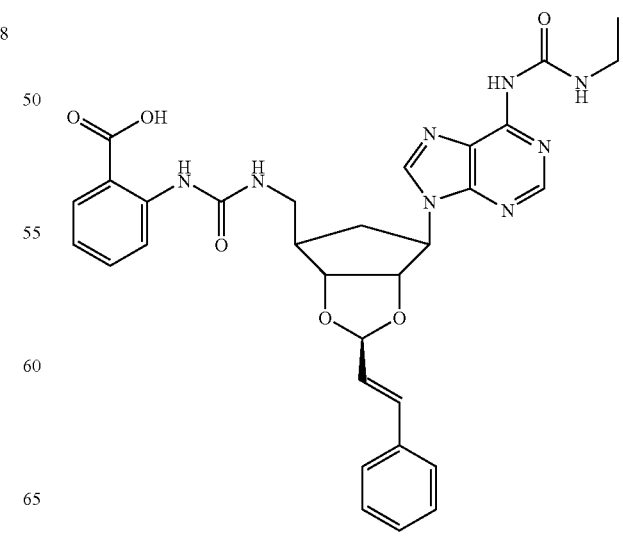

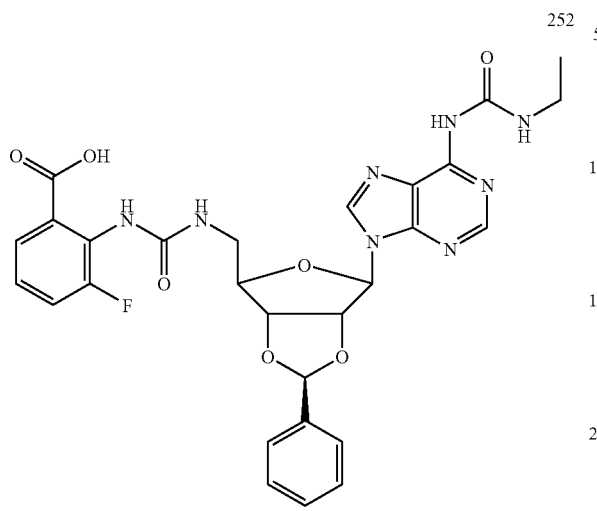
252
253
254
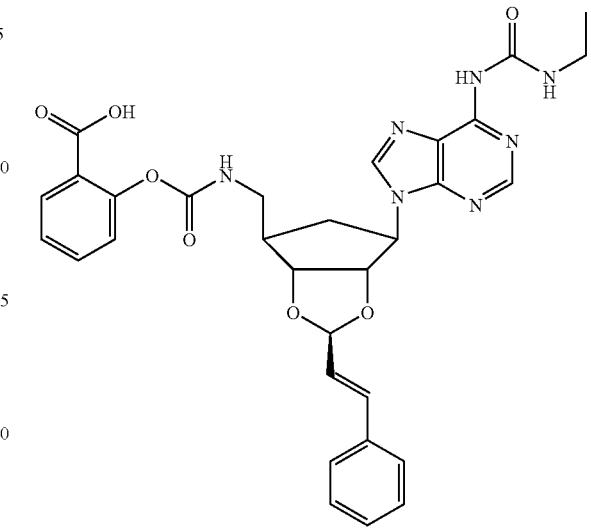
255
256
257
In another embodiment of the present invention, the compound of Formula I is a compound of Formula XI:

Formula XI

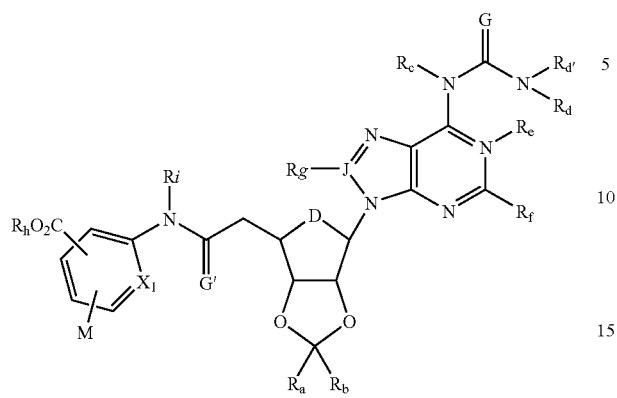

wherein:

$R_a$, $R_b$, $R_c$, G, D, $R_d$, $R_{d'}$, $R_f$, J, M, $R_g$ and $R_h$ are as defined in Formulae I and II;

$R_i$ is H or alkyl;

G' is O or S, such that the moiety C(G')-$NR_i$ is an amide or thioamide; and $X_1$ is C or N.

Preferred compounds of Formula XI are wherein:

G=G'=O;

D=O or C;

$R_a$=$R_c$$R_d$=$R_f$=$R_g$=$R_h$=H;

$R_e$ is absent;

$R_i$=H or methyl;

$R_{d'}$=$C_{1-4}$ alkyl, or $C_{3-6}$ cycloalkyl;

$X_1$=C or N;

$R_b$=phenyl, benzyl, or styryl; and

M=H, halogen, $C_{1-4}$ alkyl, $C_{1-4}$ alkoxy, $CF_3$, cyano, or amino.

Some of the preferred compounds falling under the definition of Formula XI are:

258

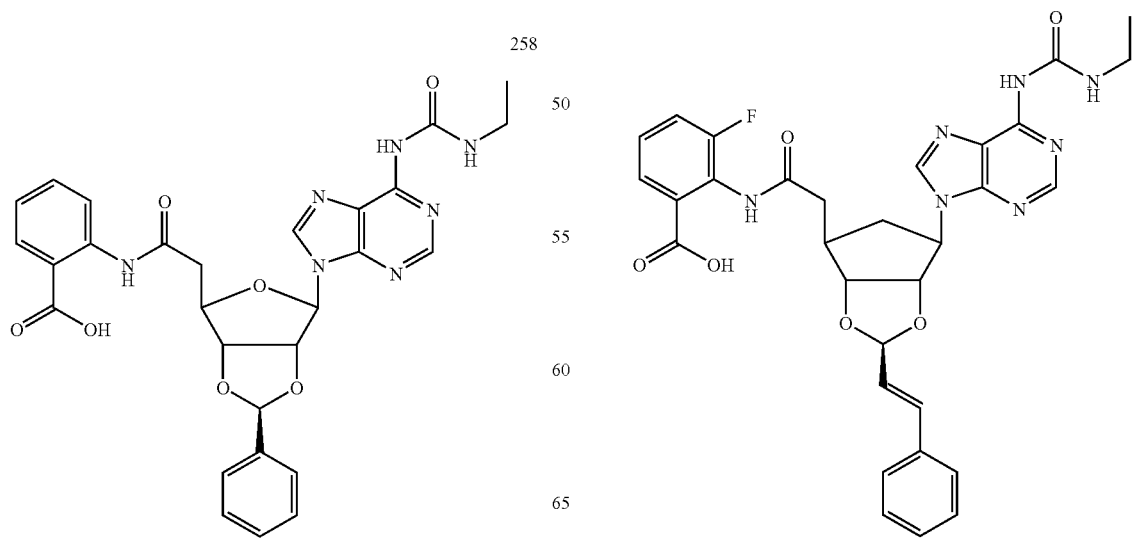

259

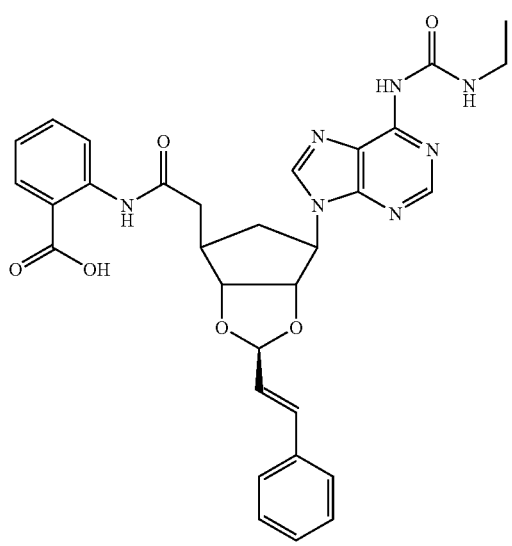

260

261

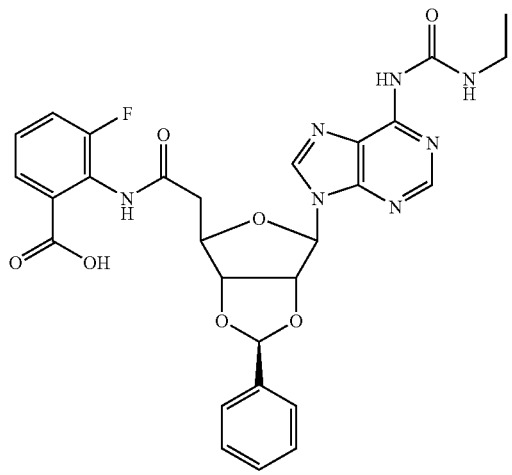

107 108
262
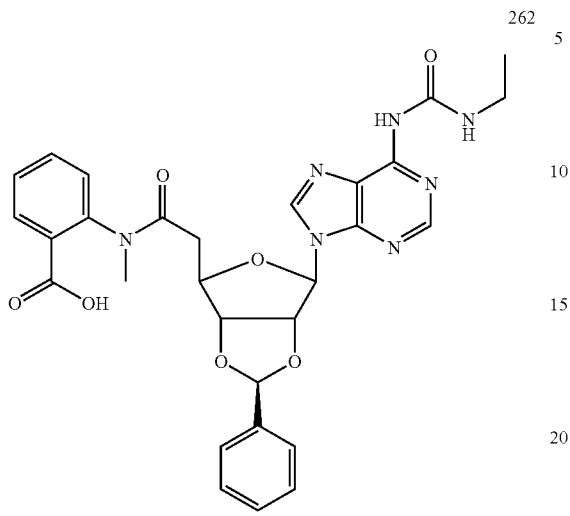
263
265
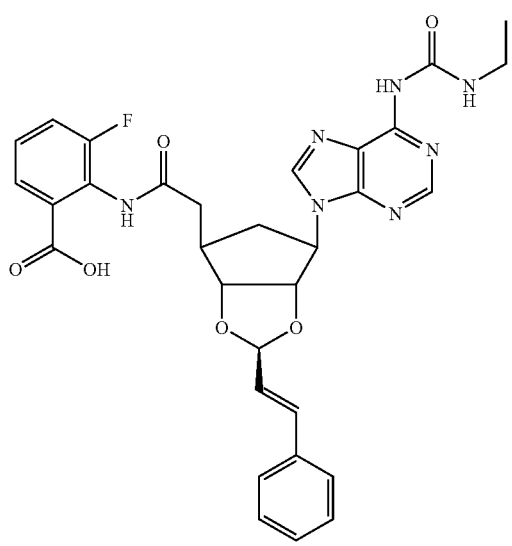
266
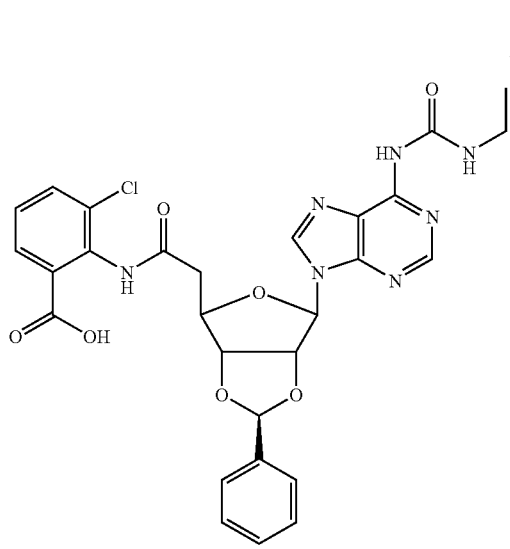
264
267
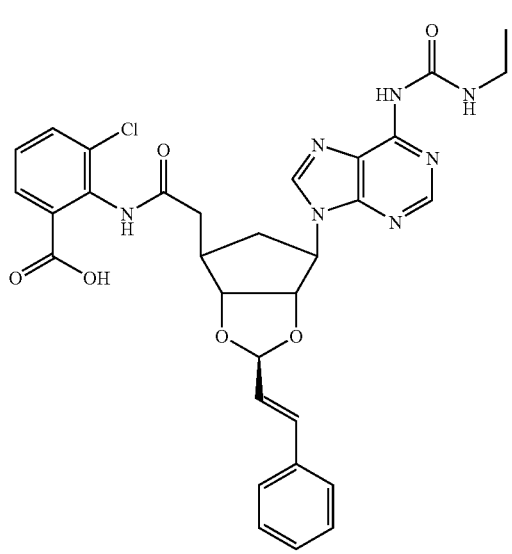

268

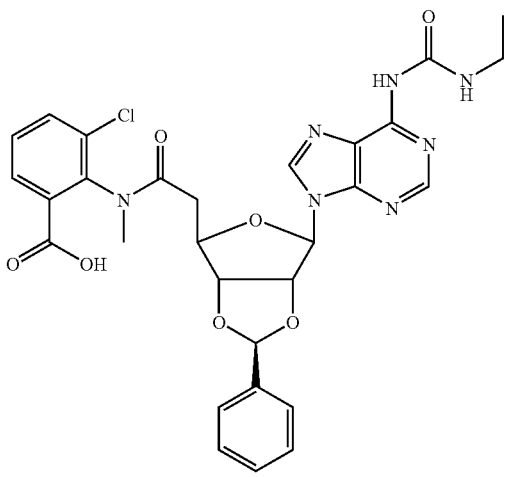

269

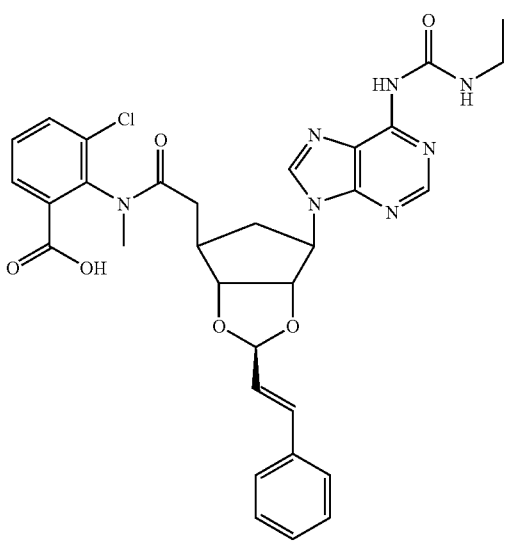

In another embodiment of the present invention, the compound of Formula I is a compound of Formula XII:

Formula XII

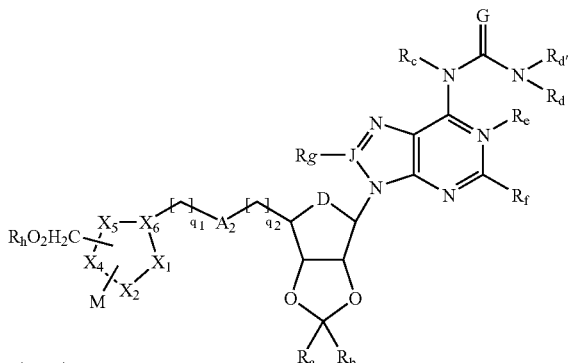

wherein:

$R_a$, $R_b$, $R_c$, G, D, $R_d$, $R_{d'}$, $R_e$, $R_f$, J, M, $R_g$ and $R_h$ are as defined in Formulae I and II;

$X_1$, $X_2$, $X_4$, $X_5$, and $X_6$ are taken to mean a ring with or without unsaturation and are independently selected from the group consisting of: N, C, S, or O; and $X_1$-$X_6$ are taken to mean a ring of from three to five atoms;

$q_1$ and $q_2$ are independently 0, 1, or 2;

$A_2$ is C, O, S, S(O), $SO_2$, or N, or $A_2$ is absent;

such that when $q_1$ and $q_2$=0 and $A_2$ is absent, the ring described by $X_1/X_2/X_4/X_5/X_6$ is directly bonded to the 4' position of the ribose.

Preferred compounds of Formula XII are wherein:

G=O;

D=O or C;

$R_a$=$R_c$=$R_d$=$R_f$=$R_g$=$R_h$=H;

$R_e$ is absent;

$q_1$ and $q_2$=0 or 1;

$A_2$=$CH_2$, O, NH, or absent;

$R_{d'}$, $C_{1-4}$ alkyl, or $C_{3-6}$ cycloalkyl;

$R_b$=phenyl, benzyl, or styryl; and

M=H.

Some of the preferred compounds falling under the definition of Formula XII are:

270

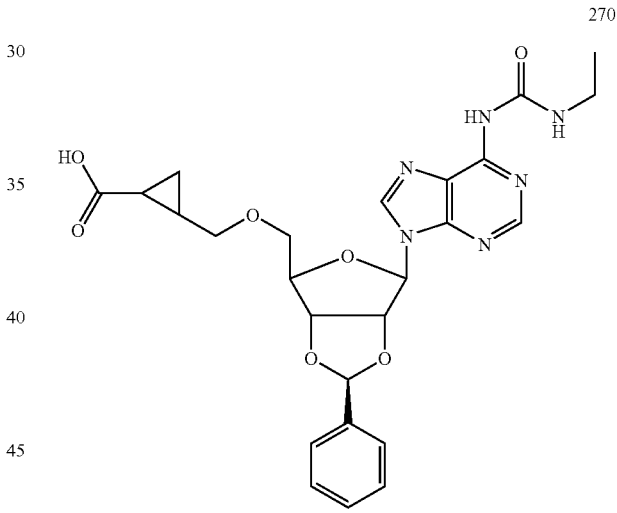

271

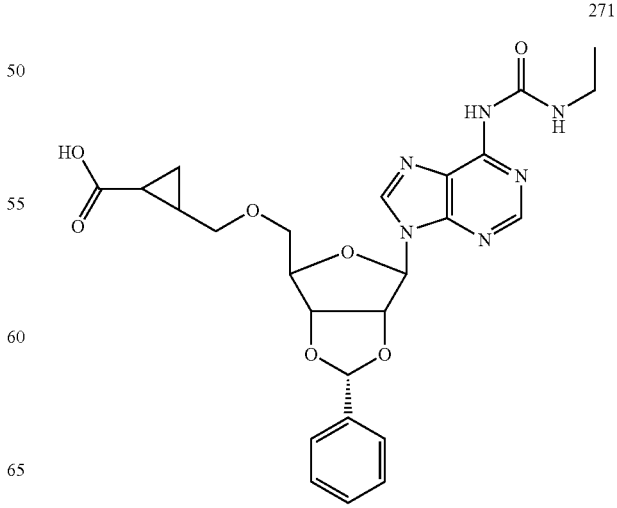

272
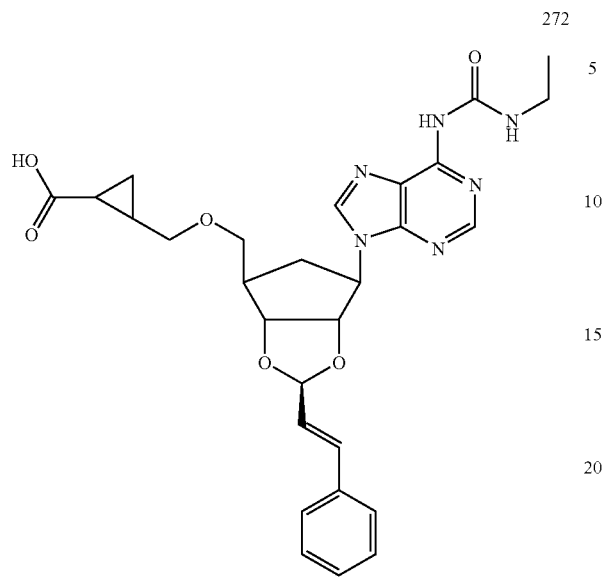
275
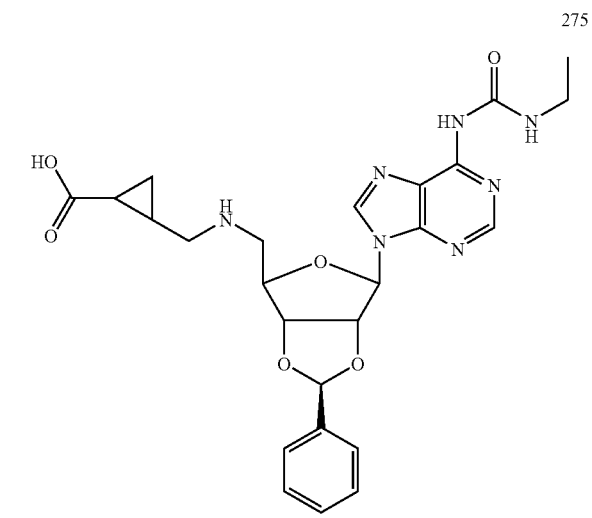
273
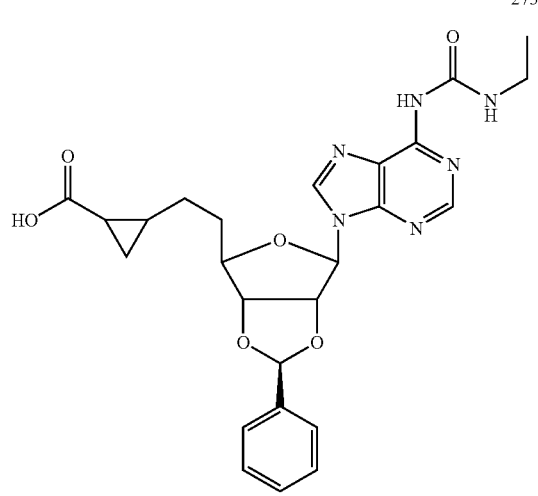
276
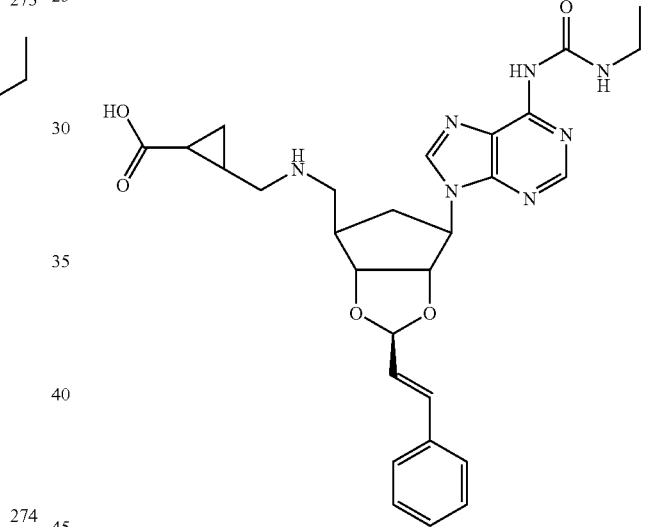
274
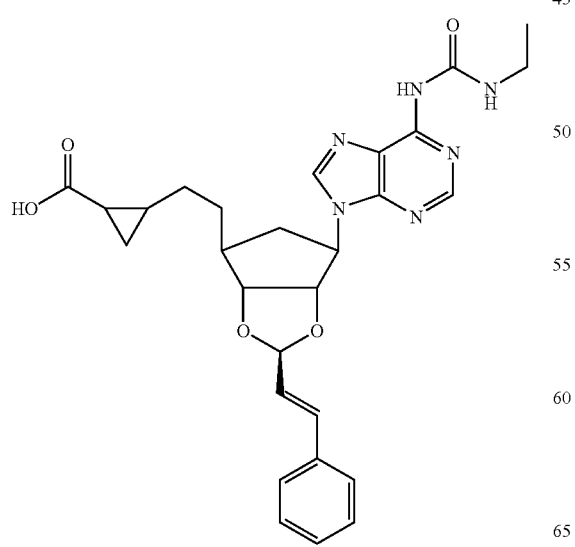
277

-continued
278
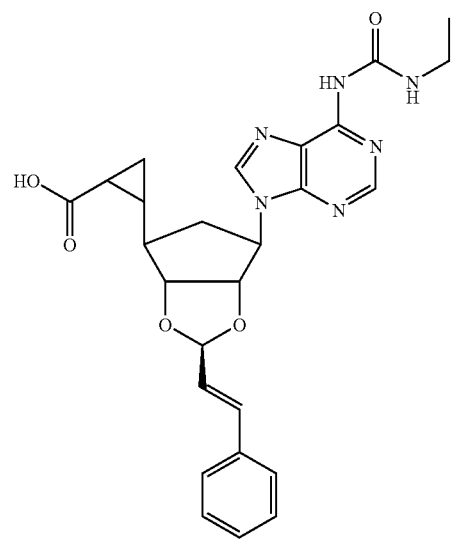
279
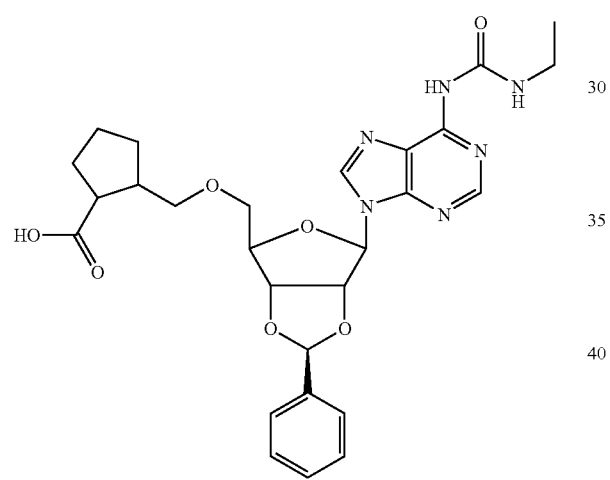
280
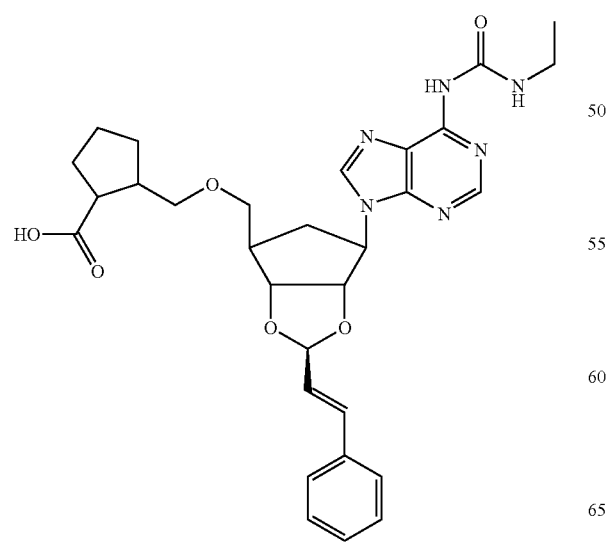
-continued
281
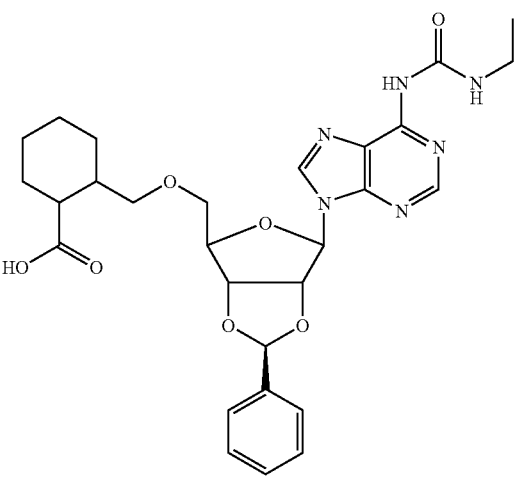
282
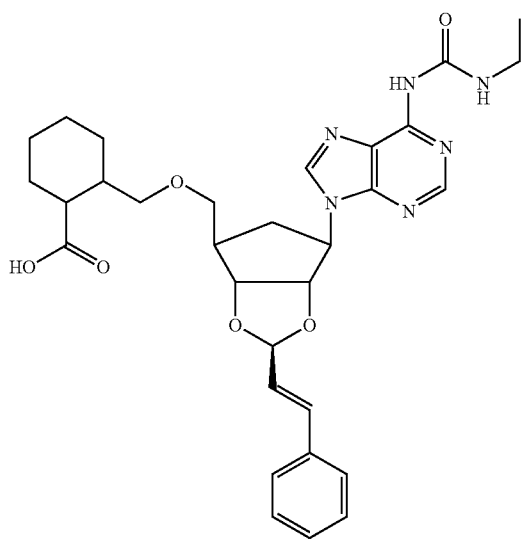
283
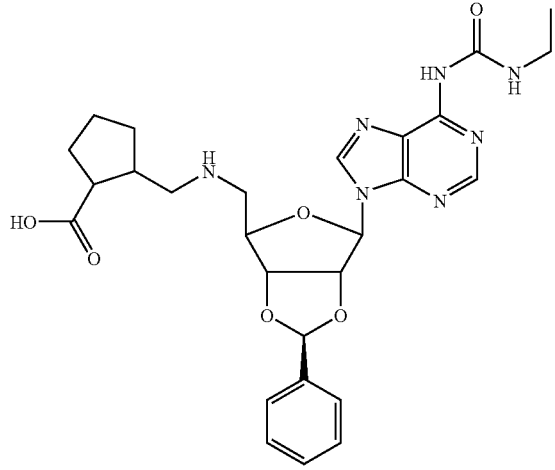

284
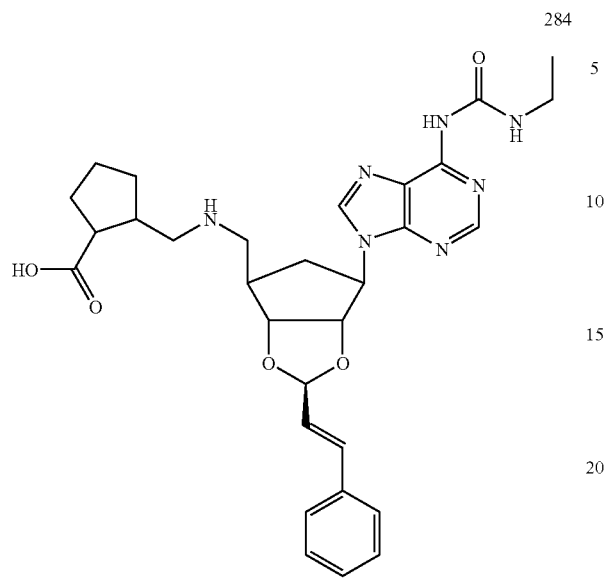
285
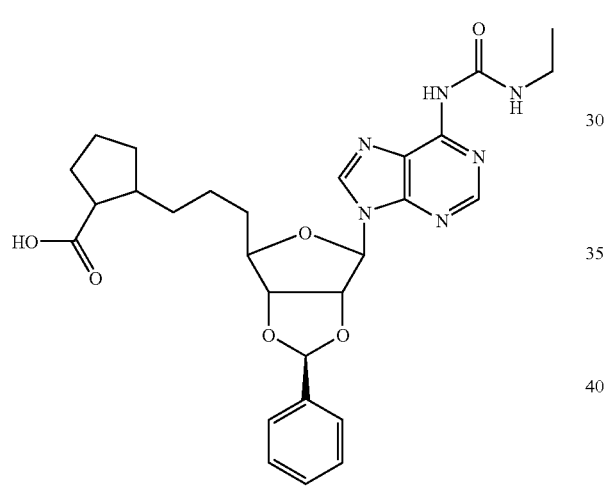
286
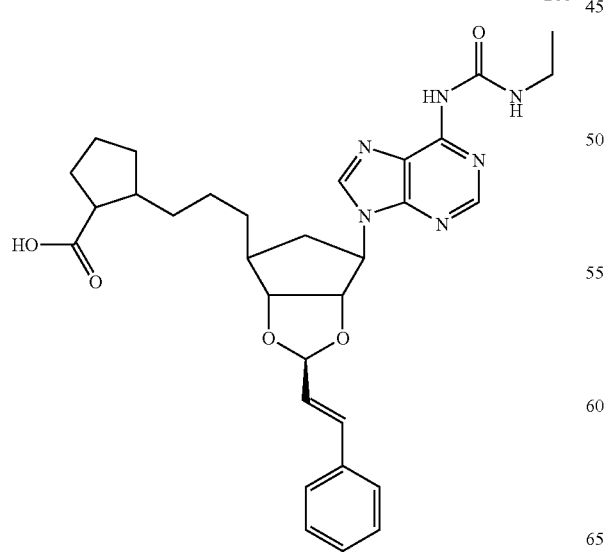
287
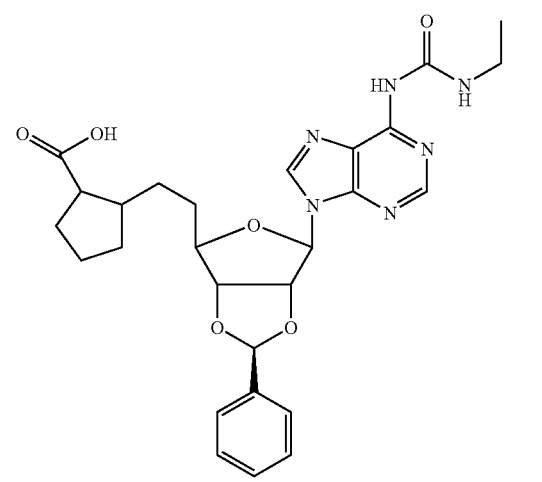
288
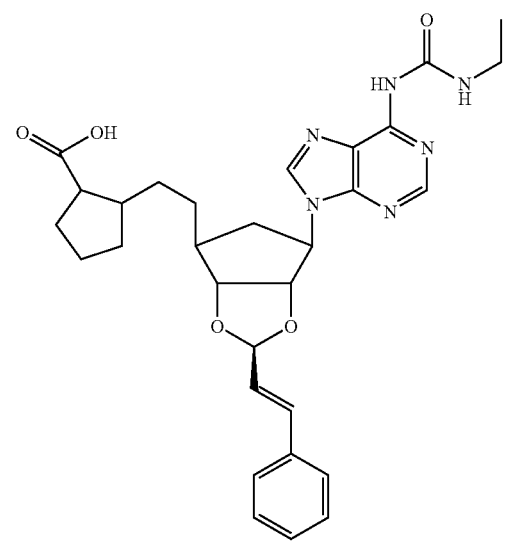
289
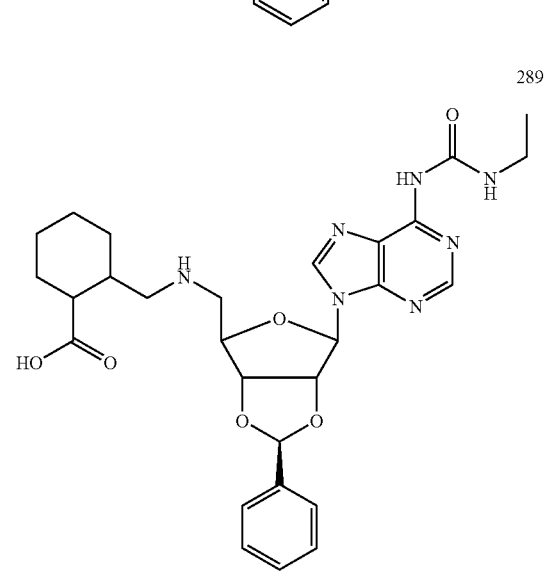

-continued
290
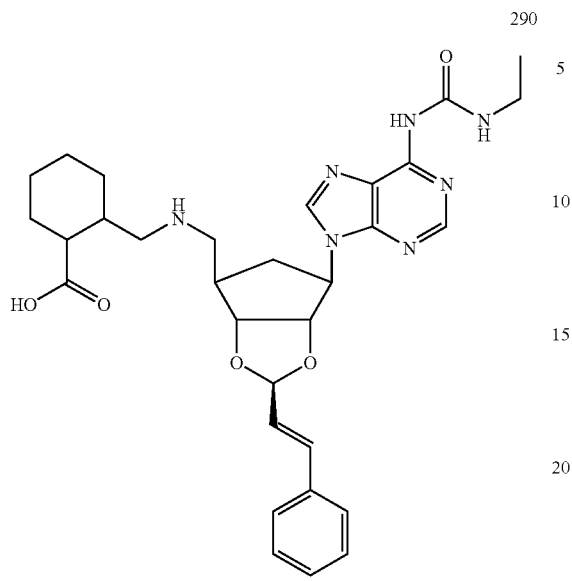
291
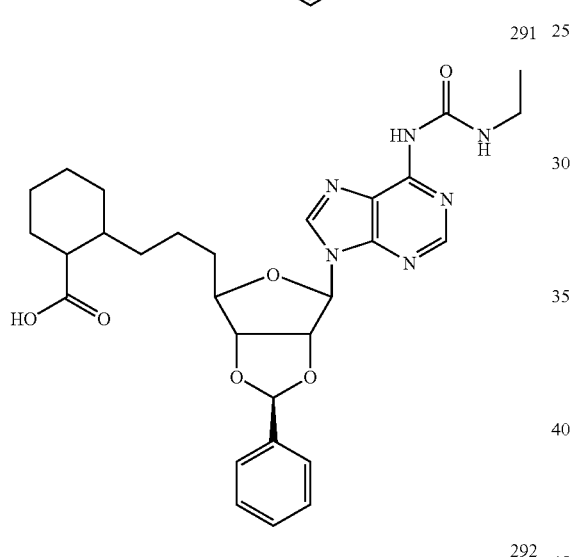
292
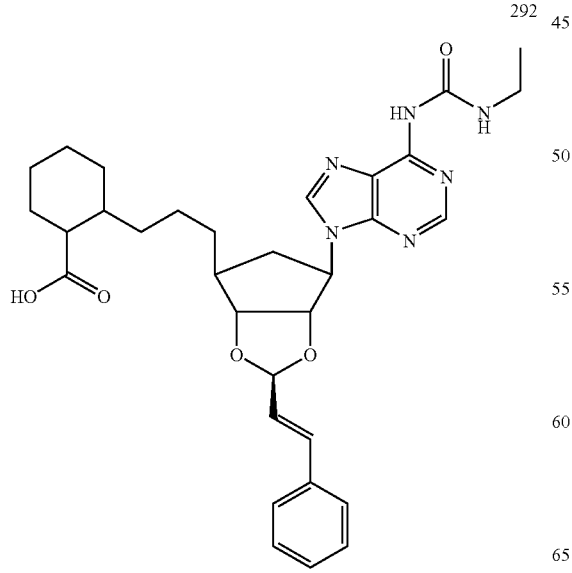
-continued
293
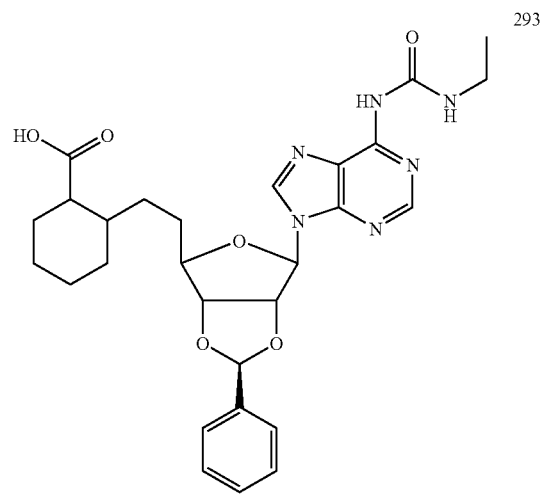
294
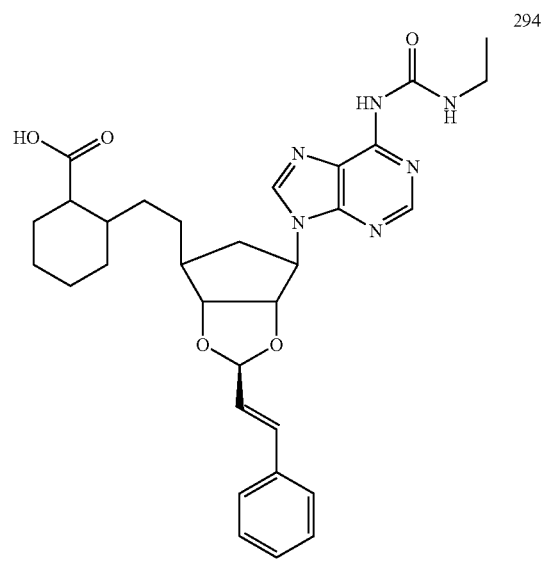
295
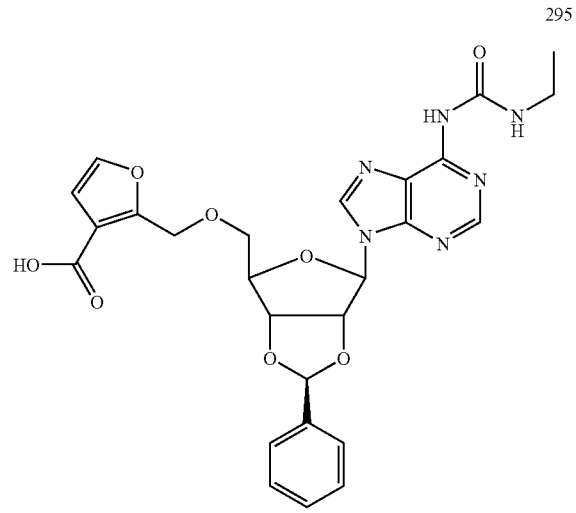

-continued
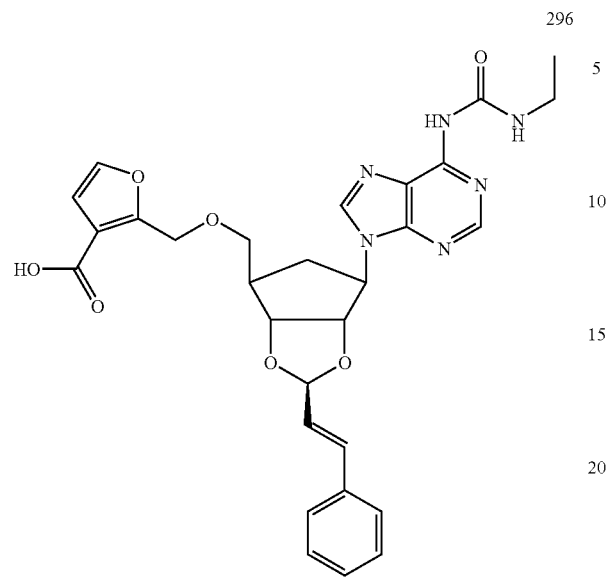
296
297
298
-continued
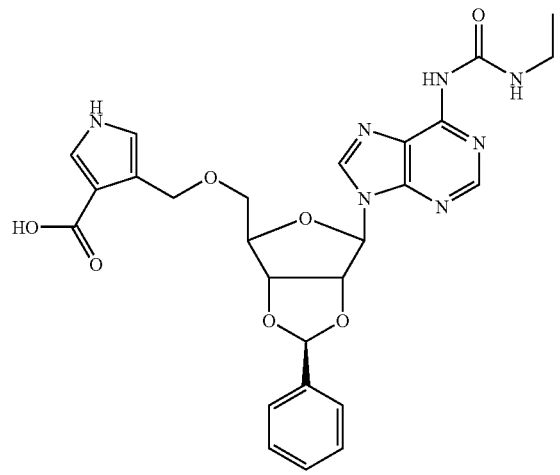
299
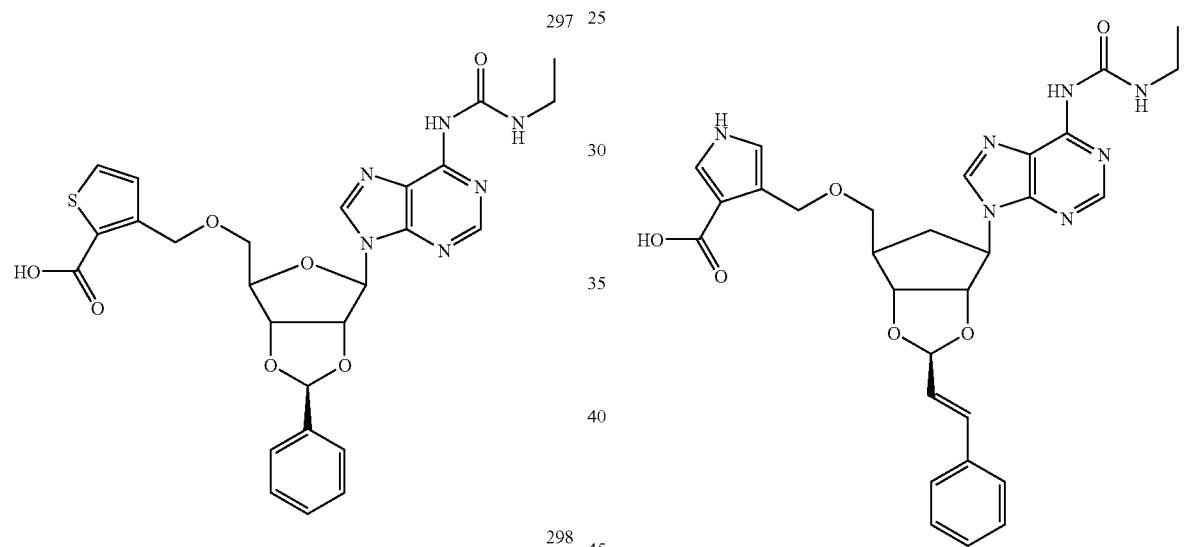
300
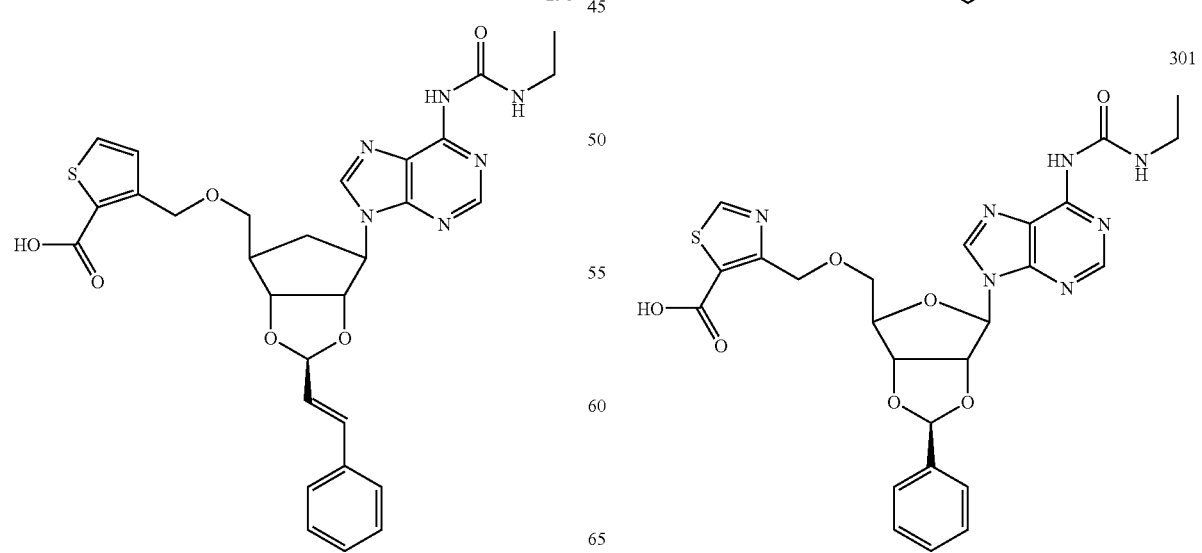
301

121
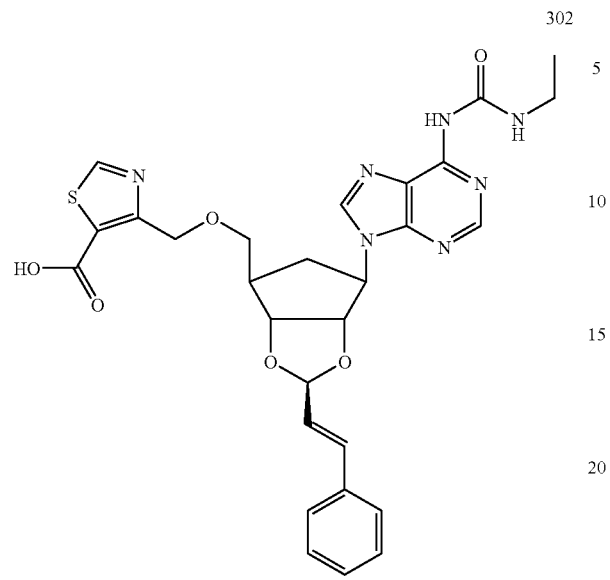
302
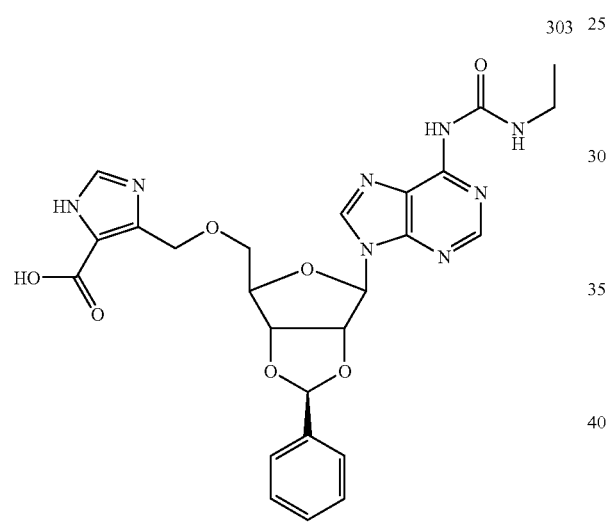
303
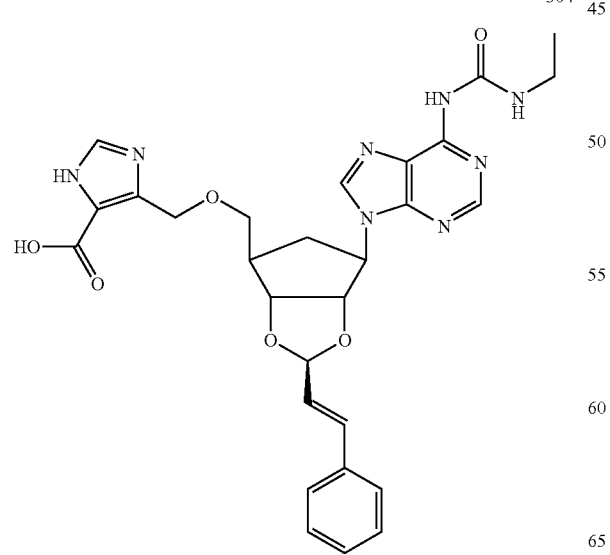
304
122
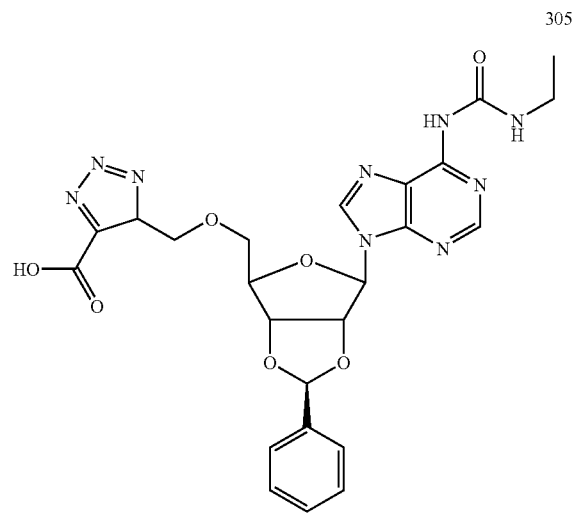
305
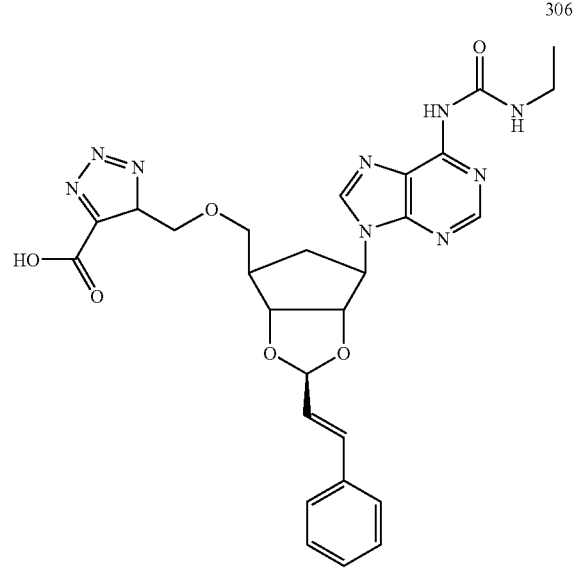
306
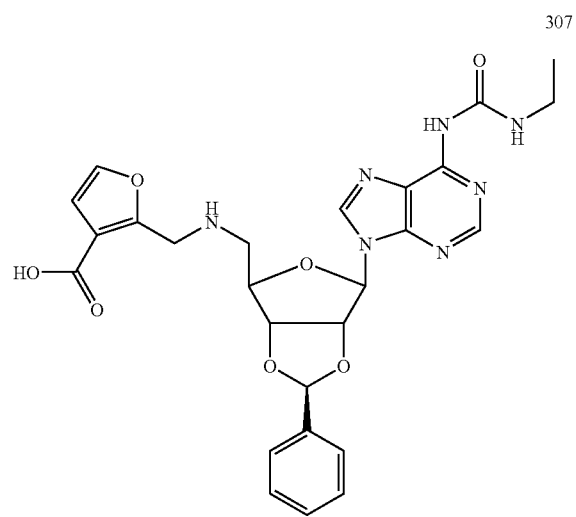
307

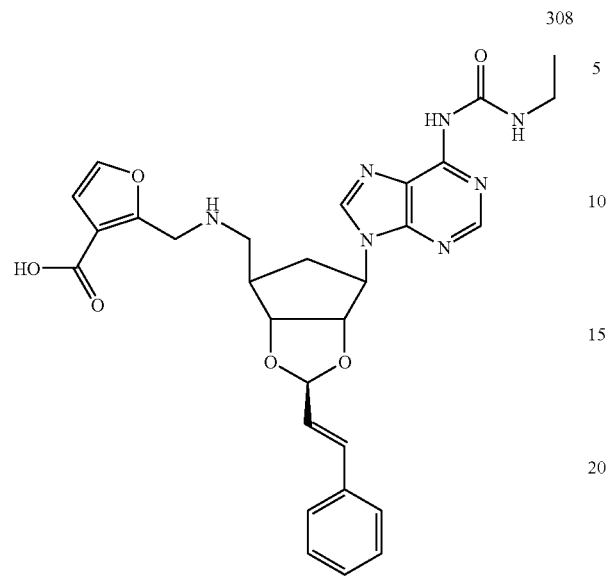
308
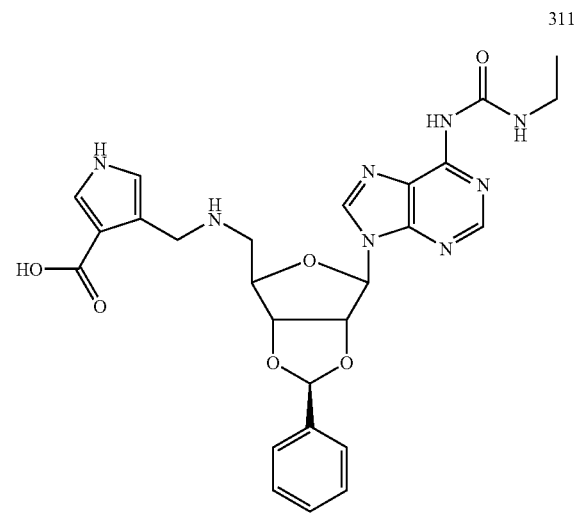
311
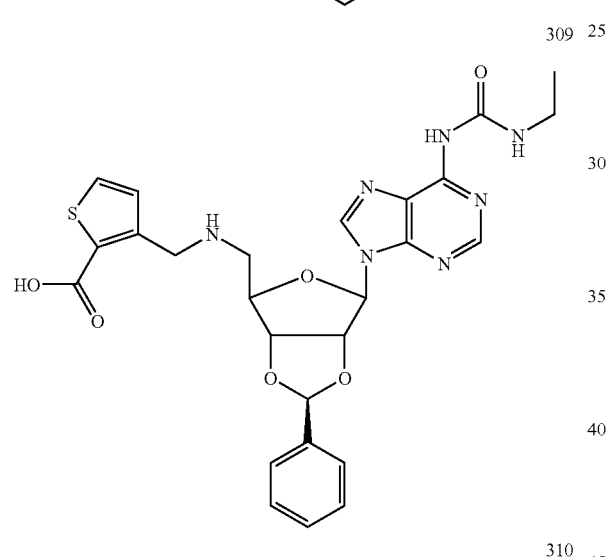
309
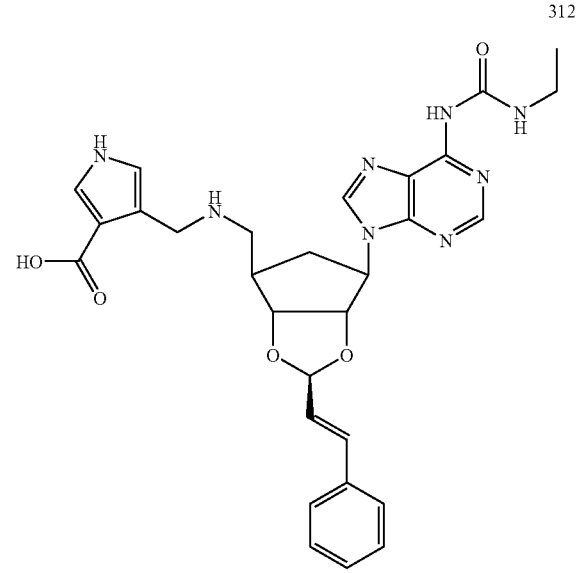
312
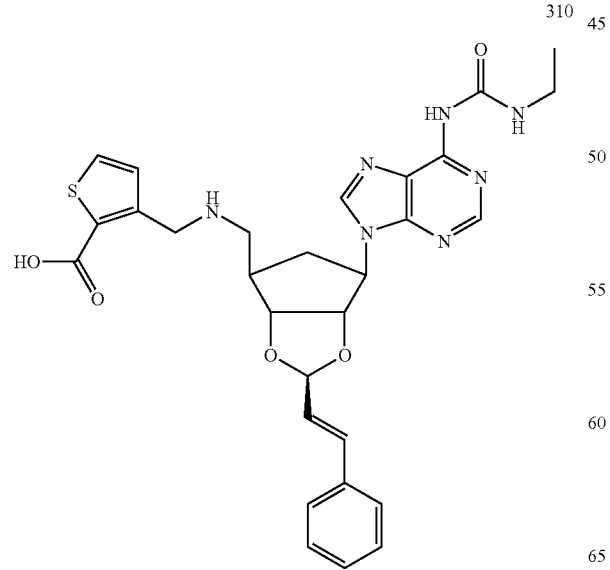
310
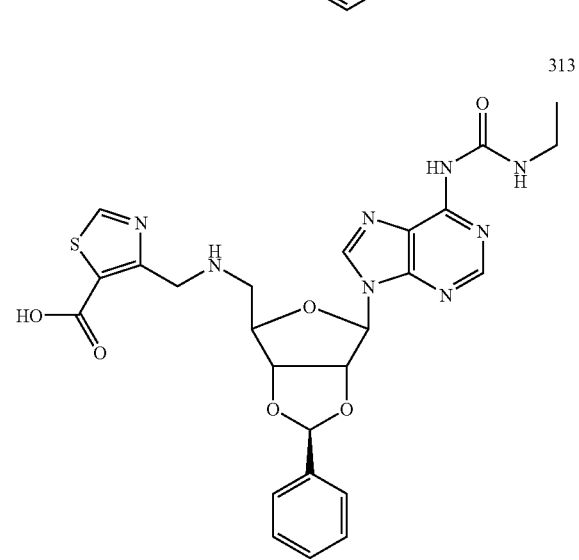
313

314
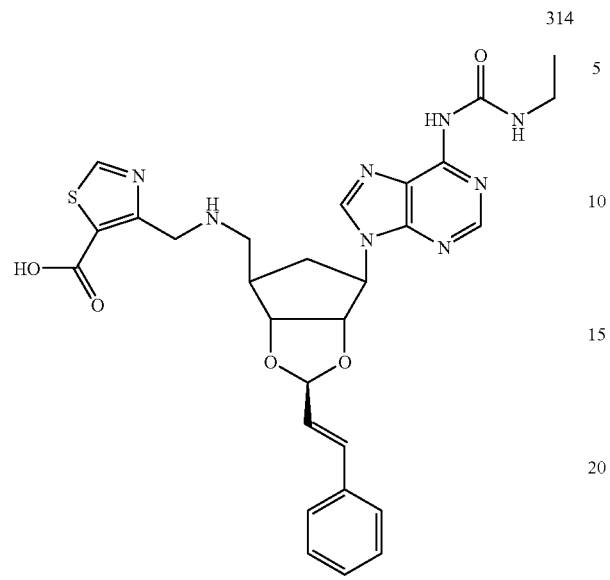
315
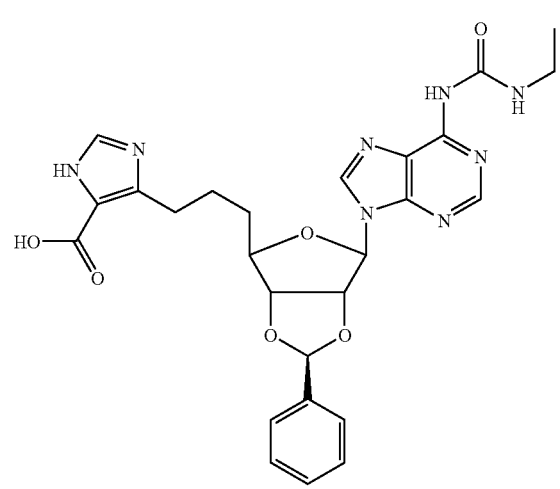
316
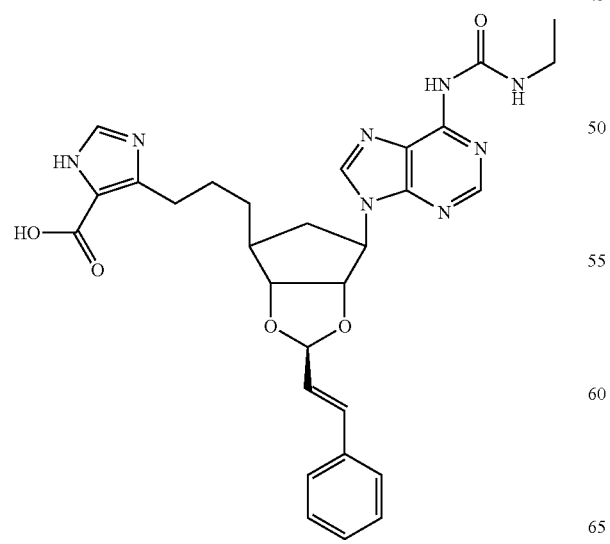
317
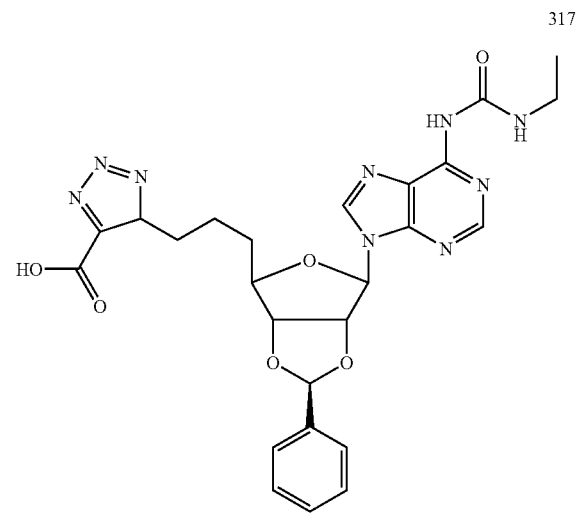
318
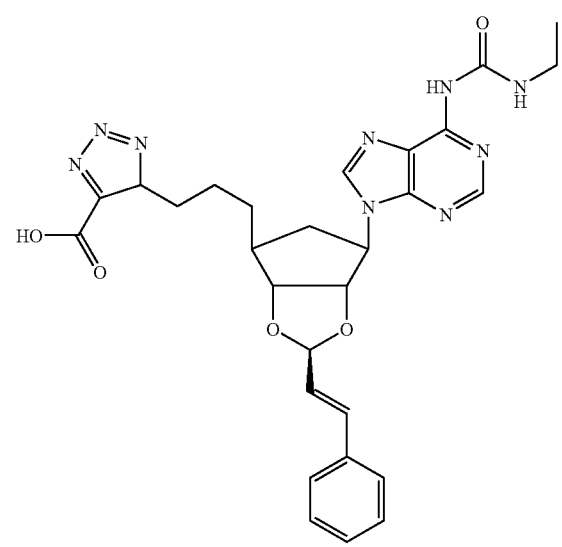
319
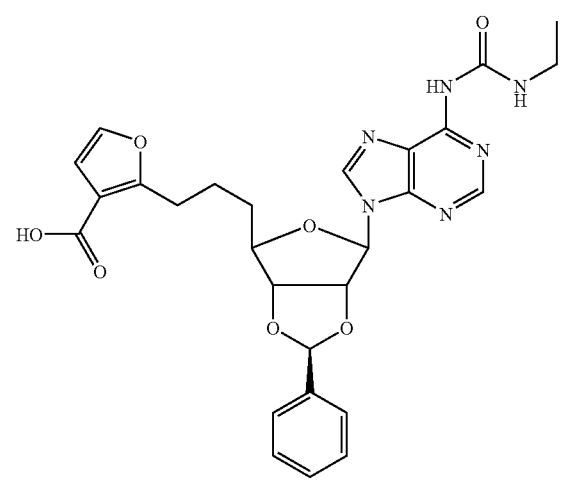

127
-continued
320
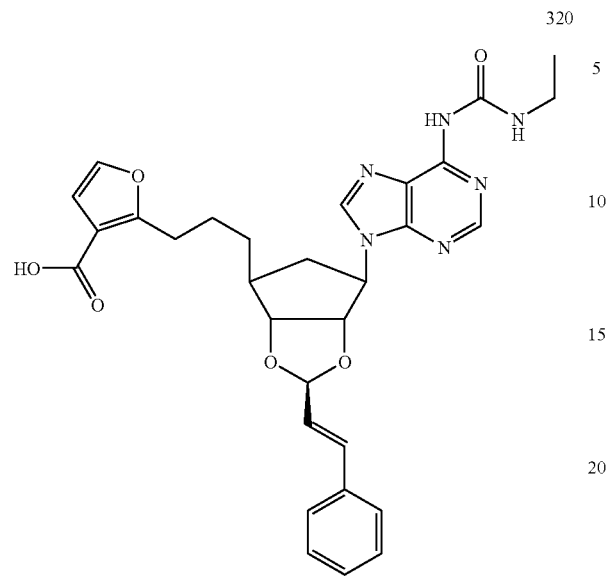
321
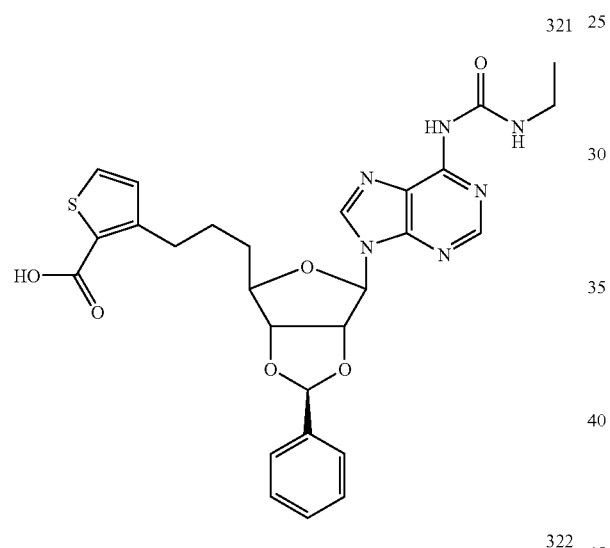
322
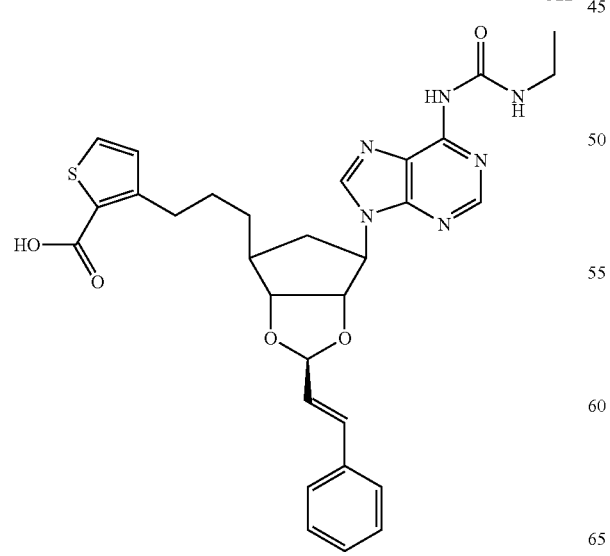
128
-continued
323
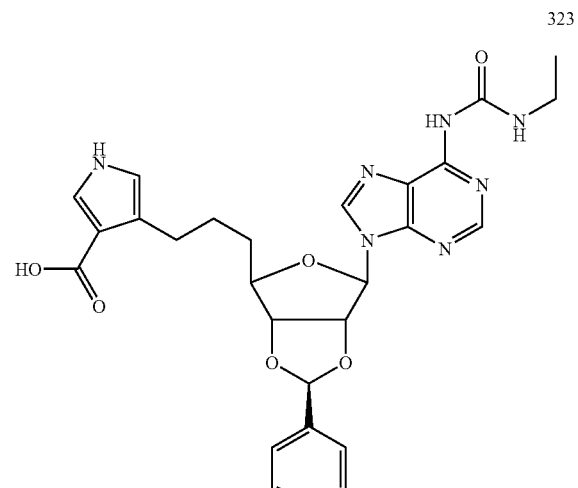
324
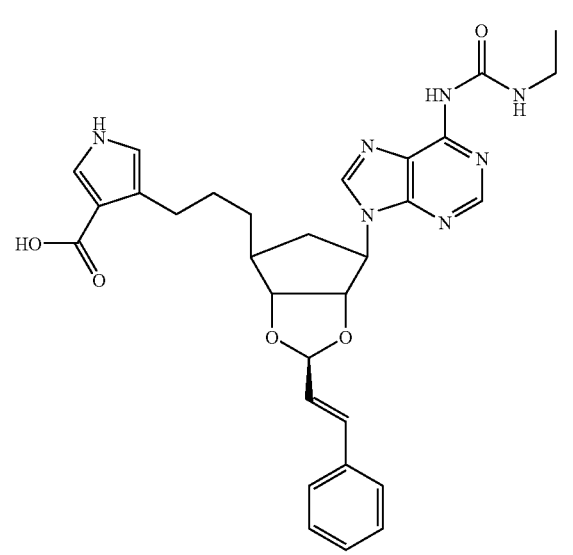
325
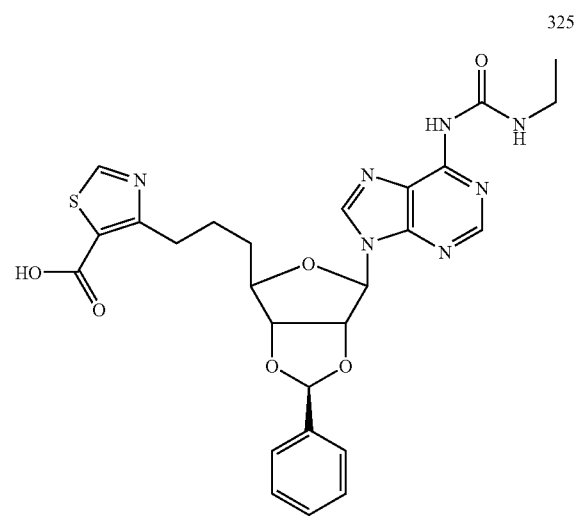

-continued

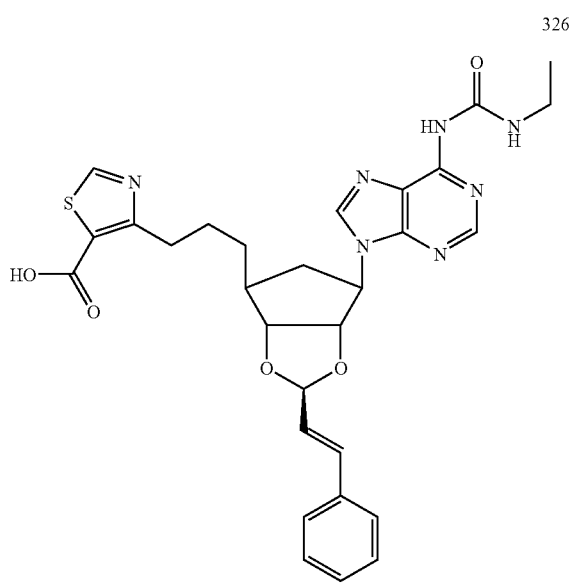

326

Pharmaceutical Formulations

The present invention additionally provides novel pharmaceutical formulations comprising a pharmaceutically acceptable carrier and compounds of Formula I, III-XI, or a pharmaceutically acceptable salt, solvate, or hydrate thereof. Pharmaceutically acceptable carriers can be selected by those skilled in the art using conventional criteria. Pharmaceutically acceptable carriers include, but are not limited to, saline solution, aqueous electrolyte solutions, isotonicy modifiers, water polyethers such as polyethylene glycol, polyvinyls such as polyvinyl alcohol and povidone, cellulose derivatives such as methylcellulose and hydroxypropyl methylcellulose, polymers of acrylic acid such as carboxypolymethylene gel, polysaccharides such as dextrans, and glycosaminoglycans such as sodium hyaluronate and salts such as sodium chloride and potassium chloride.

The pharmaceutical formulation of the present invention provides an aqueous solution comprising water, suitable ionic or non-ionic tonicity modifiers, suitable buffering agents, and a compound of Formula I, Ia, Ib, or Ic. In one embodiment, the compound is at 0.005 to 3% w/v, and the aqueous solution has a tonicity of 200-400 mOsm/kG and a pH of 4-9.

The pharmaceutical formulation can be sterilized by filtering the formulation through a sterilizing grade filter, preferably of a 0.22-micron nominal pore size. The pharmaceutical formulation can also be sterilized by terminal sterilization using one or more sterilization techniques including but not limited to a thermal process, such as an autoclaving process, or a radiation sterilization process, or using pulsed light to produce a sterile formulation. In one embodiment, the pharmaceutical formulation is a concentrated solution of the active ingredient; the formulation can be serially diluted using appropriate acceptable sterile diluents prior to intravenous administration.

In one embodiment, the tonicity modifier is ionic such as NaCl, for example, in the amount of 0.5-0.9% w/v, preferably 0.6-0.9% w/v.

In another embodiment, the tonicity modifier is non-ionic, such as mannitol, dextrose, in the amount of at least 2%, or at least 2.5%, or at least 3%, and no more than 7.5%; for example, in the range of 3-5%, preferably 3.5-5%, and more preferably 4.2-5% w/v.

Those skilled in the art will recognize various synthetic methodologies that may be employed to prepare non-toxic pharmaceutically acceptable salts and prodrugs of the compounds.

Methods of Compound Preparation

The compounds of the present invention can be synthesized by those skilled in the art using conventional synthesis methodology and well-known workup and purification procedures. The following list of references, along with references cited therein, disclose general procedures employed for the synthesis of a number of intermediates and compounds related to the present invention: Baraldi, et al., *Journal of Medicinal Chemistry*, 39(3): 802-806 (1996); Camaioni, et al., *Bioorganic & Medicinal Chemistry*, 5(12): 2267-2275 (1997); Zablocki, et al., PCT International Publication No. WO01/40243; Zablocki, et al., PCT International Publication No. WO01/40246; Mantell, et al., PCT International Publication No. WO01/94368; Jacobson, et al., *Journal of Medicinal Chemistry*, 38(10): 1720-1735 (1995); Cristalli, et al., *Journal of Medicinal Chemistry*, 38(9): 1462-1472 (1995); Secrist, III and Talekar, *Nucleosides & Nucleotides*, 9(4): 619-27 (1990); Secrist, III, U.S. Pat. No. 4,794,174 (1988); Lyga and Secrist, III, *Journal of Organic Chemistry*, 48(12): 1982-1988 (1983); Dixon, et al., PCT International Publication No. WO02/096248; Hardern, et al., PCT International Publication No. WO01/36438; Guile et al., PCT International Publication No. WO00/04021; Lee, et al., *Bioorganic & Medicinal Chemistry Letters*, 13(6): 1087-1092 (2003); Cox, et. al., U.S. Pat. No. 5,747,496 (1998).

In many cases, commercially-available starting materials can be used for the synthesis of compounds of this invention. When not available commercially, useful starting materials can either be obtained from stepwise modification of commercially-available compounds and derivatives, or they can be synthesized from simpler precursors using literature methods known in the art. In addition, the compounds of the present invention can be synthesized using the general methods shown in Schemes 1-12, or variations thereof.

Commercially-available materials include: adenosine, α-adenosine, 2',3'-isopropylidineadenosine, 5'-acetyl-2',3'-isopropylidineadenosine, $N^6$-(2-isopentenyl)adenosine, 2-chloroadenosine, 2-amino-6-chloropurine riboside, 6-chloropurine riboside, inosine, 8-bromoguanosine, 8-bromoadenosine, 8-azidoadenosine, 8-azaguanine, 8-azaadenine, protected ribonic acid lactone derivatives and protected furanose derivatives. Other appropriate intermediates can be purchased from commercial sources and used as starting materials for compounds of the present invention, or can be synthesized as described in the chemical literature.

As disclosed above, commercially available compounds, or their derivatives can be employed as starting materials for the methods of Schemes 1-12.

Scheme 1.
Preparation of 5'-modified ethers by nucleophilic aromatic substitution.

Scheme 2.
Preparation of 5'-modified ethers by Mitsunobu coupling of phenols.

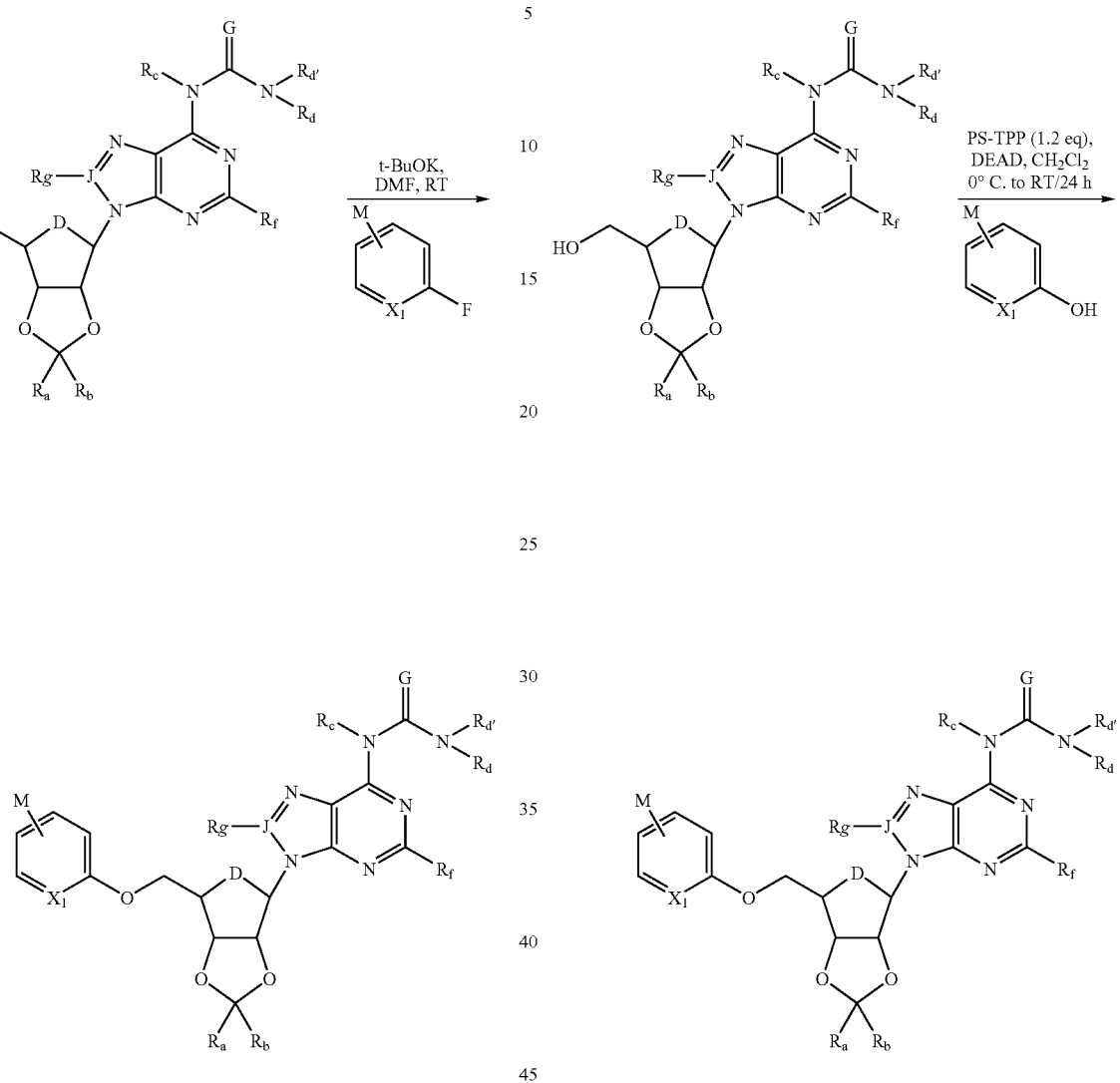

Scheme 1, for example, discloses a useful method for the synthesis of 5'-aryl- or 5'-heteroaryl-ether derivatives by substitution of an appropriately functionalized adenosine analogue or 8-azapurine derivative for a halogen on an appropriately-substituted halogenated aromatic compound or a related heteroaromatic derivative. Groups not defined in Scheme 1 are defined as in Formula I. Preferred substituents at M of the aromatic-/heteroaromatic-group in Scheme 1 are hydrogen, or halogen, or groups containing carboxylic acid derivatives such as: —$CO_2R_3$; but they can also be halogen, or esters or amides of alkylcarboxylic acids, arylcarboxylic acids, —O-(alkylcarboxylic acids), —NR-(alkylcarboxylic acids), and the like. When M is halogen in Scheme 1, preferred halogens are chloro and fluoro.

5'-Substituted aryl derivatives can also be prepared via Mitsunobu coupling of phenols (Mitsunobu, *Synthesis* 1-28 (1981); Brown, et al., *J. Med. Chem.* 37 (5), 674-88 (1994); Santosh and Balasubramanian, *Synthetic Communications*, 24(8), 1049-62 (1994)) to derivatives of adenosine, 8-azaadenosine, guanosine, 8-azaguanosine, etc., as provided in Scheme 2. Groups in Scheme 2 are defined as in Formula I. Some preferred substituents at M of the aromatic/heteroaromatic-group in Scheme 2 independently can be hydrogen, halogen, alkyl, alkoxy, aryl or groups containing carboxylic acid derivatives such as: —$CO_2R_3$; but esters or amides of alkylcarboxylic acids, arylcarboxylic acids, —O-(alkylcarboxylic acids), —NR-(alkylcarboxylic acids), and the like are also included. When M is halogen in Scheme 2, preferred halogens are chloro and fluoro.

Scheme 3.
Preparation of 5'-modified isoxazole ethers by Mitsunobu coupling of isoxazole derivatives.

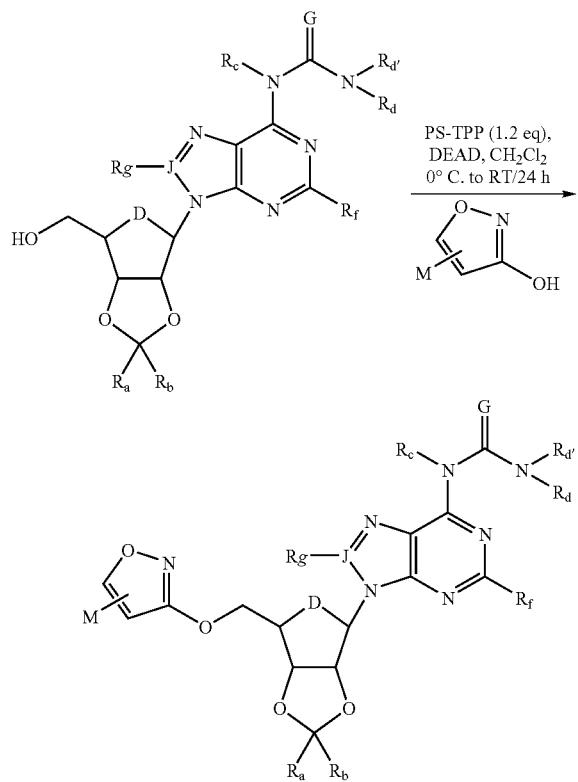

Alternatively, the Mitsunobu coupling can be carried out using hydroxyisoxazoles as provided in Scheme 3. Groups in Scheme 3 are defined as in Formula I.

Some examples of preferred substituents at M of the isoxazole derivatives of Scheme 3 independently include hydrogen, alkoxy, or halogen, or groups containing carboxylic acid derivatives such as: —$CO_2R_3$; but esters or amides of alkylcarboxylic acids, arylcarboxylic acids, —O-(alkylcarboxylic acids), —NR-(alkylcarboxylic acids), and the like are also included. When M is halogen in Scheme 3, preferred halogens are chloro and fluoro.

When the products of any of Schemes 1, 2 or 3 comprise esters, said esters can be useful in the invention. Said ester derivatives can be purified by methodologies well-known in the art, such as by normal phase, or reverse phase chromatography, or in suitable circumstances, using crystallization techniques. Alternatively, said ester derivatives can be used in the synthesis of other derivatives such as amides, hydroxamic acids, and different alkyl esters by well-known methods in the art.

Optionally, said esters can be hydrolysed under basic conditions, or cleaved using other methods known in the art, which cleave esters selectively in the presence of ketals or acetals to provide acid salts. These salts are also useful in the invention.

If desired, said acid salts can be converted into acids upon mild acid treatment. Workup by common techniques, and purification by methods well known in the art, including purification by crystallization or chromatography can be used to give the purified acids. Said acids can also be converted into other useful derivatives such as amides, hydroxamic acids, aryl esters, etc., by methods known to those skilled in the art of chemical synthesis. These acid derivatives are also useful in the invention, and are also purified using well-known methods such as crystallization or chromatography.

Scheme 4.
Transformation of 2', 3'-acetals and -ketals into new acetal and ketal derivatives using solid phase techniques.

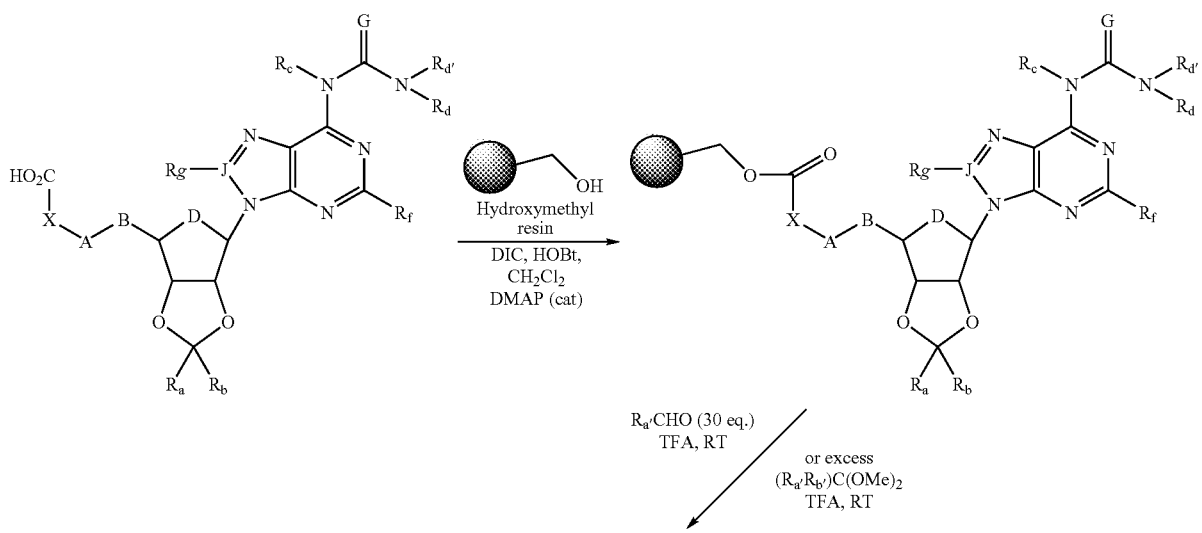

-continued

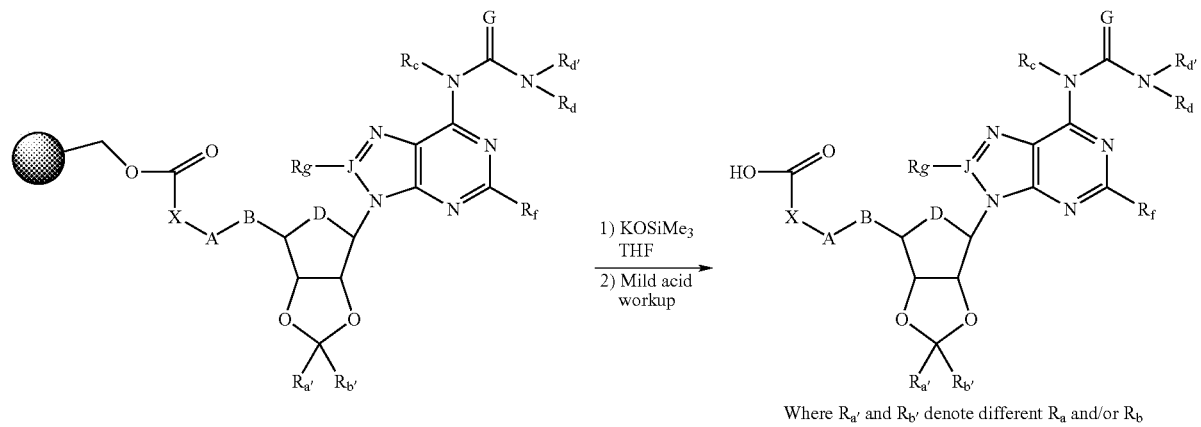

Where $R_{a'}$ and $R_{b'}$ denote different $R_a$ and/or $R_b$

Diversity using common intermediates can be introduced into the 2',3'-acetal or -ketal position of compounds encompassed in Formula I, as well as at the $N^6$-position of compounds of Formula I using solid-phase synthetic methods. Schemes 4 and 5 exemplify transketalization procedures using polymer-bound relatives of compounds of Formula I. These methods can be used to transform one class of 2',3'-ketal or -acetal into other useful 2',3'-acetal or -ketal derivatives of adenosine, guanosine, 8-azaadenosine, etc. These polymer-bound approaches are very useful, for after the desired reaction is complete, excess reagents can be washed away using one to several solvent washes. The desired material remains attached to the resin, in a pre-purified form, until it is cleaved from the solid phase using the appropriate conditions. Final purification of the desired product is then accomplished by conventional techniques like chromatography or crystallization.

Scheme 5.
Transformation of 6-chloro derivatives into 6-urea, 6-thiourea and 6-guanidine derivatives; subsequent conversion (when desired) of 2', 3'-acetals and -ketals into new acetal and ketal derivatives using solid phase techniques.

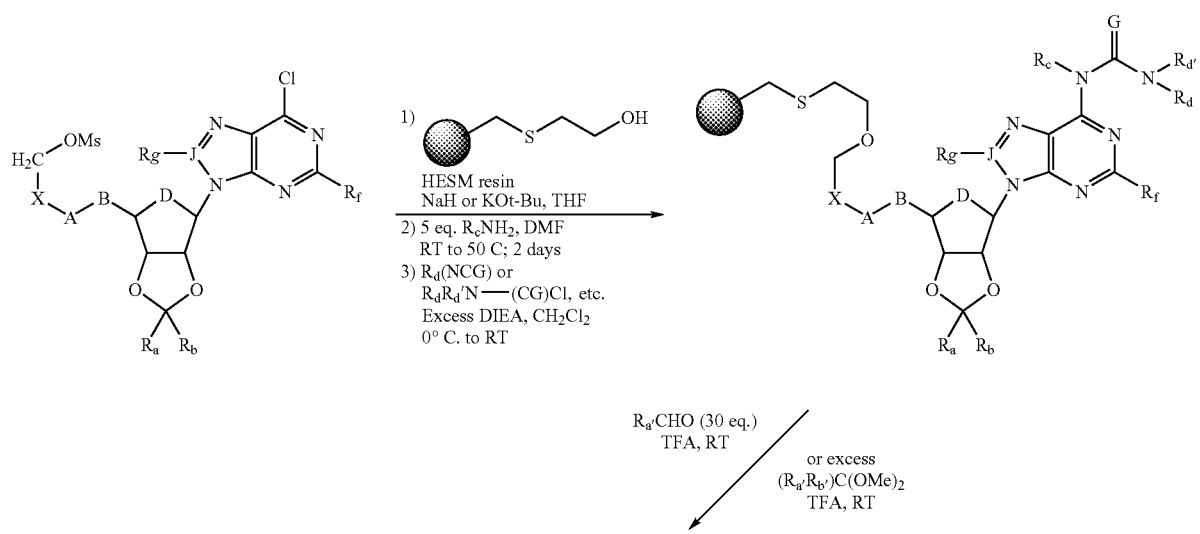

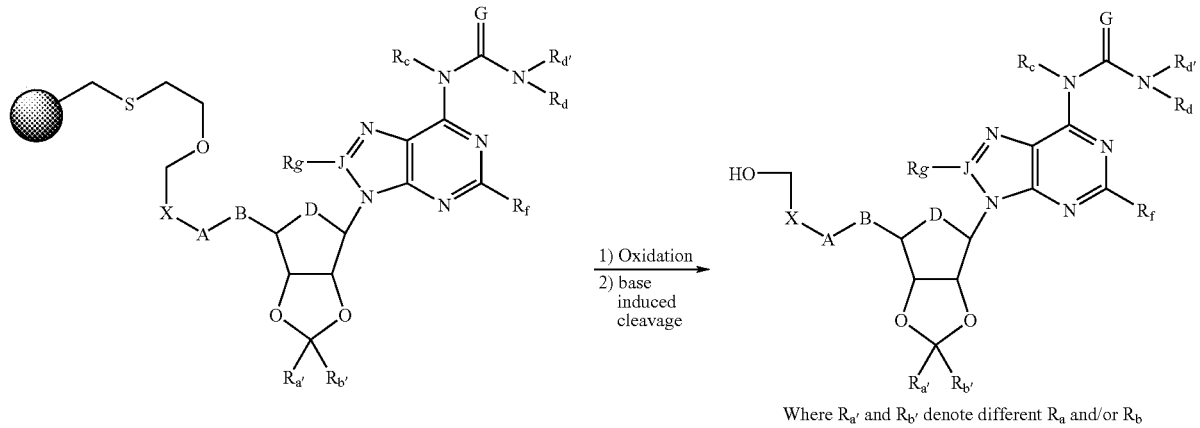

Where $R_{a'}$ and $R_{b'}$ denote different $R_a$ and/or $R_b$

Scheme 5 shows another variation of compound preparation employing resin-bound materials of Formula I. It outlines a solid-phase procedure that is useful for the introduction of functionality at the 6-position, as well as for transketalization at the 2',3'-position, if desired. It should be noted that the chemistry procedures used in these solid phase approaches are similar to methods known and used for solution-phase chemical transformations involving the synthesis of adenosine, guanosine, 8-azaadenosine, etc., derivatives. The primary differences are the necessity of attachment of a starting material to a resin, the simplicity of resin-based purification techniques (filtration and washing by compatible solvents) compared to solution-phase techniques (chromatography, crystallization, etc.), and the requirement for cleavage of a compound of the invention, or an intermediate useful for the synthesis of a compound of the invention from a resin prior to final purification and/or use of a compound so cleaved.

In Scheme 5, an early intermediate, such as a 6-chloroadenosine-2',3'-ketal or -acetal derivative, or a 6-chloro-8-azaadenosine-2',3'-ketal or -acetal derivative is attached to a resin such as polystyrene resin via a β-thioethanol linker (e.g., hydroxyethylsulfanylmethyl polystyrene; HESM polystyrene resin; Garcia-Echeverria, *Tetrahedron Lett.*, 38, 8933-7 (1997)). After workup by filtration and rinsing with a useful solvent like dimethylformamide (DMF), the resin bound material is treated with a primary amine, ammonia or a hydroxylamine derivative to introduce an amino group via displacement of the 6-chloride. As with solution phase techniques, subsequent introduction of an ureido-, thioureido-, or guanidino-group at N can be made in one step using an excess of an appropriate isocyanate, isothiocyanate, carbodiimide, carbamoyl chloride, or 2-alkyl-2-thiopseudourea; or using a chemical equivalent of such materials. Alternatively, a two-step approach can be used to introduce a group at $N^6$, which comprises treatment of an appropriate 6-amino derivative, synthesized as in Scheme 5, with a solution of a small excess of phosgene or thiophosgene and a tertiary amine such as diisopropylethylamine in a suitable solvent such as dichloromethane or toluene at a temperature which allows reaction, followed by treatment with an excess of a primary or secondary amine to give a resin-bound urea or thiourea after workup. If desired, transketalization can be performed on a bound substrate of Scheme 5 in a manner similar to that shown in Scheme 4. Or, if a desired acetal or ketal moiety of a 6-chloroadenosine, 6-chloroguanosine, 6-chloro-8-azaadenosine, etc., derivative is used to begin with, then no transketalization is necessary. Cleavage from the β-thioethanol linker of the solid phase, as shown for the HESM polystyrene resin in Scheme 5 is performed in two steps: oxidation of the thioether-linker using an oxidizing agent like m-chloroperbenzoic acid in a solvent such as dichloromethane gives a sulfone-linker, and cleavage of the β-ether moiety from the oxidized linker occurs upon treatment with a strong base like DBU in a solvent like dichloromethane and yields a compound which can be purified by techniques known in the art. Preferred oxidizing agents include peracids like m-chloroperbenzoic acid (MCPBA) and peracetic acid, but other oxidizing agents like hydrogen peroxide, permanganate salts, or persulfate salts can be used to oxidize a thioether to a sulfone. Preferred elimination conditions include DBU in dichloromethane, and 10% ammonium hydroxide in trifluoroethanol.

Following cleavage from the solid phase, a compound formed using the procedures in Scheme 5 can be used in the present invention, or can be further modified by well-known methods for functional-group transformations to generate new compounds which are also useful for this invention.

Preferred aldehydes, aldehyde acetals and ketone ketals useful in the transketalization methods shown in Schemes 4 and 5 comprise the below said carbonyl compounds and/or derivatives of: benzaldehyde, biphenyl-3-carboxaldehyde, biphenyl-4-carboxaldehyde, biphenyl-4-yl-acetaldehyde, 2-bromobenzaldehyde, benzo[b]thiophene-3-carbaldehyde, cyclohexanecarbaldehyde, cyclopentanecarbaldehyde, 2,5-dimethylbenzaldehyde, 2,6-difluorobenzaldehyde, 2-fluorobenzaldehyde, naphthalene-2-carbaldehyde, phenyl acetaldehyde, phenyl propynal, 3-phenyl propenal, 3-phenyl propionaldehyde, 2-trifluoromethyl benzaldehyde, cyclohexanone, cyclopentanone, 4-ethyl cyclohexanone, 3,4-dihydro-1H-naphthalen-2-one, and indan-2-one. Useful derivatives for transketalization of the above ketones comprise ketals like dimethoxy- or diethoxy-ketals, etc.

In addition to the introduction of amines on the $C^6$-position using solid phase techniques as provided in Scheme 5, diversity can also be introduced at the 6-position of an adenosine, 8-azaadenosine, guanosine, etc., analog via the intermediacy of a 6-halogenated-purine derivative using solution phase methods. Scheme 6 exemplifies the preparation of 5'-isoxazole ethers, introducing ammonia, various amines or hydroxylamine derivatives at the 6-position of the purine/8-azapurine ring by displacement of a chloride leaving group (a 6-chloride is shown in Schemes 5 and 6, but the leaving group at $C^6$ could also be another type, useful for such a transformation, e.g., a 6-bromide or 6-mesylate moiety) by such materials. Amines and amine-like compounds useful for displacement of a 6-halogen intermediate as contemplated for these schemes comprise ammonia, methylamine and other N-alkyl amines; N-aralkylamines; N-cyclopropylamine and other N-cycloalkylamines; anilines; ethers and other O-derivatives of hydroxylamine; aminopyridines and other heteroaromatic amines; heterocyclic compounds having a pendant —$NHR_c$-group; and N-alkyl amines which have one or more heteroatom units like O, NR, and/or S substituted for carbon units in the alkyl chain. Such $N^6$-products can be further transformed into ureas, thioureas, or guanidines by literature methods or by methods disclosed for such transformations in Schemes 5 and 6. The materials can be purified by methods typically used in the literature, such as by chromatography or, in certain cases, by crystallization Preferred substituents at $N^6$ are ureas.

When M of an isoxazole derivative as provided in Scheme 6 contains an ester group [e.g., —C(CO)O-(alkyl), —C(CO)O-(aryl), —$(CH_2)_m$C(CO)O-(alkyl), —O$(CH_2)_m$C(CO)O-(aryl), etc., where "m" defines a carbon chain length of a compound of Formula I], said ester can be used in the present invention, or it can be converted into an acid using a method which is compatible with an acetal or ketal moiety and a desired group at $N^6$. For example, an ester of Scheme 6 can be hydrolysed at room temperature (RT) in several hours using an excess of aqueous 2M lithium hydroxide solution dissolved in dioxane and/or methanol to give a carboxylate salt. Purification of said salt or a corresponding acid of said salt can be accomplished as previously disclosed. These acids and acid derivatives are also useful in this invention. Scheme 6 is exemplified using ammonia and primary amines (including hydroxylamine derivatives) as choices for nucleophiles in the displacement of a leaving group (like chloride) at $C^6$. Further modification of the $N^6$-group of a compound of Scheme 6 with a —[(CG)$NR_dR_d'$]-group yields a compound useful in the invention.

Scheme 6.
Solution phase synthesis of 5'-heteroaromatic ether-$N^6$-derivatives by Mitsunobu reaction, 6-chloride displacement, and $N^6$-amine derivatization.

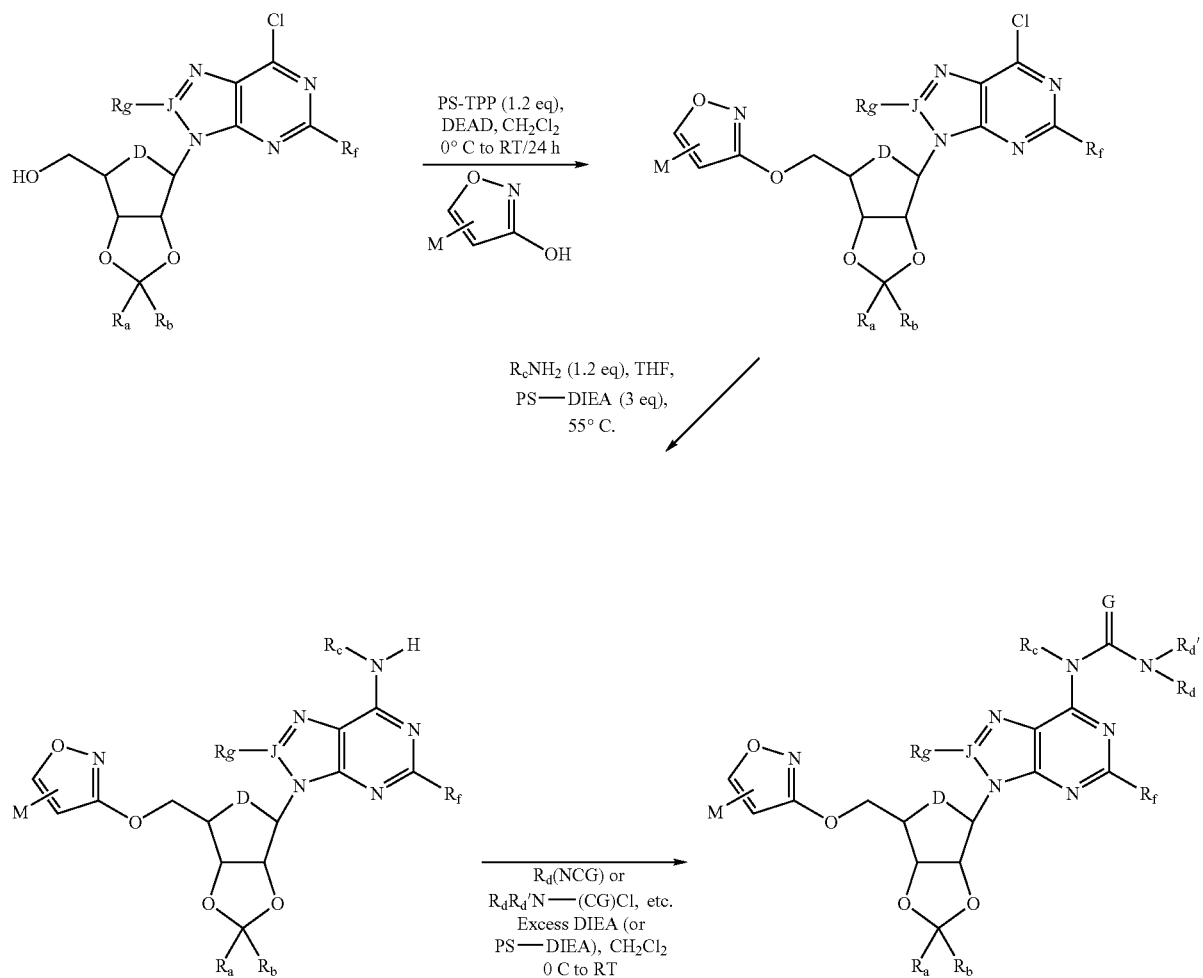

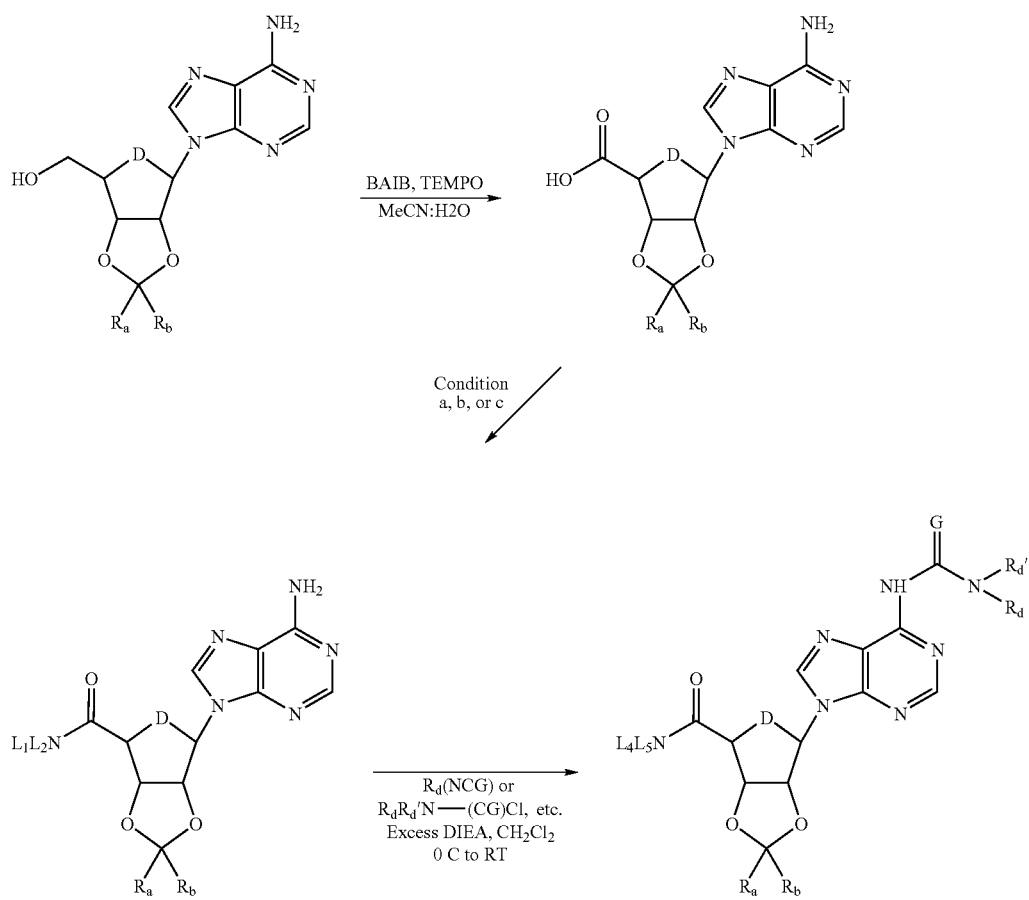

Scheme 7.
Synthesis of 2′, 3′-O-Isopropylideneadenosine-5′-carboxylic acid, related acetals and ketals, and their use as intermediates for the synthesis of compounds of this invention.

Condition a = L$_1$L$_2$NH, EDC, HOBt CH$_2$Cl$_2$, RT;
Condition b = L$_4$L$_5$NH, PyBop CH$_2$Cl$_2$, RT;
Condition c = L$_3$SO$_2$NHL$_4$, DCC, DMAP, CH$_2$Cl$_2$, RT;

2′,3′-O-Isopropylideneadenosine-5′-carboxylic acid and related acetals and ketals are useful intermediates for the preparation of various amides and sulfonamide derivatives. An intermediate of this type can be used in both solution phase and solid phase synthetic schemes to prepare compounds with various substituents at the 5′-, 2′, 3′-acetal/ketal-, and 6-positions- of adenosines or related purine derivatives as provided in Scheme 7. The methods shown in Scheme 7 are also useful for the preparation of substituted purine derivatives, and/or 8-azapurine derivatives.

Compounds containing the adenosine 5′-carboxylic acid unit shown in Scheme 7, or related N$^6$-substituted-adenosine-5′-carboxylic acids and 8-azaadenosine-5′carboxylic acids can also be used for the synthesis of esters or other materials useful in this invention using literature methods. In addition, the N$^6$-amine of such an acid can be transformed into a urea, thiourea, or guanidine, or into a protected group such as a benzamide, and the acid moiety which is at, or linked to, the 5′-position of the furanose derivative can be coupled to a solid phase resin such as a 4-sulfamylbutyryl resin, hydroxymethyl resin, or a pegylated-hydroxy resin, etc., using techniques well-known in the peptide literature and/or solid phase organic synthesis literature to give a resin-bound material. The benefits of solid-phase chemistry can then be gained for modification of a resin-bound material by transketalization techniques similar to those shown in Schemes 4 and 5. If a protecting group is used on the N$^6$-position of such an acid, it can be removed subsequent to a transketalization procedure, and a N$^6$-amine so formed can be converted into a urea, thiourea or guanidine by methods disclosed herein, or by methods in the literature. Cleavage from the solid support using known methods then yields a compound of the invention which can be purified, if needed, by employing commonly-used techniques.

Scheme 8.
N⁶-modification of adenosine derivatives, followed by oxidation to a 5′-carboxylic acid, and 5′-amide formation.

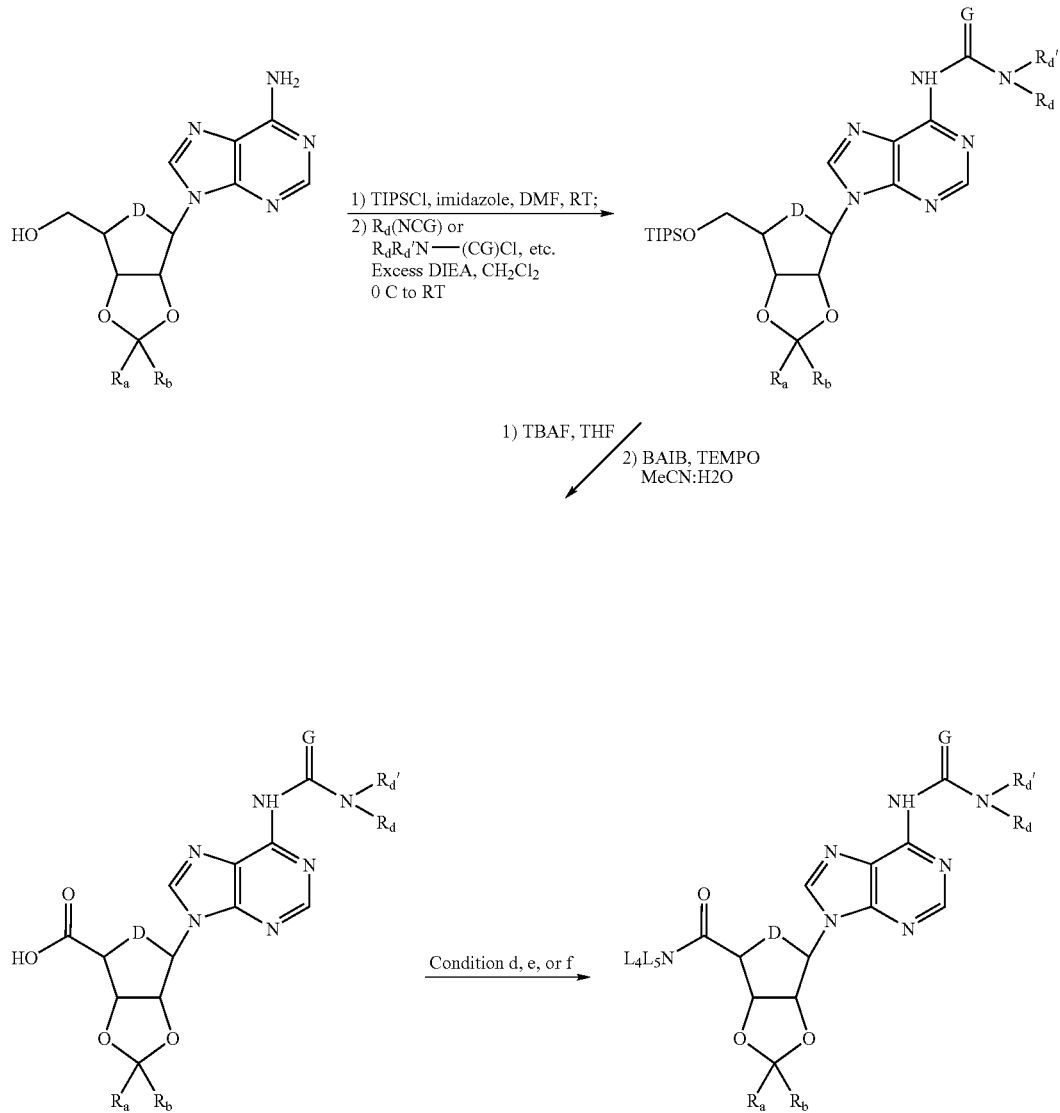

Condition d = L₄L₅NH, EDC, HOBt, CH₂Cl₂, RT;
Condition e = L₄L₅NH, HATU, CH₂Cl₂, RT;
Condition f = L₃SO₂NHL₄, DCC, DMAP, CH₂Cl₂, RT;

A variation of the method disclosed in Scheme 7, useful for the introduction of a group at N⁶ prior to oxidation of the 5′-position of an adenosine derivative or an 8-azaadenosine derivative, is shown in Scheme 8. Although Scheme 8 shows an adenine unit, it will be understood by chemistry practitioners that the methods of Scheme 8 are generally applicable to substituted members of the adenine family and also to the 8-azaadenines.

Preferred amines and amine derivatives for the 5′-amide-forming reactions shown in Schemes 7 and 8 are: trifluoromethanesulfonamide, methanesulfonamide, serine, glycine, proline, anthranilic acid and its regioisomers, and methyl anthanilate and its regioisomers.

Scheme 9.
Amino acid amides of 5'-adenosinecarboxylic acid derivatives and 8-azaadenosine-5'-carboxylic acid derivatives using solid phase techniques.

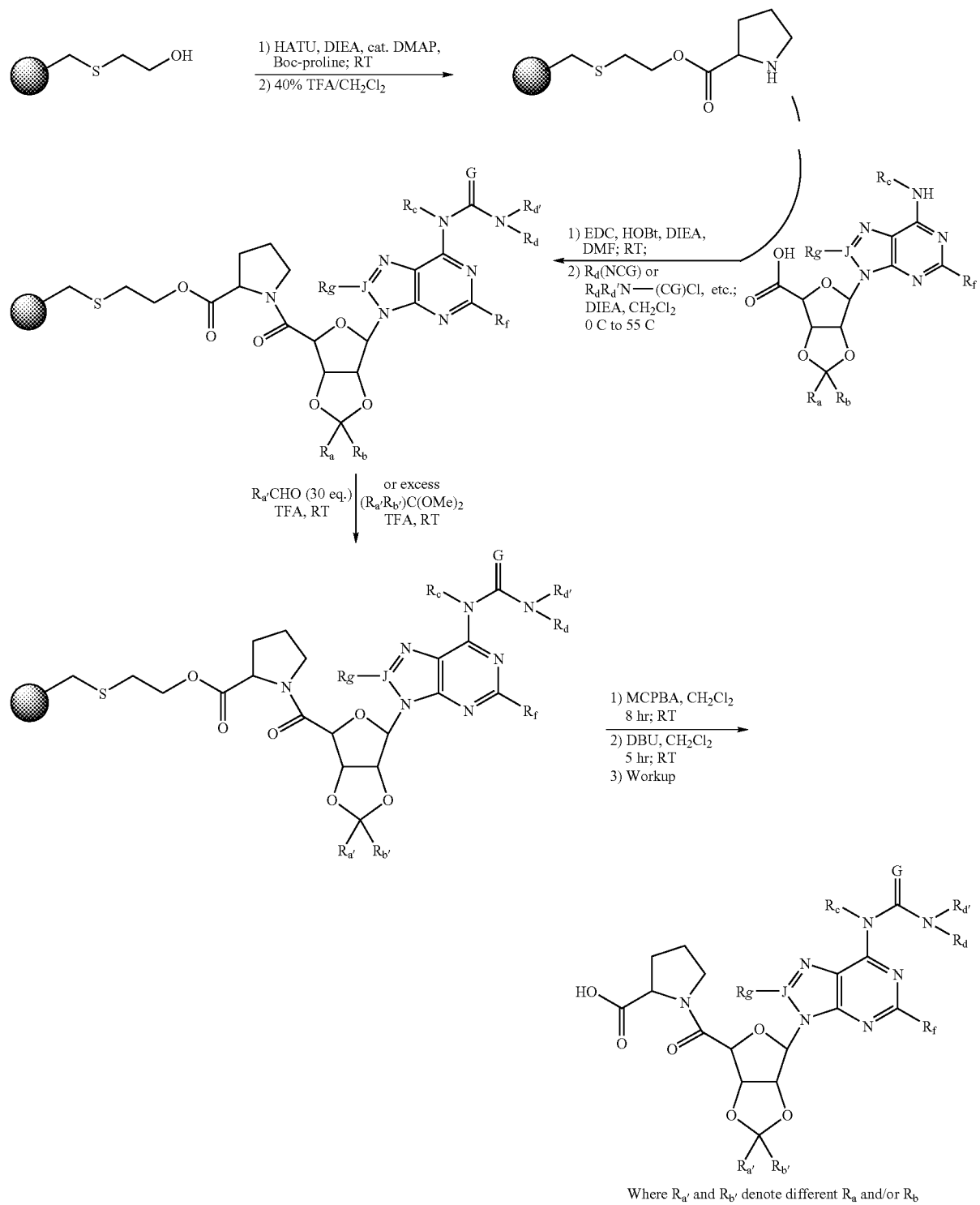

Where $R_{a'}$ and $R_{b'}$ denote different $R_a$ and/or $R_b$

Amide derivatives of 5'-carboxylic acids (e.g., those shown in Scheme 7 and Scheme 8) or amide derivatives of acid moieties linked at the 5'-position of Formula I can also include amides derived from amino acids, peptides, aminoalcohols and the like. A convenient way of attaching naturally-occurring, as well as synthetically-derived amino acids and peptides, or derivatives, to a 5'-carboxylic acid or related homologue is exemplified in Scheme 9 using the amino acid, proline.

An example of the method is shown in Scheme 9 utilizing a resin-linker combination like the polystyrene/HESM as a solid phase. Other solid phase/linkers known in the art can also be used in this method. Attachment of a group, such as an amino acid, (e.g., proline, as shown) or a series of amino acids, or a peptide, by well-known methods in the art of solid phase synthesis yields a resin-linked amine. Said amine can then be reacted with an adenosine 5'-carboxylic acid, or another type of derivative useful for making compounds of this invention, to yield a coupled product. The said coupled product, if it bears an amine at the 6-position, can then be treated with one of the various reagents described previously, or with a reagent known in the literature, to yield a urea, thiourea or guanidine at the adenosine 6-position. Alternatively, if a 5'-carboxylic acid derivative used in a coupling to a solid phase has a urea, etc., already installed at the 6-position, then the latter said modification at $N^6$ need not be performed. If desired, a coupled 5'-amide/$N^6$-derivatized product can be converted into a variety of different acetals or ketals using solid phase methods such as described for Schemes 4 and 5. When a synthesis is complete, cleavage of a compound of the invention from a solid phase can be performed by a variety of methods known in the art; such cleavage conditions depending upon the type of linker used. Cleavage methodologies useful for cleaving peptide- or amino acid derivatives of 5'-linked-adenosine compounds comprise the linker oxidation/elimination procedures given in Schemes 5 and 9; treatment with a hydroxide source, such as lithium hydroxide, using conditions as for the ester hydrolysis described in Scheme 6; and hydrolysis using potassium trimethylsilanolate, as described in Scheme 4; as well as others known in the art (including aminolysis to form amides). If desired, a compound useful in this invention can be obtained in purified form by cleaving it from a resin and purifying it as described previously.

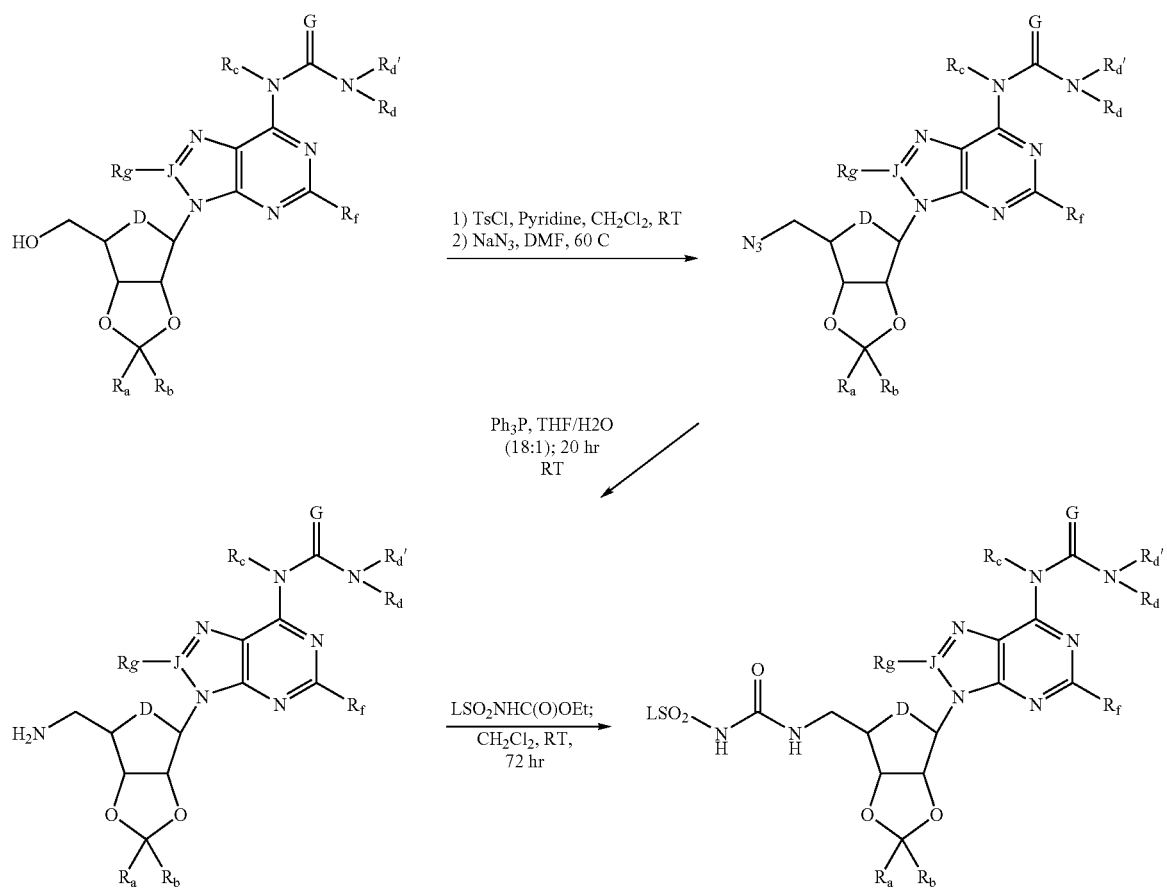

In another embodiment, an amino group can be installed at the 5'-position of an adenosine or 8-azaadenosine analogue, or on the chain of a 5'-homologue of such a material. This amine can be utilized to form amide-, sulfonamide-, and other derivatives. Scheme 10 illustrates how a sulfonylurea can be synthesized at the 5'-position using a 5'-amine, or at related positions on homologous amine derivatives. In addition, an amine introduced at the 5'-position or on the 5'-chain of a homologue is also useful for the synthesis of amides, ureas, sulfonamides and other amine derivatives using methods known in the art for such processes.

Scheme 11.
Homologation of adenosine derivatives, including steps involving oxidation,
Wittig or Horner-Emmons Reaction, reduction and coupling with amines.

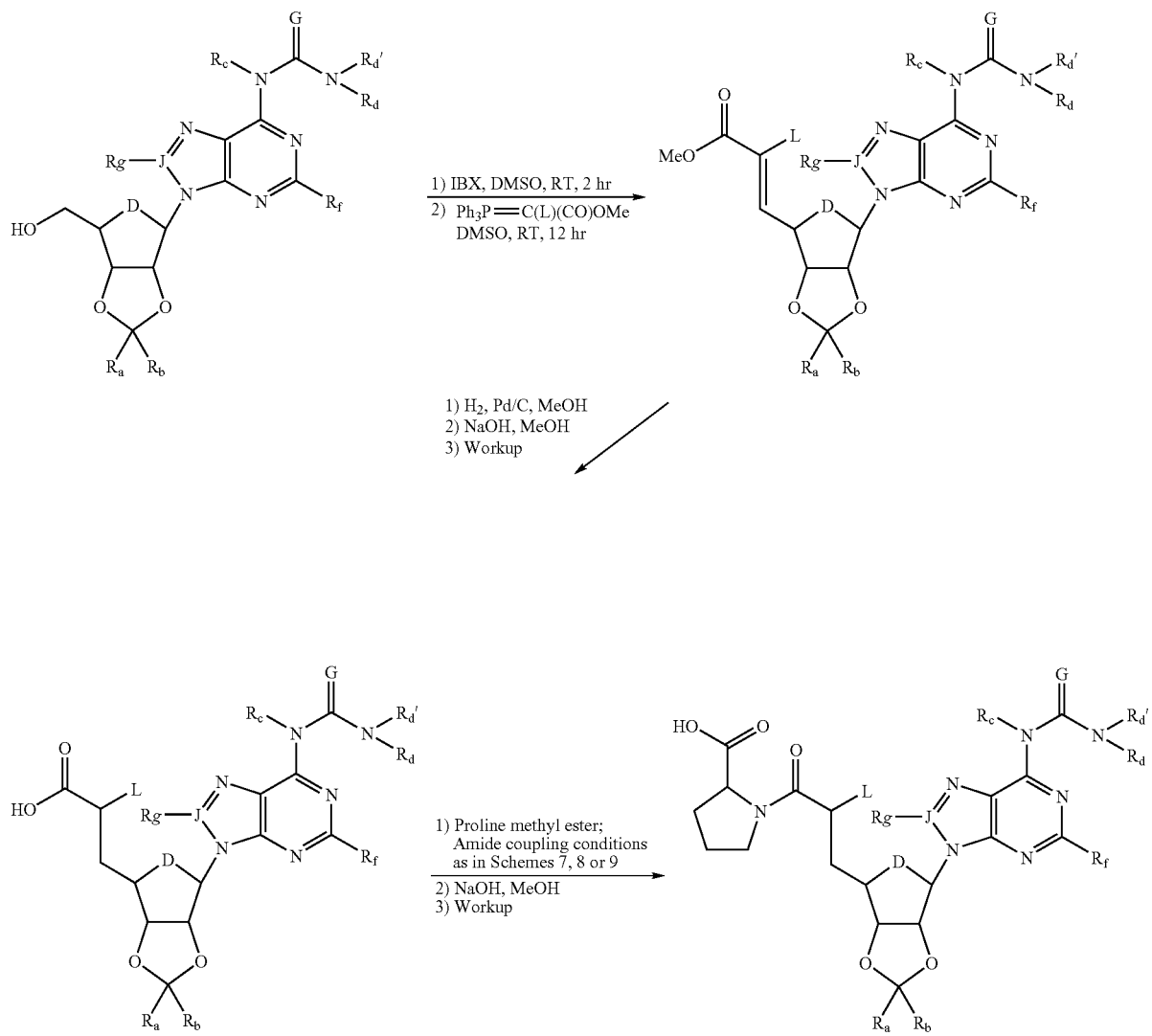

In still another embodiment, the 5'-position of the nucleoside derivative or 8-azanucleoside derivative is homologated with one or more carbon atoms, affording compounds with different distances between the atoms of the tetrahydrofuran ring and the homologated group. Scheme 11 illustrates the preparation of a class of homologated adenosine analogs which are useful for the invention. Or, if desired, such a homologue can subsequently be coupled with an amino acid to give other compounds useful for this invention. In Scheme 11, proline is used to exemplify the amide coupling, but other amines or amino acid derivatives can be employed. In Scheme 12, the reduction step of Scheme 11 is omitted, which generates unsaturated homologues useful in this invention.

Scheme 12. Preparation of 5'-substituted ethers.

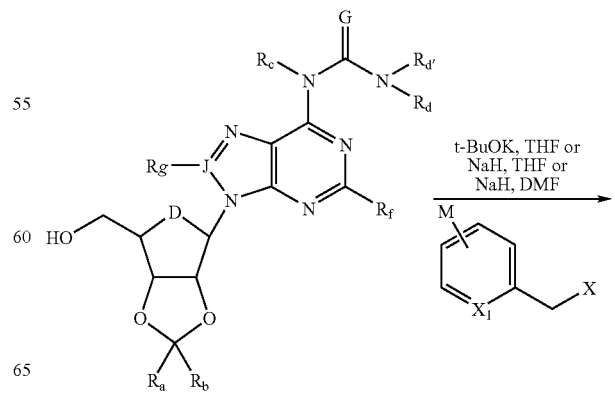

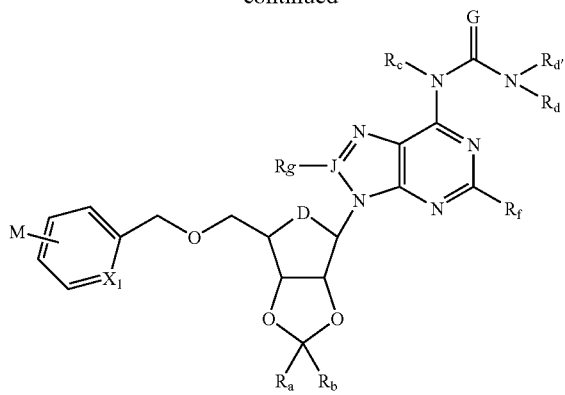

Scheme 12, for example, discloses a useful method for the synthesis of aryl- or heteroaryl-nucleoside ethers from purine or 8-azapurine carbocyclic nucleoside acetals by substitution of an appropriately functionalized adenosine analogue or 8-azapurine derivative with a halogenated on an appropriately-substituted halogenated aryl, alkyl, or alkylaryl compound or a related heteroaromatic derivative. Preferred substituents at M of the aromatic/heteroaromatic-group in Scheme 12 are independently hydrogen, or halogen, or groups containing carboxylic acid derivatives such as: —CO$_2$R$_3$; but they can also be halogen, or esters or amides of alkylcarboxylic acids, arylcarboxylic acids, —O-(alkylcarboxylic acids), —NR-(alkylcarboxylic acids), and the like. When M is halogen in Scheme 1, preferred halogens are chloro and fluoro.

The method disclosed in Scheme 12 can also be extended to a wide range of alkyl or aralkyl halides, making it a useful method for the general preparation of 5' substituted ethers.

Scheme 13. Preparation of 2, 3-acetals and -ketals.

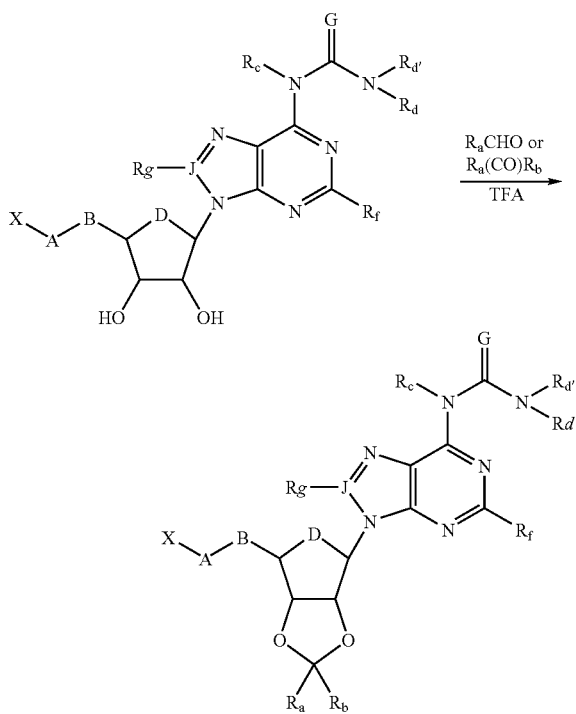

Diversity using common intermediates can be introduced into the 2,3-acetal or -ketal position (Scheme 14) of compounds encompassed in Formula I, as well as at the N$^6$-position of compounds of Formula I. Final purification of the desired product is then accomplished by conventional techniques like chromatography or crystallization.

Preferred aldehydes, aldehyde acetals and ketone ketals useful in the transketalization methods shown in Schemes 2 comprise the below said carbonyl compounds and/or derivatives of: benzaldehyde, biphenyl-3-carboxaldehyde, biphenyl-4-carboxaldehyde, biphenyl-4-yl-acetaldehyde, 2-bromobenzaldehyde, benzo[b]thiophene-3-carbaldehyde, cyclohexanecarbaldehyde, cyclopentanecarbaldehyde, 2,5-dimethylbenzaldehyde, 2,6-difluorobenzaldehyde, 2-fluorobenzaldehyde, naphthalene-2-carbaldehyde, phenyl acetaldehyde, phenyl propynal, 3-phenyl propenal, 3-phenyl propionaldehyde, 2-trifluoromethyl benzaldehyde, cyclohexanone, cyclopentanone, 4-ethyl cyclohexanone, 3,4-dihydro-1H-naphthalen-2-one, and indan-2-one.

Those having skill in the art will recognize that the starting materials can be varied and additional steps employed to produce compounds encompassed by the present invention, as shown in the above schemes and as demonstrated by the examples which follow. In some cases, protection of certain reactive functionalities can be necessary to achieve some of the above transformations. In general, the need for such protecting groups as well as the conditions necessary to attach and remove such groups will be apparent to those skilled in the art.

Use of P2Y$_{12}$ Receptor Antagonist Compounds

This invention provides a method of preventing or treating diseases or conditions associated with platelet aggregation and/or platelet activation. This invention also provides a method for solving treatment problems or limited treatment options caused by the aggregation of platelets or by the irreversible inhibition of platelet aggregation.

This invention provides methods of preventing or treating thrombosis and related disorders, such as venous thrombosis, established peripheral arterial disease, thrombophlebitis, arterial embolism, coronary and cerebral arterial thrombosis, unstable angina, myocardial infarction, stroke, cerebral embolism, renal embolism, pulmonary embolism and other embolism- or thrombosis-related afflictions produced by but not limited to procedural or surgical interventions. This invention further provides methods for the prevention of embolism or thrombosis during percutaneous coronary interventions, placement of coronary stents, coronary angioplasty, coronary endarectomy, carotid endarectomy, or due to platelet-aggregation complications related to atherosclerosis, inflammation, exposure of blood to artificial devices, drug effects.

This invention further provides methods of inhibiting platelet aggregation in blood and blood products comprising platelets, such as stored blood.

The method comprises administering to a subject or blood and blood products a composition comprising an effective amount of P2Y$_{12}$ receptor antagonist compound, wherein said amount is effective to bind the P2Y$_{12}$ receptors on platelets and inhibit platelet aggregation, preferably in a reversible manner.

The invention further provides useful methods of treating patients to inhibit platelet aggregation in a reversible manner, especially in patients that are subject to a procedure such as percutaneous coronary interventions, stent placement, balloon angioplasty, coronary atherectomy, coronary endarterectomy, carotid endarterectomy, thrombolytic therapy, coronary or other vascular graft surgery, dialysis, etc. In those patients, it is important that platelet aggregation inhibition can be rapidly reversed (within hours for oral administration and within minutes for intravenous administration) if necessary. The method comprises the steps of: (a) providing a patient in need of rapid reversal of platelet aggregation inhibition; (b) administering a therapeutically effective amount of a compound of Formula I, Ia, or Ic to the patient; (c) submitting the patient to a procedure selected from the group consisting of: percutaneous coronary interventions, stent placement, balloon angioplasty, coronary atherectomy, coronary endarterectomy, carotid endarterectomy, thrombolytic therapy, coronary or other vascular graft surgery, and dialysis, (d) discontinuing the administering of said compound to the patient; and (e) allowing the amount of said compound in the patient's blood to reduce to below an therapeutically effective amount. In step (b), the administration of the compound can be either continuous or intermittent as long as it provides a therapeutically effective amount of the compound in the patient's blood. The amount of the compound in the patient's blood is monitored.

The compounds of general Formulae I, III-XII are antagonists of the effect of ADP on its platelet membrane receptor, the $P2Y_{12}$ receptor. The compounds of general Formula I are useful in therapy, in particular in the prevention or treatment of platelet aggregation. The compounds provide efficacy as antithrombotic agents by their ability to block ADP from acting at its platelet receptor site and thus prevent platelet aggregation. The compounds provide a more efficacious antithrombotic effect than aspirin, but with less profound effects on bleeding than antagonists of the fibrinogen receptor.

The $P2Y_{12}$ receptor antagonists of this invention, in contrast with currently available marketed products clopidogrel (Plavix®) and ticlopidine (Ticlid®), bind to the $P2Y_{12}$ receptor in a reversible fashion and therefore, the effects of the treatment with compounds described in this invention are reversed by the simple discontinuation of the treatment, restoring the hemostatic functionality of the platelet as necessary. Since platelets are non-nucleated cell particles that lack the ability to synthesize new proteins, treatment of subjects with irreversible $P2Y_{12}$ antagonists results in the impairment of platelet function that lasts for the lifespan of the platelet (approximately 8 to 10 days). The use of irreversible $P2Y_{12}$ antagonists such as clopidogrel has been associated with increases in blood loss, transfusion requirements and rate of reoperation after cardiac surgery (Kapetanakis, et al., *Eur Heart J.* 26: 576-83, 2005). To avoid these complications, subjects undergoing elective surgeries are required to discontinue the treatment with irreversible antagonists for at least five days prior to the surgery, which increases the risk of a thrombotic event during this period. Therefore, the compounds described in this invention represent an advantage over the currently marketed compounds.

The ADP-induced platelet aggregation is mediated by the simultaneous activation of both $P2Y_{12}$ and $P2Y_1$ receptors, thus the combined administration of the Formula I compounds with antagonists of platelet $P2Y_1$ receptors can provide a more efficacious antithrombotic effect at concentrations of each antagonist that are below the effective concentrations to block each receptor subtype in other systems, resulting in a decrease of the potential manifestation of adverse effects. In addition, these compounds can be used in conjunction with lower doses of other platelet aggregation inhibitors, which work by different mechanisms, to reduce the possible side effects of said agents.

The compounds of the present invention are useful as antithrombotic agents, and are thus useful in the treatment or prevention of unstable angina, coronary angioplasty (PTCA) and myocardial infarction.

The compounds of the present invention are useful in the treatment or prevention of primary arterial thrombotic complications of atherosclerosis such as thrombotic stroke, peripheral vascular disease, and myocardial infarction without thrombolysis.

The compounds of the invention are useful for the treatment or prevention of arterial thrombotic complications due to interventions in atherosclerotic disease such as angioplasty, endarterectomy, stent placement, coronary and other vascular graft surgery.

The compounds of the invention are useful for the treatment or prevention of thrombotic complications of surgical or mechanical damage such as tissue salvage following surgical or accidental trauma, reconstructive surgery including skin flaps, and "reductive" surgery such as breast reduction.

The compounds of the present invention are useful for the prevention of mechanically-induced platelet activation in vivo, for example, caused by cardiopulmonary bypass, which results in temporary platelet dysfunction (prevention of microthromboembolism). The compounds of the present invention are useful for prevention of mechanically-induced platelet activation in vitro. For example, the compounds are useful in the preservation of blood products, e.g. platelet concentrates, prevention of shunt occlusion such as renal dialysis and plasmapheresis, and thrombosis secondary to vascular damage/inflammation such as vasculitis, arteritis, glomerulonephritis and organ graft rejection.

The compounds of the present invention are useful in disorders with a diffuse thrombotic/platelet consumption component such as disseminated intravascular coagulation, thrombotic thrombocytopenic purpura, hemolytic uremic syndrome, heparin-induced thrombocytopenia and pre-eclampsia/eclampsia.

The compounds of the invention are useful for the treatment or prevention of venous thrombosis such as deep vein thrombosis, veno-occlusive disease, hematological conditions such as thrombocythemia and polycythemia, and migraine.

The compounds of the present invention are useful in treating a mammal to alleviate the pathological effects of atherosclerosis and arteriosclerosis, acute MI, chronic stable angina, unstable angina, transient ischemic attacks and strokes, peripheral vascular disease, arterial thrombosis, preeclampsia, embolism, restenosis or abrupt closure following angioplasty, carotid endarterectomy, and anastomosis of vascular grafts.

The compounds of the present invention are useful in treating chronic or acute states of hyper-aggregability, such as disseminated intravascular coagulation (DIC), septicemia, surgical or infectious shock, post-operative and post-partum trauma, cardiopulmonary bypass surgery, incompatible blood transfusion, abruptio placenta, thrombotic thrombocytopenic purpura (TTP), snake venom and immune diseases, are likely to be responsive to such treatment.

The compounds of the present invention are useful in treating diseases or conditions associated with platelet activation and/or aggregation produced by the contact of blood with an artificial device. In one embodiment, the artificial device is a paracorporeal artificial lung and an extracorporeal membrane oxigenation device. In another embodiment, the artificial device is an internal implantable artificial heart. In another embodiment, the artificial device is an apheresis instrument used to remove or isolate a specific component of the blood, and returning the remaining blood components to the donor. In yet another embodiment, the artificial device is a hemodialysis instrument.

The compounds of the present invention are useful in vitro to inhibit the aggregation of platelets in blood and blood products, e.g. for storage, or for ex vivo manipulations such as in diagnostic or research use. In such applications, the compounds are administered to the blood or blood product.

Finally, if the compounds of the present invention have sufficient binding affinity and bear a fluorescent moiety, they are useful as biochemical probes for the $P2Y_{12}$ receptor.

In a preferred embodiment, the compounds are used in the treatment of unstable angina, coronary angioplasty and myocardial infarction.

In another preferred embodiment, the compounds are useful as adjunctive therapy in the prevention or treatment of thrombotic disorders, such as coronary arterial thrombosis during the management of unstable angina, coronary angioplasty and acute myocardial infarction, for example, as adjuvants of thrombolytic therapy. The compounds are also administered in combination with other antiplatelet and/or anticoagulant drugs such as heparin, aspirin, GP IIb/IIIa antagonists, or thrombin inhibitors.

This invention provides a method of inhibiting platelet aggregation and clot formation in a mammal, especially a human, which comprises administering to the subject a compound of Formula (I) and a pharmaceutically acceptable carrier.

This invention further provides a method for inhibiting the reocclusion of an artery or vein and the formation of new blood clots following fibrinolytic therapy, which comprises administering to a subject a compound of Formula (I) and a fibrinolytic agent. When used in the context of this invention, the term fibrinolytic agent is intended to mean any compound, whether a natural or synthetic product, which directly or indirectly causes the lysis of a fibrin clot. Plasminogen activators are a well known group of fibrinolytic agents. Useful plasminogen activators include, for example, anistreplase, urokinase (UK), pro-urokinase (pUK), streptokinase (SK), tissue plasminogen activator (tPA) and mutants, or variants thereof, which retain plasminogen activator activity, such as variants which have been chemically modified or in which one or more amino acids have been added, deleted or substituted or in which one or more functional domains have been added, deleted or altered such as by combining the active site of one plasminogen activator or fibrin binding domain of another plasminogen activator or fibrin binding molecule. The increased clinical efficacy of the combination of the compounds described in this invention with fibrinolytic agents allows to use lower concentrations of the fibrinolytic agent and decrease the risk of hemorrhagic events. This in turn, allows the administration of fibrinolytic therapy over an extended period of time after a heart attack or stroke.

Extracorporeal circulation is routinely used for cardiovascular surgery in order to oxygenate blood. Platelets adhere to surfaces of the extracorporeal circuit. Platelets released from artificial surfaces show impaired hemostatic function. Compounds of the invention can be administered to prevent adhesion.

Other applications of these compounds include prevention of platelet thrombosis, thromboembolism and reocclusion during and after thrombolytic therapy and prevention of platelet thrombosis, thromboembolism and reocclusion after angioplasty of coronary and other arteries and after coronary artery bypass procedures.

The active compounds can be administered systemically to target sites in a subject in need such that the extracellular concentration of a $P2Y_{12}$ antagonist is elevated to block the binding of ADP to $P2Y_{12}$ receptor, thus inhibit the platelet aggregation. The term systemic as used herein includes subcutaneous injection, intravenous, intramuscular, intrasternal injection, intravitreal injection, infusion, inhalation, transdermal administration, oral administration, rectal administration and intra-operative instillation.

For systemic administration such as injection and infusion, the pharmaceutical formulation is prepared in a sterile medium. The active ingredient, depending on the vehicle and concentration used, can either be suspended or dissolved in the vehicle. Adjuvants such as local anesthetics, preservatives and buffering agents can also be dissolved in the vehicle. The sterile injectable preparation can be a sterile injectable solution or suspension in a non-toxic acceptable diligent or solvent. Among the acceptable vehicles and solvents that can be employed are sterile water, saline solution, or Ringer's solution.

Another method of systemic administration of the active compound involves oral administration, in which pharmaceutical compositions containing active compounds are in the form of tablets, lozenges, aqueous or oily suspensions, viscous gels, chewable gums, dispersible powders or granules, emulsion, hard or soft capsules, or syrups or elixirs.

For oral use, an aqueous suspension is prepared by addition of water to dispersible powders and granules with a dispersing or wetting agent, suspending agent one or more preservatives, and other excipients. Suspending agents include, for example, sodium carboxymethylcellulose, methylcellulose and sodium alginate. Dispersing or wetting agents include naturally-occurring phosphatides, condensation products of an allylene oxide with fatty acids, condensation products of ethylene oxide with long chain aliphatic alcohols, condensation products of ethylene oxide with partial esters from fatty acids and a hexitol, and condensation products of ethylene oxide with partial esters derived from fatty acids and hexitol anydrides. Preservatives include, for example, ethyl, and n-propyl p-hydroxybenzoate. Other excipients include sweetening agents (e.g., sucrose, saccharin), flavoring agents and coloring agents. Those skilled in the art will recognize the many specific excipients and wetting agents encompassed by the general description above.

For oral application, tablets are prepared by mixing the active compound with nontoxic pharmaceutically acceptable excipients suitable for the manufacture of tablets. These excipients can be, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets can be uncoated or they can be coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil. Formulation for oral use can also be presented as chewable gums by embedding the active ingredient in gums so that the active ingredient is slowly released upon chewing.

Additional means of systemic administration of the active compound to the target platelets of the subject would involve a suppository form of the active compound, such that a therapeutically effective amount of the compound reaches the target sites via systemic absorption and circulation.

For rectal administration, the compositions in the form of suppositories can be prepared by mixing the active ingredient with a suitable non-irritating excipient which is solid at ordinary temperatures but liquid at the rectal temperature and will therefore melt in the rectum to release the compound. Such excipients include cocoa butter and polyethylene glycols.

The active compounds can also be systemically administered to the platelet aggregation sites through absorption by the skin using transdermal patches or pads. The active compounds are absorbed into the bloodstream through the skin. Plasma concentration of the active compounds can be controlled by using patches containing different concentrations of active compounds.

One systemic method involves an aerosol suspension of respirable particles comprising the active compound, which the subject inhales. The active compound would be absorbed into the bloodstream via the lungs, and subsequently contact the target platelets in a pharmaceutically effective amount. The respirable particles can be liquid or solid, with a particle size sufficiently small to pass through the mouth and larynx upon inhalation; in general, particles ranging from about 1 to 10 microns, but more preferably 1-5 microns, in size are considered respirable.

Another method of systemically administering the active compounds to the platelet aggregation sites of the subject involves administering a liquid/liquid suspension in the form of eye drops or eye wash or nasal drops of a liquid formulation, or a nasal spray of respirable particles that the subject inhales. Liquid pharmaceutical compositions of the active compound for producing a nasal spray or nasal or eye drops can be prepared by combining the active compound with a suitable vehicle, such as sterile pyrogen free water or sterile saline by techniques known to those skilled in the art.

Intravitreal delivery can include single or multiple intravitreal injections, or via an implantable intravitreal device that releases $P2Y_{12}$ antagonists in a sustained capacity. Intravitreal delivery can also include delivery during surgical manipulations as either an adjunct to the intraocular irrigation solution or applied directly to the vitreous during the surgical procedure.

For systemic administration, plasma concentrations of active compounds delivered can vary according to compounds; but are generally $1 \times 10^{-10}$-$1 \times 10^{-4}$ moles/liter, and preferably $1 \times 10^{-8}$-$1 \times 10^{-5}$ moles/liter.

The pharmaceutical utility of $P2Y_{12}$ antagonist compounds of this invention is indicated by their inhibition of ADP-induced platelet aggregation. This widely used assay, as described in S. M. O. Hourani et al. *Br. J Pharmacol.* 105, 453-457 (1992) relies on the measurement of the aggregation of a platelet suspension upon the addition of an aggregating agent such as ADP.

$P2Y_{12}$ Receptor Antagonist Compound-Eluting Stents

Coating stents with pharmaceutical agents has an inherent advantage over systemic administration, due to the ability to precisely deliver a much lower dose of the drug to the target area thus achieving high tissue concentration while minimizing the risk of systemic toxicity.

The present invention is also directed to a drug-eluting stent, which is a stent coated with one or more non-nucleotide $P2Y_{12}$ receptor antagonist compounds of Formula I, or III-XII, or a pharmaceutically acceptable salt, solvate, or hydrate thereof. When the stent is placed in a narrowed or damaged arterial vessel, a therapeutically effective amount of the compound(s) is eluted continuously from the stent to the local environment of the stent. Local delivery to vasculature facilitates the achievement of high regional drug concentrations, achieves a continuous exposure of the tissue to the drug, and reduces potential adverse effects and systemic toxicity due to lower systemic doses. The drug can be targeted directly to the required site. A therapeutically effective amount of the $P2Y_{12}$ receptor antagonist compound is an amount that is effective in preventing thrombosis and maintaining blood flow rate of the stented vessel, by decreasing in shear forces, relaxing vascular smooth muscle, and reducing narrowing of the vascular lumen restenosis.

By coating with one or more $P2Y_{12}$ receptor antagonist compounds, it is meant that the stent is coated with the $P2Y_{12}$ receptor antagonist compound itself (without a carrier), or the stent is coated with the compound in a carrier, i.e., the compound is in the form of a component of a mixture or matrix. In one embodiment, the stent is coated with a carrier that comprises at least one $P2Y_{12}$ receptor antagonist compound. The carrier is usually a biocompatible and non-toxic polymer. The polymer is preferably a biodegradable polymer or a biostable polymer.

Biodegradable polymers suitable for this invention can be chosen from, but are not limited to, polycaprolactone, polylactic acid (D/L or L), poly(lactide-co-glycolide), poly(hydroxybutyrate), poly(hydroxybutyrate-covalerate), polydioxanone, polyorthoester, polyanhydride, poly(glycolic acid), poly(glycolic acid-cotrimethylene carbonate), polyphosphoester, polyphosphoester urethane, poly(amino acids), poly(trimethylene carbonate), poly(iminocarbonate), cyanoacrylates, polyalkylene oxalates, polyphosphazenes, and aliphatic polycarbonates. Alternately, natural biomolecules such as cellulose, starch, dextran, hyaluronic acid, and collagen can also be used.

Biostable polymers can be chosen from, but are not limited to, polyurethanes, polyesters, polyamides, polyolefins, polycaprolactam, polyvinyl chloride, polyvinyl alcohol, poly(ethylene-vinyl alcohol), polyethers, silicones, acrylate polymers and copolymers, polyvinylmethyl ether, polyimide, and polyacrylonitrile.

The concentration of the $P2Y_{12}$ receptor antagonist compound in the stent is in general in the range of 0.001-20, preferably 0.01-10, and more preferably 0.1-5 µg/mm². Alternatively, the concentration of the $P2Y_{12}$ receptor antagonist compound in the stent is 1-500, preferably 10-100 µg/mm. Muni, et al. (*American Heart Journal*, 149:415-433, (2005)) have reported stent drug carriers, drug concentrations, stent sizes, and types of lesions; the article is incorporated herein by reference in its entirety.

In one embodiment, the elution of the $P2Y_{12}$ receptor antagonist compound is slow release and long-acting, i.e., the compound is eluted constantly and provides a local therapeutically effective amount at least until the epithelium damaged by the stent placement is healed. The local elution of the $P2Y_{12}$ receptor antagonist compound into the tissue surrounding the stent is preferably over a period of 3 to 6 months, and preferably 6 months. When the stent is coated with biodegradable polymers, the elution of the compound from the stent directly relates to the rate of degradation of the polymer.

$P2Y_{12}$ receptor antagonists useful in this invention are compounds that do not require hepatic, renal or any other metabolic transformation to become pharmacologically active. The compound can be a prodrug if the conversion of the prodrug into the active species is carried out locally in the release area. For example, an ester prodrug can be converted into an active drug by tissue esterases such as endothelial esterases. All ester forms of $P2Y_{12}$ receptor antagonists are included in the application.

Recently, Wihlborg et al. describe the presence of $P2Y_{12}$ receptors in vascular smooth muscle (*Arterioscler. Thromb.*

Vasc. Biol. 2004; 24: 1810-1815). The activation of these $P2Y_{12}$ receptors by endogenously released ADP results in vasoconstriction. This effect contributes to tonic contraction of smooth muscle cells by circulating ADP, or by released ADP from adhering platelets, endoethelial cells and leukocytes attracted to the damaged area as part of the healing process. $P2Y_{12}$ receptor activation is associated with an increase in cell proliferation and the onset of inflammation; both of these effects contribute to in-stent restenosis observed in approximately 10% of the patients treated with currently marketed stents.

Applicants have discovered the therapeutic benefits of $P2Y_{12}$ receptor antagonists-eluting stents. The elution of $P2Y_{12}$ receptor antagonists to local stented tissues can prevent the stenosis of stented arteries by relaxing the arterial smooth muscle, which results in an increase in blood flow rate of the stented artery and a decrease in shear forces that could promote thrombosis. Additionally, the inhibition of vascular smooth muscle contraction in stented arteries can decrease the risk of ischemia and thrombosis. Therefore, the use of $P2Y_{12}$ receptor antagonists-eluting stents improves the therapeutic benefit of current stents by decreasing the incidence of thrombosis and restenosis and improving of the flow rate of perfusion of the stented artery due to the relaxing activity of smooth muscle cells.

$P2Y_{12}$ receptor antagonist compound-eluting stents can be used as in situ antithrombotics to decrease the risk of stent thrombosis by a constant delivery of the $P2Y_{12}$ antagonist for several months. This treatment decreases the risk of thrombosis by inhibiting the aggregation of platelets in the stented artery. $P2Y_{12}$ receptor antagonist compounds are useful to coat all types of stents, including coronary stents, cerebral arterial stents (basilar or vertebral arteries), other arterial stents (aortic, carotid, renal, peripheral, etc), and vein stents (portal, renal, including vein graft conduits). Peripheral artery is defined as an artery that carries blood to upper and lower extremities. $P2Y_{12}$ receptor antagonist eluting stents are useful for saphenous vein grafts previously grafted in coronary arteries, which have reduced patency due to restenosis or thrombosis. Preferred stents for this invention are coronary stents.

Marketed $P2Y_{12}$ antagonists such as PLAVIX® and TICLID® are not suitable for coating stents because PLAVIX® and TICLID® need to be metabolized in the liver in order to generate the active metabolites. The $P2Y_{12}$ receptor antagonists of the present invention do not require metabolism for activation, and therefore they are capable of exerting their antithrombotic and smooth muscle relaxing activity in situ.

P2Y12 receptor antagonist compound-eluting stents provide the advantages of inhibiting the contraction of vascular smooth muscle cells, inhibiting cell proliferation, and reducing inflammation. P2Y12 receptor antagonist compound-eluting stents are useful in preventing the thrombosis and restenosis observed on patients after placement of bear metal and other drug-eluting stents.

Currently, patients who receive stents require the prophylactic treatment with anti thrombotic drugs for at least 3 months to reduce the risk of thrombosis. The local delivery of an antiplatelet and vascular smooth muscle relaxant drug with potential for anti-inflammatory effects (due to the inhibition of platelet activation and release of pro-inflammatory substances) such as the P2Y12 receptor antagonists of the present invention provide additional benefit compared with the current stent therapy.

The present invention provides a method for treating blocked or narrowed arteries. The method comprises the step of placing a P2Y12 receptor antagonist compound-eluting stent according to claim 1 in a narrowed or blocked artery of a patient, whereby a therapeutically effective amount of the compound is eluted to the stented area, whereby the blood flow is resumed by the stent and the restenosis and thrombosis are prevented by the P2Y12 receptor antagonist compound. The artery can be, for example, coronary artery, cerebral artery, or peripheral artery, which has been narrowed or blocked by a plaque or a plaque rupture, respectively. The inserted stent delivers P2Y12 receptor antagonist compound locally to the stented area, and decreases the incidence of thrombosis and restenosis. The method optionally comprises the step of monitoring the patient to ensure patency of the stented artery. For example, when the stent is inserted into the coronary artery, the patient can be monitored by clinical symptoms of the cardic function, e.g., electrocardiogram (EKG), to determine if the blood flow in the heart muscle is restored. When the stent is inserted into the carotid artery, the patient can be monitored by ultrasound to determine if the narrowed artery is restored, and by evaluation of clinical symptoms such as headache, facial droop, loss of coordination, vertigo and depressed mental status. When the stent is inserted into the cerebral arteries, the patient can be monitored by neurological examinations including clinical symptoms such as headache, facial droop, loss of coordination, vertigo and depressed mental status.

Preparation of $P2Y_{12}$ Receptor Antagonist Compound-Eluting Stents

Stents are frequently made from stainless steel. Stents can be made of any biocompatible metal, including, but not limited to, steel, cobalt, titanium, tantalum, chromium, zirconium, niobium, tungsten, platinum, palladium, vanadium, silver, gold, molybdenum, nickel, or magnesium, and alloys thereof in any combination. Alternately, stents can be constructed of non-metallic biocompatible materials, such as bioabsorbable or biostable polymers.

The preparation of drug-eluting stents has been described in Kavanagh, et al. (*Pharmacology & Therapeutics,* 102: 1-15, 2004), Doorty, et al. (*Cardiovascular Pathology,* 12: 105-110, 2003), Hossainy (U.S. Pat. No. 6,908,624). Both articles are incorporated herein by reference in their entirety.

In general, $P2Y_{12}$ receptor antagonist compounds of the present invention are preferably not attached directly (covalently of non-covalently) to the surface of an unmodified stent. In order to deliver the compounds of the present invention to the site of action, the stent is preferably coated with an organic or inorganic polymer (or polymers) or some other substance (such as an inorganic coating) that is able to retain the compound to be delivered and release it at a desired rate. The nature of this retention can be covalent or non-covalent, with the latter being preferred.

In one embodiment, the stent is first modified by coating it with an inorganic substance or an organic or inorganic polymer which is capable of binding the compound to the stent surface. For example, when the $P2Y_{12}$ receptor antagonist compound bears a phosphate or other acidic moiety, the stent is first coated with a substance or a polymer that bears a basic moiety, and the compound is bound to the modified stent by an ionic interaction. When the $P2Y_{12}$ receptor antagonist compound bears a basic moiety, the stent is first coated with a substance or a polymer that bears an acidic moiety, and the compound is bound to the modified stent by an ionic interaction.

In another embodiment, the $P2Y_{12}$ receptor antagonist compound is first incorporated into a compatible polymer matrix, which is then used to coat a stent. The advantage of this approach is that the elution of the $P2Y_{12}$ receptor antagonist compound from the stent depends on the property of the polymer, thus one can select a suitable polymer, which provides controlled and sustained release of the $P2Y_{12}$ receptor antagonist compound to the site of action. The polymer can be hydrophilic, hydrophobic, biodegradable, or biostable, thus one can further select a polymer to optimize the desired therapeutic effect.

The present invention provides a composition comprising at least one biodegradable polymer and at least one $P2Y_{12}$ receptor antagonist compound of general Formula I, wherein said biodegradable polymer is selected from the group consisting of polycaprolactone, polylactic acid, poly(lactide-co-glycolide), poly(hydroxybutyrate), poly(hydroxybutyrate-covalerate), polydioxanone, polyorthoester, polyanhydride, poly(glycolic acid), poly(glycolic acid-cotrimethylene carbonate), polyphosphoester, polyphosphoester urethane, poly (amino acids), poly(trimethylene carbonate), poly(iminocarbonate), cyanoacrylates, polyalkylene oxalates, polyphosphazenes, aliphatic polycarbonates, cellulose, starch, dextran, hyaluronic acid, and collagen.

The present invention further provides a composition comprising at least one biostable polymer and at least one $P2Y_{12}$ receptor antagonist compound of general Formula I, wherein said biostable polymer is selected from the group consisting of polyurethanes, polyesters, polyamides, polyolefins, polycaprolactam, polyvinyl chloride, polyvinyl alcohol, poly(ethylene-vinyl alcohol), polyethers, silicones, acrylate polymers and copolymers, polyvinylmethyl ether, polyimide, and polyacrylonitrile.

When biodegradable polymers are used, the $P2Y_{12}$ receptor antagonist compound is incorporated into the polymer matrix and released in a controlled manner by a gradual degradation of the polymer matrix. This degradation can occur by various processes, including hydrolysis, metabolism, bulk erosion, or polymer surface erosion. When biostable polymers are used, the $P2Y_{12}$ receptor antagonist compound is uniformly distributed in the polymer or encapsulated within the polymer, from which the compound is eluted via diffusion processes or through pores of the polymer structure.

The $P2Y_{12}$ receptor antagonist compound can be incorporated into the polymer via processes known to those skilled in the art. These include, but are not limited to, encapsulation of the compound within a polymer matrix during polymer synthesis prior to application of the polymer to the stent, dissolving both polymer and the compound in an appropriate solvent and applying the solution to a stent, after which the solvent is allowed to evaporate and the stent is allowed to dry, or precoating a stent with a polymer, after which the therapeutic agent is applied as a solution in an appropriate solvent. Application methods can include, but are not limited to, spraying, dipping, or spin coating processes.

The invention is illustrated further by the following examples that are not to be construed as limiting the invention in scope to the specific procedures described in them.

EXAMPLES

Example 1

Preparation of 5'-aryl ether derivatives

5-Amino-2-{2-benzyl-6-[6-(3-phenyl-ureido)-purin-9-yl]-tetrahydro-furo[3,4-d][1,3]dioxol-4-yl-methoxy}-benzoic acid (2)

Adenosine (10 g, 37 mmol was dissolved in N,N-dimethyl formamide (100 mL) and dimethoxypropane (25 mL) followed by addition of Amberlyst $15H^+$ resin. The mixture was stirred 3 h at 55° C. The resin was removed by filtration and the solvents removed in vacuo, affording 2',3'-di-O-isopropylidene adenosine (11 g, 95%).

This product (6 g, 20 mmol) was dissolved in N,N-dimethyl formamide (22 mL) and stirred with triisopropylsilyl chloride and imidazole 16 h at 23° C. The solution was partitioned between ether (200 mL) and brine (100 mL) and the ether phase washed with additional brine (2×50 mL). The ether was dried over magnesium sulfate and evaporated, affording 5'-O-triisopropylsilyl-2',3'-di-O-isopropylidene adenosine.

This residue was dissolved in toluene (20 mL) and treated with phenylisocyanate (3.6 g, 30 mmol) for 16 h at 25° C. A solution of sodium bicarbonate (1 mL of 10 M) was added and the mixture evaporated to dryness. The residue was partitioned between ethyl acetate (100 mL) and water (25 mL). The organic phase was dried with magnesium sulfate and evaporated to dryness. The solid was dissolved in tetrahydrofuran (20 mL) and stirred with tetrabutyl ammonium fluoride in tetrahydrofuran (20 mL of a 1 M solution) for 1 h in a dry ice/acetone bath. Removal of the solvent in vacuo followed by washing with hexane afforded the 5'-alcohol (5.3 g).

A portion of the above phenylurea product (0.41 g, 0.96 mmol) was suspended in 25 mL of 20% aqueous acetic acid and 5 mL of tetrahydrofuran /dioxane (1:1) and was stirred at 50° C. for 24 h. The white suspension became a clear yellow solution. The mixture was concentrated and then lyophilized, to give 0.360 g (97% yield) of 1-[9-(3,4-dihydroxy-5-hydroxymethyl-tetrahydro-furan-2-yl)-9H-purin-6-yl]-3-phenyl-urea as a yellow solid. MW calculated for $C_{17}H_{18}N_6O_5$ ($MH^+$) 387. found 387 by LCMS.

A small amount of 4A flame dried molecular sieves (cooled down by a flow of argon) was added to a vial containing a portion of the product immediately above (0.131 g, 0.34 mmol). The mixture was capped with a rubber septum and cooled down to 0° C. To this mixture trifluoroacetic acid (2.5 mL) was added via syringe and the mixture stirred at this temperature for 15 min. Phenyl acetaldehyde dimethylacetal (0.230 ml, 4 eq.) was added dropwise and the mixture stirred at 0° C. for 2 h. One more equivalent of phenyl acetaldehyde dimethyl acetal was added and stirred an additional five hours. The volatiles were evaporated off and the residue was purified by flash chromatography (hexane:ethyl acetate, 8:2, 1% triethylamine) to give 0.095 g of product (60% yield) as a yellow solid. MW calculated for $C_{25}H_{24}N_6O_5$ ($MH^+$) 489. found 489 by LCMS.

A portion of this acetal product (0.068 g, 0.14 mmol) was dissolved in dry N,N-dimethyl formamide (2.5 mL) and potassium tert-butoxide (0.084 g, 5 eq) was added to give a yellow solution. To this mixture was added 2-fluoro-5-nitrobenzoic acid (0.046 g, 1.8 eq). After 2.5 h of stirring at room temperature the mixture was concentrated and purified by preparative HPLC to give the nucleoside analog as a white powder. MW calculated for $C_{32}H_{27}N_7O_9$ ($MH^+$) 654. found 654 by LCMS.

The nitro group of the product immediately above was reduced under a hydrogen atmosphere with a catalytic amount of 10% Pd/C in methanol during 6 h. Filtration through Celite followed by HPLC purification yielded 52 mg (62% yield) of the title compound as clear semisolid.

Example 2

Preparation of 5'-heteroaryl ether derivatives

2-{2,2-Dimethyl-6-[6-(3-phenyl-ureido)-purin-9-yl]-tetrahydro-furo[3,4-d][1,3]dioxol-4-ylmethoxy}-nicotinic acid To a stirred solution of 1-[9-(6-hydroxymethyl-2,2-dimethyl-tetrahydro-furo[3,4-d][1,3]dioxol-4-yl)-9H-purin-6-yl]-3-phenyl-urea (43 mg, 0.1 mmol) in dry N,N'-dimethylformamide (1 mL) at 23° C. was added potassium tert-butoxide (45 mg, 0.4 mmol). After 30 min, 2-chloronicotinic acid (60 mg, 0.4 mmol) was added to the solution. The resulting mixture was stirred at 23° C. for 15 h and then quenched with water (1 mL), suspended in ethyl acetate (50 mL), washed with brine (3×), dried over anhydrous sodium sulfate, filtered and concentrated in vacuo to give the crude product. Preparative reverse-phase HPLC was used to obtain the pure compound (15 mg, 27% yield) as a white solid. $^1$H NMR (300 MHz, DMSO-$d_6$) δ 11.76 (s, 1H), 10.15 (s, 1H), 9.16 (s, 1H), 8.65 (s, 1H), 8.05 (dd, J=8.5 Hz, 3.5 Hz, 1H), 7.94 (dd, J=9.0 Hz, 3.0 Hz, 1H), 7.60 (d, J=2.0 Hz, 1H), 7.57 (d, J=2.0 Hz, 1H), 7.32 (t, J=12.5 Hz, 2H), 7.05 (t, J=12.5 Hz, 1H), 6.96 (dd, J=12.5 Hz, 8.5 Hz, 1H), 6.25 (d, J=6.0 Hz, 1H), 5.80 (t, J=7.5 Hz, 1H), 5.10 (dd, J=9.0 Hz, 2.5 Hz, 1H), 4.67 (m, 1H), 4.53 (dd, J=20.0 Hz, 4.0 Hz, 1H), 4.36 (dd, J=20.0 Hz, 4.0 Hz, 1H), 1.59 (s, 3H), 1.38 (s, 3H). MW calculated for $C_{26}H_{25}N_7O_7$ (MH$^+$) 548. found 548 by LCMS. Similarly, other 5'-substituted pyridines were prepared:

6-{2,2-Dimethyl-6-[6-(3-phenyl-ureido)-purin-9-yl]-tetrahydro-furo[3,4-d][1,3]dioxol-4-ylmethoxy}-nicotinic acid: (9 mg, 8% yield) as a white solid. $^1$H NMR (300 MHz, DMSO-$d_6$) δ 11.68 (s, 1H), 10.20 (s, 1H), 8.71 (s, 1H), 8.64 (d, J=3.0 Hz, 2H), 8.12 (dd, J=15.0 Hz, 3.5 Hz, 1H), 7.63 (d, J=2.0 Hz, 1H), 7.61 (d, J=1.5 Hz, 1H), 7.36 (t, J=13.0 Hz, 2H), 7.09 (t, J=12.5 Hz, 1H), 6.84 (dd, J=13.5 Hz, 1.0 Hz, 1H), 6.33 (d, J=3.5 Hz, 1H), 5.61 (dd, J=10.0 Hz, 4.0 Hz, 1H), 5.20 (dd, J=10.0 Hz, 4.5 Hz, 1H), 4.64 (m, 1H), 4.54 (m, 2H), 1.60 (s, 3H), 1.40 (s, 3H). MW calculated for $C_{26}H_{25}N_7O_7$ (MH$^+$) 548. found 548 by LCMS.

6-{2,2-Dimethyl-6-[6-(3-phenyl-ureido)-purin-9-yl]-tetrahydro-furo[3,4-d][1,3]dioxol-4-ylmethoxy}-pyridine-2-carboxylic acid: (5 mg, 4.6% yield) as a white solid. $^1$H NMR (300 MHz, DMSO-$d_6$) δ 11.64 (s, 1H), 10.15 (s, 1H), 8.68 (s, 1H), 8.60 (s, 1H), 7.83 (dd, J=13.5 Hz, 12.5 Hz, 1H), 7.62 (m, 3H), 7.34 (t, J=12.5 Hz, 2H), 7.06 (t, J=12.5 Hz, 1H), 6.96 (dd, J=13.0 Hz, 1.0 Hz, 1H), 6.30 (d, J=4.0 Hz, 1H), 5.59 (dd, J=10.0 Hz, 4.5 Hz, 1H), 5.17 (dd, J=10.0 Hz, 4.5 Hz, 1H), 4.64 (m, 1H), 4.50 (m, 2H), 1.58 (s, 3H), 1.38 (s, 3H). MW calculated for $C_{26}H_{25}N_7O_7$ (MH$^+$) 548. found 548 by LCMS.

5-Chloro-6-{2,2-dimethyl-6-[6-(3-phenyl-ureido)-purin-9-yl]-tetrahydro-furo[3,4-d][1,3]dioxol-4-ylmethoxy}-nicotinic acid: (11 mg, 1.5% yield) as a white solid. MW calculated for $C_{26}H_{24}ClN_7O_7$ (MH$^+$) 582. found 582 by LCMS.

6-Chloro-2-{2,2-dimethyl-6-[6-(3-phenyl-ureido)-purin-9-yl]-tetrahydro-furo[3,4-d][1,3]dioxol-4-ylmethoxy}-nicotinic acid (isomer A) & 2-Chloro-6-{2,2-dimethyl-6-[6-(3-phenyl-ureido)-purin-9-yl]-tetrahydro-furo[3,4-d][1,3]dioxol-4-ylmethoxy}-nicotinic acid (isomer B)

Two isomer were obtained from the reaction with 2,6-dichloronicotinic acid. The major product was A (80 mg, 69% yield). LC-MS calculated for $C_{26}H_{24}ClN_7O_7$ (MH$^+$) 582. found 582. The minor product was B (20 mg, 17% yield). MW calculated for $C_{26}H_{24}ClN_7O_7$ (MH$^+$) 582. found 582 by LCMS.

2-Chloro-6-{2,2-dimethyl-6-[6-(3-phenyl-ureido)-purin-9-yl]-tetrahydro-furo[3,4-d][1,3]dioxol-4-ylmethoxy}-isonicotinic acid: (60 mg, 52% yield) as a white solid. $^1$H NMR (300 MHz, DMSO-$d_6$) δ 11.63 (s, 1H), 10.18 (s, 1H), 8.68 (s, 1H), 8.61 (s, 1H), 7.6 (s, 1H), 7.59 (s, 1H), 7.36 (s, 1H), 7.33 (t, J=13.0 Hz, 2H), 7.06 (t, J=13.5 Hz, 1H), 6.29 (d, J=3.5 Hz, 1H), 5.63 (dd, J=10.0 Hz, 4.0 Hz, 1H), 5.17 (dd, J=10.0 Hz, 4.5 Hz, 1H), 4.64 (m, 1H), 4.47 (m, 2H), 1.60 (s, 3H), 1.38 (s, 3H). MW calculated for $C_{26}H_{24}ClN_7O_7$ (MH$^+$) 582. found 582 by LCMS.

6-{2,2-Dimethyl-6-[6-(3-phenyl-ureido)-purin-9-yl]-tetrahydro-furo[3,4-d][1,3]dioxol-4-ylmethoxy}-nicotinamide: (15 mg, 14% yield) as a white solid. $^1$H NMR (300 MHz, DMSO-$d_6$) δ 11.70 (s, 1H), 10.10 (s, 1H), 8.69 (s, 1H), 8.61 (s, 1H), 8.60 (d, J=4.0 Hz, 1H), 8.09 (dd, J=10.0 Hz, 4.0 Hz, 1H), 7.95 (s, 1H), 7.62 (s, 1H), 7.59 (s, 1H), 7.39 (s, 1H), 7.34 (t, J=15.0 Hz, 2H), 7.07 (t, J=12.5 Hz, 1H), 6.80 (d, J=14.0 Hz, 1.0 Hz, 1H), 6.31 (d, J=4.0 Hz, 1H), 5.59 (dd, J=10.5 Hz, 4.5 Hz, 1H), 5.17 (dd, J=10.0 Hz, 4.5 Hz, 1H), 4.63 (m, 1H), 4.49 (m, 2H), 1.59 (s, 3H), 1.39 (s, 3H). MW calculated for $C_{26}H_{26}N_8O_6$ (MH$^+$) 547. found 547 by LCMS.

6-Chloro-2-{2,2-dimethyl-6-[6-(3-phenyl-ureido)-purin-9-yl]-tetrahydro-furo[3,4-d][1,3]dioxol-4-ylmethoxy}-5-fluoro-nicotinic acid: (35 mg, 19% yield) as a white solid. MW calculated for $C_{26}H_{23}ClFN_7O_7$ (MH$^+$) 600. found 600 by LCMS.

1-{9-[6-(3-Hydroxy-pyridin-2-yloxymethyl)-2,2-dimethyl-tetrahydro-furo[3,4-d][1,3]dioxol-4-yl]-9H-purin-6-yl}-3-phenyl-urea Dry argon was bubbled through a solution of 1-{9-[6-(3-Benzyloxy-pyridin-2-yloxymethyl)-2,2-dimethyl-tetrahydro-furo[3,4-d][1,3]dioxol-4-yl]-9H-purin-6-yl}-3-phenyl-urea (18 mg, 0.03 mmol, prepared as above) in methanol/ethyl acetate (1:1 v/v, 10 mL) at 23° C. for 10 min. Palladium on activated carbon (10%) was added and the suspension was degassed by argon for another 5 min. Hydrogen (H$_2$) was conducted to the solution via a balloon, and the reaction proceeded for 5 h. The mixture was filtered and concentrated in vacuo to give the crude product. Preparative reverse-phase HPLC was used to obtain the pure compound (5 mg, 31% yield) as a white solid. MW calculated for $C_{25}H_{25}N_7O_6$ (MH$^+$) 520. found 520 by LCMS.

2-{2-Benzyl-6-[6-(3-phenyl-ureido)-purin-9-yl]-tetrahydro-furo[3,4-d][1,3]dioxol-4-ylmethoxy}-nicotinic acid 2-{2,2-Dimethyl-6-[6-(3-phenyl-ureido)-purin-9-yl]-tetrahydro-furo[3,4-d][1,3]dioxol-4-ylmethoxy}-nicotinic acid (180 mg, 0.33 mmol) was dissolved in a mixture of trifluoroacetic acid and water (TFA/H$_2$O, 4:1 v/v, 20 mL), and the suspension was stirred at 23° C. for 30 min. The solvents were removed under reduced pressure to give the intermediate diol product (120 mg, 72% yield) as a white solid. MW calculated for $C_{23}H_{21}N_7O_7$ (MH$^+$) 508. found 508 by LCMS.

To a stirred solution of the diol immediately above (0.23 mmol) in dry trifluoroacetic acid (5 mL) at 23° C. was added phenyl acetaldehyde (130 mg, 1.1 mmol). The resulting mixture was stirred at 23° C. for 6 h. After the removal of most trifluoroacetic acid by evaporation under reduced pressure, the reaction was quenched with saturated sodium bicarbonate solution (10 mL). The product was extracted using ethyl acetate (50 mL), washed with brine (3×), dried over anhydrous sodium sulfate, filtered and concentrated in vacuo to give the crude product. Preparative reverse-phase HPLC was used to obtain the pure acetal compound (7 mg, 5% yield) as a white solid. $^1$H NMR (300 MHz, DMSO-$d_6$) δ 11.67 (s, 1H), 10.50 (s, 1H), 8.68 (s, 1H), 8.51 (s, 1H), 8.27 (dd, J=8.0 Hz, 3.0 Hz, 1H), 8.10 (dd, J=10.0 Hz, 4.0 Hz, 1H), 7.60 (dd, J=14.0 Hz, 2.0 Hz, 1H), 7.30 (m, 7H), 7.08 (m, 3H), 6.21 (d, J=4.5 Hz, 1H), 5.51 (dd, J=10.5 Hz, 4.0 Hz, 1H), 5.32 (t, J=8.0 Hz, 1H), 5.06 (dd, J=10.0 Hz, 3.0 Hz, 1H), 4.70 (m, 1H), 4.62

(dd, J=20.0 Hz, 5.0 Hz, 1H), 4.45 (dd, J=20.0 Hz, 5.0 Hz, 1H), 3.10 (d, J=8.5 Hz, 2H). MW calculated for $C_{31}H_{27}N_7O_7$ (MH$^+$) 610. found 610 by LCMS.

Other 5'-substituted pyridine-ethers were transformed to various 2',3'-acetals using methods similar to those given immediately above.

Example 3

Synthesis of 5'-isoxazole Derivatives

3-[6-(6-Chloro-purin-9-yl)-2,2-dimethyl-tetrahydro-furo[3,4-d][1,3]dioxol-4-ylmethoxy]-isoxazole-5-carboxylic acid methyl ester To a solution of [6-(6-Chloro-purin-9-yl)-2,2-dimethyl-tetrahydro-furo[3,4-d][1,3]dioxol-4-yl]-methanol (0.570 g, 1.74 mmol) in 16 mL of dry dichloromethane was added polymer-bound triphenylphosphine (PS-TPP; Argonaut Tech., 2.14 mmol/g, 0.91 g, 1.2 eq), followed by methyl-3-hydroxy-5-isoxazolecarboxylate (0.248 g, 1 eq). The mixture was sonicated for 15 minutes then stirred at room temperature for 1 h under argon. The reaction mixture was cooled to 0° C. and under argon flow diethylazodicarboxylate (0.33 g, 1.1 eq), dissolved in 1 ml of dichloromethane, was added dropwise via syringe. The mixture was protected from light and stirred at 0° C. for 30 min. then at room temperature for 20 h. The resin was washed liberally with dichloromethane and methanol. The organic solution obtained from the washes was concentrated to give, after flash chromatography purification, 0.740 g of the product as a white solid (95% yield). $^1$H NMR (300 MHz, CDCl$_3$) δ 8.76 (s, 1H), 8.23 (s, 1H), 6.42 (s, 1H), 6.23 (d, J=2.1 Hz, 1H), 5.43 (dd, J=2.1 Hz, 1H), 5.14 (dd, J=3.6 Hz, 1H), 4.7 (m, 1H), 4.61 (dd, J=3.9 Hz, 1H), 4.49 (dd, J=5.7 Hz, 1H), 3.93 (s, 3H), 1.65 (s, 3H), 1.42 (s, 3H). MW calculated for $C_{18}H_{18}ClN_5O_7$ (MH$^+$) 452. found 452 by LCMS.

3-{6-[6-(N-Benzyl-N-methyl-amino)-purin-9-yl]-2,2-dimethyl-tetrahydro-furo[3,4-d][1,3]dioxol-4-yl-methoxy}-isoxazole-5-carboxylic acid To a solution of 3-[6-(6-Chloro-purin-9-yl)-2,2-dimethyl-tetrahydro-furo[3,4-d][1,3]dioxol-4-ylmethoxy]-isoxazole-5-carboxylic acid methyl ester (0.106 g, 0.23 mmol) in tetrahydrofuran (1.2 mL) was added polymer-bound diisopropylethylamine (PS-DIEA; Argonaut Tech., 3.83 mmol/g, 0.190 g, 3 eq), followed by addition of 0.040 mL of N-methyl-N-benzylamine (1.2 eq). The resulting mixture was stirred at room temperature overnight. The PS-DIEA resin was washed three times with dichloromethane and the solution obtained from the washes was concentrated to yield 3-{6-[6-(N-Benzyl-N-methyl-amino)-purin-9-yl]-2,2-dimethyl-tetrahydro-furo[3,4-d][1,3]dioxol-4-ylmethoxy}-isoxazole-5-carboxylic acid methyl ester as yellow oil. This material (0.23 mmol) was dissolved in 1,4-dioxane (1.2 mL) and 0.250 mL of an aqueous 2M lithium hydroxide solution added. The mixture was stirred at room temperature for 4 h. The crude product, isolated after acid workup, was used without further purification in the following step. MW calculated for $C_{25}H_{26}N_6O_7$ (MH$^+$): 523. found 523 by LCMS.

3-{2-Benzyl-6-[6-(N-methyl-N-benzyl-amino)-purin-9-yl]-tetrahydro-furo[3,4-d][1,3]dioxol-4-ylmethoxy}-isoxazole-5-carboxylic acid A solution of the above acetonide (0.075 g, 0.140 mmol) dissolved in 1.5 mL of dry dichloromethane was cooled in an ice bath to 0° C. To this clear mixture was added 1.8 mL of trifluoroaceic acid. The mixture was stirred at 0° C. for 5 h to afford the intermediate diol as a yellow semisolid after evaporative workup. This crude product (0.23 mmol) was dissolved at 0° C. in 1 mL of dry trifluoroacetic acid in the flask. To this mixture was added a small amount of 3 A molecular sieves (previously dried by flame in situ and cooled by a stream of argon). The flask was capped with a rubber septum and cooled to 0° C., then 0.1 mL of phenyl acetaldehyde dimethyl acetal was added and the mixture stirred for 18 h at 0° C. At that point, 0.1 mL more of acetal was added and stirred an additional 6 h. Purification by HPLC yielded 52 mg of the desired product as a clear semisolid (62% yield). MW calculated for $C_{30}H_{28}N_6O_7$ (MH$^+$): 585. found 585 by LCMS.

Example 4

Solution Phase Synthesis of 5'-carboxamide Adenosine Analogs 2',3'-O-Isopropylideneadenosine-5'-carboxylic acid In a reaction vessel, bis-acetoxyiodobenzene (BAIB, 1.15 g, 3.58 mmol), 2,2,6,6-tetramethyl-1-piperidinyloxy (TEMPO, 0.051 g, 0.325 mmol), and 2',3'-isopropylideneadenosine (0.500 g, 1.63 mmol) were combined, and 3 mL of 1:1 acetonitrile: water mixture was added to the reaction vessel. The reaction mixture was stirred at ambient temperature under argon for 1 h then filtered. The white crystalline product was washed with acetonitrile:water mixture (1:1) and dried in vacuo, to yield 0.464 g of product, 89%. $^1$H NMR (300 MHz, CD$_3$SOCD$_3$) δ 12.77 (br s, 1H), 8.22 (s, 1H), 8.06 (s, 1H), 7.27 (s, 2H), 6.32 (s, 1H), 5.52 (dd, J1=5.7 Hz, J2=1.8 Hz, 1H), 5.45 (d, J=9.5 Hz, 1H), 4.67 (d, J=1.5 Hz, 1H), 1.52 (s, 3H), 1.35 (s, 3H).

2-({2,2-Dimethyl-6-[6-(3-phenyl-ureido)-purin-9-yl]-tetrahydro-furo[3,4-d][1,3]dioxole-4-carbonyl}-amino)-benzoic acid methyl ester To a vial containing 2',3'-O-Isopropylideneadenosine-5'-carboxylic acid (0.241 g, 0.75 mmol) was added 3-aminobenzoic acid methyl ester (0.144 g, 0.75 mmol) in one portion at RT followed by heating at 50° C. overnight. The reaction mixture was diluted with 100 ml of ethyl acetate, washed with 1N hydrochloric acid, saturated sodium bicarbonate, brine, and dried over MgSO$_4$. Upon removal of solvent, the solid residue was purified with chromatography with 2-5% methanol in dichloromethane to give 90 mg (26%) of the carboxamide as white solid. MW calculated for $C_{21}H_{22}N_6O_6$ (MH$^+$) 455. found 455 by LCMS. This carboxamide product (90 mg, 0.20 mmol) was dissolved in DMF (2 mL) and added to a flask containing phenyl isocyanate (35 mg, 0.30 mmol) in 2 ml of toluene at 50° C. The reaction was stirred at 50° C. overnight. Additional phenyl isocyanate (35 mg, 0.20 mmol) was then added in several portions until nearly complete consumption of the starting material was noted by TLC analysis. The reaction mixture was then diluted with ethyl acetate (100 ml), washed with saturated sodium bicarbonate, brine, and dried over magnesium sulfate. The crude product was purified by a chromatography with 0-2% methanol in dichloromethane to give 57 mg (50%) of pure product and recovered starting material (10 mg). $^1$H NMR (300 MHz, CDCl$_3$) δ 11.53 (s, 1H), 9.21 (s, 1H), 8.54 (s, 1H), 8.36 (s, 1H), 8.21 (s, 1H), 7.72 (m, 1H), 7.58 (m, 2H), 7.38 (m, 2H), 7.24 (m, 1H), 7.12 (m, 1H), 6.29 (d, J=2.1 Hz, 1H), 5.66 (dd, J=6.3, 1.5 Hz, 1H), 5.56 (dd, J=6.3, 1.5 Hz, 1H), 4.88 (d, J=1.8 Hz, 1H), 3.78 (s, 3H), 1.65 (s, 3H), 1.44 (s, 3H). MW calculated for $C_{28}H_{27}N_7O_7$ (MH$^+$): 574. found 574 by LCMS.

3-({2,2-Dimethyl-6-[6-(3-phenyl-ureido)-purin-9-yl]-tetrahydro-furo[3,4-d][1,3]dioxole-4-carbonyl}-amino)-benzoic acid To a vial containing 2',3'-O-Isopropylideneadenosine-5'-carboxylic acid (250 mg, 0.778 mmol), triethylamine (1.57 mg, 1.56 mmol), and 3-amino-benzoic acid allyl ester (0.276 mg, 1.56 mmol) in 0.5 ml of N,N-dimethyl formamide at 0° C. was added PyBOP (0.443 mg, 0.856 mmol) in one portion. Reaction was continued at 0° C. for 4 h and at ambient for 4 h. Additional PyBOP (50 mg) was added and the reaction continued overnight at ambient temperature. The reaction mixture was diluted with ethyl acetate (100 ml), washed with saturated sodium bicarbonate, brine, and dried over magnesium sulfate. The crude was purified by a chromatography with 0-2% methanol in dichloromethane to give the desired amide product. MW calculated for $C_{23}H_{24}N_6O_6$ (MH$^+$) 481. found 481 by LCMS.

Phenyl isocyanate was coupled with the amide product using a method similar to those described above, affording the intermediate phenylurea compound. MW calculated for $C_{30}H_{29}N_7O_7$ (MH$^+$) 600. found 600 by LCMS.

This phenylurea compound (36 mg, 0.057 mmol) and morpholine (0.015 mg, 0.17 mmol) were dissolved in tetrahydrofuran (5 ml) followed by addition of tetrakis(triphenylphosphine)palladium (5 mg, 0.004 mmol). Reaction was completed in 4 h at RT. After removal of the solvent, the crude product mixture was purified by preparative HPLC to give the desired product. $^1$H NMR (300 MHz, CDCl$_3$) δ 11.52 (s, 1H), 9.99 (s, 1H), 9.60 (s, 1H), 8.61 (s, 1H), 8.42 (s, 1H), 7.94 (s, 1H), 7.72 (m, 4H), 7.34 (m, 2H), 7.23 (m, 1H), 7.06 (m, 1H), 6.56 (s, 1H), 5.56 (m, 2H), 4.88 (s, 1H), 1.58 (s, 3H), 1.39 (s, 3H).

Example 5

Solution Phase Synthesis of a Sulfonamide

N-{2,2-Dimethyl-6-[6-(3-phenyl-ureido)-purin-9-yl]-tetrahydro-furo[3,4-d][1,3]dioxole-4-carbonyl}-methanesulfonamide To a vial containing 2',3'-O-Isopropylideneadenosine-5'-carboxylic acid (20 mg, 0.045 mmol), dimethylaminopyridine (5 mg, 0.045 mmol), and methanesulfonamide (0.009 mg, 0.091 mmol) in dichloromethane (0.5 ml) was added dicyclohexylcarbodiimide (10 mg, 0.05 mmol). The mixture was stirred for 2 days at RT. Additional dicyclohexylcarbodiimide (10 mg, 0.05 mmol) and dimethylaminopyridine (5 mg, 0.045 mmol) were added and the reaction was continued at RT overnight. To the reaction mixture was added ethyl acetate (75 ml), which was washed with 1 N hydrochloric acid, water, saturated sodium bicarbonate, brine, and dried over magnesium sulfate. Upon removal of solvent, the residue was purified by prep. HPLC to yield 13 mg of desired product (55%). MW calculated for $C_{21}H_{23}N_7O_7S$ (MH$^+$) 518. found 518 by LCMS.

Example 6

Solid Phase Synthesis of Ureas and Acetals from Polymer Bound 5'-proline-amides of Adenosine Commercially available hydroxymethylsulfanylmethyl (HESM) polystyrene resin (1.4 mmol/g, 200 mesh, NovaBiochem; 2.82 g, 3.95 mmol) was swelled for 15 minutes in 50 mL. In a separate reaction vessel, Boc-Pro-OH (3.40 g, 15.8 mmol), HATU (5.7 g, 15.0 mmol), dimethylaminopyridine (0.24 g, 1.98 mmol), and diisopropylethylamine (3.5 mL, 19.8 mmol) were dissolved in 40 mL of N,N-dimethyl formamide and stirred for 15 minutes. N,N-dimethyl formamide was drained from the HESM resin and the solution of activated proline derivative was added to the resin. The resin was agitated at RT for 17 h. The solvent was then drained and the resin washed with N,N-dimethyl formamide (3×30 mL), dichloromethane (3×30 mL), methanol (3×30 mL), dichloromethane (2×30 mL), methanol (3×30 mL) and dried in vacuo overnight. Mass of resin: 3.42 g, 93% loading.

Removal of BOC Protecting Group:

Resin obtained in the previous step was agitated with a 40% trifluoroacetic acid/dichloromethane solution (75 mL) for 15 minutes. The solvent was drained, and a fresh solution of 40% trifluoroacetic acid in dichloromethane was added, and resin was agitated for another 15 minutes. After this the resin was washed with dichloromethane (5×40 mL), 20% diisopropylethylamine/dichloromethane (2×30 mL), dichloromethane (3×30 mL), and methanol (5×40 mL). The resin was dried under vacuum. A chloranil test indicated the presence of a free amino group, and this proline-bound resin was carried over to the next step.

The proline resin product from the previous step was swelled in 50 mL N,N-dimethyl formamide for 30 minutes, after that the N,N-dimethyl formamide was drained. In a separate reaction vessel, 2',3'-O-Isopropylideneadenosine-5'-carboxylic acid (1.40 g, 4.35 mmol), dichloroethane (0.91 g, 4.74 mmol), HOBtH$_2$O (0.73 g, 4.74 mmol), and diisopropylethylamine (3.5 mL, 19.8 mmol) were dissolved in 55 mL of N,N-dimethyl formamide. The solution was stirred for 15 minutes, and then added to the proline resin. The resin was agitated at RT for 17 h. The solvent was drained, the resin was washed with N,N-dimethyl formamide (3×30 mL), dichloromethane (3×30 mL), methanol (3×30 mL), dichloromethane (2×30 mL), methanol (3×30 mL), and dried in vacuo for 48 h. A chloranil test performed on a few sample beads indicated that coupling had occurred. A small amount of resin was cleaved using the following procedure to verify attachment of the carboxylic acid, and analysed by LCMS. Calculated mass for $C_{18}H_{22}N_6O_6$ (MH$^+$): 419. found 419 by LCMS. Mass of resin: 3.66 g, 0.55 mmol/g, 82% in three steps.

General Cleavage Procedure for Analysis of HESM Resin:

A small amount of resin is suspended in a solution of 5-6 equivalents of m-chloroperbenzoic acid in dichloromethane and agitated for 7-8 hours at RT. The solution is then drained, and the resin is washed 5-6 times with fresh dichloromethane. Then resin is suspended in a solution of 4-5 equivalents of DBU in dichloromethane, and agitated at RT for 4-5 hours. The resin is then filtered and the solution is analyzed by LC/MS, HPLC or another method. The compounds are recovered from solution by rotary evaporation.

The adenosine-proline amide-derivatized resin from the previous resin-synthesis step (0.5 g, 0.275 mmol) was suspended in anhydrous N,N-dimethyl formamide (10 mL). Ethyl isocyanate was added (0.43 mL, 5.5 mmol), and the reaction mixture was heated in a capped vial at 55° C. for 16 h. The resin was then drained and washed with N,N-dimethyl formamide (3×10 mL), dichloromethane (3×10 mL), methanol (3×10 mL), dichloromethane (2×10 mL), methanol (3×10 mL), and the procedure was repeated once again then the resin dried in vacuo for 24 h. A negative chloranil test indicated complete reaction. A small amount of this resin (bound to the 5'-adenosine-(2',3'-acetonide)-proline amide-derivatized as the 6-ethylurea) was cleaved by the procedure described for cleavage of HESM resin, and the isolated product was analyzed by LCMS. Mass calculated for $C_{21}H_{27}N_7O_7$ (MH$^+$): 490. found 490 by LCMS. Loading 0.52 mmol/g, mass 0.52 g, 98%.

The procedure described above was also used to prepare N$^6$-ureas with $R_d$=—$C_6H_{11}$, -Ph, —CH$_2$Ph, —CH$_2$CH$_2$Ph, -cyclopentyl, and trans-2-phenyl-cycloprop-1-yl groups using the appropriate isocyanates.

1-{6-[6-(3-Ethyl-ureido)-purin-9-yl]-2-phenyl-tetrahydro-furo[3,4-d][1,3]dioxole-4-carbonyl}-pyrrolidine-2-carboxylic acid The resin described above (0.05 g, 0.026 mmol) was suspended in trifluoroacetic acid, then benzaldehyde (0.095 g, 0.9 mmol) was added all at once. The resin was agitated in a tightly closed vial for 24 h. The resin was drained, washed with dichloromethane (5×3 mL), 20% diisopropylethylamine/dichloromethane (2×3 mL), dichloromethane (3×3 mL), and methanol (5×3 mL), then dried in vacuo for 3 h. The resin was cleaved using the cleavage procedure described above, the crude product was collected, analyzed by LCMS and purified by preparative HPLC. Calculated MW for $C_{25}H_{27}N_7O_7$ (MH$^+$): 538. found: 538 by LCMS.

The following analogs were prepared in a similar manner to that described above, using appropriate combinations of isocyanates and aldehydes. Compounds analyzed by LCMS.

$R_d$=ethyl, $R_a$=benzyl Calculated MW for C26H29N7O7: 552.55 (MH$^+$). found: 552.4.

$R_d$=ethyl, $R_a$=4-biphenyl Calculated MW for C31H31N7O7: 614.62 (MH$^+$). found: 614.3

$R_d$=ethyl, $R_a$=3-biphenyl Calculated MW for C31H31N7O7: 614.62 (MH$^+$). found: 614.3

$R_d$=ethyl, $R_a$=2-naphthyl Calculated MW for C29H29N7O7: 588.58 (MH$^+$). found: 588.1.

$R_d$=n-hexyl, $R_a$=phenyl Calculated MW for C29H35N7O7: 594.63 (MH$^+$). found: 594.3.

$R_d$=n-hexyl, $R_a$=benzyl Calculated MW for C30H37N7O7: 608.65 (MH$^+$). found: 608.2.

$R_d$=n-hexyl, $R_a$=4-biphenyl Calculated MW for C35H39N7O7: 670.73 (MH$^+$). found: 670.3.

$R_d$=n-hexyl, $R_a$=3-biphenyl Calculated MW for C35H39N7O7: 670.73 (MH$^+$). found: 670.3.

$R_d$=n-hexyl, $R_a$=2-naphthyl Calculated MW for C33H37N7O7: 644.69 (MH$^+$). found: 644.3.

$R_d$=cyclopentyl, $R_a$=benzyl Calculated MW for C29H33N7O7: 592.62 (MH$^+$). found: 592.3.

$R_d$=cyclopentyl, $R_a$=phenyl Calculated MW for C28H31N7O7: 578.59 (MH$^+$). found: 578.3.

$R_d$=cyclopentyl, $R_a$=4-biphenyl Calculated MW for C34H35N7O7: 654.68 (MH$^+$). found: 654.3.

$R_d$=cyclopentyl, $R_a$=3-biphenyl Calculated MW for C34H35N7O7: 654.68 (MH$^+$). found: 654.3.

$R_d$=cyclopentyl, $R_a$=2-naphthyl Calculated MW for C32H33N7O7: 628.65 (MH$^+$). found: 628.4.

$R_d$=benzyl, $R_a$=benzyl Calculated MW for C31H31N7O7: 614.62 (MH$^+$). found: 614.3.

$R_d$=benzyl, $R_a$=phenyl Calculated MW for C30H29N7O7: 600.59 (MH$^+$). found: 600.3.

$R_d$=benzyl, $R_a$=2-naphthyl Calculated MW for C34H31N7O7: 650.65 (MH$^+$). found: 650.3.

$R_d$=benzyl, $R_a$=4-biphenyl Calculated MW for C36H33N7O7: 676.69 (MH$^+$). found: 676.3.

$R_d$=benzyl, $R_a$=3-biphenyl Calculated MW for C36H33N7O7: 676.69 (MH$^+$). found: 676.3.

$R_d$=ethylphenyl, $R_a$=benzyl Calculated MW for C32H33N7O7: 628.65 (MH$^+$). found: 628.3.

$R_d$=ethylphenyl, $R_a$=phenyl Calculated MW for C31H31N7O7: 614.62 (MH$^+$). found: 614.5.

$R_d$=ethylphenyl, $R_a$=4-biphenyl Calculated MW for C37H35N7O7: 690.72 (MH$^+$). found: 690.4.

$R_d$=ethylphenyl, $R_a$=3-biphenyl Calculated MW for C37H35N7O7: 690.72 (MH$^+$). found: 690.5.

$R_d$=ethylphenyl, $R_a$=2-naphthyl Calculated MW for C35H33N7O7: 664.68 (MH$^+$). found: 664.4.

$R_d$=cyclopropyl-trans-2-phenyl, $R_a$=benzyl Calculated MW for C33H33N7O7: 640.66 (MH$^+$). found: 640.3.

$R_d$=cyclopropyl-trans-2-phenyl, $R_a$=3-biphenyl Calculated MW for C38H35N7O7: 702.73 (MH$^+$). found: 702.6.

$R_d$=cyclopropyl-trans-2-phenyl, $R_a$=2-naphthyl Calculated MW for C36H33N7O7: 676.69 (MH$^+$). found: 676.6.

$R_d$=phenyl, $R_a$=benzyl Calculated MW for C30H29N7O7: 600.59 (MH$^+$). found: 600.3.

$R_d$=phenyl, $R_a$=phenyl Calculated MW for C29H27N7O7: 586.57 (MH$^+$). found: 586.2.

$R_d$=phenyl, $R_a$=2-naphthyl Calculated MW for C33H29N7O7: 636.63 (MH$^+$). found: 636.5.

$R_d$=phenyl, $R_a$=4-biphenyl Calculated MW for C35H31N7O7: 662.66 (MH$^+$). found: 662.5.

$R_d$=phenyl, $R_a$=3-biphenyl Calculated MW for C35H31N7O7: 662.66 (MH$^+$). found: 662.5.

$R_d$=phenyl, $R_a$=3-thianaphthene Calculated MW for C31H27N7O7S: 642.65 (MH$^+$). found: 642.0.

$R_d$=ethylphenyl, $R_a$=3-thianaphthene Calculated MW for C33H31N7O7S: 670.71 (MH$^+$). found: 670.0.

$R_d$=ethylphenyl, $R_a$=3-thianaphthene Calculated MW for C32H29N7O7S: 656.68 (MH$^+$). found: 656.1.

$R_d$=n-hexyl, $R_a$=3-thianaphthene Calculated MW for C31H35N7O7S: 650.72 (MH$^+$). found: 650.2.

$R_d$=n-hexyl, $R_a$=CHCHPh Calculated MW for C31H37N7O7: 620.67 (MH$^+$). found: 620.4.

$R_d$=n-hexyl, $R_a$=CCPh Calculated MW for C31H35N7O7: 618.65 (MH$^+$). found: 618.0.

$R_d$=cyclopropyl-trans-2-phenyl, $R_a$=CCPh Calculated MW for C34H31N7O7: 650.65 (MH$^+$). found: 650.1.

$R_d$=ethylphenyl, $R_a$=CCPh Calculated MW for C33H31N7O7: 638.64 (MH$^+$). found: 638.1.

$R_d$=benzyl, $R_a$=CCPh Calculated MW for C32H29N7O7: 624.62 (MH$^+$). found: 624.1.

$R_d$=ethyl, $R_a$=CCPh Calculated MW for C27H27N7O7: 562.55 (MH$^+$). found: 562.0.

$R_d$=cyclopropyl-trans-2-phenyl, $R_a$=4-biphenyl Calculated MW for C38H35N7O7: 702.73 (MH$^+$). found: 702.1.

$R_d$=cyclopropyl-trans-2-phenyl, $R_a$=phenyl Calculated MW for C32H31N7O7: 626.63 (MH$^+$). found: 626.0.

$R_d$=cyclopropyl-trans-2-phenyl, $R_a$=CHCHPh Calculated MW for C34H33N7O7: 652.67 (MH$^+$). found: 652.1.

$R_d$=ethylphenyl, $R_a$=CHCHPh Calculated MW for C33H33N7O7: 640.66 (MH$^+$). found: 640.3.

Example 7

Synthesis of a 5' Sulfonylurea as in Scheme 10

1-[9-(2-Benzyl-6-ureidomethyl-tetrahydro-furo[3,4-d][1,3]dioxol-4-yl)-9H-purin-6-yl]-3-phenyl-urea methylsulfonamide In a reaction vessel were combined 2',3'-O-benzylidene-N6-(phenylurea)adenosine ((0.200 g, 0.409 mmol), p-toluene sulfonyl chloride (0.148 g, 0.778 mmol), and 4.0 mL of pyridine. The mixture was stirred for 4 h at RT. The solvent was removed in vacuo and the tosylate (0.260 g, 99%) was recovered as a yellow solid. MW calculated for $C_{32}H_{30}N_6O_7S$: 643.19 ($MH^+$). found 642.9.

This tosylate product (0.260 g, 0.409 mmol) was dissolved in 3 mL of anhydrous N,N-dimethyl formamide, sodium azide (0.266 g, 4.09 mmol) was added, and the mixture was heated at 80° C. in a closed vial for 7 h while being stirred. The mixture was diluted with 50 mL of dichloromethane and extracted with 5% sodium bicarbonate solution and brine. The organic layer was separated, dried over anhydrous sodium sulfate and solvent was removed in vacuo. The azide derivative was recovered (0.183 g, 87%) as a white solid. MW calculated for $C_{25}H_{23}N_9O_4$: 514.19 ($MH^+$). found 514.1.

This residue containing the azide (0.180 g, 0.351 mmol) was dissolved in 6 mL of tetrahydrofuran/water mixture (18:1), polystyrene-bound triphenylphospine was added (2.19 mmol/g, 0.800 g, 1.75 mmol), and the reaction mixture was stirred at RT under argon for 24 h. The reaction mixture was then filtered, the solvent was removed in vacuo and the crude product was chomatographed on a silica gel column (2 cm×15 cm). The column was eluted with dichloromethane/methanol/triethylamine (88:10:2) to give 0.072 g (42%) of the amine as a white solid. MW calculated for $C_{25}H_{25}N_7O_4$: 488.20 ($MH^+$). found 488.0.

A portion of the amine product above (0.022 g, 0.046 mmol) was dissolved in 2 mL of dichloromethane (anhydrous) and methylsulfonylethylcarbamate (0.008 g, 0.046 mmol) was added. The reaction was stirred at RT under argon for 72 h. Solvent was then removed in vacuo, and the crude product was purified by preparative HPLC (acetonitrile/0.1% trifluoroacetic acid//water/0.1% trifluoroacetic acid buffer). 0.016 g (59%) of product was recovered as a white solid. MW calculated for $C_{27}H_{28}N_8O_7S$: 609.18 ($MH^+$). found 609.4. $^1H$ NMR (300 MHz, $CD_3SOCD_3$) δ 11.69 (br s, 1H), 10.22 (br s, 1H), 8.69 (s, 1H), 8.65 (s, 1H), 7.60 (d, J=7.8 Hz, 2H), 7.36-7.21 (m, 6H), 7.07 (t, J=7.5 Hz, 1H), 6.90-6.87 (m, 1H), 6.57 (s, 1H), 6.22 (d, J=2.4 Hz, 1H), 5.75 (s, 1H), 5.45 (dd, J1=6.3 Hz, J2=2.1 Hz, 1H), 5.31 (t, J=5.1 Hz, 1H), 4.92 (dd, J1=6.6 Hz, J2=3.3 Hz, 1H), 4.16-4.02 (m, 5H), 3.11 (s, 3H).

Example 8

5'-Homologated Derivatives as in Scheme 11

3-{2,2-Dimethyl-6-[6-(3-phenyl-ureido)-purin-9-yl]-tetrahydro-furo[3,4-d][1,3]dioxol-4-yl}-acrylic acid methyl ester To a vial containing the starting compound, 1-[9-(6-Hydroxymethyl-2,2-dimethyl-tetrahydro-furo[3,4-d][1,3]dioxol-4-yl)-9H-purin-6-yl]-3-phenyl-urea (1.07 g, 2.5 mmol), in 10 ml of dimethylsulfoxide was added IBX (1.06 g, 3.75 mmol) in one portion at RT. The white solid gradually dissolved as the reaction proceeded. After stirring at RT for 2 hours, methyl(triphenylphosphorylidene) acetate (0.84 g, 2.5 mmol) was added in one portion. The reaction was run at RT overnight. To the reaction mixture was added ethyl acetate (100 ml), which was washed with saturated $NaHCO_3$, brine, and dried over $MgSO_4$. After removal of solvent, the residue was recrystallized with isopropyl alcohol to provide the title compound. MW calculated for $C_{23}H_{24}N_6O_6$ ($MH^+$) 481.5. found 481.3 by LCMS.

3-{2,2-Dimethyl-6-[6-(3-phenyl-ureido)-purin-9-yl]-tetrahydro-furo[3,4-d][1,3]dioxol-4-yl}-propionic acid To a round bottom flask containing product from the previous step (1.2 g, 2.5 mmol) and palladium on carbon (10% w/w, 10 mg) under nitrogen was added methanol (20 ml). After flushing with hydrogen gas, the reaction mixture was stirred under a hydrogen atmosphere using a hydrogen balloon overnight at RT. Upon filtration and removal of solvent, the crude white solid product was recrystallized from isopropyl alcohol to give the desired methyl ester compound. MW calculated for $C_{23}H_{26}N_6O_6$ ($MH^+$) 483.5. found 483.2.

The methyl ester (500 mg, 1.04 mmol) was dissolved in 4 ml of methanol and sodium hydroxide (83 mg, 2.1 mmol) was then added. The reaction was stirred overnight at RT. After removal of methanol, acetic acid (2.1 mmol, 120 mmol) was added and a white solid precipitated. The solvent was removed under vacuum. The residue was recrystallized from water to provide the pure desired product as a white solid (0.4 g, 83%). MW calculated for $C_{22}H_{24}N_6O_6$ (M-1) 467.5 found 467.4 by LCMS.

1-(3-{2,2-Dimethyl-6-[6-(3-phenyl-ureido)-purin-9-yl]-tetrahydro-furo[3,4-d][1,3]dioxol-4-yl}-propion-1-yl)-pyrrolidine-2-carboxylic acid To a vial containing the carboxylic acid product from the previous step (0.117 g, 0.25 mmol), thionyl chloride (0.3 g, 2.5 mmol) was added at 0° C. After addition, the cold bath was removed followed by addition of two drops of N,N-dimethyl formamide. The reaction mixture was heated to 50° C. for 30 minutes. The excess of thionyl chloride was removed under vacuum and the solid residue was washed with ethyl ether to give the acid chloride. The acid chloride (61 mg, 0.125 mmol) was added to a vial containing L-proline methyl ester (23 mg, 0.138 mmol) and triethylamine (28 mg, 0.275 mmol) in 1 mL of dichloromethane at 0° C. The reaction was gradually warmed to RT overnight. To the reaction mixture was added ethyl acetate (75 ml), which was washed with 1 N hydrochloric acid, saturated sodium bicarbonate, and dried over magnesium sulfate. The residue was purified by elution from a silica column using 2% methanol in dichloromethane to give purified prolylmethyl ester product (10 mg, 14%). MW calculated for $C_{28}H_{33}N_7O_7$ ($MH^+$) 580.6 found 580.3 by LCMS. The prolylmethyl ester (6 mg, 0.010 mmol) was dissolved in tetrahydrofuran (0.1 ml) followed by addition of 6 μl of 15% sodium hydroxide. After stirring at RT for 2 hrs, ethyl acetate (50 ml) was added and enough 1 N hydrochloric acid was added to adjust the pH to 3. The organic layer was washed with brine and dried over magnesium sulfate. After removal of solvent, the title compound was obtained as a white powder. MW calculated for $C_{27}H_{31}N_7O_7$ ($MH^+$) 566.6 found 566.3 by LCMS.

Example 9

Enzymatic Synthesis of a Mixture of 1-Ethyl-3-[9-(6-hydroxymethyl-2-styryl-tetrahydro-furo[3,4-d][1,3]dioxol-4-yl)-9H-purin-6-yl]-urea isomers from the corresponding isomeric mixture of 5'-AMP acetal/urea derivatives The 2',3'-(cinnamylacetal)-$N^6$-(ethylurea) derivative of AMP (0.750 g, 0.14 mmol) as a mixture of acetal diastereoisomers was dissolved in water (25 mL, 1.4 mol) in a round bottom flask and the pH was adjusted to 8.3 with NaOH. The temperature was adjusted to 35 C, and alkaline phosphatase (0.003 g, 0.00004 mol) was added. Within 15 minutes, the mixture became rather heterogenous, and methanol (20 mL, 0.5 mol) was added to resolubilize the nucleoside product. After 4 h the reaction was judged essentially complete by HPLC. The reaction was worked up by adding more MeOH (20 mL), heating to 60 C to denature the enzyme, and filtering through a 0.22 uM filter. The methanol was evaporated in vacuo, and a white, fine-particle solid precipitated from the remaining solvent. This mixture was cooled in an ice bath and filtered. Washing the material with water, followed by drying over $P_2O_5$ in a dessicator afforded the title product as a mixture of acetal diastereomers. Dry weight 440 mg (0.10 mmol, 71% yield).

Example 10

3-{6-[6-(3-Ethyl-ureido)-purin-9-yl]-2-styryl-tetrahydro-furo[3,4-d][1,3]dioxol-4-yl}-acrylic acid methyl ester 1-Ethyl-3-[9-(6-hydroxymethyl-2-styryl-tetrahydro-furo[3,4-d][1,3]dioxol-4-yl)-9H-purin-6-yl]-urea (5.0 g, 11 mmol) was suspended in dry acetonitrile (50 mL) and Dess-Martin periodinate (6.7 g, 16 mmol) was added. The suspension was stirred 2 h, after which time proton NMR of an aliquot showed complete conversion to the aldehyde. (Methoxycarbonylmethylene)triphenylphosphorane (3.9 g, 12 mmol) was added and stirring was continued overnight. The reaction mixture was then diluted with ethyl acetate (300 mL), washed with saturated sodium bicarbonate/thiosulfate solution (100 mL), dried with sodium sulfate and filtered. The filtrate was evaporated and the solid was dissolved in hot isopropyl alcohol (50 mL). It was allowed to cool, then heptane was added and it was stirred overnight. The resulting precipitate was washed with heptane and dried under vacuum, affording the desired product (2.9 g, 71%). $^1$H-NMR (300 MHz, $d_6$DMSO) δ 1.15 (t, 3H, J=7 Hz), 3.21 (q, 2H, J=7 Hz), 3.59 (s, 3H), 4.98 (m, 1H), 5.28 (ψt, 1H, J=6 Hz), 5.51 (dd, 1H, J=6 Hz, <2 Hz), 5.70 (d, 1H, J=16 Hz), 5.90 (d, 1H, J=6 Hz), 6.30 (dd, 1H, J=6 Hz, 16 Hz), 6.45 (d, 1H, J=2 Hz), 6.95 (d, 1H, J=15 Hz), 7.35 (m, 3H), 7.45 (d, 2H, J=7 Hz), 8.50 (s, 1H), 8.60 (s, 1H), 9.30 (t, 1H, J=6 Hz), 9.60 (s, 1H).

Example 11

3-{6-[6-(3-Ethyl-ureido)-purin-9-yl]-2-styryl-tetrahydro-furo[3,4-d][1,3]dioxol-4-yl}-propionic acid methyl ester 3-{6-[6-(3-Ethyl-ureido)-purin-9-yl]-2-styryl-tetrahydro-furo[3,4-d][1,3]dioxol-4-yl}-acrylic acid methyl ester (250 mg, 0.5 mmol) was dissolved in dry methanol (3 mL). Copper (II) sulfate (90 mg, 0.5 mmol) was added followed by sodium tetrahydroborate (90 mg, 2.5 mmol) and the reaction was stirred 48 h. The reaction was diluted with water, filtered, and concentrated in vacuo. The residue was dissolved in ethyl acetate and precipitated with heptane. The precipitate was dissolved in dichloromethane and was chromatographed on silica gel with dichloromethane-methanol (95:5) as eluent, affording the title compound (125 mg, 50%). $^1$H-NMR (300 MHz, $d_6$ DMSO) δ 1.15 (t, 3H, J=7 Hz), 1.90 (m, 2H), 2.19 (m, 2H), 3.21 (q, 2H, J=7 Hz), 3.55 (s, 3H), 4.20 (m, 1H), 4.98 (dd, 1H, J=4 Hz, 6 Hz), 5.45 (dd, 1H, J=3 Hz, 7 Hz), 5.85 (d, 1H, J=6 Hz), 6.25 (d, 1H, J=3 Hz), 6.27 (dd, 1H, J=6 Hz, 16 Hz), 6.90 (d, 1H, J 16 Hz), 7.35 (m, 3H), 7.50 (d, 2H, J=7 Hz), 8.56 (s, 1H), 8.57 (s, 1H), 9.30 (t, 1H, J=5 Hz), 9.60 (s, 1H).

Example 12

3-{6-[6-(3-Ethyl-ureido)-purin-9-yl]-2-styryl-tetrahydro-furo[3,4-d][1,3]dioxol-4-yl}-propionic acid 3-{6-[6-(3-Ethyl-ureido)-purin-9-yl]-2-styryl-tetrahydro-furo[3,4-d][1,3]dioxol-4-yl}-propionic acid methyl ester (5.0 g, 10 mmol) was dissolved in tetrahydrofuran (300 mL). Water (100 mL) was added, followed by lithium hydroxide (1.0 g, 25 mmol). The solution was allowed to stir 16 h at room temperature. It was acidified to pH 5 with acetic acid, concentrated in vacuo, then extracted with chloroform (300 mL). The organic extract was evaporated, redissolved in ethyl acetate and precipitated with heptane to afford the title compound (3.9 g, 80%), as a mixture of acetal diastereomers. Compound 183, which is the trans diastereomer contained within the acetal mixture, was obtained by separation on a chiral HPLC column. (Phenomenex Synergi Polar RP chiral $C_{18}$ column). Alternately, Compound 183 was obtained by subjecting the diastereomeric mixture of acetals to aqueous acid conditions (for example 65% aqueous acetic acid at 50° C. or aqueous p-toluenesulfonic acid at 30° C.), which cleaved the less stable cis diastereomer, leaving the trans isomer (Compound 183) intact. $^1$H-NMR of the diastereomeric mixture of acetals(300 MHz, $d_6$DMSO) δ 1.14 (t 3H, J=7 Hz), 1.90 (m, 2H), 2.19 (m, 2H), 3.26 (q, 2H, J=6 Hz), 4.17 (m, 1H), 4.93 (ψt, 1H, J=6 Hz), 5.43 (dd, 1H, J=3 Hz, 7 Hz), 5.84 (d 1H, J=6 Hz), 6.24 (d, 1H, J=3 Hz), 6.28 (dd, 1H, J=7 Hz, 13 Hz), 6.90 (d, 1H, J 16 Hz), 7.35 (m, 3H), 7.51 (d, 2H, J=7 Hz), 8.56 (s, 1H), 8.61 (s, 1H), 9.30 (t, 1H, J=6 Hz).

Example 13

Synthesis of 5'-Ethers as in Scheme 12

3-Chloro-2-{6-[6-(3-ethyl-ureido)-purin-9-yl]-2-trans-styryl-tetrahydro-furo[3,4-d][1,3]dioxol-4-ylmethoxymethyl}-benzoic acid 1-Ethyl-3-[9-(6-hydroxymethyl-2-trans-styryl-tetrahydro-furo[3,4-d][1,3]dioxol-4-yl)-9H-purin-6-yl]-urea (0.200 g, 0.44 mmol) was suspended in tetrahydrofuran (5 mL) and sodium hydride (60% w/w in oil, 0.106 g, 2.65 mmol) added. Once the bubbling ceased, added methyl-2-bromomethyl-3-chloro-benzoate (0.233 g, 0.88 mmol) and stirred the reaction mixture overnight at room temperature. Mass spectral analysis indicated that the reaction was complete and that the product was the title compound, arising from in situ hydrolysis of the methyl ester. The pH was lowered to 5 with acetic acid, and the mixture partitioned between ethyl acetate (40 mL) and 50% saturated sodium chloride (50 mL). The layers were separated and the ethyl acetate layer concentrated to dryness. The residue was reconstituted in aqueous acetonitrile and the product purified on preparative HPLC ($C_{18}$ column, gradient from 0.05 M ammonium acetate (pH 6.5) to acetonitrile over 20 minutes). The solvent was removed from the fraction containing the product, giving the title compound (Compound 115) after overnight lyophilization (0.194 g, 70%)

MW calculated for $C_{30}H_{29}ClN_6O_7$ (MH$^-$) 620.0 found 619.6 by LCMS. $^1$H-NMR (300 MHz, CDCl$_3$) δ1.29 (t 3H), 3.42 (q, 2H), 3.77 (dd, 1H), 3.97 (dd, 1H), 4.70 (s, 1H), 4.90 (d, 1H), 5.05 (d, 1H), 5.19 (d, 1H), 5.60 (dd, 1H), 5.86 (d, 1H), 6.18 (dd, 1H), 6.28 (d, 1H), 6.83 (d, 1H), 7.36 (m, 7H), 7.89 (d, 1H), 8.52 (s, 1H), 8.57 (s, 1H), 9.33 (s, 1H), 9.56 (t, 1H).

Example 14

Inhibition of ADP-Induced Platelet Aggregation

Isolation of Platelets: Human blood is obtained from informed healthy adult volunteers. Blood is collected into one-sixth volume of acid/citrate/dextrose (ACD) buffer (85 mM sodium citrate, 65 mM citric acid, and 100 mM glucose). Collected blood is placed in a water bath at 37° C. for 30 minutes. Blood is then centrifuged at 275×g for 16 minutes at room temperature and the platelet-rich plasma is removed and centrifuged at 2200×g for 13 minutes at room temperature. The platelet pellet is resuspended in 40 mL of HEPES-buffered Tyrode's solution (137 mM NaCl, 2.7 mM KCl, 1 mM $MgCl_2$, 2 mM $CaCl_2$, 12 mM $NaHCO_3$, 0.36 mM $NaH_2PO_4$, 5.5 mM glucose, 5 mM HEPES pH 7.4, 0.35% bovine serum albumin or 0.35% human serum albumin) containing 10 U/mL heparin and 5 µM (final concentration) prostaglandin 12 ($PGI_2$). The platelet suspension is incubated in a 37° C. water bath for 10 minutes and then 5 µM (final conc.) $PGI_2$ is added just before centrifugation at 1900×g for 8 minutes. The resulting pellet is resuspended in 40 mL of HEPES-buffered Tyrode's solution containing 5 µM (final concentration) $PGI_2$ and then is incubated for 10 minutes in a 37° C. water bath. A small aliquot (500 µL) of the platelet suspension is removed for platelet counting. Prior to centrifugation 5 µM (final concentration) $PGI_2$ is added to the suspension and then the suspension is centrifuged at 1900×g for 8 minutes. The pellet is resuspended at a density of $5 \times 10^8$ cells/mL in HEPES-buffered Tyrode's solution containing 0.05 U/mL apyrase.

Aggregation Studies: ADP-induced platelet aggregation is determined by measuring the transmission of light through a 0.5 ml suspension of stirred (1000 rpm) washed platelets in a lumi-aggregometer at 37° C. (Chrono-Log Corp. Havertown, Pa.). The baseline of the instrument is set using 0.5 ml of Hepes-buffered Tyrode's solution. Prior to aggregation measurements, the platelet suspension is supplemented with 1 mg/ml fibrinogen. Platelet aggregation is initiated by the addition of indicated concentrations of ADP or other agonists, and the light transmission is continuously recorded for at least 8 min. When inhibitors of platelet aggregation are tested, platelets are incubated for 2 min in the presence of indicated concentrations of inhibitor before addition of ADP or other agonists, and the response is recorded for at least 8 min. The potency of agonists and inhibitors of platelet aggregation is calculated from both the rate of aggregation and the maximal extent of aggregation obtained for each determination by fitting the data to a four-parameter logistic equation using the GraphPad software package (GraphPad Corp. San Diego, Calif.).

When a broad range of concentrations of $P2Y_{12}$ antagonist is tested (usually from 1 nM to 100 µM), an $IC_{50}$ value is also obtained. $IC_{50}$ values represent the concentration of antagonist necessary to inhibit by 50% the aggregation elicited by a given concentration of ADP.

Example 15

Inhibition of ADP-Induced Platelet Aggregation in Whole Blood

Human blood is obtained from informed healthy adult volunteers. Blood is collected into syringes containing heparin, sodium citrate, PPACK or hirudin as anticoagulant. Blood is carefully transferred to a conical tube and maintained at room temperature. Assays are conducted within 60 min from the collection of the blood sample. ADP-induced platelet aggregation is performed using the impedance mode of an aggregometer (Chrono-Log Corp. Havertown, Pa.). Blood is gently mixed and an aliquot of 500 µL is transferred to a measurement cuvette, then, 450 µL of warm sterile saline is added to each cuvette and the sample is stirred at 1000 rpm. The impedance probe is introduced into the cuvette and the sample is allowed to warm for approx. 3-4 minutes in the aggregometer. The basal impedance is recorded for 1 minute and then 50 µL of the appropriate concentrations of ADP are added to generate an ADP dose response curve. For the evaluation of $P2Y_{12}$ receptor antagonists on platelet aggregation, after the basal impedance is recorded for 1 minute as indicated above, blood samples are supplemented with 50 µL of the antagonist or vehicle and after 2 minutes, 50 µL of ADP ($EC_{90}$; usually 5-10 µmol/L ADP) are added and the impedance is recorded for up to 8 minutes. The potency of agonists and inhibitors of platelet aggregation is calculated from the impedance values obtained in each sample by fitting the data to a four-parameter logistic equation using the GraphPad software package (GraphPad Corp. San Diego, Calif.).

Example 16

Effects on Platelet Aggregation In Vivo

To evaluate the ability of these compounds to inhibit platelet aggregation in vivo, an experimental protocol similar to the method of R. G. Humphries et al. (Br. J. Pharmacol. 115:1110-1116, 1995) is performed.

Surgical Preparation and Instrumentation: Male Sprague-Dawley rats are anesthetized. Body temperature is maintained at 37±0.5° C. with a heating lamp. Animals breathe spontaneously and a tracheotomy is performed to ensure a patent airway. A cannula containing heparinized saline is introduced into the left femoral artery and connected to a transducer to record blood pressure and heart rate. Cannulae containing non-heparinized saline are introduced into the left common carotid artery and left jugular vein for withdrawal of arterial blood samples and intravenous administration of compounds, respectively. Experimental Protocol: Either compound or vehicle is administered to each animal as an infusion. Blood samples are taken immediately prior to the first infusion, at the end of each infusion and 20 min after cessation of the final infusion for measurement of platelet aggregation ex vivo. Immediately after sampling, ADP-induced platelet aggregation is measured in duplicate in 0.5 ml blood samples diluted 1:1 with saline and incubated at 37° C. for 4 min. For the final minute of this period, cuvettes are transferred to a lumi-aggregometer and the sample stirred at 900 rpm. ADP (3 µM) is added in a volume of 20 µl and the aggregation response is recorded using the impedance mode of the aggregometer.

Example 17

Inhibition of Thrombus Formation in Anesthetized Rats

To evaluate the effect of these compounds on thrombus formation in vivo, the following experimental protocol is performed.

Rats (CD-1; male; approximately 350 grams; Charles River, Raleigh, N.C.), are anesthetized with sodium pentobarbital (70 mg/kg i.p.). The abdomens are shaved and a 22 gauge intravenous catheter is inserted into a lateral tail vein. A midline incision is made and the intestines are wrapped in saline-soaked gauze and positioned so the abdominal aorta is accessible. The inferior vena cava and abdominal aorta are carefully isolated and a section (approximately 1 cm) of the abdominal aorta (distal to the renal arteries proximal to the bifurcation) is dissected. All branches from the aorta in this section are ligated with 4-0 silk suture. A 2.5 mm diameter flow probe connected to a Transonic flow meter is placed on the artery and a baseline (pre-stenosis) flow is recorded. Two clips are placed around the artery decreasing the vessel diameter by approximately 80%. A second baseline flow measurement is taken (post-stenosis) and the hyperemic response is tested. Animals are then treated with either compound or saline intravenously via tail vein catheter. Thrombosis is induced five minutes after treatment by repeated external compressions of the vessel with hemostatic forceps. Two minutes post-injury, the vessel compressions are repeated and a 10 minute period of flow monitoring is started. Animals are monitored continuously for a minimum of the first ten minutes post-injury. After twenty minutes (post-injury), a flow measurement is repeated and the animals are euthanized. The section of the aorta that includes the injured section is harvested and placed in 10% formalin for possible histologic evaluation.

Example 18

In Vivo PK/PD Measurements Following Oral Administration

To evaluate the ability of these compounds to be absorbed orally and to inhibit platelet aggregation in vivo, the following experimental protocol is conducted.

Male Sprague-Dawley rats are anesthetized using an inhaled anesthetic. A cannula containing heparinized saline is introduced into the jugular vein for withdrawal of venous blood samples. Animals are allowed a 48-hour recovery period prior to dose administration.

Either compound or vehicle is administered to each animal as an oral gavage. Blood samples are taken immediately prior to compound administration, and at up to 12 time points ranging from 15 min to 24 hours following compound administration. HPLC-MS/MS is used to measure the amount of compound and/or metabolite in the blood samples.

Example 19

Inhibition of Thrombus Formation in Anesthetized Dogs

To evaluate the effect of the compounds of this invention on dynamic thrombus formation in vivo, the following experimental protocol, similar to the method of J. L. Romson et al. (*Thromb. Res.* 17:841-853, 1980), is performed.

Surgical Preparation and Instrumentation: Briefly, purpose-bred dogs are anesthetized, intubated and ventilated with room air. The heart is exposed by a left thoracotomy in the fifth intercostal space and suspended in a pericardial cradle. A 2-3 cm segment of the left circumflex coronary artery (LCCA) is isolated by blunt dissection. The artery is instrumented from proximal to distal with a flow probe, a stimulation electrode, and a Goldblatt clamp. The flow probe monitors the mean and phasic LCCA blood flow velocities. The stimulation electrode and its placement in the LCCA and the methodology to induce an occlusive coronary thrombus have been described previously (J. K. Mickelson et al., *Circulation* 81:617-627, 1990; R. J. Shebuski et al., Circulation 82:169-177, 1990; J. F. Tschopp et al., Coron. Artery Dis. 4:809-817, 1993).

Experimental Protocol: Dogs are randomized to one of four treatment protocols (n=6 per treatment group) in which the control group receives saline intravenously and the three drug-treated groups are administered compound intravenously. Upon stabilization from the surgical interventions, dogs receive either saline or compound. After approximately 30 minutes, an anodal current is applied to the LCCA for 180 min. The number and frequency of cyclic flow variations (CFV) that precede formation of an occlusive thrombus are recorded. These cyclic phenomena are caused by platelet thrombi that form in the narrowed lumen as a result of platelet aggregation (J. D. Folts et al., Circulation 54:365-370, 1976; Bush et al., Circulation 69:1161-1170, 1984). Zero flow in the LCCA for a minimum of 30 minutes indicates a lack of antithrombotic efficacy (L. G. Frederick et al., *Circulation* 93:129-134, 1996).

Example 20

$IC_{50}$ values for representative compounds of the present invention. Platelet $IC_{50}$ data were determined using washed human platelets, according to the protocol of example 14. Agonist challenge (ADP) typically in the range of 1-5 µM. Data are presented in µM and are from the average of two experiments or more.

TABLE 1

| Compound # | PLATELET DATA IC50 (uM) Washed Platelets |
|---|---|
| 1 | 6.6 |
| 14 | 8.1 |
| 19 | 18 |
| 24 | 2.15 |
| 26 | 1 |
| 36 | 0.75 |
| 37 | 15 |
| 65 | 0.728 |
| 69 | 0.441 |
| 70 | 0.397 |
| 107 | 0.057 |
| 108 | 0.098 |
| 109 | 0.03 |
| 110 | 0.023 |
| 112 | 0.009 |
| 115 | 0.012 |
| 127 | 0.032 |
| 128 | 0.042 |
| 130 | 0.057 |
| 158 | 8 |
| 183 | 0.376 |
| 189 | 0.243 |
| 191 | 0.512 |
| 210 | 0.163 |
| 233 | 0.503 |
| 239 | 0.086 |
| 298 | 0.081 |

TABLE 2

| Compound # | Compound Name |
|---|---|
| 1 | 4-{2,2-Dimethyl-6-[6-(3-phenyl-ureido)-purin-9-yl]-tetrahydro-furo[3,4-d][1,3]dioxol-4-ylmethoxy}-isophthalic acid |
| 14 | 2-[6-[6-(3-Phenyl-ureido)-purin-9-yl]-2-(2-trifluoromethyl-phenyl)-tetrahydro-furo[3,4-d][1,3]dioxol-4-ylmethoxy]-nicotinic acid |
| 19 | 2-{2-Naphthalen-2-yl-6-[6-(3-phenyl-ureido)-purin-9-yl]-tetrahydro-furo[3,4-d][1,3]dioxol-4-ylmethoxy}-nicotinic acid |
| 24 | 2-{6-[6-(3-Hexyl-ureido)-purin-9-yl]-2-phenyl-tetrahydro-furo[3,4-d][1,3]dioxol-4-ylmethoxy}-nicotinic acid |
| 26 | 2-{6-[6-(3-Ethyl-ureido)-purin-9-yl]-2-phenylethynyl-tetrahydro-furo[3,4-d][1,3]dioxol-4-ylmethoxy}-nicotinic acid |
| 36 | 1-{2-Benzyl-6-[6-(3-cyclopentyl-ureido)-purin-9-yl]-tetrahydro-furo[3,4-d][1,3]dioxole-4-carbonyl}-pyrrolidine-2-carboxylic acid |
| 37 | 1-(9-{2-Benzyl-6-[(3-methylsulfonyl-ureido)-methyl]-tetrahydro-furo[3,4-d][1,3]dioxol-4-yl}-9H-purin-6-yl)-3-phenyl-urea |
| 65 | 1-{6-[6-(3-Ethyl-ureido)-purin-9-yl]-2-trans-phenyl-tetrahydro-furo[3,4-d][1,3]dioxole-4-carbonyl}-L-pyrrolidine-2-carboxylic acid |
| 69 | 1-{6-[6-(3-Ethyl-ureido)-purin-9-yl]-2-trans-phenyl-tetrahydro-furo[3,4-d][1,3]dioxole-4-carbonyl}-L-pyrrolidine-2-carboxylic acid |
| 70 | 1-{6-[6-(3-Ethyl-ureido)-purin-9-yl]-2-trans-styryl-tetrahydro-furo[3,4-d][1,3]dioxole-4-carbonyl}-D-pyrrolidine-2-carboxylic acid |
| 107 | 2-{6-[6-(3-Ethyl-ureido)-purin-9-yl]-2-trans-phenyl-tetrahydro-furo[3,4-d][1,3]dioxol-4-ylmethoxymethyl}-benzoic acid |
| 108 | 2-{6-[6-(3-Ethyl-ureido)-purin-9-yl]-2-cis-phenyl-tetrahydro-furo[3,4-d][1,3]dioxol-4-ylmethoxymethyl}-benzoic acid |

TABLE 2-continued

| Compound # | Compound Name |
|---|---|
| 109 | 2-{6-[6-(3-Ethyl-ureido)-purin-9-yl]-2-trans-styryl-tetrahydro-cyclopenta[1,3]dioxol-4-ylmethoxymethyl}-benzoic acid |
| 110 | 2-{6-[6-(3-Ethyl-ureido)-purin-9-yl]-2-trans-phenyl-tetrahydro-furo[3,4-d][1,3]dioxol-4-ylmethoxymethyl}-3-fluoro-benzoic acid |
| 112 | 2-{6-[6-(3-Ethyl-ureido)-purin-9-yl]-2-trans-styryl-tetrahydro-cyclopenta[1,3]dioxol-4-ylmethoxymethyl}-3-fluoro-benzoic acid |
| 115 | 3-Chloro-2-{6-[6-(3-ethyl-ureido)-purin-9-yl]-2-trans-styryl-tetrahydro-cyclopenta[1,3]dioxol-4-ylmethoxymethyl}-benzoic acid |
| 127 | 2-{6-[6-(3-Ethyl-ureido)-purin-9-yl]-2-trans-styryl-tetrahydro-cyclopenta[1,3]dioxol-4-ylmethoxymethyl}-isophthalic acid |
| 128 | 2-{6-[6-(3-Ethyl-ureido)-purin-9-yl]-2-trans-phenyl-tetrahydro-furo[3,4-d][1,3]dioxol-4-ylmethoxymethyl}-nicotinic acid |
| 130 | 2-{6-[6-(3-Ethyl-ureido)-purin-9-yl]-2-trans-styryl-tetrahydro-cyclopenta[1,3]dioxol-4-ylmethoxymethyl}-nicotinic acid |
| 158 | 2-(2-{6-[6-(3-Ethyl-ureido)-purin-9-yl]-2-trans-phenyl-tetrahydro-furo[3,4-d][1,3]dioxol-4-yl}-ethyl)-3-fluoro-benzoic acid |
| 183 | 3-{6-[6-(3-Ethyl-ureido)-purin-9-yl]-2-trans-styryl-tetrahydro-cyclopenta[1,3]dioxol-4-yl}-propionic acid |
| 189 | {6-[6-(3-Ethyl-ureido)-purin-9-yl]-2-trans-styryl-tetrahydro-cyclopenta[1,3]dioxol-4-ylmethoxy}-acetic acid |
| 191 | ({6-[6-(3-Ethyl-ureido)-purin-9-yl]-2-trans-styryl-tetrahydro-furo[3,4-d][1,3]dioxol-4-ylmethyl}-amino)-acetic acid |
| 210 | 6-[6-(3-Ethyl-ureido)-purin-9-yl]-2-trans-styryl-tetrahydro-furo[3,4-d][1,3]dioxole-4-carboxylic acid |
| 233 | {6-[6-(3-Ethyl-ureido)-purin-9-yl]-2-trans-styryl-tetrahydro-cyclopenta[1,3]dioxol-4-ylmethoxythiocarbonylamino}-acetic acid |
| 239 | N-{6-[6-(3-Ethyl-ureido)-purin-9-yl]-2-trans-styryl-tetrahydro-cyclopenta[1,3]dioxol-4-ylmethyl}-phthalamic acid |
| 298 | 3-{6-[6-(3-Ethyl-ureido)-purin-9-yl]-2-styryl-tetrahydro-cyclopenta[1,3]dioxol-4-ylmethoxymethyl}-thiophene-2-carboxylic acid |

The data in Table 1 illustrates that a diverse set of compounds of the present invention show activity as antagonists of $P2Y_{12}$-mediated platelet aggregation. For example, compounds falling under Formula I (1, 14, 19, 24, 26, 36, 37) show $P2Y_{12}$ antagonist activity, despite having differing moieties at the 4' and 2'/3' (acetal) positions of the ribose, and/or 6 (urea) position of the base. Additionally, compounds falling under preferred Formula IV (65, 69, and 70) illustrate that diastereomerically-pure molecules containing a prolinamide residue at the 4' position, a phenyl or styryl acetal moiety at the 2'/3' position, and an ethyl urea at the 6 position have improved potency relative to the less preferred compounds previously listed as falling under Formula I. Further, compounds falling under a more preferred Formula V and Formula II (107, 108, 109, 110, 112, 115, 127, 128, and 130) show dramatically better potency ($IC_{50}$ data below 0.1 and even below 0.01 for Compound 112) believed to be as a result of their containing a benzyl ether (with or without substituents falling under the definition of M) or 2-nicotinylmethyl moiety at the 4' position, in addition to the preferred acetals and urea previously listed for preferred compounds falling under Formula IV.

Table 1 also shows that replacing the oxygen of the benzyl ether moiety and reducing the linking group between the ribose ring 4' position and the terminal phenyl ring falling under the definition of V and Formula II to two total atoms instead of three (158) still lead to active molecules. Yet further, preferred compounds falling under Formula VII (183, 189, 191 and 210) show that $P2Y_{12}$ antagonist activity can be obtained by modification of the ribose 4' position with simple, acyclic, non-aromatic moieties, in conjunction with the preferred styryl acetal and ethyl urea moieties previously described. Even further, preferred compounds falling under Formula IX (233) show $P2Y_{12}$ antagonist activity when one of the linking groups at the 4' position falling under the definition of A and B in Formula I is a thiocarbamate moiety. In another illustration, preferred compounds falling under Formula X (239) show potent activity when part of the linking group between the 4' position of the ribose and the phenyl ring falling under the definition of moiety X in Formula I and Formula II is an amide. In yet another illustration, compounds falling under the definition of Formula XII (298) are active when the moiety defined by X in Formula I and Formula II is a 5-membered heterocyclic ring. Taken together, Table 1 illustrates that a wide variety of molecules falling under the definitions of Formulae IV-XII are useful as antagonists of $P2Y_{12}$ mediated platelet aggregation, and consequently useful as therapeutics in diseases where inhibition of platelet aggregation is beneficial.

Example 21

Coating of a Stent with a Polymer Incorporating a $P2Y_{12}$ Antagonist Compound A stent is coated with a $P2Y_{12}$ antagonist compound with procedures modified from that described in Example 4 of U.S. Pat. No. 6,908,624 (Hossainy). A stent is suspended in isopropanol and cleaned in an ultrasonic bath for 30 minutes. The stent is dried and cleaned in a plasma chamber. A poly (ethylene-vinyl alcohol) solution is made by dissolving one part poly(ethylene-vinyl alcohol) in seven parts dimethylsulfoxide, with stirring and shaking at 60° C. for 24 hours. A $P2Y_{12}$ antagonist compound (for example compound 41; typically in the range of 2-10% by weight of the total) is added to the poly(ethylene-vinyl alcohol)/dimethyl sulfoxide solution and the solution is mixed, vortexed and placed in a tube. The stent is attached to a mandrel wire and dipped into the solution. The coated stent is briefly passed over a hotplate at 60° C., then is cured for 6 hours at ambient temperature, after which it is dried for 24 hours in a vacuum oven at 40-60° C. The above process is repeated two or three times to give two or three layers. Following final drying, the stent is optionally sterilized by electron beam radiation.

The invention, and the manner and process of making and using it, are now described in such full, clear, concise and exact terms as to enable any person skilled in the art to which it pertains, to make and use the same. It is to be understood that the foregoing describes preferred embodiments of the present invention and that modifications can be made therein without departing from the scope of the present invention as set forth in the claims. To particularly point out and distinctly claim the subject matter regarded as invention, the following claims conclude this specification.

What is claimed:

1. A drug-eluting stent, wherein the stent is coated with one or more non-nucleotide P2Y12 receptor antagonist compound of general Formula I, or a pharmaceutically acceptable salt thereof, wherein a therapeutically effective amount of the compound is eluted to the local environment when the stent is placed in a vessel,

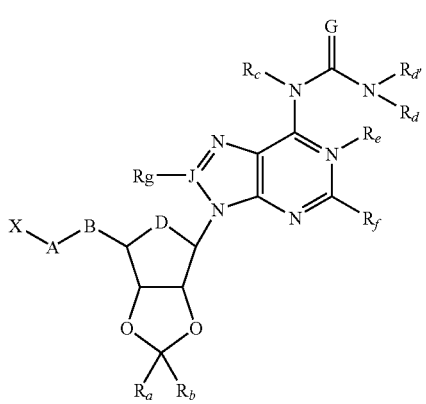

Formula I wherein $R_a$ and $R_b$ are each independently selected from the group consisting of: hydrogen, $C_{1-8}$ alkyl, $C_{1-8}$ alkenyl, $C_{1-8}$ alkynyl, $C_{3-7}$ cycloalkyl, $C_{4-7}$ cycloalkenyl, aralkyl, aryl, and saturated or unsaturated $C_{3-6}$ heterocycle; where all rings or chains optionally bear one or more substituents selected from the group consisting of alkyl, aryl, halogen, aralkyl, carboxy, alkoxycarbonyl, hydroxyl, acyloxy, alkoxy, aryloxy, and aralkoxy; or $R_a$ and $R_b$ are taken together to form a ring of 3 to 7 members, with or without substitution, and with or without heteroatoms in place of ring carbon atoms;

$R_c$=H, $C_{1-8}$ alkyl, $C_{3-7}$ cycloalkyl, aryl, or heterocycle, or R(CO)—;

where R is selected from the group consisting of: $C_{1-8}$ alkyl, $C_{1-8}$ alkenyl, $C_{1-8}$ alkynyl, $C_{3-7}$ cycloalkyl, $C_{4-7}$ cycloalkenyl, aryl, aralkyl, heteroaryl, and saturated or unsaturated $C_{3-6}$ heterocycle; where all rings or chains optionally bear one or more substituents selected from the group consisting of alkyl, aryl, halogen, aralkyl, carboxy, alkoxycarbonyl, hydroxyl, acyloxy, alkoxy, aryloxy, and aralkoxy;

G=O, S, or $NR_d$, where $R_d$ is defined as below;

$R_d$ and $R_{d'}$ are independently selected from the group consisting of: H, $C_{1-8}$ alkyl, $C_{1-8}$ alkenyl, $C_{1-8}$ alkynyl, $C_{3-7}$ cycloalkyl, $C_{4-7}$ cycloalkenyl, $C_{4-11}$ alkylcycloalkyl, $C_{5-11}$ alkylcycloalkenyl, with 1 to 4 carbons in the alkyl portion, aralkyl, aryl, heteroaryl, and saturated or unsaturated $C_{3-6}$ heterocycle; or $R_d$ and $R_{d'}$ groups are taken together to form a ring of 4 to 7 members, with or without unsaturation and with or without heteroatoms in place of ring-carbon units; or $R_d$ or $R_{d'}$ and $R_c$ are taken together to form a ring of 4 to 7 members, with or without unsaturation and with or without heteroatoms in place of ring-carbon units;

$R_e$=O or absent;

$R_f$=H, halogen, $C_{1-8}$ alkyl, $C_{1-8}$ alkenyl, $C_{1-8}$ alkynyl, $C_{3-7}$ cycloalkyl, $C_{4-7}$ cycloalkenyl, $C_{4-11}$ alkylcycloalkyl, $C_{5-11}$ alkylcycloalkenyl, with 1 to 4 carbons in the alkyl portion, aryl, aralkyl, heteroaryl, saturated or unsaturated $C_{3-6}$ heterocycle, —OH, $C_{1-6}$ alkoxy, aryloxy, —SH, $C_{1-6}$ thioalkyl, thioaryl, —[(CO)OR], —[(CO)NRR], amino, —N-substituted amino, or N,N-disubstituted amino; wherein each said substituent on said N-substituted-amino group, or N,N-disubstituted-amino-group of $R_f$ is independently selected from the group consisting of: $C_{1-8}$ alkyl, $C_{1-8}$ alkenyl, $C_{1-8}$ alkynyl, $C_{3-7}$ cycloalkyl, $C_{4-7}$ cycloalkenyl, aryl, aralkyl, heteroaryl, $C_{3-6}$ heterocycle, —[(CO)R] and —[(CO)—NRR]; wherein each R is independently as defined above; or when $R_f$ is —NRR, —[NH(CO)NRR], —[N($C_{1-8}$ alkyl) (CO)NRR], —[N(aryl)(CO)NRR], or [N(aralkyl)(CO) NRR], the R groups of said —NRR unit (N,N-disubstituted-amino-group) in $R_f$ can be taken together such that a ring of 3 to 7 members is formed, with or without heteroatoms in place of the ring-carbon units;

J=N or C, with the proviso that when J=N, then $R_g$ is absent;

when J=C, $R_g$ is selected from the group consisting of: —H, halogen, $C_{1-8}$ alkyl, $C_{1-8}$ alkenyl, $C_{1-8}$ alkynyl, $C_{3-7}$ cycloalkyl, $C_{4-7}$ cycloalkenyl, aralkyl, aryl, —OH, $C_{1-6}$ alkoxy, aryloxy, —SH, $C_{1-6}$ thioalkyl, thioaryl, —[(CO) OR], —[(CO)NRR], and —NRR; wherein each R is independently as defined above; or when $R_g$ is —[(CO)NRR] or —NRR, the R groups of said —NRR unit in $R_g$ are taken together such that a ring of 3 to 7 members is formed, with or without heteroatoms in place of the ring-carbon units;

D is O, NH, N-acyl, N-alkyl, or C;

A and B are each independently selected from the group consisting of: C, N, substituted N, O, S, S(O), $SO_2$, —$C_{1-3}$ alkylene-, —$C_{1-3}$ heteroalkylene, wherein each said —$C_{1-3}$ alkylene- unit of A and B independently can be saturated or unsaturated, and each carbon of a —$C_{1-3}$ alkylene- unit of B independently can be substituted with 0 to 2 fluorine groups, 0 to 1 methyl groups, 0 to 2 —[(CO)OR] groups, and 0 to 1 —(OR) groups, —$CF_2$—, —(CO)—; —NH(CO)—, —NR(CO)—, —(CO)NH—, —(CO)NR—, —NH(CO)NH—, —NH (CS)NH—, —N(NH)NH—, —N(NR)NH—, —NH (CO)O—, —NH(CS)O—, —O(CO)NH—, —O(CS) NH—, provided that no —S—S— or —O—O— bonds are formed by combination of the -A- and —B— groups; or A and/or B are absent;

X is a group as provided in Formula II:

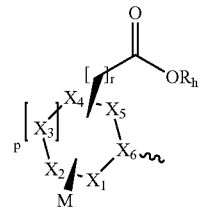

Formula II wherein:

$X_6$ is the attachment point to the moiety defined by A-B;

the ring defined by $X_1$-$X_6$ is a ring with or without unsaturation;

$X_1$-$X_6$ are independently C, N, O, or S; and when any of $X_1$-$X_5$ is C, the carbon atom bears an H when doubly bonded in an unsaturated ring, or a substituent M, as defined below; or when any of $X_1$-$X_5$ is C, the carbon atom bears two H when singly bonded in a saturated ring, or one H plus one substituent M, or two substituents M without H, with the proviso that any such moiety with one or two M substituents is of sufficient chemical stability;

when any of $X_1$-$X_5$ is N in an saturated ring, the nitrogen atom bears an H, an alkyl or an acyl; or any of $X_1$-$X_5$ is absent, with the proviso that at least two of $X_1$-$X_5$ are present, such that the ring described by $X_1$-$X_6$ consists of at least three atoms;

with the provisos that no two adjacent atoms $X_1$-$X_6$ are O—O or S—S, and that the ring shown in Formula II contains no more than four heteroatoms, and that the shown pendant —$CO_2R_h$ unit in Formula II is a substituent on the ring described in Formula II;

p=0, 1, or 2;

r=0 or 1;

$R_h$ is H, a physiologically-relevant cation forming a carboxylate salt, alkyl, aryl, or aralkyl;

M is —H, halogen, or —[(CO)OR], and one or more moiety M is present.

2. The drug-eluting stent according to claim 1, wherein said compound is Compound 1, which is 4-[2,2-Dimethyl-6-[6-(3-phenyl-ureido)-purin-9-yl]-tetrahydro-furo[3,4-d]-[1,3]dioxol-4-ylmethoxy]-isophthalic acid; Compound 14, which is 2-[6-[6-(3-Phenyl-ureido)-purin-9-yl]-2-(2-trifluoromethyl-phenyl)-tetrahydro-furo[3,4-d][1,3]dioxol-4-yl-methoxy]-nicotinic acid; Compound 19, which is 2-[2-Naphthalen-2-yl-6-[6-(3-phenyl-ureido)-purin-9-yl]-tetrahydro-furo[3,4-d][1,3]dioxol-4-ylmethoxy]-nicotinic acid; Compound 24, which is 2-[6-[6-(3-Hexyl-ureido)-purin-9-yl]-2-phenyl-tetrahydro-furo[3,4-d][1-,3]dioxol-4-yl-methoxy]-nicotinic acid; Compound 26, which is 2-[6-[6-(3-Ethyl-ureido)-purin-9-yl]-2-phenylethynyl-tetrahydro-furo[3,4-d][1,3]dioxol-4-ylmethoxy]-nicotinic acid; or Compound 36; which is 1-[2-Benzyl-6-[6-(3-cyclopentyl-ureido)-purin-9-yl]-tetrahydro-furo[3,4-d-][1,3]dioxole-4-carbonyl]-pyrrolidine-2-carboxylic acid.

3. The drug-eluting stent according to claim 1, wherein said compound of Formula I is a compound of Formula III:

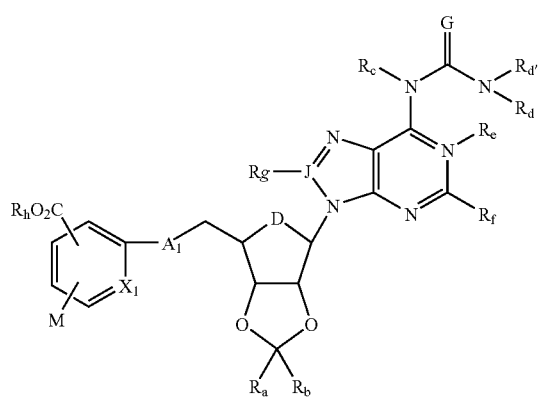

Formula III wherein $R_a$, $R_b$, $R_c$, G, $R_d$, $R_d{}'$, $R_e$, $R_f$, J, $R_g$, and $R_h$ are as defined in claim 1;

$A_1$ is O or $CH_2$;

D is O or $CH_2$;

$X_1$ is selected from the group consisting of: N and C-M; and

M is independently selected from the group consisting of: —H, halogen, —$CF_3$, $C_{1-8}$ alkyl, cyano, $C_{1-8}$ alkenyl, $C_{1-8}$ alkynyl, $C_{3-7}$ cycloalkyl, $C_{3-7}$ cycloalkenyl, aryl, aralkyl, heteroaryl, saturated or unsaturated $C_{2-6}$ heterocycle, —OH, saturated or unsaturated $C_{1-6}$ alkoxy, aralkoxy, aryloxy, —SH, $C_{1-6}$ thioalkyl, thioaryl, —[(CO)OR], —[(CO)NRR], amino, —N-substituted amino, and N,N-disubstituted amino; wherein each said substituent on said amino of M is independently selected from the group consisting of: $C_{1-8}$ alkyl, $C_{3-7}$ cycloalkyl, aryl, aralkyl, heteroaryl, $C_{2-6}$ heterocycle, —[(CO)R], —[(CO)O—($C_{1-8}$ alkyl)], and —[(CO)—NRR]; and when M is —[(CO)NRR], —[NH(CO)NRR], —[N($C_{1-8}$ alkyl)(CO)NRR], —[N(aryl)(CO)NRR], or —[N(aralkyl)(CO)NRR], the R groups of any said —NRR unit (N,N-disubstituted-amino group) in M are optionally taken together such that a ring of 3 to 7 members is formed, with or without heteroatoms in place of the ring-carbon units.

4. The drug-eluting stent according to claim 1, wherein said compound of Formula I is a compound of Formula IV:

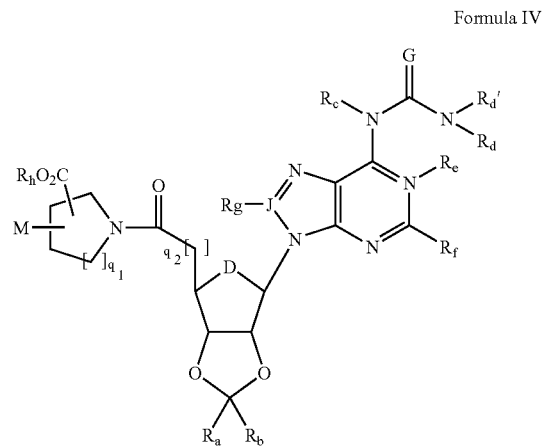

Formula IV wherein $R_a$, $R_b$, $R_c$, G, D, $R_d$, $R_d{}'$, $R_e$, $R_f$, J, M, $R_g$ and $R_h$ are as defined in claim 1;

$q_1$ and $q_2$ are 0, 1, or 2;

the M and —$CO_2R_h$ groups are independently and optionally attached to any carbon of the pyrrolidine ring; and M is H, $C_{1-4}$ alkyl, $C_{3-6}$ cycloalkyl, or $C_{1-4}$ alkoxy.

5. The drug-eluting stent according to claim 4, wherein said compound of Formula IV is Compound 65, which is 1-{6-[6-(3-Ethyl-ureido)-purin-9-yl]-2-trans-phenyl-tetrahydro-furo[3,4-d][1,3]dioxole-4-carbonyl}-L-pyrrolidine-2-carboxylic acid; Compound 69, which is 1-{6-[6-(3-Ethyl-ureido)-purin-9-yl]-2-trans-styryl-tetrahydro-furo[3,4-d][1,3]dioxole-4-carbonyl}-L-pyrrolidine-2-carboxylic acid; or Compound 70, which is 1-{6-[6-(3-Ethyl-ureido)-purin-9-yl]-2-trans-styryl-tetrahydro-furo[3,4-d][1,3]dioxole-4-carbonyl}-D-pyrrolidine-2-carboxylic acid.

6. The drug-eluting stent according to claim 1, wherein said compound of Formula I is a compound of Formula V:

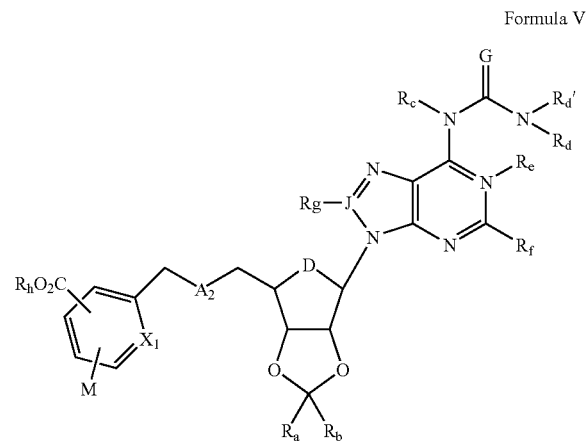

Formula V wherein $R_a$ and $R_b$ are each independently selected from the group consisting of: hydrogen, $C_{1-8}$ alkyl, $C_{1-8}$ alkenyl, $C_{1-8}$ alkynyl, $C_{3-7}$ cycloalkyl, $C_{4-7}$ cycloalkenyl, aralkyl, aryl, and saturated or unsaturated $C_{3-6}$ heterocycle; where all rings or chains optionally bear one or more substituents selected from the group consisting of alkyl, aralkyl, carboxy, alkoxycarbonyl, hydroxyl, acyloxy, alkoxy, aryloxy, and aralkoxy;

$R_c$=H, $C_{1-8}$ alkyl, $C_{3-7}$ cycloalkyl, aralkyl, aryl, or heterocycle, or R(CO)—;

where R is selected from the group consisting of: $C_{1-8}$ alkyl, $C_{1-8}$ alkenyl, $C_{1-8}$ alkynyl, $C_{3-7}$ cycloalkyl, $C_{4-7}$ cycloalkenyl, aryl, aralkyl, heteroaryl, and saturated or unsaturated $C_{3-6}$ heterocycle; where all rings or chains optionally bear one or more substituents selected from the group consisting of alkyl, aryl, halogen, aralkyl, carboxy, alkoxycarbonyl, hydroxyl, acyloxy, alkoxy, aryloxy, and aralkoxy;

G=O, S, or $NR_d$;

$R_d$ and $R_{d'}$ are independently selected from the group consisting of: H, $C_{1-8}$ alkyl, $C_{1-8}$ alkenyl, $C_{1-8}$ alkynyl, $C_{3-7}$ cycloalkyl, $C_{4-7}$ cycloalkenyl, $C_{4-11}$ alkylcycloalkyl, $C_{5-11}$ alkylcycloalkenyl, with 1 to 4 carbons in the alkyl portion, aralkyl, aryl, heteroaryl, and saturated or unsaturated $C_{3-6}$ heterocycle;

$R_e$=O or absent;

$R_f$=H, halogen, $C_{1-8}$ alkyl, $C_{1-8}$ alkenyl, $C_{1-8}$ alkynyl, $C_{3-7}$ cycloalkyl, $C_{4-7}$ cycloalkenyl, $C_{4-11}$ alkylcycloalkyl, $C_{5-11}$ alkylcycloalkenyl, with 1 to 4 carbons in the alkyl portion, aryl, aralkyl, heteroaryl, saturated or unsaturated $C_{3-6}$ heterocycle, —OH, $C_{1-6}$ alkoxy, aryloxy, —SH, $C_{1-6}$ thioalkyl, thioaryl, —[(CO)OR], —[(CO)NRR], amino, —N-substituted amino, or N,N-disubstituted amino;

J=N or C, with the proviso that when J=N, then $R_g$ is absent;

when J=C, $R_g$ is selected from the group consisting of: —H, halogen, $C_{1-8}$ alkyl, $C_{1-8}$ alkenyl, $C_{1-8}$ alkynyl, $C_{3-7}$ cycloalkyl, $C_{4-7}$ cycloalkenyl, aralkyl, aryl, —OH, $C_{1-6}$ alkoxy, aryloxy, —SH, $C_{1-6}$ thioalkyl, thioaryl, —[(CO)OR], —[(CO)NRR], and —NRR; wherein each R is independently as defined above;

D is O, NH, N-acyl, N-alkyl, or C;

$X_1$ is C, N, O, or $R_h$ is H, a physiologically-relevant cation forming a carboxylate salt, alkyl, aryl, or aralkyl;

$A_2$ is $CH_2$, O, S, S(O), $SO_2$, or NH, where the hydrogen on C is optionally substituted with alkyl, and the hydrogen on N is optionally substituted with alkyl, or acyl; or $A_2$ is absent.

7. The drug-eluting stent according to claim 6, wherein said compound of Formula V is Compound 107, which is 2-{6-[6-(3-Ethyl-ureido)-purin-9-yl]-2-trans-phenyl-tetrahydro-furo[3,4-d][1,3]dioxol-4-ylmethoxymethyl}-benzoic acid; Compound 108, which is 2-{6-[6-(3-Ethyl-ureido)-purin-9-yl]-2-cis-phenyl-tetrahydro-furo[3,4-d][1,3]dioxol-4-yl-methoxymethyl}-benzoic acid; Compound 109, which is 2-{6-[6-(3-Ethyl-ureido)-purin-9-yl]-2-trans-styryl-tetrahydro-cyclopenta[1,3]dioxol-4-ylmethoxymethyl}-benzoic acid; Compound 110, which is 2-{6-[6-(3-Ethyl-ureido)-purin-9-yl]-2-trans-phenyl-tetrahydro-furo[3,4-d][1,3]dioxol-4-ylmethoxymethyl}-3-fluoro-benzoic acid; Compound 112, which is 2-{6-[6-(3-Ethyl-ureido)-purin-9-yl]-2-trans-styryl-tetrahydro-cyclopenta[1,3]dioxol-4-ylmethoxymethyl}-3-fluoro-benzoic acid; Compound 115, which is 3-Chloro-2-{6-[6-(3-ethyl-ureido)-purin-9-yl]-2-trans-styryl-tetrahydro-cyclopenta[1,3]dioxol-4-ylmethoxymethyl}-benzoic acid; Compound 127, which is 2-{6-[6-(3-Ethyl-ureido)-purin-9-yl]-2-trans-styryl-tetrahydro-cyclopenta[1,3]dioxol-4-ylmethoxymethyl}-isophthalic acid; Compound 128, which is 2-{6-[6-(3-Ethyl-ureido)-purin-9-yl]-2-trans-phenyl-tetrahydro-furo[3,4-d][1,3]dioxol-4-ylmethoxymethyl}-nicotinic acid; or Compound 130, which is 2-{6-[6-(3-Ethyl-ureido)-purin-9-yl]-2-trans-styryl-tetrahydro-cyclopenta[1,3]dioxol-4-ylmethoxymethyl}-nicotinic acid.

8. The drug-eluting stent according to claim 1, wherein said compound of Formula I is a compound of Formula VI:

Formula VI wherein:

$R_a$, $R_b$, $R_c$, G, D, $R_d$, $R_{d'}$, $R_e$, $R_f$, J, M, $X_1$, $R_g$ and $R_h$ are as defined in claim 1;

$A_3$ is $CH_2$, where the hydrogen on C is optionally substituted with alkyl; or $A_3$ is absent;

$R_i$ is H or alkyl.

9. The drug-eluting stent according to claim 1, wherein said compound of Formula I is a compound of Formula X:

Formula X wherein:

$R_a$, $R_b$, $R_c$, G, D, $R_d$, $R_{d'}$, $R_e$, $R_f$, J, M, $X_1$, $R_g$ and $R_h$ are as defined in claim 1;

G' is O or S;

$A_6$ is C, N, O, S, or absent; and $R_i$ is H or alkyl;

such that the moiety described by $A_6$/C(G')/$NR_i$ is an amide, thioamide, carbamate, thiocarbamate, urea, or thiourea.

10. The drug-eluting stent according to claim 9, wherein said compound of Formula X is Compound 239, which is N-{6-[6-(3-Ethyl-ureido)-purin-9-yl]-2-trans-styryl-tetrahydro-cyclopenta[1,3]dioxol-4-ylmethyl}-phthalamic acid.

11. The drug-eluting stent according to claim 1, wherein said compound of Formula I is a compound of Formula XI:

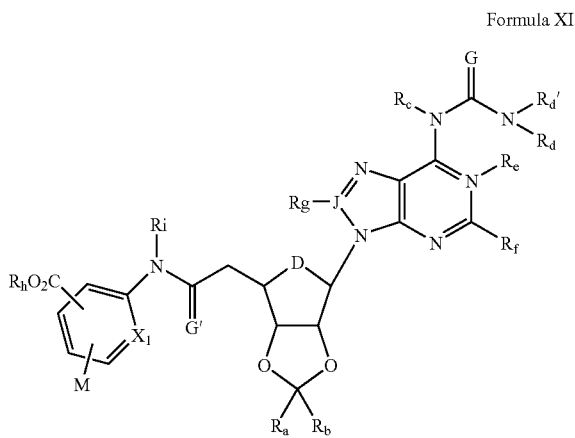

Formula XI wherein:

$R_a$, $R_b$, $R_c$, G, D, $R_d$, $R_{d'}$, $R_e$, $R_f$, J, M, $R_g$ and $R_h$ are as defined in Formulae I and II;

$R_i$ is H or alkyl;

G' is O or S, such that the moiety C(G')-$NR_i$ is an amide or thioamide; and $X_1$ is C or N.

12. The drug-eluting stent according to claim 1, wherein said compound of Formula I is a compound of Formula XII:

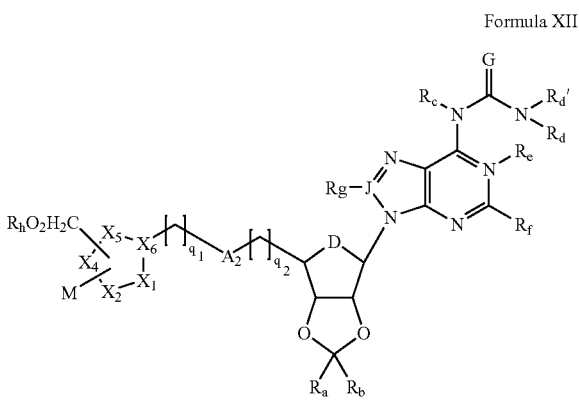

Formula XII wherein:

$R_a$, $R_b$, $R_c$, G, D, $R_d$, $R_{d'}$, $R_e$, $R_f$, J, M, $R_g$ and $R_h$ are as defined in Formulae I and II;

$X_1$, $X_2$, $X_4$, $X_5$, and $X_6$ are taken to mean a ring with or without unsaturation and are independently selected from the group consisting of: N, C, S, or O; and $X_1$-$X_6$ are taken to mean a ring of from three to five atoms;

$q_1$ and $q_2$ are independently 0, 1, or 2;

$A_2$ is C, O, S, S(O), $SO_2$, or N, or $A_2$ is absent;

such that when $q_1$ and $q_2$=0 and $A_2$ is absent, the ring described by $X_1/X_2/X_4/X_5/X_6$ is directly bonded to the 4' position of the ribose.

13. The drug-eluting stent according to claim 12, wherein said compound of Formula XII is Compound 298, which is 3-{6-[6-(3-Ethyl-ureido)-purin-9-yl]-2-styryl-tetrahydrocyclopenta[1,3]dioxol-4-ylmethoxymethyl}-thiophene-2-carboxylic acid.

14. The drug-eluting stent according to claim 6, wherein said stent is a coronary stent, a cerebral arterial stent, a carotid stent, aortic stent, renal artery stent, or a peripheral artery stent.

15. The drug-eluting stent according to claim 14, wherein said stent is a coronary stent.

16. A method for treating blocked or narrowed arteries, comprising the step of placing a P2Y.sub.12 receptor antagonist compound-eluting stent according to claim 1 in a narrowed or blocked artery of a patient, whereby a therapeutically effective amount of the compound is eluted to the stented area, whereby the blood flow is resumed and the restenosis and thrombosis are treated.

17. The method according to claim 16, which further comprises the step of monitoring the patient to ensure patency of the stented artery.

18. The drug-eluting stent according to claim 6, wherein

G=O;

D=O or C;

$R_a$=$R_c$=$R_d$=$R_f$=$R_g$=H;

$R_e$ is absent;

$R_h$=H or ethyl;

$R_{d'}$=$C_{1-4}$ alkyl, or $C_{3-6}$ cycloalkyl;

$A_2$ is $CH_2$, O, NH, N-methyl, N-acetyl, or absent;

$X_1$=C or N;

$R_b$=phenyl, benzyl, or styryl; and

M=H, halogen, or COOR.

19. The drug-eluting stent according to claim 6, wherein said Compound is

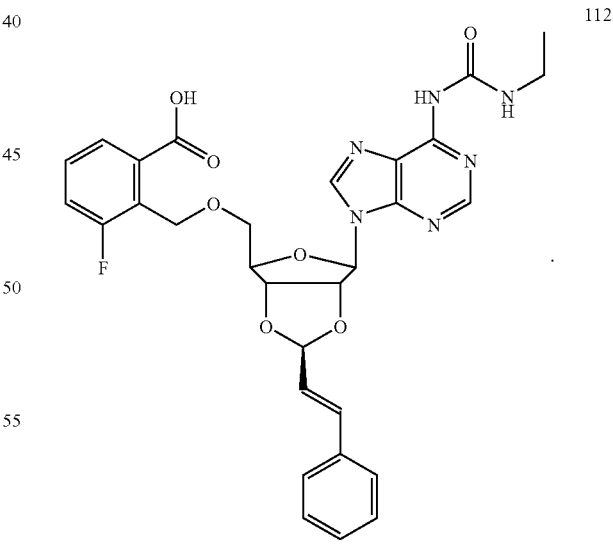

112

* * * * *